US012364721B2

(12) United States Patent
Cook et al.

(10) Patent No.: US 12,364,721 B2
(45) Date of Patent: Jul. 22, 2025

(54) COMPOSITIONS AND METHODS FOR TREATMENT OF INFLAMMATORY AND IMMUNE DISEASES

(71) Applicant: Prolacta Bioscience, Inc., City of Industry, CA (US)

(72) Inventors: David N. Cook, City of Industry, CA (US); Gregory McKenzie, City of Industry, CA (US); Julie E. Button, City of Industry, CA (US)

(73) Assignee: Prolacta Bioscience, Inc., Duarte, CA (US)

( * ) Notice: Subject to any disclaimer, the term of this patent is extended or adjusted under 35 U.S.C. 154(b) by 547 days.

(21) Appl. No.: 17/638,137

(22) PCT Filed: Sep. 24, 2020

(86) PCT No.: PCT/US2020/052501
§ 371 (c)(1),
(2) Date: Feb. 24, 2022

(87) PCT Pub. No.: WO2021/061991
PCT Pub. Date: Apr. 1, 2021

(65) Prior Publication Data

US 2023/0068960 A1 Mar. 2, 2023

Related U.S. Application Data

(60) Provisional application No. 63/053,224, filed on Jul. 17, 2020, provisional application No. 63/028,743, filed on May 22, 2020, provisional application No. 63/027,739, filed on May 20, 2020, provisional application No. 62/905,256, filed on Sep. 24, 2019.

(51) Int. Cl.

| | |
|---|---|
| ***A61K 35/745*** | (2015.01) |
| ***A61K 31/702*** | (2006.01) |
| ***A61P 3/04*** | (2006.01) |
| ***A61P 3/10*** | (2006.01) |
| ***A61P 37/06*** | (2006.01) |

(52) U.S. Cl.
CPC .......... *A61K 35/745* (2013.01); *A61K 31/702* (2013.01); *A61P 3/04* (2018.01); *A61P 3/10* (2018.01); *A61P 37/06* (2018.01)

(58) Field of Classification Search
CPC .......... A61K 35/745; A61P 37/06; A61P 3/04; A61P 3/10
See application file for complete search history.

(56) References Cited

U.S. PATENT DOCUMENTS

| | | | |
|---|---|---|---|
| 2,567,898 | A | 9/1951 | Hilding |
| 2,798,053 | A | 7/1957 | Brown |
| 3,946,113 | A | 3/1976 | Seiberling |
| 4,362,697 | A | 12/1982 | Tabb et al. |
| 4,455,483 | A | 6/1984 | Schonhuber |
| 4,485,040 | A | 11/1984 | Roger et al. |
| 4,544,750 | A | 10/1985 | Brandstrom et al. |
| 4,758,579 | A | 7/1988 | Kohl et al. |
| 4,762,822 | A | 8/1988 | Ettinger |
| 4,772,262 | A | 9/1988 | Grant et al. |
| 4,876,100 | A | 10/1989 | Holm et al. |
| 4,948,599 | A | 8/1990 | Sagara et al. |
| 5,045,552 | A | 9/1991 | Souda et al. |
| 5,064,674 | A | 11/1991 | Girsh |
| 5,169,766 | A | 12/1992 | Schuster et al. |
| 5,256,437 | A | 10/1993 | Degen et al. |
| 5,303,598 | A | 4/1994 | Binder et al. |
| 5,334,822 | A | 8/1994 | Sanford |
| 5,374,730 | A | 12/1994 | Slemon et al. |
| 5,386,032 | A | 1/1995 | Brandstrom |
| 5,401,523 | A | 3/1995 | Degen et al. |
| 5,505,955 | A | 4/1996 | Peterson et al. |
| 5,541,065 | A | 7/1996 | Erlich et al. |
| 5,576,040 | A | 11/1996 | Moller et al. |
| 5,589,168 | A | 12/1996 | Allen et al. |
| 5,605,689 | A | 2/1997 | Ammann |
| 5,616,483 | A | 4/1997 | Bjursell et al. |
| 5,670,196 | A | 9/1997 | Gregory |
| 5,683,733 | A | 11/1997 | Krabsen et al. |

(Continued)

FOREIGN PATENT DOCUMENTS

| | | | |
|---|---|---|---|
| CA | 2642976 | C | 9/2007 |
| CN | 102300575 | A | 12/2011 |

(Continued)

OTHER PUBLICATIONS

Arthur et al., "Intestinal inflammation targets cancer-inducing activity of the microbiota," Science 338(6103):120-123 (2012).
Cuevas-Ramos et al., "*Escherichia coli* induces DNA damage in vivo and triggers genomic instability in mammalian cells," Proceedings of the National Academy of Sciences, 107(25):11537-11542 (2010).
Kobata, "Exo-and endoglycosidases revisited," Proceedings of the Japan Academy, Series B, 89(3):97-117 (2013).

(Continued)

*Primary Examiner* — Mary Maille Lyons
(74) *Attorney, Agent, or Firm* — MEDLER FERRO WOODHOUSE & MILLS PLLC

(57) ABSTRACT

Provided herein are compositions, methods, strategies, kits, and articles of manufacture that are useful, inter alia, in the treatment or prevention of diseases or conditions such as those which may be associated with inflammation, infection, allergy, immune dysfunction, or dysbiosis of the intestinal microbiome. In some aspects, the invention provides a synergistic combination of a prebiotics, e.g., a mixture of human milk oligosaccharides, and a probiotic strain, such as a strain capable of internalizing and consuming the rebiotics, e.g., *B. longum* subsp. *infantis*.

11 Claims, 6 Drawing Sheets

Specification includes a Sequence Listing.

(56) References Cited

U.S. PATENT DOCUMENTS

| | | | |
|---|---|---|---|
| 5,707,678 | A | 1/1998 | Gregory |
| 5,972,337 | A | 10/1999 | Ceriani et al. |
| 5,983,198 | A | 11/1999 | Mowery et al. |
| 5,989,463 | A | 11/1999 | Tracy et al. |
| 6,001,558 | A | 12/1999 | Backus et al. |
| 6,004,288 | A | 12/1999 | Hochstedler et al. |
| 6,017,511 | A | 1/2000 | Wong et al. |
| 6,020,015 | A | 2/2000 | Gaull |
| 6,056,978 | A | 5/2000 | Beck et al. |
| 6,183,803 | B1 | 2/2001 | Morcol et al. |
| 6,194,009 | B1 | 2/2001 | Kamarel |
| 6,203,797 | B1 | 3/2001 | Perry |
| 6,270,827 | B1 | 8/2001 | Gaull et al. |
| 6,288,222 | B1 | 9/2001 | Roth et al. |
| 6,294,206 | B1 | 9/2001 | Barrett-Reis et al. |
| 6,613,367 | B1 | 9/2003 | Wells et al. |
| 6,635,296 | B1 | 10/2003 | Nissen et al. |
| 6,652,900 | B2 | 11/2003 | Lindquist |
| 6,670,124 | B1 | 12/2003 | Chow et al. |
| 6,737,096 | B2 | 5/2004 | Lindquist |
| 6,780,987 | B1 | 8/2004 | Herman et al. |
| 6,835,376 | B1 | 12/2004 | Neeser et al. |
| 6,846,298 | B1 | 1/2005 | Carr et al. |
| 6,910,594 | B2 | 6/2005 | Foley et al. |
| 7,829,130 | B2 | 11/2010 | Tossavainen et al. |
| 7,867,541 | B2 | 1/2011 | McMahon et al. |
| 7,914,822 | B2 | 3/2011 | Medo |
| 7,943,315 | B2 | 5/2011 | Medo et al. |
| 7,951,410 | B2 | 5/2011 | McMahon et al. |
| 8,197,872 | B2 | 6/2012 | Mills et al. |
| 8,278,046 | B2 | 10/2012 | Medo et al. |
| 8,377,455 | B2 | 2/2013 | Ceri et al. |
| 8,545,920 | B2 | 10/2013 | Medo et al. |
| 8,628,921 | B2 | 1/2014 | Medo et al. |
| 8,927,027 | B2 | 1/2015 | Fournell et al. |
| 9,149,052 | B2 | 10/2015 | Medo et al. |
| 9,433,651 | B2 | 9/2016 | Jones |
| 9,956,282 | B2 | 5/2018 | Cook et al. |
| 10,064,900 | B2 | 9/2018 | Maltzhan et al. |
| 10,076,546 | B2 | 9/2018 | Henn et al. |
| 10,098,903 | B2 | 10/2018 | Morrow et al. |
| 10,226,431 | B2 | 3/2019 | Jones et al. |
| 10,258,655 | B2 | 4/2019 | Henn et al. |
| 10,391,064 | B2 | 8/2019 | Jones et al. |
| 2001/0034614 | A1 | 10/2001 | Fletcher-Haynes et al. |
| 2001/0049096 | A1 | 12/2001 | Brown |
| 2002/0155445 | A1 | 10/2002 | Jarvik |
| 2002/0182243 | A1 | 12/2002 | Medo |
| 2003/0093171 | A1 | 5/2003 | Soehnlen |
| 2003/0129278 | A1 | 7/2003 | Stahl et al. |
| 2003/0152942 | A1 | 8/2003 | Fors et al. |
| 2003/0175701 | A1 | 9/2003 | Griffiths et al. |
| 2003/0219812 | A1 | 11/2003 | Quay et al. |
| 2004/0181205 | A1 | 9/2004 | Morton et al. |
| 2004/0265462 | A1 | 12/2004 | Carlson |
| 2005/0053707 | A1 | 3/2005 | Kopf et al. |
| 2005/0096295 | A1 | 5/2005 | McMahon et al. |
| 2005/0100634 | A1 | 5/2005 | Medo |
| 2005/0214358 | A1 | 9/2005 | Mikoshiba et al. |
| 2005/0220894 | A1 | 10/2005 | Williams et al. |
| 2006/0040893 | A1 | 2/2006 | Harn et al. |
| 2006/0115558 | A1 | 6/2006 | Lamothe |
| 2006/0204632 | A1 | 9/2006 | Barrett-Reis et al. |
| 2006/0233915 | A1 | 10/2006 | Puski et al. |
| 2007/0098863 | A1 | 5/2007 | Medo et al. |
| 2007/0098871 | A1 | 5/2007 | Dunker et al. |
| 2007/0104700 | A1 | 5/2007 | Garcia-Rodenas et al. |
| 2007/0166447 | A1 | 7/2007 | Ur-Rehman et al. |
| 2007/0192878 | A1 | 8/2007 | Perreault |
| 2007/0203802 | A1 | 8/2007 | Medo et al. |
| 2008/0118615 | A1 | 5/2008 | Hartmann et al. |
| 2008/0124430 | A1 | 5/2008 | Medo et al. |
| 2008/0187619 | A1 | 8/2008 | Hartmann et al. |
| 2008/0227101 | A1 | 9/2008 | Medo et al. |
| 2008/0254165 | A1 | 10/2008 | Patel et al. |
| 2008/0274230 | A1 | 11/2008 | Johns et al. |
| 2009/0035813 | A1 | 2/2009 | Sprenger et al. |
| 2009/0098240 | A1 | 4/2009 | Mills et al. |
| 2009/0181848 | A1 | 7/2009 | Lenz et al. |
| 2009/0203592 | A1 | 8/2009 | Beermann et al. |
| 2009/0258121 | A1 | 10/2009 | Medo |
| 2010/0268658 | A1 | 10/2010 | Medo et al. |
| 2010/0280115 | A1 | 11/2010 | Medo et al. |
| 2011/0206684 | A1 | 8/2011 | Medo |
| 2011/0206806 | A1 | 8/2011 | Ur-Rehman et al. |
| 2011/0256233 | A1 | 10/2011 | Fournell et al. |
| 2011/0256269 | A1 | 10/2011 | Medo et al. |
| 2011/0311689 | A1 | 12/2011 | Medo et al. |
| 2012/0040051 | A1 | 2/2012 | Chen et al. |
| 2012/0149584 | A1 | 6/2012 | Olle et al. |
| 2012/0171165 | A1 | 7/2012 | Buck et al. |
| 2012/0171166 | A1 | 7/2012 | Chow et al. |
| 2013/0059815 | A1 | 3/2013 | Fournell et al. |
| 2014/0037785 | A1 | 2/2014 | Barboza et al. |
| 2014/0087021 | A1 | 3/2014 | Berrocal et al. |
| 2014/0377421 | A1 | 12/2014 | Kambouris et al. |
| 2015/0010670 | A1 | 1/2015 | Mills et al. |
| 2015/0037847 | A1 | 2/2015 | Bertelsen et al. |
| 2015/0140175 | A1 * | 5/2015 | Fournell ................ A23C 9/158 426/587 |
| 2015/0238545 | A1 | 8/2015 | Borody |
| 2015/0335577 | A1 | 11/2015 | Bazo et al. |
| 2015/0359894 | A1 | 12/2015 | Weinrich |
| 2018/0092374 | A1 | 4/2018 | Fournell et al. |
| 2018/0104279 | A1 | 4/2018 | Elster et al. |
| 2019/0154465 | A1 | 5/2019 | Moriya et al. |
| 2019/0247447 | A1 | 8/2019 | Button et al. |
| 2020/0054035 | A1 | 2/2020 | Sun et al. |
| 2020/0093870 | A1 | 3/2020 | Santiago et al. |

FOREIGN PATENT DOCUMENTS

| | | | |
|---|---|---|---|
| CN | 104144613 | A | 11/2014 |
| EP | 1637043 | A1 | 3/2006 |
| EP | 0975235 | B1 | 5/2006 |
| EP | 3450443 | A1 | 3/2019 |
| JP | 1451747 | A | 10/1976 |
| JP | S56-36494 | A | 4/1981 |
| JP | S 61-33895 | U | 1/1986 |
| JP | S64-67141 | A | 3/1989 |
| JP | H01-168693 | A | 7/1989 |
| JP | H06-303900 | A | 11/1994 |
| JP | 2001-517949 | A | 10/2001 |
| JP | 2002-532074 | A | 10/2002 |
| JP | 2002-540806 | A | 12/2002 |
| JP | 2003-047402 | A | 2/2003 |
| JP | 2003-113087 | A | 4/2003 |
| JP | 2003-522539 | A | 7/2003 |
| JP | 2005-525116 | A | 8/2005 |
| JP | 2008-512398 | A | 4/2008 |
| JP | 2012-510476 | A | 5/2010 |
| JP | 2012-520325 | A | 9/2012 |
| RU | 2430631 | C2 | 10/2011 |
| SE | 380422 | B | 11/1975 |
| TW | I280101 | B | 5/2007 |
| WO | 1998/057549 | A1 | 12/1998 |
| WO | 2000/043550 | A2 | 7/2000 |
| WO | 2005/013709 | A1 | 2/2005 |
| WO | 2005/051088 | A2 | 6/2005 |
| WO | 2005/084129 | A2 | 9/2005 |
| WO | 2006/026878 | A1 | 3/2006 |
| WO | 2006/026879 | A1 | 3/2006 |
| WO | 2007/035870 | A2 | 3/2007 |
| WO | 2007/051475 | A1 | 5/2007 |
| WO | 2008/027572 | A1 | 3/2008 |
| WO | 2008/067486 | A2 | 6/2008 |
| WO | 2008/073888 | A2 | 6/2008 |
| WO | 2009/077352 | A1 | 6/2009 |
| WO | 2010/030764 | A2 | 3/2010 |
| WO | 2010/065652 | A1 | 6/2010 |
| WO | 2010/105207 | A1 | 9/2010 |
| WO | 2012/097950 | A1 | 7/2012 |
| WO | 2012/124668 | A1 | 9/2012 |
| WO | 2012/160080 | A1 | 11/2012 |

(56) References Cited

FOREIGN PATENT DOCUMENTS

| | | | | |
|---|---|---|---|---|
| WO | 2013/044928 A1 | | 4/2013 | |
| WO | 2013/139344 A1 | | 9/2013 | |
| WO | 2013/182206 A1 | | 12/2013 | |
| WO | 2013/190530 A1 | | 12/2013 | |
| WO | 2013/190531 A1 | | 12/2013 | |
| WO | 2014/135167 A1 | | 9/2014 | |
| WO | 2014/167537 A1 | | 10/2014 | |
| WO | 2014/167538 A1 | | 10/2014 | |
| WO | WO-2014201037 A2 | * | 12/2014 | A23C 9/123 |
| WO | 2015/032413 A1 | | 3/2015 | |
| WO | 2015/036138 A1 | | 3/2015 | |
| WO | 2015/049331 A1 | | 4/2015 | |
| WO | 2015/106943 A1 | | 7/2015 | |
| WO | 2015/150328 A1 | | 10/2015 | |
| WO | 2015/197082 A1 | | 12/2015 | |
| WO | 2016/088589 A1 | | 6/2016 | |
| WO | 2016/168698 A1 | | 10/2016 | |
| WO | 2017/004238 A1 | | 1/2017 | |
| WO | 2017/008026 A1 | | 1/2017 | |
| WO | 2017/042382 A1 | | 3/2017 | |
| WO | 2017/091783 A2 | | 6/2017 | |
| WO | 2017/101958 A1 | | 6/2017 | |
| WO | WO-2017156550 A1 | * | 9/2017 | A61K 31/702 |
| WO | 2018/053535 A1 | | 3/2018 | |
| WO | 2018/077892 A1 | | 5/2018 | |
| WO | 2018/206434 A1 | | 11/2018 | |
| WO | 2019/008133 A1 | | 1/2019 | |
| WO | 2019/043029 A1 | | 3/2019 | |
| WO | 2019/106620 A1 | | 6/2019 | |
| WO | 2019/191390 A2 | | 10/2019 | |
| WO | 2019/191694 A1 | | 10/2019 | |
| WO | 2019/227085 A1 | | 11/2019 | |
| WO | 2019/232284 A1 | | 12/2019 | |
| WO | 2020/128948 A1 | | 6/2020 | |
| WO | 2021/061991 A1 | | 4/2021 | |
| WO | 2021/074409 A1 | | 4/2021 | |
| WO | 2021/094993 A1 | | 5/2021 | |
| WO | 2021/102090 A1 | | 5/2021 | |
| WO | 2021/149663 A1 | | 7/2021 | |
| WO | 2001/060171 A1 | | 8/2021 | |
| WO | 2022/036225 A1 | | 2/2022 | |

OTHER PUBLICATIONS

Nougayrede et al., "*Escherichia coli* Induces DNA Double-Strand Breaks in Eukaryotic Cells," Science 313(5788):848-851 (2006).
Olier et al., "Genotoxicity of *Escherichia coli* Nissle 1917 strain cannot be dissociated from its probiotic activity," 3(6):501-509 (2012).
Walsh et al., "From lab bench to formulated ingredient: Characterization, production, and commercialization of human milk oligosaccharides," Journal of Functional Foods 72:104052 (2020).
International Search Report and Written Opinion mailed Dec. 22, 2021 in International Application No. PCT/US2021/045951.
International Search Report and Written Opinion mailed May 18, 2022 in International Application No. PCT/US2022/012120.
International Search Report and Written Opinion mailed May 18, 2022 in International Application No. PCT/US2022/013313.
[Author Unknown] "Safe Handling of Milk and Dairy Products". Clemson University, Factsheet, HGIC 3510, Updated: Mar. 8, 2007, https://hgic.clemson.edu/factshee/safe-handling-of-milk-dairy-products/, 5 pages.
[Author Unknown] Oligosaccharide, Definition of Oligosaccharide by Merriam, 4 pages www.meriam-webster.com/dictionary/oligosaccharide. (Year: 2021).
[Author Unknown] Beta-galactosidase, Wikipedia, https://en.wikipedia.org/wiki/Beta-galactosidase (Mar. 12, 2021), 7 pages. (Year: 2021).
[Author Unknown] "Enteral Nutrition", Patients on Intravenous and Nasogastric Nutrition Therapy (definition, enteral), downloaded on May 13, 2019 from https:pinnt.com/Enteral-Nutrition.aspx (2019), PINNT, Dorset, England, 2 pgs.
[Author Unknown], "CARE + WEAR" What is TPN and How is it Administered? Definition: Total Parenteral Nutrition (2018), downloaded Apr. 25, 2019 from https://www.careandwear.com/blogs/commun ity/124683651-what-is-tpn-and-how-is-it-administered, 5 pages.
[Author Unknown] "Incidence and Prevalence", Advanced Renal Education (2012); pp. 1-2, advancedrenaleducation.com/content/incidence-and-prevalence.
[Author Unknown], "Neonatal Parenteral Nutrition", UCSF Children's Hospital, Intensive Care Nursery House Staff Manual, 2004-2006, The Regents of the University of California; pp. 136-142, 7 pages.
[Author Unknown] "Home parenteral nutrition". Mayo Clinic / Mayo Foundation for Medical Education and Research (MFMER) 1998-2019, pp. 1-3, downloaded Oct. 29, 2019, https://www.mayoclinic.org/tests-procedures/total-parenteral-nutrition/about/pac-20385081?p= 1.
[Author Unknown] "The benefits of probiotics bacteria". Harvard Medical School (Jun. 2, 2017), https://www.health.harvard.edu/staying-healthy/the-benefits-of-probiotics, 8 pages.
Adhikari, et al., Viability of Microencapsulated Bifidobacteria in Set Yogurt During Refrigerated Storage. Journal of Dairy Science (Sep. 1, 2000); 83(9): 1946-1951.
Aoyama, et al. "Improved outcome of allogeneic bone marrow transplantation due to breastfeeding-induced tolerance to maternal antigens." Blood (2009); 113.8: 1829-1833.
Arnold, "How North American Donor Banks Operate: Results of a Survey: Part 1," J. Hum. Lact. 13(2):159-162 (1997).
Arnold, "How North American Donor Banks Operate: Results of a Survey: Part 2," J. Hum. Lact. 13(3):243-246 (1997).
Arnold, "How to Order Banked Donor Milk in the United States: What the Health Care Provider Needs to Know," J. Hum. Lact. 14(1):65-67 (1998).
Arnold, Human Milk in the NICU. Policy Into Practice. Jones & Bartlett Publishers. pp. 3-11, pp. 15-46; pp. 191-207; pp. 311-367, 121 pages (2010).
Autran, et al., "Human milk oligosaccharide composition predicts risk of necrotising enterocolitis in preterm infants." Gut 67(6):1064-1070 (2018).
Bao, et al., "Simultaneous quantification of sialyloligosaccharides from human milk by capillary electrophoresis" Anal Biochem. 370(2): 206-214 (2007).
Bendich, "Symposium: Antioxidants, Immune Response, and Animal Function. Physiological Role of Antioxidants in the Immune System" J Dairy Sci. 76(9): 2789-2794 (1993).
Bernshaw, "Milk Banking: An Idea That has Come of Age. Non-Profit Milk Banking," Seminar delivered on Aug. 29, 2006. Retrieved from the internet: http://www.utahbreastfeeding.org/business/2006_08_MilkBankNotes.pdf.
Bin-Nun, et al., "Oral Probiotics Prevent Necrotizing Enterocolitis in Very Low Birth Weight Neonates", J Pediatr. 147(2):192-196 (2005).
Black, et al., "Incremental Hospital Costs Associated With Comorbidities of Prematurity". Managed Care Magazine Online (Dec. 2015); downloaded on Jan. 25, 2017 at https://www.managedcaremag.com/linkout/2015/12/54, 14 pages.
Bloom, "Safety of donor milk: a brief report" Journal of Perinatology 36(5):392-393 (2016).
Bode, et al., "Overcoming the limited availability of human milk oligosaccharides: challenges and opportunities for research and application". Nutr Rev. 74(10):635-644 (2016).
Bode, L., "Human milk oligosaccharides: Every baby needs a sugar mama". Glycobiology; 22(9):1147-1162 (2012).
Bode and Jantscher-Krenn, "Structure-function relationships of human milk oligosaccharides." Advances in Nutrition: An International Review Journal 3.3:383S-391S (2012).
Boehm and Stahl, "Oligosaccharides from Milk," The Journal of Nutrition 137(3 Suppl 2):847S-849S (2007).
Boehm, et al., "Metabolic Differences Between AGA- and SGA-Infants of Very Low Birthweight II Relationship to Protein Intake," Acta Pædiatrica 77(5):642-646 (1988).
Burger et al., "Detection of a 1% to 2% Contributor in a DNA Sample Mixture From Human Milk," International Society for Forensic Genetics 21st Congress Conference Programme and Abstracts

(56) References Cited

OTHER PUBLICATIONS

[online], Sep. 12-17, 2005 [retrieved on Mar. 26, 2007]. Retrieved from the Internet: http://www.ipatimup.pt/isfg2005/PROGRAMME.pdf; p. 75.
Burger et al., "Detection of a Minor contributor in a DNA Sample Mixture from Human Milk," International Congress Series 1288:547-549 (2006).
Carey et al., "Growth and phosphorus metabolism in premature infants fed human milk, fortified human milk, or special premature formula. Use of serum procollagen as a marker of growth," Am. J. Dis. Children 141(5):511-515 (1987).
Casey, "The nutritive and metabolic advantages of homologous milk," Proc. Nutr. Soc. 48:271-281 (1989).
Chaturvedi, et al., "Fucosylated human milk oligosaccharides vary between individuals and over the course of lactation" Glycobiology 11(5): 365-372 (2001).
Chen et al., "The Role of Intestinal Microbiota in Acute Graft-versus-Host Disease". Journal of Immunology Research pp. 1-9 (2015).
Coppa et al., "Oligosaccharides in human milk during different phases of lactation." Acta Paediatr Suppl. 88(430):89-94 (1999).
Cowan et al., "Milk permeate as a dietary supplement for lactating dairy cows," Aus. J. Exp. Agric. 30(6):807-810 (1990).
Database Medline [Online] US National Library of Medicine (NLM), Bethesda, MD, US; Jul. 1979 (Jul. 1979), Jenness R: "The composition of human milk." Database accession No. NLM392766, XP002785943, 2 pages.
Davidson et al., "Fucosylated Oligosaccharides in Human Milk in Relation to Gestational Age and Stage of Lactation". Adv Exp Med Biol. 554:427-430 (2004).
Davies, Stella M., "A Pilot Study of Donor Enteral Human Milk to Modulate the Gut Microbiome in Children Receiving Stem Cell Transplant", 2015 BMT Tandem Meetings, Feb. 11, 2015, San Diego, CA, Poster Abstract—Copyright 2011, BMT Tandem, XP055518062, Retrieved from the Internet: URL:https://bmt.confex.com/tandem/2015/webprogram/Paper5173.html [retrieved on Oct. 23, 2018], 2 pages. Optima.
Definition of "drink", Oxford Dictionary (2021), 7 pages.
Edmond and Bahl, "Optimal feeding of low-birth-weight infants." World Health Organization pp. 1-121, 131 pages (2006).
Fessler et al., "Enteral Nutrition for Patients With Head and Neck Cancer." Today's Dietitian vol. 10, No. 6, p. 46, 6 pages (Jun. 2008).
Ford et al., "Improved feeding tolerance and growth are linked to increased gut microbial community diversity in very-low-birth-weight infants fed mother's own milk compared with donor breast milk," The American Journal of Clinical Nutrition 109(4):1088-1097 (2019).
Fredricks, "The gut microbiota and graft-versus-host disease," J Clin Invest. 129(5):1808-1817 (2019).
Friis et al., "Rate of inactivation of cytomegalovirus in raw banked milk during storage at −20°C. and pasteurisation," Br. Med. J. 285:1604-1605 (1982).
Fuji et al., "Systematic Nutritional Support in Allogeneic Hematopoietic Stem Cell Transplant Recipients," Biology of Blood and Marrow Transplantation 21(10):1707-1713 (2015).
Fukushima et al., "Consumption of cow milk and egg by lactating women and the presence of β-lactoglobulin and ovalbumin in breast milk," Am. J. Clin. Nutr. 65:30-35 (1997).
Gabrielli et al., "Preterm Milk Oligosaccharides During the First Month of Lactation," Pediatrics 128(6): e1520-1531 (2011).
Ganapathy, "Long term healthcare costs of infants who survived neonatal necrotizing enterocolitis: a retrospective longitudinal study among infants enrolled in Texas Medicaid". BMC Pediatrics 13(1):1-11 (2013).
Gartner et al., "Breastfeeding and the use of human milk," Pediatr. 115(2):496-506 (2005).
Geilman et al., "Production of an electrolyte beverage from milk permeate," J. Dairy Sci. 75(9):2364-2369 (1992).
Gerbitz et al., "Probiotic effects on experimental graft-versus-host disease: let them eat yogurt," Blood 103(11):4365-4367 (2004).
German et al., "Human milk oligosaccharides: Evolution, structures and bioselectivity as substrates for intestinal bacteria," Nestle Nutr. Workshop Ser. Pediatr. Program 62:205-222 (2008).
Ghosh, et al., "Quantitation of Human Immunodeficiency Virus Type 1 in Breast Milk". J Clin Microbiol. 41(6): 2465-2470 (2003).
Gotoh et al., "Sharing of human milk oligosaccharides degradants within bifidobacterial communities in faecal cultures supplemented with Bifidobacterium bifidum", Sci Rep. 8(1):1-14 (2018).
Grandison et al., "The use of dead-end and cross-flow nanofiltration to purify prebiotic oligosaccharides from reaction mixtures". Songklanakarin J. Sci. Technol. 24(Suppl.):915-928 (2002).
Hagelberg et al., "Amino Acid Levels in the Critically Ill Preterm Infant Given Mother's Milk Fortified with Protein from Human or Cow's Milk" Acta Paediatr. Scand. 79:1163-1174 (1990).
Hagelberg et al., "The Protein Tolerance of Very Low Birth Weight Infants Fed Human Milk Protein Enriched Mothers' Milk" Acta Paediatr. Scand. 71: 597-601 (1982).
Hair et al., "Beyond Necrotizing Enterocolitis Prevention: Improving Outcomes with an Exclusive Human Milk-Based Diet". Breastfeeding Medicine 11(2): 70-74 (2016).
Hair et al., "Beyond Necrotizing Enterocolitis: Other Clinical Advantages of an Exclusive Human Milk Diet," Breastfeeding Medicine 13(6): 408-411 (2018).
Han et al., "Application of Electrospray Ionization-Collision Induced Dissociation Tandem Mass Spectrometry in Differentiation Isomers of Human Milk Oligosaccharides," Chinese Journal Analytical Chemistry, 34(9):1213-1218 (2006) (with English Abstract).
Hartmann et al., "Best Practice Guidelines for the Operation of a Donor Human Milk Bank in an Australian NICU," Early Human Devel. 83:667-673 (2007).
Heiman and Schanler, "Benefits of maternal and donor human milk for premature infants." Early Human Development 82(12): 781-787 (2006).
Henrick et al., "Colonization by B. infantis EVC001 modulates enteric inflammation in exclusively breastfed infants," Pediatric Research 86: 749-757 (2019).
Herrmann and Carroll, "An Exclusively Human Milk Diet Reduces Necrotizing Enterocolitis," Breastfeeding Medicine 9(4):184-190 (2014).
Hicks et al., "Calcium Absorption in Very Low Birth Weight Infants with and without Bronchopulmonary Dysplasia," The Journal of Pediatrics 158(6):885-890 (2011).
Huston et al., "Decreasing Necrotizing Enterocolitis and Gastrointestinal Bleeding in the Neonatal Intensive Care Unit: The Role of Donor Human Milk and Exclusive Human Milk Diets in Infants ≤1500 g Birth Weight," ICAN: Infant, Child, & Adolescent Nutrition 6(2): 86-93 (2014).
Huston, et al., "Improving Growth for Infants ≤1250 Grams Receiving an Exclusive Human Milk Diet," Nutrition in Clinical Practice 33(5):671-678 (2018).
Hylmö, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.
Itabashi et al., "Fortified preterm human milk for very low birth weight infants," Early Hum. Devel. 29:339-343 (1992).
Jacobson, et al., "A Gut Commensal-Produced Metabolite Mediates Colonization Resistance to *Salmonella* Infection", Cell Host Microbe 24(2): 296-307.e7 (2018).
Jenness et al., "Substances Adsorbed on the Fat Globules in Cream and Their Relation to Churning. V. Composition of the 'Membrane' and Distribution of the Adsorbed Substances in Churning," J. Dairy Science 28(8):611-623 (1945).
Jensen et al., "Lipids in Human Milk and Infant Formulas," Ann. Rev. Nutr. 12:417-441 (1992).
Jensen et al., "Lipids of Bovine and Human Milks: A Comparison," J. Dairy Science 73:223-240 (1990).
Jenq et al., "Regulation of intestinal inflammation by microbiota following allogeneic bone marrow transplantation," J Exp Med. 209(5): 903-911 (2012).
Jones et al., "History of North American Donor Milk Banking: One Hundred Years of Progress," J Hum Lact. 19(3):313-318 (2003).

(56) References Cited

OTHER PUBLICATIONS

Khandelwal et al., "A Pilot Study of Human Milk to Reduce Intestinal Inflammation After Bone Marrow Transplant," Breastfeeding Medicine 14(3):193-202 (2019).
Klein, "Nutrient Requirements for Preterm Infant Formulas," J. Nutr. 132:1395S-1577S (2002).
Kobata, "Structures and application of oligosaccharides in human milk". Proc Jpn Acad Ser B Phys Biol Sci. 86(7):731-747 (2010).
Kornhauser and Schneiderman, "How Plans Can Improve Outcomes and Cut Costs for Preterm Infant Care," Managed Care 19(1): 28-30 (2010).
Krukovsky et al., "The Effects of Nordihydroguaiaretic Acid, Salt, and Temperature of Storage on the Stability of Fat and Fat-Soluble Vitamins in Cream and Butter," J. Dairy Science 32(7):679-687 (1949).
Kunz et al., "Bioactivity of Human Milk Oligosaccharides," Food Oligosaccharides: Production, Analysis and Bioactivity, First Edition. Edited by Dr. F. Javier Moreno and Dr. María Luz Sanz. JohnWiley & Sons, Ltd., Ch. I, pp. 5-20, 18 pages (2014).
Kunz et al., "Lactose-derived oligosaccharides in the milk of elephants: comparison with human milk," Br J Nutr. 82(5): 391-399 (1999).
Kunz et al., "Oligosaccharides in Human Milk: Structural, Functional, and Metabolic Aspects," Annu Rev Nutr. 20: 699-722 (2000).
Kuzma-O'Reilly et al., "Evaluation, Development, and Implementation of Potentially Better Practices in Neonatal Intensive Care Nutrition," Pediatrics 111(4): e461-e470 (2003).
Ladas et al., "The safety and feasibility of probiotics in children and adolescents undergoing hematopoietic cell transplantation," Bone Marrow Transplant 51(2): 262-266 (2016).
Ladirat et al., "High-throughput analysis of the impact of antibiotics on the human intestinal microbiota composition", Journal of Microbiological Methods 92(3):387-397 (2013).
Ladirat et al., "Impact of galacto-oligosaccharides on the gut microbiota composition and metabolic activity upon antibiotic treatment during in vitro fermentation," FEMS Microbiol Ecol 87:41-51 (2014).
Lapillione et al., "Mineral balance and whole body bone mineral content in very low-birth-weight infants," Acta Pediatrica 84 (s405):117-122 (1994).
Lara-Villoslada et al., "Beneficial effects of probiotic bacteria isolated from breast milk," British Journal of Nutrition 98 Suppl. 1: S96-100 (2007).
Laterza et al., "The Gut Microbiota and Immune System Relationship in Human Graft-Versus-Host Disease," Mediterranean Journal of Hematology and Infectious Diseases 8(1): e2016025 (2016).
Lawley et al., "Differentiation of Bifidobacterium longum subspecies longum and infantis by quantitative PCR using functional gene targets, " PeerJ 5: e3375 (2017).
Lawrence, "Storage of human milk and the influence of procedures on immunological components of human milk," Acta Pædiatr. 88:14-18 (1999).
Lin et al., "Oral Probiotics Reduce the Incidence and Severity of Necrotizing Enterocolitis in Very Low Birth Weight Infants," Pediatrics; 115(1): 1-4 (2005).
Lindblad et al., "Blood Levels of Critical Amino Acids in Very Low Birthweight Infants on a High Human Milk Protein Intake" Acta Paediatr. Scand. 296:24-27 (1982).
Locascio, et al., "Broad Conservation of Milk Utilization Genes in *Bifidobacterium longum* subsp. *infantis* as Revealed by Comparative Genomic Hybridization", Applied and Environmental Microbiology 76(22):7373-7381 (2010).
Lönnerdal, "Biochemistry and physiological function of human milk proteins," Am. J. Clin. Nutr. 42:1299-1317 (1985).
Lucas and Cole, "Medical Science Breast milk and neonatal necrotising enterocolitis, " The Lancet 336(8730-8731):1519-1523 (1980).
Lucas et al., "A human milk formula," Early Hum. Devel. 4(1):15-21 (1980).
Lucas et al., "Breast milk and subsequent intelligence quotient in children born preterm". The Lancet 339(8788): 261-264 (1992).
Lucas et al., "Randomised trial of early diet in preterm babies and later intelligence quotient," BMJ 317(7171): 1481-1487 (1998).
Luck et al., "Nicotine and cotinine concentrations in the milk of smoking mothers: influence of cigarette consumption and diurnal variation," Eur J. Pediatr. 146:21-26 (1987).
Martinez-Ferez et al., "Goats' milk as a natural source of lactose-derived oligosaccharides: Isolation by membrane technology," International Dairy Journal 16:173-181 (2006).
McKiernan et al., "The Constituents of Neonatal Milk," Pediatr. Res. 16:60-64 (1982).
Melegh et al., "Changes of Plasma Free Amino Acids and Renal Clearances of Carnitines in Premature Infants During L-Carnitine-Supplemented Human Milk Feeding," J. Pediatric Gastroenterol. Nutr. 7(3):424-429 (1998).
Moro et al., "Fortification of Human Milk: Evaluation of a Novel Fortification Scheme and of a New Fortifier," J. Ped. Gastroenterol. Nutr. 20:162-172 (1995).
Moro et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 13:150-154 (1991).
Morrow et al., "Human-Milk Glycans That Inhibit Pathogen Binding Protect Breast-feeding Infants against Infectious Diarrhea," J Nutr. 135(5):1304-1307 (2005).
Musilova et al., "Assessment of the symbiotic properties of human milk oligosaccharides and *Bifidobacterium longum* subsp. *infantis* in vitro and in humanised mice," Beneficial Microbes 8(2):281-289 (2017).
Muscaritoli et al., "Clinical and metabolic effects of different parenteral nutrition regimens in patients undergoing allogeneic bone marrow transplantation," Transplantation 66.5: 610-616 (1998).
Nash et al., "Human Milk Banking: A Review". www.breastfeedingindia.com/breastfeeding/human_milk_banks.html, pp. 1-3, downloaded Dec. 18, 2019 (indicated by the Examiner in U.S. Appl. No. 15/726,232 as being published in 2002).
Newburg et al., "Fucosylated Oligosaccharides of Human Milk Protect Suckling Mice from Heat-Stabile Enterotoxin of *Escherichia coli*," The Journal of Infectious Diseases, 162:1075-1080 (1990).
Newburg et al., "Quantitative Analysis of Human Milk Oligosaccharides by Capillary Electrophoresis," Adv Exp Med Biol. 478: 381-382 (2000).
Nieder et al., "Safety and Feasibility of Administering Lactobacillus Plantarum to Children Undergoing Myeloablative Hematopoietic Cell Transplantation (HCT)," Biology of Blood and Marrow Transplantation 21(2) (Supplement): Abstract S256, 1 page (2015).
Ninoneuvo et al., "A Strategy for Annotating the Human Milk Glycome," Journal of Agricultural and Food Chemistry 54:7471-7480 (2006).
Ogundele, "Techniques for the storage of human breast milk: implications for anti-microbial functions and safety of stored milk," Eur. J. Pediatr. 159:793-797 (2000).
O'Sullivan et al., "Correlation of rRNA gene amplicon pyrosequencing and bacterial culture for microbial compositional analysis of faecal samples from elderly Irish subjects," J Appl Microbiol 111(2): 467-473 (2011).
Ostrov, "Some ill adults use breast milk to fight disease." The Seattle Times. Dec. 30, 2004.
Panzer et al., "Immune thrombocytopenia in severe hemophilia A treated with high-dose intravenous immunoglobulin," Transfusion 26:69-72 (1986).
Pham and Lawley, "Emerging insights on intestinal dysbiosis during bacterial infections," Current Opinion in Microbiology 17: 67-74 (2014).
Pietz et al., "Prevention of Necrotizing Enterocolitis in Preterm Infants: A 20-Year Experience," Pediatrics 119 (1): e164-e170 (2007).
Polberger, "Fortified Human Milk for Very Low Birth Weight Infants: Effects on Growth and Metabolism," Dept. Pediatrics, University of Lund, Malmo pp. 1-148 (1990).
Polberger et al., "Amino Acid Concentrations in Plasma and Urine in Very Low Birth Weight Infants Fed Non-Protein-Enriched or Human Milk Protein-Enriched Human Milk," Department of Pedi-

(56) References Cited

OTHER PUBLICATIONS atrics, University of Lund, Malmö General Hospital, S-21401 Malmö Sweden, Pediatrics 86:131-148. (1990).

Polberger et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.

Polberger et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 79(8-9): 729-736 (1990).

Polberger et al., "Growth of Very Low Birth Weight Infants on Varying Amounts of Human Milk Protein," Department of Pediatrics, University of Lund, Malmö General Hospital, S-21401 Malmö Sweden, 25(4):69-87; Pediatr Res (1989).

Polberger et al., "Urinary and Serum Urea as Indicators of Protein Metabolism in Very Low Birth Weight Infants Fed Varying Human Milk Protein Intakes," Department of Pediatrics, University of Lund, Malmö General Hospital, S-21401 Malmö Sweden, pp. 89-99. Acta Paediatr Scand. 79(8-9): 737-742 (1990).

Prentice, "Constituents of Human Milk," Food and Nutrition Bulletin, the United Nations University Press, 17(4), Dec. 1996. Retrieved from the internet: http://www.inffoundation.org/FNB/FNBIndexNEW.html.

Prudden et al., "Synthesis of asymmetrical multiantennary human milk oligosaccharides," PNAS 114(27): 6954-6959 (2017).

Pubchem Compound Summary, 3-Fucosyllactose, $C_{18}H_{32}O_{15}$, 2005, pp. 1-16, downloaded Dec. 18, 2019, https://pubchem.ncbi.nlm.nih.gov/compound/3_-Fucosyllactose.

Pubchem Compound Summary, 2-Fucosyllactose, Unii-XO2533XO8R, $C_{18}H_{32}O_{15}$, 2005, pp. 1-17, downloaded Dec. 18, 2019, https://pubchem.ncbi.nIm. nih.gov/compound/170484.

Rechtman et al., "Effect of Environmental Conditions on Unpasteurized Donor Human Milk". Breastfeeding Medicine 1(1): 24-26 (2006).

Reeves et al., "TGF-β2, a Protective Intestinal Cytokine, is Abundant in Maternal Human Milk and Human-Derived Fortifiers but Not in Donor Human Milk," Breastfeeding Medicine 8(6):496-502 (2013).

Rönnholm et al., "Human Milk Protein and Medium-Chain Triglyceride Oil Supplementation of Human Milk: Plasma Amino Acids in Very Low-Birth-Weight Infants," Pediatrics (5):792-799 (1984).

Rönnholm et al., "Supplementation with Human Milk Protein Improves Growth of Small Premature Infants Fed Human Milk," Pediatrics 77(5):649-653 (1986).

Saiki et al., "Genetic analysis of amplified DNA with immobilized sequence-specific oligonucleotide probes," Proc. Natl. Acad. Sci. USA 86:6230-6234 (1989).

Salle et al., "Effects of Calcium and Phosphorus Supplementation on Calcium Retention and Fat Absorption in Preterm Infants Fed Pooled Human Milk," J. Pediatric Gastroenterol. (4): 638-642 (1986).

Samanta et al., "Prophylactic Probiotics for Prevention of Necrotizing Enterocolitis in Very Low Birth Weight Newborns, " J Trop Pediatr 55(2):128-131 (2009).

Sandhu et al., "Human-Based Human Milk Fortifier as Rescue Therapy in Very Low Birth Weight Infants Demonstrating Intolerance to Bovine-Based Human Milk Fortifier," Breastfeeding Medicine 12(9): 570-573 (2017).

Sarney, et al., "A Novel Approach to the Recovery of Biologically Active Oligosaccharides from Milk Using a Combination of Enzymatic Treatment and Nanofiltration". Biotechnol Bioeng. 69(4):461-467 (2000).

Schanler et al., "Feeding strategies for premature infants: beneficial outcomes of feeding fortified human milk versus preterm formula," Pediatr. 103(6 Pt 1):1150-1157 (1999).

Schanler, "Mother's Own Milk, Donor Human Milk, and Preterm Formulas in the Feeding of Extremely Premature Infants." Journal of Pediatric Gastroenterology and Nutrition (2007); 45 (Suppl 3): S175-S177.

Schanler, et al., "Randomized Trial of Donor Human Milk Versus Preterm Formula as Substitutes for Mothers' Own Milk in the Feeding of Extremely Premature Infants". Pediatrics (Aug. 2005); 116(2): 400-406.

Schanler, R., et al., "Enhanced Fecal Excretion of Selected Immune Factors in Very Low Birth Weight Infants Fed Fortified Human Milk," Pediatric Research, 1986, vol. 20, No. 8, pp. 711-715.

Schanler et al., "Fortified mothers' milk for very low birth weight infants: results in macromineral balance studies," J. Pediatrics 107(5):767-774 (1985).

Schanler et al., "Fortified mothers' milk for very low birth weight infants; results of growth and nutrient balance studies," J. Pediatrics 107(3):437-444 (1985).

Schanler et al., "Mineral balance studies in very low birth weight infants fed human milk," J. Pediatrics 113(1):230-238 (1988).

Schell, et al., "The genome sequence of Bifidobacterium longum reflects its adaptation to the human gastrointestinal tract". PNAS (Oct. 29, 2002); 99 (22): 14422-14427.

Sela, et al., "The genome sequence of *Bifidobacterium longum* subsp. *infantis* reveals adaptations for milk utilization within the infant microbiome", PNAS (Dec. 2, 2008); 105(48): 18964-18969.

Smilowitz, et al., "Breast milk oligosaccharides: structure-function relationships in the neonate", Annu. Rev. Nutr. (2014); 34: 143-169. Epub May 15, 2014.

Smilowitz, et al., "Safety and tolerability of *Bifidobacterium longum* subspecies *infantis* EVC001 supplementation in healthy term breastfed infants: a phase I clinical trial", BMC Pediatr. (May 20, 2017); 17(133): 1-11. Epub May 30, 2017.

Sorbara, et al., "Inhibiting antibiotic-resistant Enterobacteriaceae by microbiota-mediated intracellular acidification", J Exp Med. (Jan. 7, 2019); 216(1): 84-98. Epub Dec. 18, 2018.

Srinivasan, L., et al., "Increased osmolality of breast milk with therapeutic additives," Arch. Dis. Child. F et al. Neonatal Ed. 2004. 89:F514-F517.

Stayner, et al., "Feeding tube placement: errors and complications." Nutr Clin Pract. Dec. 2012; 27(6):738-748. Epub Oct. 12, 2012. (Abstract).

Szilagyi, et al., "Possible Therapeutic use of Loperamide for Symptoms of Lactose Intolerance". Canadian Journal of Gastroenterology (2000); 14(7): 581-587.

Terpstra, et al., "Antimicrobial and Antiviral Effect of High-Temperature Short-Time (HTST) Pasteurization Applied to Human Milk," Breastfeeding Med. 2007. vol. 2, pp. 27-33.

Texas Tech University, "The human milk microbiota plays a role in health of the infant," http://www.infantrisk.com/content/humanmilk-microbiota-plays-role-health-infant (2012), pp. 1-2.

The Dairy Council, "The Nutritional Composition of Dairy Products," pp. 1-49, 2002.

Thum, et al., "Composition and enrichment of caprine milk oligosaccharides from New Zealand Saanen goat cheese whey". J Food Comp and Anal. (2015); 42: 30-37.

Tsitko et al., "A small in vitro fermentation model for screening the gut microbiota effects of different fiber preparations," Int. J. Mol. Sci. 20(8)1925 (2019).

Tully, "Is Pasteurized Mother's Own or Donor Milk an Answer to the HIV Crisis," J. Hum. Lact. 15(4):345-346 (1999).

Ubeda, et al., "Vancomycin-resistant Enterococcus domination of intestinal microbiota is enabled by antibiotic treatment in mice and precedes bloodstream invasion in humans", J Clin Invest (Dec. 2010); 120(12): 4332-4341. Epub Nov. 22, 2010.

UCSF Children's Hospital, "Feeding of Preterm Infants", Intensive Care Nursery House Staff Manual, 2004 pp. 50-53).

U.S. National Library of Medicine: "Archive History for NCT02025478 Human Breastmilk in Children Receiving a Bone Marrow Transplant", Mar. 25, 2015 (Mar. 25, 2015), XP055518058, Retrieved from the Internet: URL:https://clinicaltrials.gov/ct2/history/NCT02025478?V2=View#StudyPageTop [retrieved on Oct. 23, 2018], 6 pages.

(56) References Cited

OTHER PUBLICATIONS

Underwood, et al., "*Bifidobacterium longum* subspecies *infantis*: champion colonizer of the infant gut", Pediatr Res. (Jan. 2015); 77(1): 229-235. Published online Oct. 10, 2014.

Urashima, et al., "Recent Advances in Studies on Milk Oligosaccharides of Cows and Other Domestic Farm Animals." Bioscience, Biotechnology, and Biochemistry (2013); 77(3): 455-466.

Virus Safety Services, Sanquin Research, Final Report FR4500, "Process Validation Breast Milk Step 1 for Inactivation of BVDV/HAV/HIV/PSR," May 27, 2002. pp. 1-33.

Visuthranukul et al., "Premature small for gestational age infants fed an exclusive human milk-based diet achieve catch-up growth without metabolic consequences at 2 years of age". Arch Dis Child Fetal Neonatal Ed. (May 2019); 104(3): F242-F247. Epub Nov. 13, 2018.

Voyer et al., "Human Milk Lacto-Engineering," Acta Paediatr. Scand. 1984. vol. 73, pp. 302-306.

Ward, R.E., "Isolation of Milk Oligosaccharides using Solid-Phase Extraction". Open Glycoscience (2009); 2: 9-15.

Wight, N.E., et al., Best Medicine: Human Milk in the NICU (2008); pp. xi-xiv, pp. 1-7, pp. 9-32, pp. 43-96, 91 pages.

Wilhelm, et al., "Drying and Dehydration." Chapter 10 in Food & Process Engineering Technology, 259-284, American Society of Agricultural Engineers, 2005.

Williams, et al., "Human Milk Banking," J. Trop. Pediatr. 31:185-190 (1985).

Wilson, et al., "Parenteral Nutrition Utilization in Bone Marrow Transplant Recipients". Journal of Nutrition and Health Sciences (May 20, 2014); vol. 1, Issue 1, pp. 1-4.

Wisconsin Center for Dairy Research, Dried Dairy Ingredients, May 15, 2008, pp. 1-60.

Wu, et al., "Development of an Annotated Library of Neutral Human Milk Oligosaccharides." Journal of Proteome Research (2010); 9(8): 4138-4151.

Xiao, et al., "Human Milk Oligosaccharide 2'-Fucosyllactose Improves Innate and Adaptive Immunity in an Influenza-Specific Murine Vaccination Model". Frontiers in Immunology (Mar. 9, 2018); 9:452. eCollection 2018.

Zivkovic, et al., "Human milk glycobiome and its impact on the infant gastrointestinal microbiota". PNAS (Mar. 15, 2011); 108 (Supplement 1): 4653-4658; first published Aug. 2, 2010.

Altmann et al., "Genome Analysis and Characterisation of the Exopolysaccharide Produced by *Bifidobacterium longum* subsp. *longum* 35624TM," PLoS ONE 11(9):e0162983 (2016).

Ayechu-Muruzabal et al., "Diversity of Human Milk Oligosaccharides and Effects on Early Life Immune Development," Frontiers in Pediatrics 6:239 (2018).

Belenguer et al., "Two Routes of Metabolic Cross-Feeding between Bifidobacterium adolescentis and Butyrate-Producing Anaerobes from the Human Gut," Applied and Environmental Microbiology, 72(5), 3593-3599 (2006).

Bergmann, "Bifidobacteria Stabilize Claudins at Tight Junctions and Prevent Intestinal Barrier Dysfunction in Mouse Necrotizing Enterocolitis," The American Journal of Pathology, 182(5):1595-1606 (2013).

Bokulich et al., "Antibiotics, birth mode, and diet shape microbiome maturation during early life," Science Translational Medicine, 8(343) (2016).

Bouhnik et al., "Short-Chain Fructo-Oligosaccharide Administration Dose-Dependently Increases Fecal Bifidobacteria in Healthy Humans," The Journal of Nutrition, 129(1):113-116 (2019).

Brandt et al., "An overview of fecal microbiota transplantation: techniques, indications, and outcomes," Gastrointestinal endoscopy, 78(2):240-249 (2013).

Browne et al., "Culturing of 'unculturable' human microbiota reveals novel taxa and extensive sporulation," Nature 533(7604):543-546 (2016).

Casaburi et al., "Early-life gut microbiome modulation reduces the abundance of antibiotic-resistant bacteria," Antimicrobial Resistance & Infection Control 8(1):131 (2019).

Comstock et al., "Select human milk oligosaccharides directly modulate peripheral blood mononuclear cells isolated from 10-d-old pigs," The British Journal of Nutrition, 111(5):819-828 (2014).

Coulet et al., "Pre-clinical safety evaluation of the synthetic human milk, nature-identical, oligosaccharide 2'-O-Fucosyllactose (2'FL)," Regulatory Toxicology and Pharmacology 68(1), 59-69 (2014).

Coulet et al., "Pre-clinical safety assessment of the synthetic human milk, nature-identical, oligosaccharide Lacto-N-neotetraose (LNnT)," Food and Chemical Toxicology 62:528-537 (2013).

Dinleyici et al., "Lactobacillus reuteri DSM 17938 effectively reduces the duration of acute diarrhoea in hospitalised children," Acta paediatrica 103(7):e300-5 (2014).

Duar et al., "Colonization Resistance in the Infant Gut: The Role of B. infantis in Reducing pH and Preventing Pathogen Growth," High-Throughput, 9(2):7 (2020).

Duncan et al., "Contribution of acetate to butyrate formation by human faecal bacteria," The British Journal of Nutrition 91(6), 915-923 (2004).

Duncan et al., "Lactate-Utilizing Bacteria, Isolated from Human Feces, That Produce Butyrate as a Major Fermentation Product. Applied and Environmental Microbiology," 70(10), 5810-5817 (2004).

Eguchi et al., "Perioperative synbiotic treatment to prevent infectious complications in patients after elective living donor liver transplantation: a prospective randomized study," Am J Surg. 201(4):498-502 (2011).

Elison et al., "Oral supplementation of healthy adults with 2'-O-fucosyllactose and lacto-N-neotetraose is well tolerated and shifts the intestinal microbiota," The British Journal of Nutrition 116(8):1356-1368 (2016).

Ewaschuk et al., "Secreted bioactive factors from Bifidobacterium infantis enhance epithelial cell barrier function," American Journal of Physiology-Gastrointestinal and Liver Physiologyn295(5):G1025-G1034 (2008).

Falony et al., "Cross-Feeding between Bifidobacterium longum BB536 and Acetate-Converting, Butyrate-Producing Colon Bacteria during Growth on Oligofructose," Applied and Environmental Microbiology 72(12):7835-7841 (2006).

Fukuda et al., "Bifidobacteria can protect from enteropathogenic infection through production of acetate," Nature, 469(7331):543-547 (2011).

Garrido et al., "Consumption of human milk glycoconjugates by infant-associated bifidobacteria: mechanisms and implications," Microbiology 159(Pt 4):649-664 (2013).

Goehring et al., "Similar to Those who are Breastfed, Infants fed a Formula Containing 2'- Fucosyllactose Have Lower Inflammatory Cytokines in a Randomized Controlled Trial. The Journal of Nutrition," 146(12):2559-2566 (2016).

Golob et al., "Stool Microbiota at Neutrophil Recovery is Predictive for Severe Acute Graft vs Host Disease After Hematopoietic Cell Transplantation," Clin Infect Dis. 65(12):1984-1991 (2017).

Grady et al., "Microbial therapeutic interventions", Seminars in Fetal and Neonatal Medicine, 21(6):418-423 (2016).

Groeger et al., "Bifidobacterium infantis 35624 modulates host inflammatory processes beyond the gut," Gut Microbesc4(4):325-339 (2013).

Greub, "Culturomics: a new approach to study the human microbiome," Clinical Microbiology and Infection 18(12):1157-1159 (2012).

Hanlon et al., "A 3-week pre-clinical study of 2'-fucosyllactose in farm piglets," Food and Chemical Toxicology 74:343-348 (2014).

Henrick et al., "Elevated Fecal pH Indicates a Profound Change in the Breastfed Infant Gut Microbiome Due to Reduction of Bifidobacterium over the Past Century," MSphere, 3(2), e00041-18 (2018).

Hill et al., "Evolution of gut microbiota composition from birth to 24 weeks in the INFANTMET Cohort," Microbiome 5(1):4 (2017).

Holler et al., "Metagenomic analysis of the stool microbiome in patients receiving allogeneic stem cell transplantation: loss of diversity is associated with use of systemic antibiotics and more pronounced in gastrointestinal graft-versus-host disease," Biology of Blood and Marrow Transplantation, 20(5):640-645 (2014).

Huda et al., "Bifidobacterium Abundance in Early Infancy and Vaccine Response at 2 Years of Age," Pediatrics, 143(2), e20181489 (2019).

(56) References Cited

OTHER PUBLICATIONS

Huda et al., "Stool microbiota and vaccine responses of infants," Pediatrics, 134(2), e362-372 (2014).
Jang et al., "Fecal microbial transplantation and a high fiber diet attenuates emphysema development by suppressing inflammation and apoptosis," Experimental & molecular medicine, 52(7):128-1139 (2020).
Jantscher-Krenn et al., "Human milk oligosaccharides are differentially metabolised in neonatal rats," The British Journal of Nutrition, 110(4):640-650 (2013).
Jenq et al., "Intestinal Blautia is Associated with Reduced Death from Graft-versus-Host Disease. Biology of Blood and Marrow Transplantation," 21(8):1373-1383 (2015).
Johnsen et al., "Gas chromatography—mass spectrometry data processing made easy," J Chromatogr A 1503:57-64 (2017).
Kaito et al., "Fecal microbiota transplantation with frozen capsules for a patient with refractory acute gut graft-versus-host disease," Blood Advances 2(22), 3097-3101 (2018).
Kakihana et al., "Fecal microbiota transplantation for patients with steroid-resistant acute graft-versus-host disease of the gut," Blood 128(16):2083-2088 (2016).
Kim et al., "Toxicological evaluation of 3'-sialyllactose sodium salt," Regulatory Toxicology and Pharmacology, 94:83-90 (2018).
Konieczna et al., "Bifidobacterium infantis 35624 administration induces Foxp3 T regulatory cells in human peripheral blood: potential role for myeloid and plasmacytoid dendritic cells," Gut 61(3):354-66 (2012).
Lei et al., "Effect of probiotics and prebiotics on immune response to influenza vaccination in adults: a systematic review and meta-analysis of randomized controlled trials," Nutrients 9(11):1175 (2017).
Locascio et al., "Glycoprofiling of bifidobacterial consumption of human milk oligosaccharides demonstrates strain specific, preferential consumption of small chain glycans secreted in early human lactation," Journal of Agricultural and Food Chemistry 55(22)8914-8919 (2007).
Marcobal and Sonnenburg, "Human milk oligosaccharide consumption by intestinal microbiota," Clinical Microbiology and Infection 18:12-15 (2012).
Marriage et al., "Infants fed a lower calorie formula with 2' FL show growth and 2' FL uptake like breast-fed infants," Journal of Pediatric Gastroenterology and Nutrition 61(6):649 (2015).
Matsuki et al., "Distribution of bifidobacterial species in human intestinal microflora examined with 16S rRNA-gene-targeted species-specific primers," Applied and Environmental Microbiology 65(10):4506-4512 (1999).
Mattarelli et al., "Proposal to reclassify the three biotypes of *Bifidobacterium longum* as three subspecies: *Bifidobacterium longum* subsp. *longum* subsp. nov., *Bifidobacterium longum* subsp. *infantis* comb. nov. and *Bifidobacterium longum* subsp. *suis* comb. nov." International Journal of Systematic and Evolutionary Microbiology 58(4):767-772 (2008).
Medina et al., "Prebiotics mediate microbial interactions in a consortium of the infant gut microbiome," International Journal of Molecular Sciences, 18(10):2095 (2017).
Mi et al., "Bifidobacterium infantis ameliorates chemotherapy-induced intestinal mucositis via regulating T cell immunity in colorectal cancer rats," Cellular Physiology and Biochemistry 42(6):2330-2341 (2017).
Newburg and Morelli, "Human milk and infant intestinal mucosal glycans guide succession of the neonatal intestinal microbiota," Pediatric Research, 77(1):115-120 (2015).
O'Callaghan and Van Sinderen, "Bifidobacteria and their role as members of the human gut microbiota," Frontiers in Microbiology 7:925 (2016).
O'Hara et al., "Functional modulation of human intestinal epithelial cell responses by Bifidobacterium infantis and Lactobacillus salivarius," 118(2):202-215 (2006).
Palm et al., "Immunoglobulin A coating identifies colitogenic bacteria in inflammatory bowel disease," Cell 158(5):1000-1010 (2014).
Pamer et al., "Impact of the intestinal microbiota on infections and survival following hematopoietic stem cell transplantation," Blood 124(21): SCI-48 (2014).
Patel and Dupont, "New approaches for bacteriotherapy: prebiotics, new-generation probiotics, and synbiotics," 60(suppl_2):S108-S121 (2015).
Peled, "Microbiota as Predictor of Mortality in Allogeneic Hematopoietic-Cell Transplantation," New England Journal of Medicine 382(9):822-834 (2020).
Petrovsky and Cooper, "Carbohydrate-based immune adjuvants," Expert Review of Vaccines, 10(4):523-537 (2011).
Phipps et al., "Safety evaluation of a mixture of the human-identical milk oligosaccharides 2'-fucosyllactose and difucosyllactose," Food and Chemical Toxicology 120:552-565 (2018).
Picard et al., "Review article: bifidobacteria as probiotic agents—physiological effects and clinical benefits," Alimentary Pharmacology & Therapeutics 22(6):495-512 (2005).
Pokusaeva et al., "Carbohydrate metabolism in Bifidobacteria," Genes & Nutrition 6(3), 285-306 (2011).
Reuter, "Designation of Type Strains for *Bifidobacterium* Species," International Journal of Systematic Bacteriology 21(4):273-275 (1971).
Riviere et al., "Bifidobacteria and Butyrate-Producing Colon Bacteria: Importance and Strategies for Their Stimulation in the Human Gut", Frontiers in Microbiology 7(28):979 (2016).
Rivière et al., "Mutual Cross-Feeding Interactions between *Bifidobacterium longum* subsp. *longum* NCC2705 and Eubacterium rectale ATCC 33656 Explain the Bifidogenic and Butyrogenic Effects of Arabinoxylan Oligosaccharides," Applied and Environmental Microbiology 81(22), 7767-7781 (2015).
Routy et al., "The influence of gut-decontamination prophylactic antibiotics on acute graft-versus-host disease and survival following allogeneic hematopoietic stem cell transplantation," Oncoimmunology 6(1):e1258506 (2017).
Salminen, "Regulatory Aspects of Human Milk Oligosaccharides," in E. Isolauri, P. M. Sherman, & W. A. Walker (Eds.), Nestlé Nutrition Institute Workshop Series 88:161-170 (2017).
Schmutz et al., "Safe Handling of Milk & Dairy Products," Clemson University, Factsheet, HGIC 3510, Updated: Mar. 8, 2007, https://hgic.clemson.edu/factshee/safe-handling-of-milk-dairy-products/, 5 pages.
Sheng et al., "Synbiotic supplementation containing Bifidobacterium infantis and xylooligosaccharides alleviates dextran sulfate sodium-induced ulcerative colitis," Food Funct. 11(5):3964-3974 (2020).
Mizuno et al., "Bifidobacterium-Rich Fecal Donor may be a Positive Predictor for Successful Fecal Microbiota Transplantation in Patients with Irritable Bowel Syndrome", Digestion 96(1):29-38 (2017).
Shono et al., Increased GVHD-related mortality with broad-spectrum antibiotic use after allogeneic hematopoietic stem cell transplantation in human patients and mice, Science Translational Medicine 8(339):339ra71 (2016).
Smart et al., "Analytical platform for metabolome analysis of microbial cells using methyl chloroformate derivatization followed by gas chromatography—mass spectrometry," Nat Protoc 5(10):1709-1729 (2010).
Sprenger et al., "Production of human milk oligosaccharides by enzymatic and whole-cell microbial biotransformations," Journal of Biotechnology 258:79-91 (2017).
Tanabe et al., "Bifidobacterium infantis suppresses proinflammatory interleukin-17 production in murine splenocytes and dextran sodium sulfate-induced intestinal inflammation," International Journal of Molecular Medicine, 22(2):181-185 (2008).
Taur et al., "Intestinal Domination and the Risk of Bacteremia in Patients Undergoing Allogeneic Hematopoietic Stem Cell Transplantation. Clinical Infectious Diseases," 55(7):905-914 (2012).
Taur et al., "The effects of intestinal tract bacterial diversity on mortality following allogeneic hematopoietic stem cell transplantation," Blood, 124(7):1174-1182 (2014).

(56) References Cited

OTHER PUBLICATIONS

Taur et al., "Reconstitution of the gut microbiota of antibiotic-treated patients by autologous fecal microbiota transplant. Science Translational Medicine," 10(460):eaap9489 (2018).
Underwood et al., "Prebiotic Oligosaccharides in Premature Infants," Journal of Pediatric Gastroenterology and Nutrition 58(3):352-360 (2014).
Underwood et al., "*Bifidobacterium longum* subspecies *infantis*: champion colonizer of the infant gut," Pediatric Research, 77(1-2):229-235 (2015).
Van Berlo et al., "Safety assessment of biotechnologically produced 2'-Fucosyllactose, a novel food additive," Food and Chemical Toxicology 118:84-93 (2018).
Vos et al., "Dietary supplementation of neutral and acidic oligosaccharides enhances Th1-dependent vaccination responses in mice. Pediatric allergy and immunology: official publication of the European Society of Pediatric Allergy and Immunology," 18(4):304-312 (2007).
Ward et al., "In Vitro Fermentation of Breast Milk Oligosaccharides by Bifidobacterium infantis and Lactobacillus gasseri," Applied and Environmental Microbiology, 72(6):4497-4499 (2006).
"Why is B. infantis so important for your baby?" Web blog post. LoveBug Probiotics, Jul. 31, 2019 accessed at <https://lovebugprobiotics.com/blogs/news/why-is-b-infantis-so-important-for-your-baby>.
Xiong et al., "Distinct Contributions of Neutrophils and CCR2+ Monocytes to Pulmonary Clearance of Different Klebsiella pneumoniae Strains," Infect Immun 83(9):3418-3427 (2015).
Zabel et al., "Novel Genes and Metabolite Trends in *Bifidobacterium longum* subsp. *infantis* Bi-26 Metabolism of Human Milk Oligosaccharide 2'-fucosyllactose," Scientific Reports 9(1):1-11 (2019).
Zhou et al., "Bifidobacterium infantis Induces Protective Colonic PD-L1 and Foxp3 Regulatory T Cells in an Acute Murine Experimental Model of Inflammatory Bowel Disease," Gut Liver 13(4):430-439 (2019).
Zuo et al., "Bifidobacterium infantis attenuates colitis by regulating T cell subset responses," World J Gastroenterol 20(48):18316-18329 (2014).
Chakrabarti et al., "Clostridium difficile infection in allogeneic stem cell transplant recipients is associated with severe graft-versus-host disease and non-relapse mortality," Bone Marrow Transplantation 26:871-876 (2000).
Frese et al., "Persistence of Supplemented *Bifidobacterium longum* subsp. *infantis* EVC001 in Breastfed Infants," mSphere 2(6):e00501-17 (2017).
Thonogram et al., "Human milk oligosaccharide consumption by probiotic and human-associated bifidobacteria and lactobacilli," Journal of Dairy Science 100(10):7825-7833 (2017).
International Preliminary Report on Patentability for International Application No. PCT/US2009/066430, mailed Jun. 7, 2011, 10 pages.
International Search Report and Written Opinion for International Application No. PCT/US2006/036827, mailed Sep. 5, 2007.
International Search Report and Written Opinion for International Application No. PCT/US2007/019234, mailed Jan. 18, 2008.
International Search Report and Written Opinion for International Application No. PCT/US2007/085969, mailed May 8, 2008.
International Search Report and Written Opinion for International Application No. PCT/US2007/086973, mailed May 5, 2008.
International Search Report and Written Opinion for International Application No. PCT/US2009/066430, mailed Jan. 26, 2010.
International Search Report and Written Opinion for International Application No. PCT/US2012/049590, mailed Oct. 1, 2012.
International Preliminary Report on Patentability for International Application No. PCT/US2017/052332, dated Mar. 19, 2019, 9 pages.
International Search Report and Written Opinion for International Application No. PCT/US2017/052332, mailed Nov. 20, 2017, 11 pages.
International Search Report and Written Opinion for International Application No. PCT/US2020/052501, mailed Mar. 18, 2021, 27 pages.

* cited by examiner

COMPOSITIONS AND METHODS FOR TREATMENT OF INFLAMMATORY AND IMMUNE DISEASES

CROSS-REFERENCE TO RELATED APPLICATIONS

This application is the National Stage of International Application No. PCT/US2020/052501, filed Sep. 24, 2020, entitled "Compositions and Methods for Treatment of Inflammatory and Immune Diseases", which claims priority from U.S. provisional application No. 62/905,256 filed Sep. 24, 2019, entitled "Compositions and Methods for Treatment of Graft Versus Host Disease", U.S. provisional application No. 63/027,739 filed May 20, 2020, entitled "Compositions for Treatment of Hyperammonemia", U.S. provisional application No. 63/028,743 filed May 22, 2020, entitled "Compositions and Methods for Treatment of Inflammatory and Immune Disease", and U.S. provisional application No. 63/053,224 filed Jul. 17, 2020, entitled "Compositions and Methods for Treatment of Inflammatory and Immune Disease", the contents of each of which is incorporated by reference in its entirety.

INCORPORATION BY REFERENCE OF SEQUENCE LISTING

The present application is being filed along with a Sequence Listing in electronic format. The Sequence Listing is provided as a file entitled PROL03703WOSEQLIST_ST25, created Sep. 21, 2020, which is 153 kilobytes in size. The information in the electronic format of the Sequence Listing is incorporated by reference in its entirety.

FIELD OF THE INVENTION

Provided herein are compositions, methods, strategies, kits, and articles of manufacture that are useful, inter alia, in the treatment or prevention of diseases, disorders, or conditions that may be associated with inflammation, infection, allergy, immune dysfunction, or dysbiosis of the intestinal microbiome, such as graft versus host disease (GVHD). In some aspects, the invention provides a synergistic combination of a prebiotic, e.g., a mixture of human milk oligosaccharides, and a probiotic strain of bacterium, such as a strain capable of internalizing and consuming the prebiotic, e.g., *Bifidobacterium longum* subsp. *infantis.*

BACKGROUND OF THE INVENTION

The microbiome is proposed to be a key modulator of human health, such as to the extent that it has been proposed to be an 'essential organ' of the human body. For most individuals, microbial colonies found on or in the body, such as in the gut, are normally benign or beneficial. These beneficial and appropriately sized microbial colonies carry out a series of helpful and necessary functions, such as aiding in digestion or preventing growth of pathogenic microbes. Changes to the microbiome composition, such as from the presence or expansion of pathogenic microorganisms or a loss of the diversity of the microflora, may result in a state of dysbiosis. While microbiome dysbiosis has been described in various diseases, safely promoting a 'healthy' microbiome has been difficult, particularly in subjects who may be vulnerable or immunocompromised. Furthermore, microbiomes may vary in healthy individuals, adding to confusion over how a "healthy" microbiome may be defined, let alone promoted or developed. What is needed in the art are compositions and methods for safely treating or ameliorating dysbiosis of the microbiome, as well as disorders or diseases involving inflammation, infection, allergy, or immune dysfunction that may be associated with dysbiosis.

SUMMARY OF THE INVENTION

Provided herein are compositions, kits, articles of manufacture, and methods of use thereof, that contain a mixture of one or more prebiotics, e.g., non-digestible carbohydrates such as human milk oligosaccharides, and one or more probiotic strains of bacteria capable of consuming the prebiotics. The provided compositions, kits, and articles of manufacture are particularly useful for treating or preventing diseases or conditions, such as those involving inflammation, immune disorders, allergy, or dysbiosis of the intestinal microbiome. In some aspects, the provided compositions, kits, and articles of manufacture are useful for treating or preventing graft versus host disease (GVHD).

Provided herein is a method for treating or preventing a disease, disorder, or condition associated with one or more of dysbiosis of the intestinal microbiome, inflammation, infection, allergy, or immune dysfunction in a subject in need thereof, the method comprising administering to the subject (i) a prebiotic mixture comprising one or more human milk oligosaccharides and (ii) at least one probiotic strain of bacterium capable of consuming the one or more human milk oligosaccharides.

In particular embodiments, the probiotic strain is capable of internalizing the one or more human milk oligosaccharides. In certain embodiments, the probiotic strain of bacterium comprises a bacterial strain of the genus *Bifidobacterium*. In some embodiments, the probiotic strain of bacterium comprises a strain of *B. longum* subsp. *infantis, B. longum* subsp. *longum, B. breve*, or *B. bifidum*. In particular embodiments, the probiotic strain of bacterium comprises *B. longum* subsp. *infantis.*

Provided herein is a method for treating or preventing a disease, disorder, or condition associated with one or more of dysbiosis of the intestinal microbiome, inflammation, infection, allergy, or immune dysfunction in a subject in need thereof, the method comprising administering to the subject (i) a prebiotic mixture comprising one or more human milk oligosaccharides and (ii) a probiotic strain of *B. longum* subsp. *infantis*. In certain embodiments, the prebiotic mixture comprises at least 5, at least 10, at least 25, at least 50, or at least 100 human milk oligosaccharides.

Provided herein is a method for treating or preventing a disease, disorder, or condition associated with one or more of dysbiosis of the intestinal microbiome, inflammation, infection, allergy, or immune dysfunction in a subject in need thereof, the method comprising administering to the subject (i) a prebiotic mixture comprising at least 5, at least 10, at least 25, at least 50, or at least 100 human milk oligosaccharides and (ii) a probiotic strain of the genus *Bifidobacterium.*

In some embodiments, the disease, disorder, or condition comprises one or more of obesity, type II diabetes, a chronic inflammatory disease, an autoimmune disease, an infection, an infectious disease domination, bowel resection, or a condition associated with chronic diarrhea. In particular embodiments, the disease, disorder, or condition comprises one or more of irritable bowel syndrome (IBS), inflammatory bowel disease (IBD), short bowel syndrome (SBS), celiac disease, small intestinal bacterial overgrowth (SIBO), gastroenteritis, leaky gut syndrome, pouchitis, or gastric lymphoma. In certain embodiments, the disease, condition, or disorder is graft versus host disease.

In some embodiments, the subject has received or will receive an allogenic hematopoietic stem cell transplant. Provided herein is a method of preventing or reducing the incidence or severity of graft versus host disease in a subject in need thereof, wherein the subject has received or will receive an allogenic hematopoietic stem cell transplant, the method comprising administering to the subject (i) a prebiotic mixture comprising at least 5, at least 10, at least 25, at least 50, or at least 100 human milk oligosaccharides and (ii) a probiotic strain of *B. longum* subsp. *infantis*. In particular embodiments, the disease, condition, or disorder is associated with an infection. In certain embodiments, the infection comprises a bacterial infection or gut domination.

Provided herein is a method for treating or preventing an infection in a subject in need thereof, the method comprising administering to the subject (i) a prebiotic mixture comprising at least 5, at least 10, at least 25, at least 50, or at least 100 human milk oligosaccharides and (ii) a probiotic strain of *B. longum* subsp. *infantis*, wherein the infection comprises a bacterial infection or gut domination.

In some embodiments, the bacterial infection or gut domination comprises an infection or gut domination by one or more species, subspecies, or strains of *Aeromonas, Bacillus, Blautia, Bordetella, Borrelia, Brucella, Burkholderia, Campylobacter, Chlamydia, Chlamydophila, Citrobacter, Clostridium, Corynebacterium, Coxiella, Ehrlichia, Enterobacter, Enterobacteriaceae, Enterococcus, Escherichia, Faecalicatena, Francisella, Haemophilus, Helicobacter, Hungatella, Klebsiella, Lachnospiraceae, Legionella, Leptospira, Listeria, Morganella, Mycobacterium, Mycoplasma, Neisseria, Orientia, Plesiomonas, Proteus, Pseudomonas, Rickettsia, Salmonella, Shigella, Staphylococcus, Streptococcus, Treponema, Vibrio*, or *Yersinia*, optionally one or more of *Aeromonas hydrophila, Bacillus cereus, Campylobacter fetus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enteropathogenic *E. coli*, enterotoxigenic *Escherichia coli, Escherichia coli* 0157:H7, *Helicobacter pylori, Klebsiellia pneumonia, Lysteria monocytogenes, Salmonella paratyphi, Salmonella typhi, Staphylococcus aureus, Vibrio cholerae, Vibrio parahaemolyticus, Vibrio vulnificus*, or *Yersinia enterocolitica.*

In particular embodiments, the bacterial infection or gut domination comprises an infection or gut domination by one or more of *Anaerostipes caccae, Anaerotruncus colihominis, Bifidobacterium longum, Blautia* spp., *Butyricicoccus pullicaecorum, Butyrivibrio crossotus, Caproiciproducens, Citrobacter freundii, Citrobacter koseri, Clostridium aldenense, Clostridium asparagiforme, Clostridium bolteae, Clostridium citroniae, Clostridium clostridioforme, Clostridium lavalense, Clostridium nexile, Clostridium populeti, Clostridium symbiosum, Coprococcus comes, Coprococcus eutactus, Dorea formicigenerans, Dorea longicatena, Enterobacter aerogenes, Enterobacter cloacae, Enterococcus faecalis, Enterococcus faecium, Escherichia coli, Ethanoligenens, Eubacterium hallii, Eubacterium rectale, Eubacterium ventriosum, Eubacterium siraeum, Faecalibacterium prausnitzii, Faecalicatena, Flavonifractor plautii, Hungatella, Klebsiella oxytoca, Klebsiella pneumoniae, Lactobacillus acidophilus, Morganella morganii, Oscillibacter, Papillibacter cinnamivorans, Papillibacter, Proteus mirabilis, Pseudoflavonifractor, Roseburia hominis, Roseburia intestinalis, Roseburia inulinivorans, Ruminococcus faecis, Ruminococcus lactaris, Ruminococcus torques, Ruminococcus bromii, Serratia marcescens, Sporobacter, Staphylococcus aureus, Staphylococcus epidermidis, Streptococcus anginosus, Streptococcus australis, Streptococcus constellatus, Streptococcus cristatus, Streptococcus gordonii, Streptococcus infantis, Streptococcus intermedius, Streptococcus mitis, Streptococcus mutans, Streptococcus oligofermentans, Streptococcus oxalis, Streptococcus parasanguinis, Streptococcus peroris, Streptococcus pneumoniae, Streptococcus pseudopneumoniae, Streptococcus salivarius, Streptococcus sanguinis, Streptococcus sobrinus, Streptococcus tigurinus, Streptococcus vestibularis, Subdoligranulum variabile, Subdoligranulum*, or *Syntrophococcus* sp.

In certain embodiments, the bacterial infection or gut domination comprises an infection or gut domination by drug-resistant bacteria. In some embodiments, the drug-resistant bacteria comprise one or more of antibiotic-resistant bacterium (ARB), Antibiotic-resistant Proteobacteria, Carbapenem-resistant Enterobacteriaceae (CRE), Extended Spectrum Beta-Lactamase producing Enterobacteriaceae (ESBL-E), fluoroquinolone-resistant Enterobacteriaceae, extended spectrum beta-lactam resistant Enterococci (ESBL), vancomycin-resistant Enterococci (VRE), multi-drug resistant *E. coli*, or multi-drug resistant *Klebsiella.*

In particular embodiments, the subject has undergone or will undergo an ileal pouch-anal anastomosis (IPAA) surgery, and wherein the disease, condition, or disorder comprises pouchitis. Provided herein is a method of preventing or reducing the incidence or severity of pouchitis in a subject in need thereof, wherein the subject has undergone or will undergo an ileal pouch-anal anastomosis (IPAA) surgery, the method comprising administering to the subject (i) a prebiotic mixture comprising at least 5, at least 10, at least 25, at least 50, or at least 100 human milk oligosaccharides and (ii) a probiotic strain of *B. longum* subsp. *infantis*, wherein the infection comprises a bacterial infection.

In certain embodiments, the prebiotic mixture comprises at least 10 human milk oligosaccharides. In some embodiments, the prebiotic mixture comprises at least 25 human milk oligosaccharides. In particular embodiments, the prebiotic mixture comprises at least 50 human milk oligosaccharides. In certain embodiments, the prebiotic mixture comprises at least 50 human milk oligosaccharides.

In some embodiments, the prebiotic mixture comprises one or more of 2'-fucosyl-lactose, 3'-fucosyl-lactose, 3'-sialyl-lactose, 6'-sialyl-lactose, Lacto-N-tetraose, lacto-N-difucohexaose I, lactodifucotetraose, Lacto-N-fucopentaose I, sialylacto-N-tetraose c, sialylacto-N-tetraose b, or disialyllacto-N-tetraose. In particular embodiments, the prebiotic mixture comprises 2'-fucosyl-lactose, 3'-fucosyl-lactose, 3'-sialyl-lactose, 6'-sialyl-lactose, Lacto-N-tetraose, lacto-N-difucohexaose I, lactodifucotetraose, Lacto-N-fucopentaose I, sialylacto-N-tetraose c, sialylacto-N-tetraose b, and disialyllacto-N-tetraose. In certain embodiments, the prebiotic mixture comprises 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, and Difucosyl-Lacto-N-hexaose b.

In some embodiments, the prebiotic mixture is, is derived from, or comprises a concentrated permeate from pooled human milk, wherein the permeate is obtained from the ultrafiltration of human skim milk, wherein the human skim milk is obtained by removing cream from pooled human milk, and wherein the pooled human milk is pooled from the milk of multiple human milk donors.

Provided herein is a method for treating or preventing a disease, disorder, or condition associated with one or more of dysbiosis of the intestinal microbiome, inflammation, infection, allergy, or immune dysfunction in a subject in need thereof, the method comprising administering to the subject (i) a prebiotic mixture comprising at least 5, at least 10, at least 25, at least 50, or at least 100 human milk oligosaccharides, wherein the prebiotic mixture is, is derived from, or comprises a concentrated human milk permeate, wherein the human milk permeate is obtained from the ultrafiltration of human skim milk obtained from pooled human milk, and wherein the pooled human milk is pooled from the milk of multiple human milk donors; and (ii) a probiotic strain of *B. longum* subsp. *infantis.*

In particular embodiments, the pooled human milk is pooled from the milk of at least 25, 50, or 100 human milk donors. In certain embodiments, the prebiotic mixture comprises at least one synthetic human milk oligosaccharide. In some embodiments, the prebiotic mixture and the probiotic strain are administered orally. In particular embodiments, the prebiotic mixture and the probiotic strain are administered on the same day for at least one day. In certain embodiments, the prebiotic mixture and the probiotic strain are administered on the same day for at least three consecutive days. In some embodiments, the prebiotic mixture and the probiotic strain are administered on the same day for at least seven consecutive days.

In particular embodiments, the method comprises at least a first treatment phase and a second treatment phase, wherein the first treatment phase comprises administering to the subject the prebiotic mixture and the probiotic strain on the same day for at least one day, and wherein the second treatment phase begins after the end of the first treatment phase, optionally immediately after, and comprises administering the prebiotic mixture for at least one day, wherein the probiotic strain is not administered during the second treatment phase.

In certain embodiments, the second treatment phase comprises administering to the subject the prebiotic mixture each day for at least three consecutive days. In some embodiments, the second treatment phase comprises administering to the subject the prebiotic mixture each day for at least seven consecutive days. In particular embodiments, the first treatment phase is between 3 and 14 days in length and wherein the second treatment phase is between 3 and 14 days in length. In certain embodiments, the first treatment phase is about 7 days in length and wherein the second treatment phase is about 7 days in length. In some embodiments, the probiotic strain is administered in an amount of at least $5\times10^6$ colony forming units (CFU) per day. In particular embodiments, the probiotic strain is administered in an amount of at least $8\times10^7$ colony forming units (CFU) per day. In certain embodiments, the prebiotic mixture is administered in an amount of at least 500 mg of total human milk oligosaccharides per day. In some embodiments, the prebiotic mixture is administered in an amount of between 0.5 g and 25 g, 1 g and 5 g, 2 g and 3 g, 3 g and 6 g, 4 g and 5 g, 5 g and 10 g, 8 g and 10 g, 10 g and 20 g, 15 g and 25 g, 15 g and 20 g, or 17 g and 19 g of total human milk oligosaccharides per day.

In particular embodiments, the prebiotic mixture and/or the probiotic strain is administered with an enteric coating. In certain embodiments, the methods further comprise administering a histamine-2 receptor antagonist, wherein the histamine-2 receptor antagonist is administered at least 1 hour prior to administration of the probiotic strain, optionally wherein the histamine-2 receptor antagonist is famotidine.

In some embodiments, the subject has not been administered a proton pump inhibitor at least about 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In particular embodiments, the subject has not been administered a benzimidazole derivative for at least about 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In certain embodiments, the subject has not been administered omeprazole for at least about 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In some embodiments, both of the probiotic strain and the prebiotic mixture are free or essentially free of a benzimidazole derivative.

In particular embodiments, the subject is a human subject at least 6 months, 12 months, 2 years, 5 years, 12 years, or 18 years of age. In certain embodiments, the subject is human subject that is a child, an adolescent, or an adult. In some embodiments, the subject is a human adult.

Provided herein is a use of a prebiotic mixture and at least one probiotic strain for the treatment or prevention of a disease, disorder, or condition associated with one or more of dysbiosis of the intestinal microbiome, inflammation, infection, allergy, or immune dysfunction in a subject in need thereof, wherein the prebiotic mixture comprises one or more human milk oligosaccharides and the probiotic strain is capable of consuming the one or more human milk oligosaccharides.

Provided herein is a prebiotic mixture and at least one probiotic strain for use in the manufacture of medicaments for the treatment or prevention of a disease, disorder, or condition associated with one or more of dysbiosis of the intestinal microbiome, inflammation, infection, allergy, or immune dysfunction, wherein the prebiotic mixture comprises one or more human milk oligosaccharides and wherein the probiotic strain is capable of consuming the one or more human milk oligosaccharides.

Provided herein is a kit comprising at least one probiotic strain of bacterium and a prebiotic mixture comprising one or more human milk oligosaccharides, wherein probiotic strain is capable of internalizing and consuming the one or more human milk oligosaccharides. In particular embodiments, the probiotic strain comprises a strain of *Bifidobacterium.* In certain embodiments, the probiotic strain comprises a strain of *B. longum* subsp. *infantis.* In some embodiments, the prebiotic mixture comprises at least 2, at least 5, at least 10, at least 25, at least 50, at least 100, at least 125, or at least 150 human milk oligosaccharides. In particular embodiments, the prebiotic mixture comprises at least 25 human milk oligosaccharides. In certain embodiments, the prebiotic mixture is free or essentially free of oligosaccharides that are not human milk oligosaccharides. In some embodiments, the prebiotic mixture is, is obtained from, or comprises a concentrated ultra-filtered permeate from pooled human milk. In particular embodiments, the probiotic strain is incorporated into one or more individual probiotic doses and wherein the prebiotic mixture is incorporated into one or more individual prebiotic doses. In certain embodiments, the one or more individual probiotic doses each comprise at least $1\times10^3$ colony forming units (CFU). In some embodiments, the one or more individual probiotic doses each comprise at least $8\times10^7$ colony forming units (CFU). In particular embodiments, the one or more prebiotic doses comprises between 500 mg and 25 g of total human milk oligosaccharides. In certain embodiments, the one or more individual prebiotic doses comprises between 0.5 g and 25 g, 1 g and 5 g, 2 g and 3 g, 3 g and 6 g, 4 g and 5 g, 5 g and 10 g, 8 g and 10 g, 10 g and 20 g, 15 g and 25 g, 15 g and 20 g, or 17 g and 19 g of total human milk oligosaccharides per day. In some embodiments, the one or more individual prebiotic doses comprises less than 0.1% lactose. Also provided herein is an article of manufacture, comprising a kit described herein and instructions for use, wherein the instructions for use describing any of the methods provided herein.

Provided herein is a method of treating hyperammonemia, comprising administering to a subject in need thereof a prebiotic mixture comprising oligosaccharides, wherein (i) the mixture is free or essentially free of oligosaccharides that incorporate an N-acetyl glucosamine residue or (ii) the percentage by weight of oligosaccharides comprising nitrogen in the mixture is less than 50%. Also provided herein is a method of decreasing the level or amount of ammonia in a subject in need thereof, comprising administering to the subject a prebiotic mixture comprising oligosaccharides, wherein (i) the mixture is free or essentially free of oligosaccharides that incorporate an N-acetyl glucosamine residue or (ii) the percentage by weight of oligosaccharides comprising nitrogen in the mixture is less than 50%.

In particular embodiments, the method further comprises administering a probiotic strain of bacterium capable of consuming each oligosaccharide of the mixture. In certain embodiments, the subject has, is at risk of having, or is suspected of having hyperammonemia, hepatic encephalopathy, or a urea cycle disorder. In some embodiments, the prebiotic mixture comprises one or more human milk oligosaccharides (HMOs). In particular embodiments, all or essentially all of the oligosaccharides of the prebiotic mixture are human milk oligosaccharides (HMOs). In certain embodiments, the prebiotic mixture is free or essentially free of oligosaccharides that incorporate an N-acetyl glucosamine residue. In some embodiments, the prebiotic mixture comprises at least 2, at least 3, at least 4, at least 5, at least 6, or at least 7 oligosaccharides. In particular embodiments, the percentage by weight of oligosaccharides in the prebiotic mixture comprising nitrogen is less than 50%, 40%, 30%, 25%, 20%, 10%, 5%, or 1%. In certain embodiments, the mixture is free or essentially free of oligosaccharides that comprise nitrogen. In some embodiments, less than 50%, 40%, 30%, 25%, 20%, 10%, 5%, or 1% by weight of the oligosaccharides in the prebiotic mixture are oligosaccharides comprising five or more monosaccharide residues.

In particular embodiments, the prebiotic mixture is free or essentially free of oligosaccharides comprising five or more monosaccharide residues. In certain embodiments, the probiotic strain is a strain of *Bifidobacterium*, optionally a strain of *B. longum* subsp. *infantis, B. longum* subsp. *longum, B. breve*, or *B. bifidum*. In some embodiments, the probiotic strain is capable of internalizing the oligosaccharides of the mixture.

Provided herein is a method of treating or preventing hyperammonemia, comprising administering to a subject in need thereof (i) a prebiotic mixture comprising oligosaccharides, wherein all or essentially all of the oligosaccharides of the prebiotic mixture are human milk oligosaccharides that do not incorporate an N-acetyl glucosamine residue, and (ii) a probiotic strain of bacterium, wherein the probiotic strain is a *Bifidobacterium* capable of internalizing HMOs. Also provided herein is a method of reducing ammonia in a subject in need thereof, comprising administering to a subject (i) a prebiotic mixture of oligosaccharides, wherein all or essentially all of the oligosaccharides of the prebiotic mixture are human milk oligosaccharides (HMOs) that do not incorporate an N-acetyl glucosamine residue, and (ii) a probiotic strain of bacterium, wherein the probiotic bacterium strain is a *Bifidobacterium* strain capable of internalizing HMOs.

In particular embodiments, the probiotic strain is a strain of *B. longum* subsp. *infantis*. In certain embodiments, the prebiotic mixture comprises one or more of 2'-fucosyllactose, 3-fucosyllactose, difucosyllactose, 3'-sialyllactose, or 6'-sialyllactose. In some embodiments, the prebiotic mixture comprises 2'-fucosyllactose, 3-fucosyllactose, difucosyllactose, 3'-sialyllactose, and 6'-sialyllactose. In particular embodiments, the oligosaccharides of the prebiotic mixture consist or consist essentially of 2'-fucosyllactose, 3-fucosyllactose, difucosyllactose, 3'-sialyllactose, and 6'-sialyllactose. In certain embodiments, the prebiotic mixture comprises one or more of 2'-fucosyllactose, 3-fucosyllactose, or difucosyllactose. In some embodiments, the prebiotic mixture comprises of 2'-fucosyllactose, 3-fucosyllactose, and difucosyllactose. In particular embodiments, the oligosaccharides of the mixture consist or consist essentially of 2'-fucosyllactose, 3-fucosyllactose, and difucosyllactose.

Provided herein is a method of treating or preventing hyperammonemia comprising administering to a subject in need thereof i) a prebiotic mixture comprising 2'-fucosyllactose, 3-fucosyllactose, difucosyllactose, 3'-sialyllactose, and 6'-sialyllactose and ii) a probiotic strain of *B. longum* subsp. *infantis*. Also provided herein is a method of treating or preventing hyperammonemia comprising administering to a subject in need thereof i) a prebiotic mixture comprising 2'-fucosyllactose, 3-fucosyllactose, and difucosyllactose and ii) a probiotic strain of *B. longum* subsp. *infantis*. In certain embodiments, the subject has, is suspected of having, or is at risk of having hepatic encephalopathy. In some embodiments, the subject has, is suspected of having, or is at risk of having a urea cycle disorder.

Provided herein is a method for treating dysbiosis in a subject in need thereof, wherein the dysbiosis is of the intestinal microbiome, the method comprising administering to the subject (i) a prebiotic mixture comprising one or more human milk oligosaccharides and (ii) at least one probiotic strain of bacterium capable of consuming the human milk oligosaccharides of the mixture.

Also provided herein is a method of preventing or reducing the incidence or severity of graft versus host disease (GVHD) in a subject in need thereof, wherein the subject has received or will receive an allogenic hematopoietic stem cell transplant, the method comprising administering to the subject (i) a prebiotic mixture comprising one or more human milk oligosaccharides and (ii) at least one probiotic strain of bacterium capable of consuming the human milk oligosaccharides of the mixture.

Additionally provided herein is a method of preventing or reducing the incidence or severity of a disease, disorder, or condition associated with inflammation, immune dysfunction, or allergy in a subject in need thereof, the method comprising administering to the subject (i) a prebiotic mixture comprising one or more human milk oligosaccharides and (ii) at least one probiotic strain of bacterium capable of consuming the human milk oligosaccharides of the mixture.

In some embodiments, the subject has, is suspected of having, or is at risk of having obesity, type II diabetes, a chronic inflammatory disease, an autoimmune disease, an infection, an infectious disease domination, bowel resection, and/or a condition associated with chronic diarrhea. In certain embodiments, the subject has, is suspected of having, or is at risk of having one or more of irritable bowel syndrome (IBS), inflammatory bowel disease (IBD), short bowel syndrome (SBS), celiac disease, small intestinal bacterial overgrowth (SIBO), gastroenteritis, leaky gut syndrome, pouchitis, or gastric lymphoma. In particular embodiments, the subject has, is suspected of having, or is at risk of having a disease, disorder, or condition is associated with a bacterial, viral, or parasitic infection or overgrowth. In some embodiments, the disease, condition, or disorder is associated with infection by drug-resistant bacteria.

Also provided herein is a method of preventing or reducing the incidence or severity of pouchitis in a subject in need thereof, wherein the subject has undergone or will undergo an ileal pouch-anal anastomosis (IPAA) surgery, the method comprising administering to the subject (i) a prebiotic mixture comprising one or more human milk oligosaccharides and (ii) at least one probiotic strain of bacterium capable of consuming the human milk oligosaccharides of the mixture.

In certain embodiments, the prebiotic mixture comprises at least 5, at least 10, at least 25, at least 30, at least 50, at least 100, or at least 150 human milk oligosaccharides. In particular embodiments, the prebiotic mixture comprises at least 25 human milk oligosaccharides. In some embodiments, the prebiotic mixture is, is derived from, or comprises a concentrated ultra-filtered permeate from pooled human milk. In certain embodiments, the pooled human milk is pooled from the milk of at least 25, 50, or 100 individual donors.

In particular embodiments, the at least one probiotic strain of bacterium comprises a bacterial strain of the genus *Bifidobacterium*. In some embodiments, the at least one probiotic strain of bacterium comprises a strain of *B. breve, B. bifidum, B. longum* subsp. *infantis*, or *B. longum* subsp. *longum*. In certain embodiments, the at least one probiotic strain of bacterium comprises *B. longum* subsp. *infantis.*

Provided herein is a method of preventing or reducing the incidence or severity of graft versus host disease (GVHD) in a subject in need thereof, wherein the subject has received or will receive an allogenic hematopoietic stem cell transplant, the method comprising administering to the subject (i) a prebiotic mixture comprising at least 25 human milk oligosaccharides and a probiotic strain of *B. longum* subsp. *infantis.*

In particular embodiments, the prebiotic mixture and the probiotic strain are administered orally. In some embodiments, the prebiotic mixture and the probiotic strain are administered on the same day for at least three consecutive days. In certain embodiments, the method comprises at least a first treatment phase and a second treatment phase, wherein the first treatment phase comprises administering to the subject the prebiotic mixture and the probiotic strain on the same day for at least three consecutive days, and wherein the second treatment phase begins immediately after the end of the first treatment phase and comprises administering the prebiotic mixture for at least three consecutive days.

In particular embodiments, the first treatment phase is between 3 and 14 days in length and wherein the second treatment phase is between 3 and 14 days in length. In some embodiments, the first treatment phase is about 7 days in length and wherein the second treatment phase is about 7 days in length. In certain embodiments, the probiotic strain is administered in an amount of at least $5\times10^6$ colony forming units (CFU) per day. In particular embodiments, the probiotic strain is administered in an amount of at least $8\times10^7$ colony forming units (CFU) per day. In some embodiments, the prebiotic mixture is administered in an amount of at least 500 mg of total human milk oligosaccharides per day. In certain embodiments, the prebiotic mixture is administered in an amount of between 1 g and 5 g, 2 g and 3 g, 3 g and 6 g, 4 g and 5 g, 5 g and 10 g, 8 g and 10 g, 10 g and 20 g, 15 g and 20 g, or 17 g and 19 g of total human milk oligosaccharides per day. In particular embodiments, the prebiotic mixture and/or the probiotic strain is administered with an enteric coating. In certain embodiments, the methods further comprise administering a proton pump inhibitor, wherein the proton pump inhibitor is administered at least 1 hour prior to administration of the probiotic strain. In some embodiments, the subject is at least 6 months, 12 months, 2 years, 5 years, 12 years, or 18 years of age. In certain embodiments, the subject is a child, an adolescent, or an adult.

In some embodiments, the subject has not been administered one or both of a proton pump inhibitor or an antacid for at least about 1 hour, 2 hours, 4 hours, 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In certain embodiments, the subject has not been administered a proton pump inhibitor or an antacid comprising bicarbonate for at least about 1 hour, 2 hours, 4 hours, 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In particular embodiments, the subject has not been administered a proton pump inhibitor comprising a benzimidazole derivative for at least about 1 hour, 2 hours, 4 hours, 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In some embodiments, the subject has not been administered a proton pump inhibitor comprising omeprazole for at least about 1 hour, 2 hours, 4 hours, 6 hours, 12 hours, 24 hours, 36 hours, 48 hours, 60 hours, 2 days, 3 days, 4 days, 5 days, 7 days, 10 days, 2 weeks, 3 weeks, or 4 weeks prior to administration of the probiotic strain. In certain embodiments, at a time when the one or more probiotic is administered, the subject's stomach has an acidic pH, optionally below 7, between 1 and 7, between 2 and 5, between 1 and 4, or between 1.5 and 3.5. In particular embodiments, both of the one or more probiotics and the prebiotic mixture are free or essentially free of some or all of a proton pump inhibitor and an antacid.

Provided herein is a kit comprising one or more probiotic strains of bacterium and a prebiotic mixture comprising one or more human milk oligosaccharides, wherein the one or more probiotic strains are capable of internalizing and consuming the one or more human milk oligosaccharides. In certain embodiments, the one or more probiotics comprises a *Bifidobacterium* probiotic. In particular embodiments, the one or more probiotics comprises one or more of a strain of *B. breve, B. bifidum, B. longum* subsp. *longum*, or *B. longum* subsp. *infantis*. In some embodiments, the prebiotic mixture comprises at least 2, at least 5, at least 10, at least 25, at least 50, at least 100, at least 125, or at least 150 different human milk oligosaccharides. In certain embodiments, the prebiotic mixture comprises at least 25 human milk oligosaccharides. In particular embodiments, the prebiotic mixture is free or essentially free of oligosaccharides that are not human milk oligosaccharides. In some embodiments, the prebiotic mixture is, is obtained from, or comprises a concentrated ultra-filtered permeate from pooled human milk.

In certain embodiments, the one or more probiotics are incorporated into one or more individual probiotic doses and the prebiotic mixture is incorporated into one or more individual prebiotic doses. In particular embodiments, the one or more individual probiotic doses each comprise at least $1\times10^3$ colony forming units (CFU). In some embodiments, the one or more individual probiotic doses each comprise at least $8\times10^7$ colony forming units (CFU). In certain embodiments, the one or more prebiotic doses comprises between 500 mg and 25 g of total human milk oligosaccharides. In particular embodiments, the one or more individual prebiotic doses comprises between 1 g and 5 g, 2 g and 3 g, 3 g and 6 g, 4 g and 5 g, 5g and 10 g, 8 g and 10 g, 10 g and 20 g, 15 g and 20 g, or 17 g and 19 g of total human milk oligosaccharides. In some embodiments, the one or more individual prebiotic doses comprises less than 0.1% lactose. In certain embodiments, the kit comprises one or more individual doses of a proton pump inhibitor.

In certain embodiments, provided herein is an article of manufacture comprising any of the kits provided herein and instructions for use, wherein the instructions for use describes any of the methods described herein.

Provided herein are compositions, methods, strategies, kits, and articles of manufacture that are useful, inter alia, in the treatment or prevention of graft versus host disease (GVHD) or related conditions and disorders. In some aspects, the provided compositions, methods, kits, or articles of manufacture are or include a prebiotic, such as a mixture of human milk oligosaccharides, and at least one strain of probiotic bacteria. In some aspects, the probiotic bacteria strain is capable of internalizing and metabolizing the human milk oligosaccharides. In particular embodiments, administration of the at least one probiotic strain and oligosaccharides to a subject in need thereof reduces or prevents incidence or severity of GVHD.

Provided herein is a method of preventing or reducing the incidence or severity of graft versus host disease (GVHD) in a subject in need thereof, wherein the subject has undergone or will undergo an allogenic transplant, the method comprising administering to the subject a mixture of non-digestible carbohydrates and a probiotic strain of bacterium capable of consuming the non-digestible carbohydrates of the mixture.

In particular embodiments, the mixture comprises at least 10, at least 25, at least 50, at least 100, at least 150, or at least 200 different non-digestible carbohydrates. In certain embodiments, the non-digestible carbohydrates are oligosaccharides. In some embodiments, the non-digestible carbohydrates are human milk oligosaccharides.

Further provided herein is a method of preventing or reducing the incidence or severity of graft versus host disease (GVHD) in a subject in need thereof, wherein the subject has received or will receive an allogenic transplant, the method comprising administering to the subject a mixture of HMOs and a probiotic strain of bacterium of the genus *Bifidobacterium.*

In some embodiments, the probiotic strain is a strain of *B. breve, B. bifidum, B. longum* subsp. *infantis*, or *B. longum* subsp. *longum*. In certain embodiments, the probiotic strain is *B. longum* subsp. *infantis*. In particular embodiments, the mixture comprises at least 10, at least 25, at least 50, at least 100, at least 150, or at least 200 different HMOs.

In some embodiments, administration of the mixture and the probiotic strain begins at the time of neutrophil engraftment, immediately after completion of an antibiotic regimen taken in association with the transplant. In certain embodiments, the mixture and the probiotic strain are administered orally. In particular embodiments, the mixture and the probiotic strain are administered orally twice a day. In some embodiments, the mixture is administered at a dose of between or between about 3 g/day and 18 g/day, inclusive. In certain embodiments, the mixture is administered at a dose of or of about 12.5 g/day.

In particular embodiments, the probiotic strain is administered at a dose of between or between about $10^4$ units/day and $10^{12}$ units/day. In some embodiments, the probiotic strain is administered at a dose of or of about $10^9$ units/day. In certain embodiments, the mixture and the probiotic strain is administered twice daily for the duration of a treatment period. In particular embodiments, the treatment period is or lasts between 7 days and 180 days, inclusive. In some embodiments, the treatment period is or lasts for at least 7 days, 14 days, 21 days, 28 days, 30 days, 60 days, 90 days, or 120 days.

In certain embodiments, one or both of the mixture and the probiotic strain comprises an enteric coating. In particular embodiments, the method further comprises administering a proton pump inhibitor. In some embodiments, administration of the mixture and the probiotic strain treats, ameliorates, or reduces dysbiosis in the subject.

Also provided herein is a kit comprising a mixture of at least 10, at least 25, at least 50, at least 100, at least 150, or at least 200 different HMOs and a probiotic strain of B. longum subsp. infantis, wherein the mixture and the probiotic strain is suitable for oral administration.

In addition, provided herein is a method of preventing or reducing the incidence or severity of pouchitis in a subject in need thereof, wherein the subject has undergone or will undergo an IPAA surgery, the method comprising administering to the subject a mixture of non-digestible carbohydrates and a probiotic strain of bacterium capable of consuming the non-digestible carbohydrates of the mixture.

In certain embodiments, provided herein is a composition or formulation comprising (i) a prebiotic mixture comprising one or more human milk oligosaccharides and (ii) at least one probiotic strain of bacterium capable of consuming the one or more human milk oligosaccharides, for use in treating or preventing a disease, disorder, or condition associated with one or more of inflammation, infection, allergy, immune dysfunction, or dysbiosis of the intestinal microbiome in a subject in need thereof. In particular embodiments, provided herein are formulations for use in accordance with the invention wherein the (i) prebiotic mixture and the (ii) probiotic strain are for administration to the subject simultaneously, separately, or sequentially.

In some embodiments, provided herein is a composition or formulation comprising (i) a prebiotic mixture comprising one or more human milk oligosaccharides and (ii) a probiotic strain of *B. longum* subsp. *infantis*, for use in treating or preventing a disease, disorder, or condition associated with one or more of inflammation, infection, allergy, immune dysfunction, or dysbiosis of the intestinal microbiome in a subject in need thereof.

In various embodiments, provided herein is a composition or formulation comprising (i) a prebiotic mixture comprising at least 5, at least 10, at least 25, at least 50, or at least 100 human milk oligosaccharides and (ii) a probiotic strain of the genus *Bifidobacterium*, for use in treating or preventing a disease, disorder, or condition associated with one or more of inflammation, infection, allergy, immune dysfunction, or dysbiosis of the intestinal microbiome in a subject in need thereof.

In certain embodiments, provided herein is a composition or formulation comprising (i) a prebiotic mixture comprising at least 5, at least 10, at least 25, at least 50, or at least 100 human milk oligosaccharides and (ii) a probiotic strain of *B. longum* subsp. *infantis*, for use in preventing or reducing the incidence or severity of graft versus host disease in a subject in need thereof, wherein the subject has received or will receive an allogenic hemopoietic stem cell transplant.

In particular embodiments, provided herein is a composition or formulation comprising (i) a prebiotic mixture comprising at least 5, at least 10, at least 25, at least 50, or at least 100 human milk oligosaccharides and (ii) a probiotic strain of *B. longum* subsp. *infantis*, for use in treating or preventing an infection in a subject in need thereof, wherein the infection comprises a bacterial infection.

In some embodiments, provided herein is a composition or formulation comprising (i) a prebiotic mixture comprising at least 5, at least 10, at least 25, at least 50, or at least 100 human milk oligosaccharides and (ii) a probiotic strain of *B. longum* subsp. *infantis*, for use in preventing or reducing the incidence or severity of pouchitis in a subject in need thereof, wherein the infection comprises a bacterial infection.

In particular embodiments, provided herein is a composition or formulation comprising (i) a prebiotic mixture comprising at least 5, at least 10, at least 25, at least 50, or at least 100 human milk oligosaccharides, wherein the prebiotic mixture is, is derived from, or comprises a concentrated human milk permeate, wherein the human milk permeate is obtained from the ultrafiltration of human skim milk obtained from pooled human milk, and wherein the pooled human milk is pooled from the milk of multiple human milk donors; and (ii) a probiotic strain of *B. longum* subsp. *infantis*, for use in treating or preventing a disease, disorder, or condition associated with one or more of inflammation, infection, allergy, immune dysfunction, or dysbiosis of the intestinal microbiome in a subject in need thereof.

In some embodiments, provided herein is a composition or formulation comprising a prebiotic mixture and at least one probiotic strain for the treatment or prevention of a disease, disorder, or condition associated with one or more of inflammation, infection, allergy, immune dysfunction, or dysbiosis of the intestinal microbiome in a subject in need thereof, wherein the prebiotic mixture comprises one or more human milk oligosaccharides and the probiotic strain is capable of consuming the one or more human milk oligosaccharides.

In certain embodiments, provided herein is a composition or formulation comprising a prebiotic mixture and at least one probiotic strain for use in the treatment or prevention of a disease, disorder, or condition associated with one or more of inflammation, infection, allergy, immune dysfunction, or dysbiosis of the intestinal microbiome, wherein the prebiotic mixture comprises one or more human milk oligosaccharides and wherein the probiotic strain is capable of consuming the one or more human milk oligosaccharides.

In some embodiments, provided herein is a prebiotic mixture comprising oligosaccharides for use treating hyperammonemia, wherein (i) the mixture is free or essentially free of oligosaccharides that incorporate an N-acetyl glucosamine residue or (ii) the percentage by weight of oligosaccharides comprising nitrogen in the mixture is less than 50%.

In particular embodiments, provided herein is a prebiotic mixture comprising oligosaccharides, wherein (i) the mixture is free or essentially free of oligosaccharides that incorporate an N-acetyl glucosamine residue or (ii) the percentage by weight of oligosaccharides comprising nitrogen in the mixture is less than 50%, for use in decreasing the level or amount of ammonia in a subject in need thereof for the treatment of hyperammonemia.

In certain embodiments, provided herein is a composition or formulation comprising (i) a prebiotic mixture comprising oligosaccharides, wherein all or essentially all of the oligosaccharides of the prebiotic mixture are human milk oligosaccharides that do not incorporate an N-acetyl glucosamine residue, and (ii) a probiotic strain of bacterium, for use in treating or preventing hyperammonemia, wherein the probiotic strain is a *Bifidobacterium* capable of internalizing HMOs.

In some embodiments, provided herein is a composition or formulation comprising (i) a prebiotic mixture of oligosaccharides, wherein all or essentially all of the oligosaccharides of the prebiotic mixture are human milk oligosaccharides (HMOs) that do not incorporate an N-acetyl glucosamine residue, and (ii) a probiotic strain of bacterium, for reducing ammonia in a subject in need thereof for the treatment of hyperammonemia, wherein the probiotic bacterium strain is a *Bifidobacterium* strain capable of internalizing HMOs.

In certain embodiments, provided herein is a composition or formulation comprising i) a prebiotic mixture comprising 2'-fucosyllactose, 3-fucosyllactose, difucosyllactose, 3'-sialyllactose, and 6'-sialyllactose and ii) a probiotic strain of *B. longum* subsp. *infantis*, for use in treating or preventing hyperammonemia.

In particular embodiments, provided herein is a composition or formulation comprising i) a prebiotic mixture comprising 2'-fucosyllactose, 3-fucosyllactose, and difucosyllactose and ii) a probiotic strain of *B. longum* subsp. *infantis*, for use in treating or preventing hyperammonemia.

DETAILED DESCRIPTION

Figure 1:
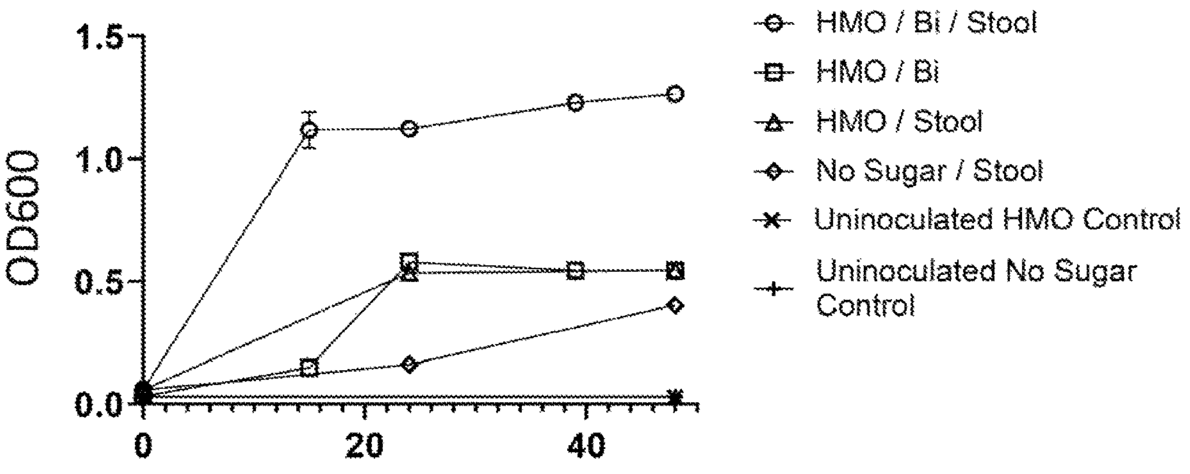
FIG. 1 provides a graph displaying optical density measurements at 600 nm (OD600) collected at various time points in cultures of *B. longum* subsp. *infantis* (BI), stool microbiota (Stool), or both (BI/Stool), incubated in the presence of a mixture of HMOs (HMO). Controls include uninoculated cultures (uninoculated) and/or cultures that were incubated in the absence of a carbon source (No Sugar).

Provided herein are compositions, kits, and articles of manufacture as well as methods of use thereof. In certain embodiments, the provided compositions, kits, and articles of manufacture contain one or more prebiotics, e.g., non-digestible carbohydrates such as human milk oligosaccharides, and at least one probiotic strain, e.g., a *Bifidobacterium* such as *B. longum* subsp. *infantis*, capable of consuming the one or more prebiotic. In certain aspects, the provided compositions, kits, and articles are manufacture are particularly useful in the treatment or prevention of diseases or conditions associated with inflammation, allergies, or immune disorders. In some aspects, the provided compositions, kits, and articles of manufacture may be administered to a subject to treat or prevent dysbiosis, e.g., of the intestinal microbiome, as well as diseases or disorders that may originate from or cause dysbiosis. In some embodiments, the provided compositions, kits, and articles of manufacture are useful for the treatment or prevention of graft versus host disease (GVHD).

In certain aspects, the maintenance of a healthy human metabolism depends on a symbiotic consortium among bacteria, archaea, viruses, fungi, and host eukaryotic cells throughout the human gastrointestinal tract. For example, microbial communities may provide enzymatic machinery and metabolic pathways that contribute to food digestion, xenobiotic metabolism, and production of a variety of bioactive molecules. Disturbances to the microbiome may result in a microbial imbalance (dysbiosis) characterized by phylum-level changes in the microbiota composition, including a marked decrease in the representation of obligate anaerobic bacteria and an increased relative abundance of facultative anaerobic bacteria. While dysbiosis is associated with numerous diseases and conditions, successfully treating dysbiosis is difficult, particularly in vulnerable or immunocompromised patients.

The provided compositions, methods, kits, and articles of manufacture address these needs. In particular, the present invention includes specific combinations of prebiotics, such as human milk oligosaccharides, and probiotics, such as probiotics that consume human milk oligosaccharides, e.g., *Bifidobacterium longum* subspecies (subsp.) *infantis* (also referred to herein as *B. longum* subsp. *infantis* or *B. infantis*), that are particularly safe and effective for treating, ameliorating, or reducing dysbiosis in the gut microbiome as well as effective in treating, ameliorating, or preventing diseases or disorders that may be accompanied by dysbiosis, such including but not limited to diseases associated with immune disorders, inflammatory disorders, or infection.

In various aspects, the provided combination of prebiotics and probiotics have several advantages over alternative treatments that target the microbiome. For example, in some aspects, the provided prebiotics, e.g., human milk oligosaccharides, provide a selective carbon and/or energy source for the provided probiotic strain, which may be a beneficial strain of bacteria, e.g., *B. longum* subsp. *infantis*, that is not typically present in the healthy adult microbiome. Thus, in contrast to treatments such as fecal matter transplants, the engraftment, expansion, and presence of the probiotic in the subject's microbiome may be controlled by the concurrent or subsequent administration of the provided prebiotics. For example, in some aspects, the expansion of the probiotic may be increased by increasing or extending the administration of the provided prebiotics. In some aspects, the duration of time that the probiotic is present within the subject's microbiome may be controlled by withdrawing or terminating administration of the prebiotic, without any need for antibiotics.

In certain aspects, administration of the provided prebiotics and probiotics promotes an environment capable of promoting or allowing the growth or expansion of other beneficial microbiota within the subject's microbiome and/or preventing the growth or expansion of potentially pathogenic bacteria. For example, in some aspects, the provided prebiotics and probiotics are administered for a limited period of time, during which time the probiotic may generate or promote an environment, such as by influencing pH and/or producing short chain fatty acids, that impairs growth of pathogenic microbiota while promoting beneficial microbiota. In certain aspects, after such a period of time, administration of the prebiotics may be withdrawn, thereby reducing the presence of the provided probiotic in the subject's microbiome. In some such aspects, the expanded presence of the beneficial microbiota may continue to sustain this healthy environment even when the provided probiotic is no longer detectable, thereby continuing to promote a healthy microbiome and/or prevent dysbiosis after administration of the provided prebiotics and probiotics has ended.

In some aspects, the probiotic strain is or includes *B. longum* subsp. *infantis*. In infants, breast feeding may result in the expansion of *B. longum* subsp. *infantis* and a subsequent reduction in other potentially deleterious species, e.g. species or strains of Enterobacteriaceae. However, *B. longum* subsp. *infantis* is not typically present in the healthy adult microbiome, nor are human milk oligosaccharides typically present in an adult diet. In certain aspects, prior to the instant invention it was not clear what, if any, benefits of *B. longum* subsp. *infantis* engraftment could have for adult health. The present invention relates, at least in part, to the surprising finding that *B. longum* subsp. *infantis* can indeed be engrafted in the adult intestinal microbiome when administered along with human milk oligosaccharides. Engraftment of *B. longum* subsp. *infantis* through this manner results in surprisingly beneficial effects for adult diseases and conditions, at least in part through one or more of a reduction of deleterious bacterial species, an increased production of short chain fatty acids, and reduction of inflammation or pro-inflammatory factors.

In some embodiments, provided herein are combinations of prebiotics, e.g., non-digestible carbohydrates such as human milk oligosaccharides, and probiotics, e.g., strains of Bifidobacteria such as *B. longum* subsp. *infantis*. In some embodiments, this prebiotic and probiotic combination synergistically (i) promotes engraftment and expansion of the probiotic; (ii) improves, reduces, treats, or ameliorates dysbiosis; (iii) promotes diversity (e.g., alpha and/or beta diversity) of the gut microbiome; (iv) promotes production of short chain fatty acids; and/or (v) reduces, improves, treats, or ameliorates inflammation or conditions associated with auto- or hyper-immunity. In certain aspects, such effects may be achieved, inter alia, by the production of lactate or acetate; reduction of intestinal pH; and/or cross-feeding of butyrate producers by the probiotic as selectively promoted by the prebiotic.

In some embodiments, the probiotic strain, e.g., *B. longum* subsp. *infantis*, is capable of internalizing oligosaccharides or non-digestible carbohydrates of the prebiotic mixture, such as for internal metabolism or hydrolysis of all or some of the prebiotic mixture. In some aspects, probiotic strains capable of internalizing non-digestible carbohydrates and oligosaccharides may have endogenous transport or import molecules as well as glycosyl hydrolases to deconstruct oligosaccharides having certain specific glycosidic linkages, e.g., linkages found in human milk oligosaccharides. In some aspects, the ability to internalize and metabolize oligosaccharides or non-digestible carbohydrates may allow for these probiotic strains to be uniquely successful in colonizing the gut of a subject administered HMOs, e.g., since the HMOs with suitable sizes and compositions are uniquely consumed by these bacteria alone. Because the oligosaccharides are internalized within the cells, monosaccharide breakdown products do not diffuse or are not consumed by other bacteria. Thus, in some embodiments, the prebiotic mixture, e.g., of human milk oligosaccharides, selectively promotes growth and expansion of the at least one probiotic strain over other bacteria, e.g., present in the gut and/or microbiome.

In certain embodiments, the non-digestible carbohydrates or oligosaccharides of the prebiotic mixture are internalized and metabolized by the probiotic strain. In some aspects, the non-digestible carbohydrates or oligosaccharides are broken down internally within the bacterial cell, such that in some aspects monosaccharides or other oligosaccharide breakdown products do not diffuse to and/or are not utilized by other bacteria. In certain embodiments, the at least one probiotic strain is a strain of *Bifidobacterium* capable of internalizing the oligosaccharides of the mixture. In certain embodiments, the at least one probiotic strain is at least one strain of *B. longum* subsp. *infantis*.

In some aspects, an advantage of the provided mixture is that the oligosaccharides, e.g., HMOs, selectively promote the growth and expansion of the probiotic strain, e.g., *B. longum* subsp. *infantis*, in the human gut or human microbiome in vivo. Particular embodiments contemplate that, in some cases, the probiotic strain may consume or internalize certain oligosaccharides in some environments, such as in vitro assays or in the gut or microbiome of non-human animals in vivo, but not in a human gut or microbiome. Thus, in some embodiments, while many kinds of oligosaccharides may promote the growth of the probiotic strain in vitro, the provided mixture of non-digestible carbohydrates promotes the engraftment, growth, and expansion of the probiotic in the human gut in vivo.

In certain aspects, the provided compositions and methods successfully treat a subject with dysbiosis or a disorder or disease related to or associated with dysbiosis, through the combination of one or more probiotic strains and prebiotics that are selectively consumed by the probiotic, thereby promoting or facilitating engraftment in the subject's, e.g., the adult subject's, intestinal microbiome. Surprisingly, administration of the prebiotic compositions provided herein result in engraftment and/or an expansion of the probiotic that may be detected days after the probiotic has been administered. Thus, in certain embodiments, the provided prebiotic compositions are surprisingly effective at supporting the engraftment, growth, expansion, and/or the persistence of the probiotic in the subject's intestinal microbiome.

In certain embodiments, provided herein is an improved strategy for treating diseases or conditions, e.g., those relating to inflammation, immune dysfunction, dysbiosis of the intestinal microbiome, by pairing the administration of a probiotic with a prebiotic, e.g., carbon source, that is selectively utilized by the probiotic with respect to microflora typically present in a healthy or dysbiotic human intestinal microbiome. Particular aspects contemplate that this strategy may be achieved with any combination of probiotic bacteria and prebiotics that are selectively consumed by the probiotic, providing that the probiotic has one or more features discussed herein, e.g., SCFA production, pH regulation, etc., thought to treat, reduce, or ameliorate dysbiosis of the intestinal microbiome or conditions or diseases, e.g., relating to dysbiosis, inflammation, or immune dysfunction, with a prebiotic that is selectively consumed by the probiotic. Certain embodiments contemplate that additional prebiotic/probiotic combinations not explicitly disclosed herein may be identified by routine methods and techniques along with the guidance provided herein.

In certain embodiments, the one or more probiotic strains are administered to a subject with an acidic pH (e.g., a stomach pH of less than 7, less than 6, 1-5, or 1.5-3.5), and/or to a subject not administered or treated with antacids or proton pump inhibitors. Particular embodiments contemplate that reducing the acidity and/or raising pH of the stomach may impair, reduce, or prevent the probability of engraftment and/or expansion of the *B. longum* subsp. *infantis* within the subject's intestinal microbiome.

Also provided herein are compositions, methods, kits, and articles of manufacture that are useful, inter alia, in the treatment or prevention of GVHD or related conditions and disorders in subjects in need thereof. In certain aspects, provided herein is one or more probiotic strains of bacterium, e.g., *Bifidobacterium* such as *B. longum* subsp. *infantis*, capable of consuming or metabolizing oligosaccharides. In certain embodiments, one or both of the at least one probiotic strain of bacterium and the oligosaccharides are administered to a subject to treat, mend, remedy, ameliorate, or prevent GVHD or one or more symptoms associated with GVHD. In certain embodiments, the at least one probiotic strain is capable of consuming or metabolizing one or more of the oligosaccharides present in the mixture.

In some aspects, allogenic transplantation such as hematopoietic stem cell transplantation (HSCT) or bone marrow transplantation (BMT) is a critical treatment of patients with high-risk hematopoietic malignancies, hematological deficiencies, and other immune diseases. In allogeneic HCT (allo-HCT), donor-derived T cells may recognize host tissues as foreign, causing graft-versus-host disease (GVHD) which is a main contributor to morbidity and mortality. The intestine is one of the organs most severely affected by GVHD. In certain aspects, some recent research has suggested an importance of bacteria, particularly the gut microbiota, in HSCT outcome and in GVHD development. Loss of intestinal bacterial diversity is common during the course of HSCT and this loss is associated with regimens of broad-spectrum antibiotics as well as with development of GVHD. Loss of intestinal diversity and outgrowth of opportunistic pathogens belonging to the phylum Proteobacteria and Enterococcus genus have also been linked to increased treatment-related mortality including GVHD, infections, and organ failure after allo-HSCT.

The provided invention addresses these needs. Administration of provided prebiotic and probiotic compositions can treat, ameliorate, or prevent dysbiosis associated with GHVD without the need for fecal matter transplantation or other treatments which may risk introducing potentially pathogenic microbiota into an already immunocompromised subject.

All publications, including patent documents, scientific articles, and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications, and other publications that are herein incorporated by reference, the definition set forth herein prevails over the definition that is incorporated herein by reference.

The section heading used herein are for organizational purposes only and are not to be construed as limiting the subject matter described.

I. COMPOSITIONS, KITS, AND ARTICLES OF MANUFACTURE

Provided herein are compositions, kits, and articles of manufacture that are or include one or both of at least one strain of probiotic bacterium (also referred to herein as a probiotic strain of bacterium, a probiotic strain, or a probiotic) and one or more prebiotics. In certain embodiments, the prebiotics are or include a mixture of two or more individual species of prebiotics (also referred to herein as a prebiotic mixture). In some embodiments, the prebiotics are or include non-digestible carbohydrates, such as oligosaccharides, e.g., human milk oligosaccharides. In some embodiments, the provided compositions, kits, and article of manufacture are or include both the at least one probiotic strain and the prebiotic mixture.

In certain embodiments, the probiotic strain(s) and the prebiotic mixture are included in separate compositions, e.g., are administered separately to a subject. Thus, in certain embodiments, provided herein are kits and articles of manufacture that include both of (i) a composition that is or includes at least one probiotic strain and (ii) a composition that is or includes a prebiotic mixture. Also provided are kits and articles of manufacture that are or include one or more compositions that each contain both the at least one probiotic strain and the prebiotic mixture.

In certain embodiments, the provided compositions, kits, and articles of manufacture contain or include any of the prebiotic mixtures of non-digestible carbohydrates, e.g., HMOs, that are described herein, such as in Section I-A. In particular embodiments, the provided compositions, kits, and articles of manufacture contain or include any of the probiotic strains, e.g., of *Bifidobacterium*, described herein, such as those described in Section I-B. In some aspects, the provided kits and articles of manufacture may also include labels or instructions for use. In some embodiments, such labels or instructions for use may describe any of the uses or methods provided herein, such as those described in Section II.

In some embodiments, the at least one probiotic strain is capable of internalizing some or all of the prebiotics, e.g., non-digestible carbohydrates such as human milk oligosaccharides, of the prebiotic mixture. In some embodiments, the at least one probiotic strain and the prebiotic mixture, e.g., of human milk oligosaccharides, are formulated to promote the growth or expansion of the at least one probiotic strain in vivo, e.g., in the gut of a human. In certain embodiments the prebiotics of the mixture selectively or exclusively serve as a carbon source for the at least one probiotic strain. In some embodiments the prebiotics of the mixture selectively or exclusively serve as an energy source for the probiotic strain(s).

Various embodiments contemplate that the administration of the prebiotic mixture and the one or more probiotic strains synergistically prevent or reduce the likelihood, probability, or risk of a disease, disorder, or condition, e.g., an inflammatory or autoimmune related disease, disorder, or condition, in a subject to a greater degree than what would be expected based on the administration of either the one or more probiotic strains or the prebiotic mixture alone.

In certain embodiments, administration of the prebiotic mixture and the one or more probiotic strains synergistically prevent or reduce the likelihood, probability, or risk of dysbiosis, e.g., of the human intestinal microbiome, to a greater degree than what would be expected based on the administration of either the one or more probiotic strains or the prebiotic mixture alone. In some embodiments, administration of the prebiotic mixture and the one or more probiotic strains synergistically treat, reduce, or ameliorate dysbiosis, and/or one or more symptoms of a disease, disorder, or condition that may be associated with dysbiosis, to a greater degree than what would be expected based on the administration of either the one or more probiotic strains or the prebiotic mixture alone. Particular embodiments contemplate that the degree of dysbiosis, as well as a reduction or decrease of dysbiosis, may be determined by those of skill in the art by routine methods, including but not limited to routine genetic techniques (e.g., 16S sequencing) to determine the presence, portion, or amount of different microbiota genera, species, and/or strains.

Particular embodiments contemplate that the administration of the prebiotic mixture and the one or more probiotic strains synergistically prevent or reduce the likelihood, probability, or risk of an incidence of GVHD in a subject, e.g., a subject who has undergone or who will undergo an allogenic transplant e.g., to a greater degree than what would be expected based on the administration of either the probiotic strain or the mixture alone. In particular embodiments, it is contemplated that the administration of the probiotic strain and the prebiotic mixture synergistically reduces, ameliorates, treats, alleviates or prevents, the severity of one or more symptoms associated with GVHD, e.g., to a greater degree than what would be expected based on the administration of either the probiotic strain or the prebiotic mixture alone.

A.) Prebiotic Mixtures

In some embodiments, the prebiotic mixture is a mixture of non-digestible carbohydrates, e.g., oligosaccharides such as human milk oligosaccharides (HMOs), that promotes the growth or expansion of the at least one probiotic strain, e.g., in vivo such as in the human gut and/or within the human gut microbiome. In certain embodiments, the prebiotic mixture, e.g., of non-digestible carbohydrates such as HMOs, promotes, e.g., selectively or exclusively, the colonization, expansion, extension, or increased presence of the at least one probiotic strain within the microbiome. In particular embodiments, the prebiotic mixture, e.g., of non-digestible carbohydrates such as HMOs, promotes the growth or expansion of a *Bifidobacterium* probiotic strain such as *B. longum* subsp. *infantis*, e.g., in vivo such as in the human gut. In certain embodiments, the prebiotic mixture is a mixture of oligosaccharides, e.g., HMOs, that promote, e.g., selectively or exclusively, the colonization, expansion, extension, or increased presence of one or more strains of *Bifidobacterium*, e.g., *B. longum* subsp. *infantis*, within the microbiome.

In some embodiments, the prebiotic mixture is or includes a mixture of non-digestible carbohydrates. In various embodiments, the prebiotic mixture is or includes a mixture of oligosaccharides. In particular embodiments, the prebiotic mixture is a mixture of one or more human milk oligosaccharides.

In some embodiments, the non-digestible carbohydrates of the prebiotic mixture are or include oligosaccharides. In particular embodiments, the non-digestible carbohydrates are or include milk oligosaccharides. In certain embodiments, the non-digestible carbohydrates are or include human milk oligosaccharides (HMOs). In some embodiments, the prebiotic mixture is a mixture of non-digestible carbohydrates that are or include human milk oligosaccharides. In particular embodiments, the prebiotic mixture is a mixture of human milk oligosaccharides, such as those that are obtained or derived from permeate, e.g., permeate derived or obtained from pooled human milk (e.g., such as a permeate described herein or produced by a method described herein such as in Section I-A-(i).

In some embodiments, the prebiotic mixture is or includes one or more oligosaccharides. In some embodiments, the oligosaccharides are capable of being internalized by one or more strain of *Bifidobacterium* such as a strain of *B. longum* subsp. *infantis*. In some embodiments, the oligosaccharides may include one or more of a fructo-oligosaccharide (FOS), galactooligosaccharide (GOS), transgalactooligosaccharide (TOS), gluco-oligosaccharide, xylo-oligosaccharide (XOS), chitosan oligosaccharide (COS), soy oligosaccharide (SOS), isomalto-oligosaccharide (IMOS), or derivatives thereof. In certain embodiments, such derivatives include those with modifications that may increase the likelihood or probability of consumption, metabolism, and/or internalization (such as by transport or import) of the oligosaccharide by the probiotic strain, e.g., *B. longum* subsp. *infantis*. Such modifications may include but are not limited to fucosylation or sialylation. In some embodiments, the oligosaccharides may include one or more of a FOS, GOS, TOS, gluco-oligosaccharide, XOS, COS, SOS, IMOS, or derivatives or any or all of the foregoing, that are capable of being metabolized, consumed, and/or internalized by one or more strains, species, or subspecies of *Bifidobacterium*, e.g., *B. longum* subsp. *infantis*. In certain embodiments, the oligosaccharides of the mixture include one or more oligosaccharides that are obtained or derived from a resistant starch, pectin, psyllium, arabinogalactan, glucomannan, galactomannan, xylan, lactosucrose, lactulose, lactitol and various other types of gums such as tara gum, acacia, carob, oat, bamboo, citrus fibers, such as by treatment with enzymes that hydrolyze fiber or polysaccharides. In some embodiments, the one or more oligosaccharides that are obtained by these means are capable of being consumed, metabolized, and/or internalized by at least one strain of *Bifidobacterium* such as *B. longum* subsp. *infantis.*

In certain embodiments, the prebiotic mixture includes one or more oligosaccharides that are or include oligosaccharides found in a mammalian milk. In some embodiments, mammalian milk oligosaccharides may be internalized and metabolized by certain strains of *Bifidobacterium*, e.g., *B. longum* subsp. *infantis*. In certain embodiments, all or a portion of the oligosaccharides of the mixture are mammalian milk oligosaccharides. In some embodiments, all of the oligosaccharides of the mixture are mammalian milk oligosaccharides. In certain embodiments, the mammalian milk oligosaccharides are derived from or found in milk that includes but is not limited to milk from dog, cat, camel, goat, cow, yak, buffalo, horse, donkey, zebu, sheep, reindeer, giraffe, elephant, non-human primate, or human.

In some embodiments, all or a portion of the oligosaccharides of the prebiotic mixture are human milk oligosaccharides, e.g., at least 25%, 50%, 75%, 90%, 95%, or 99% of the oligosaccharide by either i) the percentage of oligosaccharide species present in the mixture or ii) by total weight of the oligosaccharides in the prebiotic mixture. In certain embodiments, all or essentially all of the oligosaccharides of the prebiotic mixture are human milk oligosaccharides. In some aspects, the HMOs are oligosaccharides that are present or found in human milk. In certain aspects, all HMOs are composed of the five monosaccharides glucose (Glc), galactose (Gal), N-acetylglucosamine (GlcNAc), fucose (Fuc) and sialic acid (Sia), with N-acetylneuraminic acid (Neu5Ac) as the predominant if not only form of sialic acid. In certain aspects, HMO biosynthesis appears to follow a basic blueprint: all HMOs contain lactose (Galβ1-4Glc) at their reducing end, which can be elongated by the addition of β1-3- or β1-6-linked lacto-N-biose (Galβ1-3GlcNAc-, type 1 chain) or N-acetyllactosamine (Galβ1-4GlcNAc-, type 2 chain). Elongation with lacto-N-biose appears to terminate the chain, whereas N-acetyllactosamine can be further extended by the addition of one of the two disaccharides. A β1-6 linkage between two disaccharide units introduces chain branching. Branched structures are designated as iso-HMO; linear structures without branches as para-HMO. Lactose or the elongated oligosaccharide chain can be fucosylated in α1-2, α1-3 or α1-4 linkage and/or sialylated in α2-3 or α2-6 linkage. Particular embodiments contemplate that HMOs structures are known and identifiable, and are described, e.g., in Bode, Glycobiology (2012) 22(9): 1147-1162; Prudden et al. PNAS (2017) 114(27): 6954-6959; Kobata, Pro. Jpn. Acad., Ser B (2010) 86:731-747; and Smilowitz et al Annu Rev Nutr. (2014) 34: 143-169.

In some embodiments, the prebiotic mixture is not human milk (e.g., breastmilk or whole human milk). In certain embodiments, the prebiotic mixture may be derived from or obtained from human milk, such as with one or more steps to separate or remove macronutrients, e.g., fat, protein, and/or carbohydrates, while retaining human milk oligosaccharides. In particular embodiments, the prebiotic mixture is not a human milk fortifier, e.g., the prebiotic mixture has less than 2 g per 100 mL of protein and/or has less than 3 g per 100 mL of fat). In various embodiments, the prebiotic mixture is or includes less than 2%, 1.5%, 1%, 0.5%, or 0.1% protein (by weight/volume or w/v). In particular embodiments, the prebiotic mixture is or includes less than 3%, 2.5%, 2%, 1.5%, 1%, 0.5%, or 0.1% fat (w/v). In certain embodiments, the prebiotic mixture consists essentially of human milk oligosaccharides.

In certain embodiments, the prebiotic mixture is a mixture that is or includes at least one HMO. In some embodiments, the prebiotic mixture is a mixture of HMOs that is or includes a plurality of HMOs. In some embodiments, the prebiotic mixture is or includes a plurality of, of about, or of at least 2, 3, 5, 10, 25, 50, 75, 100, 125, 150 different individual HMOs, e.g., HMOs with different individual chemical formulas or chemical structures. In certain embodiments, the prebiotic mixture is or includes a plurality of, of about, or of at least 10, 25, 50, 75, 100, 125, 150 different individual HMOs. In some embodiments, the prebiotic mixture is or includes a plurality of, of about, or of at least 25 different individual HMOs. In some embodiments, the prebiotic mixture is or includes a plurality of, of about, or of at least 80 different individual HMOs. Particular embodiments contemplate that one of skill may determine if an oligosaccharide is an HMO, such as if the oligosaccharide has a chemical formula and structure that is identical to an oligosaccharide that is found in human milk, as a matter of routine.

In certain embodiments, the prebiotic mixture contains one or more synthetic HMOs, e.g., HMOs that are obtained, purified, or synthesized from a source other than human milk. In some aspects, synthetic HMOs, as well as methods for synthesizing oligosaccharides and HMOs, are known, and include but are not limited to those described in PCT Publication Nos.: WO2017101958, WO2015197082, WO2015032413, WO2014167538, WO2014167537, WO2014135167, WO2013190531, WO2013190530, WO2013139344, WO2013182206, WO2013044928, WO2019043029, WO2019008133, WO2018077892, WO2017042382, WO2015150328, WO2015106943, WO2015049331, WO2015036138, and WO2012097950, each of which is incorporated by reference herein in its entirety.

In some embodiments, the prebiotic mixture is a mixture of HMOs that is or is obtained from human milk or a fraction thereof. In certain embodiments, the mixture of HMOs is or is obtained from an ultra-filtered permeate from human skim milk. In some embodiments, the mixture of HMOs (e.g., a human milk permeate) is or is obtained from a process described herein, e.g., in Section-I-A-(i). In certain embodiments, the prebiotic mixture is a concentrated human milk permeate, such as those described in U.S. Pat. No. 8,927,027 or in PCT Application No. WO 2018053535, incorporated herein by reference.

In some embodiments, the prebiotic mixture is or includes a concentrated human milk permeate that contains a plurality of human milk oligosaccharides. In certain embodiments, the concentrated human milk permeate includes a plurality of, of about, or of at least 1, 2, 3, 5, 10, 25, 50, 75, 100, 125, 150 different individual HMOs, e.g., HMOs with different individual chemical formulas or chemical structures. In certain embodiments, the prebiotic mixture is or includes a plurality of, of about, or of at least 10, 25, 50, 75, 100, 125, 150 different individual HMOs. In some embodiments, the prebiotic mixture is or includes a plurality of, of about, or of at least 25 different individual HMOs. In some embodiments, the prebiotic mixture is or includes a plurality of, of about, or of at least 80 different individual HMOs.

In some embodiments, the prebiotic mixture includes some or all of 2'-fucosyl-lactose, 3'-fucosyl-lactose, 3'-sialyl-lactose, 6'-sialyl-lactose, Lacto-N-tetraose, lacto-N-difucohexaose I, lactodifucotetraose, Lacto-N-fucopentaose I, sialylacto-N-tetraose c, sialylacto-N-tetraose b, and disialyllacto-N-tetraose. In particular embodiments, the mixture includes all of 2'-fucosyl-lactose, 3'-fucosyl-lactose, 3'-sialyl-lactose, 6'-sialyl-lactose, Lacto-N-tetraose, lacto-N-difucohexaose I, lactodifucotetraose, Lacto-N-fucopentaose I, sialylacto-N-tetraose c, sialylacto-N-tetraose b, and disialyllacto-N-tetraose.

In certain embodiments, the prebiotic mixture includes some or all of 2-fucosyllactose, lacto-N-tetraorose, 3-sialyllactose, 3-fucosyllactose, lacto-N-fucopentaose I, lacto-N-fucopentaose II, and 6'sialyllactose. In particular embodiments, the prebiotic mixture includes some or all of 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, and Difucosyl-Lacto-N-hexaose b.

In certain embodiments, the prebiotic mixture includes some or all of 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose a, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, Difucosyl-Lacto-N-hexaose b, lactodifucotetraose (LD), 6'galactosyllactose, 3'galactosyllactose, 3-Sialyl-3-fucosyllactose, Sialylfucosyllacto-N-tetraose, Sialyllacto-N-fucopentaose V, disialyl-lacto-n-fucopentaose II, disialyl-lacto-n-fucopentaose V, Lacto-N-neo-difucohexaose II, 3-Fucosyl-sialylacto-N-tetraose c, para-Lacto-N-neohexose, Lacto-N-octaose, Lacto-N-neooctaose, Lacto-N-neohexaose, Lacto-N-fucopentaose V, iso-Lacto-N-octaose, para-Lacto-N-octaose, Lacto-decaose, and Sialyl-lacto-N-fucopentaose I.

In certain embodiments, the prebiotic mixture contains at least 10, 25, 50, 100, 125, or 150 HMOs which include all of 2-fucosyllactose, lacto-N-tetraorose, 3-sialyllactose, 3-fucosyllactose, lacto-N-fucopentaose I, lacto-N-fucopentaose II, and 6'sialyllactose. In particular embodiments, the prebiotic mixture contains at least 25, 50, 100, 125, or 150 HMOs which include all of 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, and Difucosyl-Lacto-N-hexaose b. In particular embodiments, the prebiotic mixture contains at least 25, 50, 100, 125, or 150 HMOs which include all of 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose a, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, Difucosyl-Lacto-N-hexaose b, lactodifucotetraose (LD), 6'galactosyllactose, 3'galactosyllactose, 3-Sialyl-3-fucosyllactose, Sialylfucosyllacto-N-tetraose, Sialyllacto-N-fucopentaose V, disialyl-lacto-n-fucopentaose II, disialyl-lacto-n-fucopentaose V, Lacto-N-neo-difucohexaose II, 3-Fucosyl-sialylacto-N-tetraose c, para-Lacto-N-neohexose, Lacto-N-octaose, Lacto-N-neooctaose, Lacto-N-neohexaose, Lacto-N-fucopentaose V, iso-Lacto-N-octaose, para-Lacto-N-octaose, Lacto-decaose, and Sialyl-lacto-N-fucopentaose I.

In certain embodiments, the prebiotic mixture has an increased amount, level, or concentration of one or more HMOs as compared to what is typically found human milk. In some embodiments, the prebiotic mixture has an increased amount, level, or concentration of one or more HMOs as compared to what is typically found human milk. In particular embodiments, the prebiotic mixture has an increased amount, level, or concentration of one or more HMOs as compared to what is typically found in untreated human milk permeate, e.g., permeate resulting from ultra-filtration of pooled human skim milk, such as described herein, or produced by a process described herein, e.g., in Section I-A-(i). In particular embodiments, the prebiotic mixture is or includes at least 25, 50, 75, 100, 125, 150, of the different HMOs found, present, or detected in pooled human milk (e.g., pooled from the milk of at least 10, 25, 50, or 100 individual donors) or in permeate (e.g., permeate resulting from ultra-filtering human milk skim) obtained from pooled human milk. In some embodiments, the prebiotic mixture is or includes at least 50%, 60%, 70%, 80%, 85%, 90%, 95%, 97%, 99%, or 99.9% of the different HMOs found, present, or detected in pooled human milk or in permeate) obtained from pooled human milk. In certain embodiments, the prebiotic mixture is or includes at least 50%, 60%, 70%, 80%, 85%, 90%, 95%, 97%, 99%, or 99.9% of the individual HMOs that may be found, present, or detected across samples of human milk. In some embodiments, the prebiotic mixture of HMOs is or includes the same or substantially the same HMOs found, present, or detected in pooled human milk or in permeate obtained from pooled human milk. In certain embodiments the prebiotic mixture is or includes a human milk permeate resulting from the ultrafiltration of human whole or skim milk pooled from at milk collected from at least 10, 25, 50, or 100 individual human milk donors that is further concentrated, e.g., by nanofiltration or reverse osmosis, to increase the concentration of total HMO (e.g., by w/w). In some embodiments, the concentration of total HMO is increased to at least 0.5%, 1%, 2%, 3%, 4%, 5%, 6%, 7%, 8%, 9%, or 10%. In certain embodiments, the concentration of total HMO is increased to at least 5% (w/w). In certain embodiments, the concentration of total HMO is increased to between 8% and 12% (w/w).

In certain embodiments, the prebiotic mixture is free or essentially free of oligosaccharides that are not HMOs.

Prebiotic mixtures of HMOs for use in the methods disclosed herein may be obtained according to methods known in the art, including, but not limited to, chemical synthesis and purification or concentration from human milk. For example, processes to obtain prebiotic mixtures of HMOs from human milk are described below and are detailed in PCT Pub. Nos. WO/2010/065652 and WO/2018/053535, the contents of which are hereby incorporated in their entirety.

In some embodiments, the prebiotic mixture is a mixture of HMOs that are or are derived from a concentrated ultra-filtered human milk permeate, e.g., any ultra-filtered human milk permeate described herein or produced by a method described herein such as in Section I-(A)-(i).

In some embodiments, the provided prebiotic mixtures are mixtures of HMOs having an HMO profile that is substantially similar both structurally and functionally to the profile of HMOs observed across the population of whole human milk. That is to say, in some aspects, since the prebiotic mixtures may be obtained from a source of human milk derived from a pool of donors, rather than an individual donor, the array of HMOs will be more diverse than in any one typical individual, and will represent or more closely represent the spectrum of HMOs that are found in human milk as opposed to the spectrum of HMOs that are found or typically found in the human milk produced by any particular individual.

In some embodiments, the prebiotic mixture is or includes a greater amount of different individual HMOs than the number of different individual HMOs found in human milk from an individual donor. In certain embodiments, the prebiotic mixture includes at least 1, 2, 3, 4, 5, 10, 15, 20, 25, 30, 35, 40, 45, or 50 more individual HMOs than the number of different individual HMOs found in human milk from an individual donor. In particular embodiments, a prebiotic mixture is or includes a greater amount of different individual HMOs than the mean or median number of different individual HMOs found in a plurality of human milk samples from individual donors. In certain embodiments, the prebiotic mixture includes at least 1, 2, 3, 4, 5, 10, 15, 20, 25, 30, 35, 40, 45, or 50 more individual HMOs than the number of different individual HMOs found in human milk from an individual donor.

In some aspects, one of the biggest variables in HMO diversity derives from the mother's Lewis blood group and specifically whether or not she has an active fucosyltrasferase 2 (FUT2) and/or fucosyltrasferase 3 (FUT3) gene. When there is an active FUT2 gene, an α1-2 linked fucose is produced, whereas fucose residues are α1-4 linked when the FUT3 gene is active. The result of this "secretor status" is, generally, that "secretors" (i.e. those with an active FUT2 gene) produce a much more diverse profile of HMOs dominated by α1-2 linked oligosaccharides, whereas "non-secretors" (i.e. those without an active FUT2 gene) may comprise a more varied array of, for example α1,-4 linked oligosaccharides (as compared to secretors), but comprise an overall decrease in diversity since they are unable to synthesize a major component of the secretor's HMO repertoire. In some embodiments, the prebiotic mixture includes human milk oligosaccharides that include α1-2 linked fucose and human milk oligosaccharides that include α1-4 linked fucose.

In some embodiments, the prebiotic mixture is or includes at least 5% total HMO (w/w). In particular embodiments, the prebiotic mixture is or includes least 5%, 6%, 7%, 8%, 9%, 10%, 11%, 12%, 15%, 20%, 25%, or 50% total HMO (w/w). In certain embodiments, the prebiotic mixture is or includes between 5% and 15%, 7.5% and 12.5%, 8% and 12%, 8.5% and 11%, or 8.4% and 10.6% total HMO (w/w). In certain embodiments, the prebiotic mixture is or includes between 8.5% and 11% total HMO (w/w). In some embodiments, the prebiotic mixture is or includes between 8.4% and 10.6% total HMO (w/w).

In some embodiments, the prebiotic mixture has a pH of between 4.0 and 5.5. In certain embodiments, the prebiotic mixture has less than 10%, 5%, 1%, or 0.1% lactose (w/w). In some embodiments, the prebiotic mixture has less than 10%, 5%, 1%, or 0.1% glucose (w/w). In particular embodiments, the prebiotic mixture has less than 10%, 5%, 1%, or 0.1% galactose (w/w). In certain embodiments, the prebiotic mixture has less than 10% galactose, less than 10% glucose, and less than 0.1% lactose.

In some embodiments, the prebiotic mixture is a liquid formulation. In some embodiments, the prebiotic mixture is in powdered form, e.g., a lyophilized or spray dried composition.

i). Methods of Generating a Prebiotic Mixture

In some embodiments, the prebiotic mixture is or includes human milk oligosaccharides (HMOs) obtained or purified from ultra-filtered permeate from donated human milk. In some embodiments, the permeate is concentrated to increase the concentration of HMOs. In certain embodiments, the donated human milk is pooled to provide a pool of human milk. In some embodiments, a pool of human milk comprises milk from two or more (e.g., ten or more) donors. In certain embodiments, the pooled human milk contains milk from at least 50, 75, 100, 150, or 200 individual donors. In certain embodiments, the pooled human milk contains human milk from at least 100 individual donors or between 100 and 300 individual donors. In some embodiments, the pooled human milk contains milk from at least ten, at least twenty-five, at least fifty, at least seventy-five, at least one hundred, or at least one hundred fifty individual human milk donors.

In some embodiments, one or more of human milk oligosaccharides that are contained or included in the prebiotic mixture are synthetic human milk oligosaccharides, such as those derived from non-human milk sources, e.g., derived or obtained as oligosaccharides or precursors from transgenic microorganisms and/or are chemically synthesized. In some aspects, synthetic oligosaccharides and HMOs, as well as methods and techniques for synthesizing oligosaccharides and HMOs, are known, and include but are not limited to those described in PCT Publication Nos.: WO2017101958, WO2015197082, WO2015032413, WO2014167538, WO2014167537, WO2014135167, WO2013190531, WO2013190530, WO2013139344, WO2013182206, WO2013044928, WO2019043029, WO2019008133, WO2018077892, WO2017042382, WO2015150328, WO2015106943, WO2015049331, WO2015036138, and WO2012097950, each of which is incorporated by reference herein in its entirety.

In some embodiments, the prebiotic mixture is or includes permeate, e.g. a concentrated, ultra-filtered permeate from pooled human milk. In some embodiments, the permeate (e.g. concentrated, ultra-filtered permeate) contains at least 10, 25, 30, 50, 75, 100, 125, 150 different individual HMO species (e.g., HMOs with different individual chemical formulas or chemical structures). In particular embodiments, the prebiotic mixture is or includes a concentrated permeate that contains at least 25, 50, or 100 different HMOs. In particular embodiments, the permeate contains at least 50 HMOs which include all of 2'-fucosyl-lactose, 3'-fucosyl-lactose, 3'-sialyl-lactose, 6'-sialyl-lactose, Lacto-N-tetraose, Lacto-N-neo-tetraose, Lacto-N-fucopentaose I, Lacto-N-fucopentaose II, Lacto-N-fucopentaose III, Sialyl-lacto-N-tetraose b, Sialyl-lacto-N-tetraose c, Lacto-N-difuco-hexaose I, Lacto-N-difuco-hexaose II, Lacto-N-hexaose, para-Lacto-N-hexaose, Disialyllacto-N-tetraose, Fucosyl-Lacto-N-hexaose, Difucosyl-Lacto-N-hexaose a, and Difucosyl-Lacto-N-hexaose b.

In some aspects, the profile of HMOs contained by the permeate is substantially similar both structurally and functionally to the profile or array of HMOs observed across the population of whole human milk. In certain embodiments, since the permeate is derived from a pool of donors rather than an individual donor, the profile or array of HMOs will be more diverse than in any one typical individual. In particular embodiments, the permeate includes HMOs produced from secretor and non-secretor mothers. In some embodiments, the permeate contains or includes α1-2 linked HMOs and α1,-4 linked HMOs.

In certain embodiments, the permeate includes about or at least 0.1%, 0.5%, 1.0%, 1.5%, 2.0%, 2.5%, 3.0%, 4.0%, 5.0%, 7.5%, or 10% or more (w/w) of human milk oligosaccharides. In some embodiments, the permeate composition is lyophilized or freeze-dried or otherwise powdered. In some embodiments, the permeate composition is an aqueous mixture.

In certain embodiments, the prebiotic mixture is produced from human milk permeate, e.g., concentrated ultra-filtered permeate from pooled human milk. In some embodiments, the prebiotic mixture contains or is formulated with human milk permeate, e.g., concentrated ultra-filtered permeate from pooled human milk. In some embodiments, the concentrated ultra-filtered permeate may be made according to any suitable method or technique known in the art. In some aspects, suitable methods and techniques include those described in U.S. Pat. No. 8,927,027 and PCT Pub. No. WO2018053535, hereby incorporated by reference in their entirety. Exemplary methods and techniques for producing the human milk compositions are briefly summarized herein.

In certain embodiments, the prebiotic mixture is or includes human milk permeate, e.g., permeate obtained by ultra-filtering human skim milk. In particular embodiments, the permeate is a concentrated ultra-filtered human milk permeate, e.g., ultra-filtered and concentrated as described herein, e.g., in Section-I-A-(i)-(a). In certain embodiments, the prebiotic mixture is, includes, or is derived from a concentrated, ultra-filtered human milk permeate that is or includes between or between about 84 g/L to 106 g/L HMO (w/v), at least 10 HMO including all of 2'-fucosyl-lactose, 3'-fucosyl-lactose, 3'-sialyl-lactose, 6'-sialyl-lactose, Lacto-N-tetraose, lacto-N-difucohexaose I, lactodifucotetraose, Lacto-N-fucopentaose I, sialylacto-N-tetraose c, sialylacto-N-tetraose b, or disialyllacto-N-tetraose. In certain embodiments, the human milk permeate is or includes no more than 1% lactose (by weight/weight or w/w), no more than 15% glucose (w/w), no more than 15% galactose (w/w), no more than 250 mg per 100 g calcium, no more than 250 mg per 100 g potassium, no more than 100 mg per 100 g magnesium, no more than 100 mg per 100 g sodium, and/or no more than 250 mg per 100 mg of phosphorus.

a). Processing Ultra-Filtered Permeate from Human Milk

In some embodiments, the donor milk is received frozen, and when desired, is thawed and pooled. In some embodiments, donor milk is then screened, e.g., to identify contaminants, by one or more of the methods discussed herein.

In some embodiments, the pooled milk is filtered, e.g., through about a 200-micron filter. In some embodiments, the pooled milk is heated, e.g., at about 63° C. or greater for about 30 minutes or more. In some embodiments, the milk is transferred to a separator, e.g., a centrifuge, to separate the cream from the skim. In some embodiments, the cream may go separation once again to yield more skim. In some embodiments, a desired amount of cream is added to the skim prior to ultra-filtration. In certain embodiments, material that did not pass through the filter is collected as the retentate fraction, and material that passes through the filter is collected as the permeate fraction.

In some embodiments, the skim fraction undergoes ultrafiltration. In some embodiments, the ultrafiltration is performed with a filter between 1 kDa and 1000 kDa to obtain a protein rich retentate and the HMO-containing permeate. Details of this process can be found, for example, in U.S. Pat. Nos. 8,545,920; 7,914,822; 7,943,315; 8,278,046; 8,628,921; and 9,149,052, each of which is hereby incorporated by reference in its entirety. In some embodiments, the ultra-filtration is performed with a filter that is between 1 kDa and 100 kDa, 5 kDa and 50 kDa, or 10 kDa and 25 kDa. In certain embodiments, the filter is about or at least 5 kDa, 10 kDa, 20 kDa, 25 kDa, 50 kDa, or 100 kDa. In some embodiments, the skim fraction undergoes ultrafiltration with a filter that is about 10 kDa. In certain embodiments, the skim fraction undergoes ultrafiltration with a filter that is about 25 kDa. In particular embodiments, the skim fraction undergoes ultrafiltration with a filter that is about 50 kDa.

In some embodiments, the ultra-filtered permeate undergoes a process for reducing lactose. In certain embodiments, a process for producing a purified HMO composition with substantially reduced levels of lactose is provided. In certain embodiments, the substantial reduction includes or requires the biochemical and/or enzymatic removal of lactose from the lactose-rich human milk permeate fraction, without loss of yield or change in molecular profile of the HMO content of human milk permeate. And, in particular embodiments, without leaving residual inactivated foreign protein, if enzymatic digestion is used to reduce lactose. In certain embodiments, about or at least 50%, 60%, 70%, 80%, 90%, 95%, 99%, 99.9%, or 99.99% of the lactose present in the permeate after ultrafiltration is removed, e.g., enzymatically digested. In certain embodiments, the permeate is free or essentially free of lactose following the enzymatic digestion.

In certain embodiments, the process for reducing lactose from human milk permeate includes one or more of the steps of a) adjusting the pH of the permeate mixture; b) heating the pH adjusted mixture; c) adding lactase enzyme to the heated permeate mixture to create a permeate/lactase mixture and incubating for a period of time; d) removing the lactase from the mixture and filtering the mixture to remove lactase; and e) concentrating human milk oligosaccharides. In some embodiments, the order of when steps (a)-(c) are performed may be varied. Thus, in some aspects, the steps may be performed in the order of (a)-(b)-(c); (a)-(c)-(b); (c)-(b)-(a); (c)-(a)-(b); (b)-(a)-(c); or (b)-(c)-(a), such that, for example, the lactase enzyme may be added prior to heating the mixture, or, alternatively at any point during the heating process. Similarly, and also by way of example only, the mixture may be heated prior to adjustment of the pH. Furthermore, several steps may be grouped into a single step, for example "enzymatically digesting lactose" or "lactases digestion of lactose" involves steps (a)-(c) as described. These steps may be performed concurrently or consecutive in any order. Therefore, as used herein "lactose digestion" refers to the performance of at least these three steps, in any order, consecutively or concurrently.

In certain embodiments, the pH of the permeate is adjusted to a pH of about 3 to about 7.5. In some embodiments, the pH is adjusted to a pH of about 3.5 to about 7.0. In particular embodiments, the pH is adjusted to a pH of about 3.0 to about 6.0. In certain embodiments, the pH is adjusted to a pH of about 4 to about 6.5. In some embodiments, pH is adjusted to a pH of about 4.5 to about 6.0. In particular embodiments, the pH is adjusted to a pH of about 5.0 to about 5.5. In certain embodiments, the pH is adjusted to a pH of about 4.3 to about 4.7, preferably 4.5. The pH may be adjusted by adding acid or base. In some embodiments, pH is adjusted by adding acid, for example HC1. In particular embodiments, pH is adjusted by adding 1N HC1 and mixing for a period of time e.g. about 15 minutes.

In some embodiments, the pH-adjusted permeate is heated to a temperature of about of about 25° C. to about 60° C. In certain embodiments, the permeate is heated to a temperature of about 30° C. to about 55° C. In some embodiments, the permeate is heated to a temperature of about 40° C. to about 50° C. In some embodiments, the permeate is heated to a temperature of about 40° C. to about 60° C., 45° C. to about 55° C., 47° C. to about 53° C., or 49° C. to about 51° C. In certain embodiments, the permeate is heated to a temperature of about 48° C. to about 50° C. In some embodiments, the permeate is heated to a temperature about 50° C. In some embodiments, the permeate is heated to a temperature less than or equal to about 40° C.

In particular embodiments, lactase enzyme is added to the pH-adjusted, heated permeate to create a permeate/lactase mixture. In certain embodiments, lactose within the permeate/lactase mixture is broken down into monosaccharides. In certain embodiments, lactase enzyme is added at about 0.1% w/w to about 0.5% w/w concentration. In certain embodiments, lactase enzyme is added at about 0.1% w/w, or 0.2% or 0.3% or 0.4% or 0.5% w/w. There are many commercially available lactase enzymes that may be used. As such, the lactase enzyme may be derived from any origin (e.g. fungal or bacterial in origin).

In some embodiments, the pH-adjusted, heated permeate is incubated with the lactase enzyme for about 5 to about 225 minutes. In certain embodiments, the incubation time is about 15 min to about 90 min. In some embodiments, the incubation time is about 30 minutes to about 90 minutes. In particular embodiments, the incubation time is about 60 minutes. Some aspects contemplate that incubation time is dependent upon myriad of factors including, but not limited to, the source of the enzyme used, the temperature and pH of the mixture and the concentration of enzyme used. Thus, in some embodiments, incubation time with the lactase enzyme may be adjusted to factor in such variables as a matter of routine. While the pH, temperature, and enzyme incubation conditions provided here are what work optimally for the process described herein, one of skill in the art would understand that modifications may be made to one or more of these variables to achieve similar results. For example, if less enzyme is used than the about 0.1% w/w to about 0.5% w/w described herein, the incubation time may need to be extended to achieve the same level of lactose digestion. Similar adjustments may be made to both the temperature and pH variables as well.

In certain embodiments, after incubation the permeate/lactase mixture is cooled to a temperature of about 20° C. to about 30° C. In a particular embodiment, the permeate/lactase mixture is cooled to a temperature of about 25° C.

In some embodiments, the permeate/lactase mixture is clarified to remove insoluble constituents. In certain embodiments, insoluble material may form throughout the change in pH and temperature. Thus, in some embodiments, it may be necessary or beneficial to clarify the mixture to remove these insoluble constituents, for example, through a depth filter. The filters may be 0.1 to 10 micron filters. In some embodiments, the filters are about 1 to about 5 micron filters. Alternatively, removal of insoluble constituents can be achieved through a centrifugation process or a combination of centrifugation and membrane filtration. The clarification step is not essential for the preparation of a diverse HMO composition, as described herein, rather, this optional step aids in obtaining a more purified permeate composition. Furthermore, the clarification step is important in the reusability of the filtration membranes and thus to the scalability of the process. Some aspects contemplate that, without adequate clarification, substantially more filter material is required, increasing the difficulty and expense to produce permeate compositions at clinical scale. However, one will understand that more or less stringent clarification may be formed at this stage in order to produce more or less purified permeate compositions, depending on formulation and application. For example, precipitated minerals may be less of a problem for a formulation destined for lyophilization.

In certain embodiments, to remove the spent and excess lactase enzyme from the clarified permeate/lactase mixture. There may, however, be some instances where the inactivated foreign protein will carry no biological risk and therefore the added steps of lactase removal or even inactivation may not be necessary. In some embodiments, the spent and excess lactase is inactivated, for example by high temperature, pressure, or both. In some embodiments, the inactivated lactase is not removed from the composition.

In other embodiments, however, a further purification to remove foreign proteins will be called for. In such embodiments lactase enzyme removal may be accomplished by ultrafiltration. In some embodiments, ultrafiltration is accomplished using an ultrafiltration membrane, for example using a membrane with molecular weight cut-off of ≤50,000 Dalton, e.g. a BIOMAX-50K, ≤25,000 Dalton, e.g. a BIOMAX-25K, or ≤10,000 Dalton e.g. a BIOMAX-10K. In some embodiments, the molecular weight cut-off less than or equal to about 10 kDa. In certain embodiments, the molecular weight cut-off less than or equal to about 25 kDa. In particular embodiments, the molecular weight cut-off less than or equal to about 50 kDa.

In certain embodiments, an additional ultrafiltration is performed through a smaller membrane than the initial a membrane) e.g., with molecular weight cut-off of ≤50,000, ≤25,000, or ≤10,000, Dalton. In some embodiments, the additional ultrafiltration is performed with a membrane with a molecular weight cut off of between 10 kDa and 50 kDa, 1 kDa and 10 kDa, 1 kDa and 5 kDa, or 2 kDa and 3 kDa. In certain embodiments, the additional ultrafiltration is performed with a membrane with a molecular weight cut off of between 2 kDa and 3 kDa. In certain embodiments, an additional ultrafiltration is not performed. In some embodiments, the additional filtration step is performed, such as to aid in the overall purity of the permeate product, such as by assisting in the removal of smaller potentially bioactive and/or immunogenic factors.

In some embodiments, the clarified mixture that has undergone at least one, and in some cases two or more rounds of ultrafiltration (or alternative lactase removal means) is further filtered to purify and concentrate human milk oligosaccharides and to reduce the mineral and monosaccharides content.

In some embodiments, filtration can be accomplished using a nanofiltration membrane. In some embodiments, the membrane has a molecular weight cut-off of ≤1,000 Dalton. In certain embodiments, the membrane has a molecular weight cut-off of between 1 kDa and 1,000 kDa. In certain embodiments, the membrane has a molecular weight cut-off of less than 600 Da. In certain embodiments, the membrane has a molecular weight cut-off between 400 Da and 500 Da. In some aspects, the additional nanofiltration removes monosaccharides, minerals, particularly calcium, and smaller molecules to produce the final purified HMO composition, e.g., the concentrated ultra-filtered human milk permeate.

In some embodiments, additional or alternative steps may be taken for the removal of minerals. Such an additional step may include, for example, centrifugation, membrane clarification (≤0.6 micron), or combination of centrifugation and membrane filtration of heated (≥40° C.) or refrigerated/frozen and thawing of concentrated ultra-filtered permeate, e.g., HMO concentrate. The collected supernatant or filtrate of these additional or alternative steps, in some embodiments, is concentrated further using a nanofiltration membrane. In some embodiments, the nanofiltration comprises filtration through a membrane with a molecular cut off of ≤600 Dalton. In some embodiments, these additional steps may be performed at any stage of the process, including but not limited to prior to or after pasteurization.

In some embodiments, the physical property of nanofiltration membranes can be modified, such as chemical modification, to selectively concentrate sialylated HMOs, for example, allowing greater efficiency of neutral HMOs removal from HMO concentrate, in instances where concentrated sialylated HMOs are preferred.

In certain embodiments, the permeate may be further processed, e.g., concentrated or diluted. In some embodiments, the permeate may be concentrated by a suitable process such as nanofiltration, reverse osmosis, or dried, e.g., lyophilized. In some embodiments, the purified HMO compositions made by the methods herein may be lyophilized or freeze-dried or otherwise powdered.

In some embodiments, the permeate is treated to reduce bioburden, such as by any means known in the art. In some embodiments, the purified HMO composition is pasteurized. In some aspects, pasteurization is accomplished at ≥63° C. for a minimum of 30 minutes. Following pasteurization, the composition is cooled to about 25° C. to about 30° C. and clarified through a 0.2 micron filter to remove any residual precipitated material.

In certain embodiments, the prebiotic mixture is or is formulated with a concentrated ultra-filtered permeate obtained from human milk. In particular embodiments, the prebiotic mixture is or is formulated with a concentrated, ultra-filtered permeate obtained from pooled human milk, e.g., milk pooled from at least 50, 100, or 150 donors. In some embodiments, the prebiotic mixture is formulated with permeate that has been ultra-filtered from the skim of pooled human milk. In certain embodiments, lactose is removed, e.g., enzymatically degraded, prior to formulation into the prebiotic mixture.

b.) Obtaining Pooled Human Milk

In some embodiments, permeate is obtained from human milk pooled from multiple qualified human milk donors. The process for obtaining, testing, and qualifying the pooled human milk is described briefly herein.

In some embodiments, the human milk is provided by donors, and the donors are pre-screened and approved before any milk is processed. In some aspects, various techniques are used to identify and qualify suitable donors. In some embodiments, a potential donor must obtain a release from her physician and her child's pediatrician as part of the approval process. This helps to insure, inter alia, that the donor is not chronically ill and that her child will not suffer as a result of the donation(s). Methods and systems for qualifying and monitoring milk collection and distribution are described, e.g., in U.S. Pat. Nos. 8,545,920; 7,943,315; 9,149,052; 7,914,822 and 8,278,046, which are incorporated herein by reference in its entirety. Donors may or may not be compensated for their donation.

In certain embodiments, the donor screening includes a comprehensive lifestyle and medical history questionnaire that includes an evaluation of prescription and non-prescription medications, testing for drugs of abuse, and testing for certain pathogens. In some embodiments, a biological sample, e.g., a blood sample and/or a milk sample, may be screened for the presence of an infectious agent such as a bacteria or virus by any suitable routine technique, e.g., qPCR or ELISA. Such infections agents may include, but are not limited to, human immunodeficiency virus Type 1 (HIV-1), HIV-2, human T-lymphotropic virus Type 1 (HTLV-I), HTLV-II, hepatitis B virus (HBV), hepatitis C virus (HCV), and syphilis.

In some embodiments, donors may continuously provide samples over a period of time, e.g., about or at least one month, three months, six months, a year, or over a year. In some embodiments, during the period of time, the donor may be requalified. In some aspects, a donor who does not requalify or fails qualification is deferred until such time as they do, or permanently deferred if warranted by the results of requalification screening. In the event of the latter situation, all remaining milk provided by that donor is removed from inventory and destroyed or used for research purposes only.

In some embodiments, once the donor has been approved, donor identity matching may be performed on donated human milk such as to ensure that the donated milk was expressed from the qualified donor and not another, e.g., when the milk was expressed by a donor away from the milk banking facility. In particular embodiments, the donor's milk may be sampled for genetic markers, e.g., DNA markers, to guarantee that the milk is truly from the approved donor. Such subject identification techniques are known in the art (see, e.g., U.S. Pat. No. 7,943,315, which is incorporated herein by reference in its entirety). In some embodiments, milk may be stored (e.g., at −20° C. or colder) and quarantined until the test results are received.

The milk is also tested for pathogens. In some embodiments, the milk is genetically screened, e.g., by polymerase chain reaction (PCR), to identify, e.g., viruses, such as HIV-1, HBV and HCV. In some embodiments, a microorganism panel that screens for various bacterial species, fungus and mold via culture may also be used to detect contaminants. In some embodiments, a microorganism panel may test for aerobic count, *Bacillus cereus, Escherichia coli, Salmonella, Pseudomonas, coliforms, Staphylococcus aureus*, yeast, and mold. In some embodiments, pathogen screening may be performed both before and after pasteurization.

In addition to screening for pathogens, the donor milk may also be tested for drugs of abuse (e.g., including but not limited to cocaine, opiates, synthetic opioids (e.g. oxycodone/oxymorphone) methamphetamines, benzodiazepine, amphetamines, and THC) and/or adulterants such as non-human proteins. In certain embodiments, an ELISA may be used to test the milk for a non-human protein, such as bovine proteins, to ensure, e.g., that cow milk or cow milk infant formula has not been added to the human milk, for example to increase donation volume when donors are compensated for donations.

In certain embodiments, adulterants may include any non-human milk fluid or filler that is added to a human milk donation, thereby causing the donation to no longer be unadulterated, pure human milk. Particular adulterants to be screened for include non-human milk and infant formula. In particular embodiments, the adulterants that are screened for include cow milk, cow milk formula, goat milk, soy milk, and soy formula. In some embodiments, methods that are known and routine by those of skill in the art may be adapted to detect non-human milk proteins, e.g., cow milk and soy proteins, in a human milk sample. In particular, immunoassays that utilize antibodies specific for a protein found in an adulterant that is not found in human milk can be used to detect the presence of the protein in a human milk sample, e.g., an enzyme-linked immunosorbent assay (ELISA), a western blot, or immunoblot.

B.) Probiotics

In particular embodiments, provided herein are compositions that are or include at least one probiotic strain of bacteria, e.g., a strain of Bifidobacteria such as *B. longum* subsp. *infantis*. In some embodiments, the at least one probiotic strain, e.g., *B. longum* subsp. *infantis*, is contained or included in the same composition as the mixture of oligosaccharides, e.g., the mixture described herein such as in Section I-A. In certain embodiments, the at least one probiotic strain, e.g., the at least one probiotic strain, e.g., *B. longum* subsp. *infantis*, is contained or included in a separate composition from the mixture.

In particular embodiments, the at least one probiotic strain is capable of consuming or metabolizing non-digestible carbohydrates, e.g., oligosaccharides such as HMOs. In particular embodiments, the at least one probiotic strain is capable of consuming or metabolizing oligosaccharides such as HMOs. In some embodiments, the at least one probiotic strain is capable of utilizing the prebiotics of the prebiotic mixture, e.g., HMOs, as a carbon source. In particular embodiments, HMOs, are preferentially consumed or metabolized by the at least one probiotic strain, e.g., as compared to other microbes or bacteria present in the gut or microbiome. In certain embodiments, the at least one probiotic strain is capable of consuming or metabolizing one or more prebiotics of the mixture, including those of any of the mixtures described herein, e.g., in Section I-A. In certain embodiments, the at least one probiotic strain is capable of consuming or metabolizing all or essentially all of the oligosaccharides of the mixture. In certain embodiments, the at least one probiotic strain is capable of consuming or metabolizing HMOs. In some embodiments, the at least one probiotic strain is capable of internalizing HMOs prior to consuming or metabolizing the HMOs. Particular embodiments contemplate that probiotic strains that consume or metabolize HMOs are known, and may be identified by routine techniques such as those described in Gotoh et al. Sci Rep. 2018 Sep. 18; 8(1):13958, incorporated by reference herein in its entirety.

In some embodiments, the at least one probiotic strain contains one or more enzymes capable of hydrolyzing the prebiotics of the mixture. In certain embodiments, the at least one probiotic strain contains one or more enzymes capable of hydrolyzing the human milk oligosaccharides. In particular embodiments, the one or more enzymes hydrolyze external oligosaccharides, e.g., oligosaccharides such as HMOs that are outside of the probiotic cell. In some embodiments, the one or more enzymes hydrolyze oligosaccharides such as human milk oligosaccharides internally or within the probiotic cell. In certain embodiments, the one or more enzymes hydrolyze internalized human milk oligosaccharides.

In particular embodiments, the at least one probiotic strain contains one or more enzymes capable of hydrolyzing one or more HMOs. In particular embodiments, the one or more enzymes hydrolyze external HMOs. In some embodiments, the one or more enzymes hydrolyze HMOs that are outside of the probiotic cell. In some embodiments, the one or more enzymes hydrolyze HMOs internally. In particular embodiments, the one or more enzymes hydrolyze HMOs within the probiotic cell. In certain embodiments, the one or more enzymes hydrolyze internalized HMOs.

In some embodiments, the at least one probiotic strain is capable of internalizing human milk oligosaccharides. In certain embodiments, the at least one probiotic strain internalizes human milk oligosaccharides prior to hydrolyzing the human milk oligosaccharides. In various embodiments, the at least one probiotic selectively or exclusively utilizes human milk oligosaccharides as a carbon source. Thus, in certain embodiments, if the at least one probiotic is administered to the subject and/or has engrafted, e.g., within the subject's microbiome (such as the intestinal microbiome), the at least one probiotic is present, expands, or increases in amount within the subject's microbiome when human milk oligosaccharides are administered to and/or ingested by the subject, and, in certain embodiments, the at least one probiotic is no longer present and/or decreases in amount within the subject's microbiome when the human milk oligosaccharides are no longer ingested or administered.

In some embodiments, the at least one probiotic strain is capable of internalizing oligosaccharides, such as to consume or metabolize the oligosaccharides. In certain embodiments, the at least one probiotic strain is capable of internalizing one or more oligosaccharides of the mixture, including those of any of the oligosaccharides or mixtures described herein, e.g., in Section I-A. In certain embodiments, the at least one probiotic strain is capable of internalizing HMOs.

In certain embodiments, the at least one probiotic strain is one or more of a *Bifidobacterium, Lactobacillis, Clostridium, Eubacterium*, or *Streptococcus* strain, e.g., capable of consuming or metabolizing HMOs. In certain embodiments, the at least one probiotic strain is or includes at least one strain of *Bifidobacterium* such as, but not limited to, *B. adolescentis, B. animalis* (e.g., *B. animalis* subsp. *animalis* or *B. animalis* subsp. *lactis*), *B. bifidum, B. breve, B. catenulatum, B. longum* (e.g., *B. longum* subsp. *infantis* or *B. longum* subsp. *longum*), *B. pseudocatanulatum, B. pseudolongum*; and/or at least one strain of *Lactobacillus*, such as *L. acidophilus, L. antri, L. brevis, L. casei, L. coleohominis, L. crispatus, L. curvatus, L. delbrueckii, L. fermentum, L. gasseri, L. johnsonii, L. mucosae, L. pentosus, L. plantarum, L. reuteri, L rhamnosus, L. sakei, L. salivarius, L. paracasei, L. kisonensis., L. paralimentarius, L. perolens, L. apis, L. ghanensis, L. dextrinicus, L. harbinensis*; and/or at least one strain of *Bacteroides* such as *Bacteroides vulgatus* or non-toxigenic *Bacteroides fragilis*; and/or at least one strain of *Clostridium* such as *C. difficile* or *C. perfringens*; and/or at least one strain of *Eubacterium* such as *E. rectale*; and/or at least one species of *Streptococcus* such as *S. thermophilus*; and/or at least one strain of *Faecalibacterium* such as *Faecalibacterium prausnitzii*, and/or at least one strain of *Pediococcus*, such as *P. parvulus, P. lolii, P. acidilactici, P. argentinicus, P. claussenii, P. pentosaceus*, or *P. stilesii*; and/or at least one strain of *Lactococcus lactis*. In some embodiments, the one or more probiotic may contain more than one strain, such as two or more of any of the species listed herein. As used herein, the terms "*B. longum* subsp. *infantis*" and "*B. infantis*" are be used interchangeably unless otherwise indicated. The terms "*B. longum* subsp. *longum*" and "*B. longum*" are also used interchangeably herein, unless indicated otherwise.

In particular embodiments, the at least one probiotic strain is one or more of a strain of *B. longum* subsp. *infantis, B. bifidum, Bacteroides fragilis, Bacteroides vulgatus, Faecalibacterium prausnitzii, Eubacterium rectale, Lactobacillus acidophilus, Lactobacillus delbrueckii, Lactococcus lactis*, or *Streptococcus thermophilus*, e.g., that is capable of consuming or metabolizing HMOs. In some embodiments, the at least one probiotic strain is one or more strains of *B. longum* subsp. *infantis, B. bifidum, Bacteroides fragilis*, or *Bacteroides vulgatus*, e.g., that is capable of consuming or metabolizing HMOs.

In particular embodiments, the species or subspecies of a given probiotic strain may be identified by routine techniques. For example, in some embodiments, the species or subspecies is identified by assessing the sequence similarity of one or more genes to corresponding sequences of known members of bacterial species or subspecies. In certain embodiments, a probiotic strain falls within a species or subspecies if all or a portion of its 16S gene has at least 97% sequence identity to all or a portion of a known 16S sequence of a known strain falling within the species. In particular embodiments, a probiotic strain falls within a species or subspecies if all or a portion of its 16S gene has at least 97% sequence identity to all or a portion of a known 16S sequence of a known strain falling within the species. Exemplary full or partial 16S sequences are summarized in Table 1.

TABLE 1

Exemplary 16S sequences

| Bacterial species or subspecies | Exemplary 16S Sequence |
|---|---|
| *B. longum* subsp. *infantis* | SEQ ID NOS: 1-7 |
| *B. adolescentis* | SEQ ID NO: 8 |
| *B. animalis* subsp. *animalis* | SEQ ID NO: 9 |
| *B. animalis* subsp. *lactis* | SEQ ID NO: 10 |
| *B. bifidum* | SEQ ID NO: 11 |
| *B. breve* | SEQ ID NO: 12 |
| *B. catenulatum* | SEQ ID NO: 13 |
| *B. longum* subsp. *longum* | SEQ ID NO: 14 |
| *B. pseudocatanulatum* | SEQ ID NO: 15 |
| *B. pseudolongum* | SEQ ID NO: 16 |
| *L. acidophilus* | SEQ ID NO: 17 |
| *L. antri* | SEQ ID NO: 18 |
| *L. brevis* | SEQ ID NO: 19 |
| *L. casei* | SEQ ID NO: 20 |
| *L. coleohominis* | SEQ ID NO: 21 |
| *L. crispatus* | SEQ ID NO: 22 |
| *L. curvatus* | SEQ ID NO: 23 |
| *L. delbrueckii* | SEQ ID NO: 24 |
| *L. fermentum* | SEQ ID NO: 25 |
| *L. gasseri* | SEQ ID NO: 26 |
| *L. johnsonii* | SEQ ID NO: 27 |
| *L. harbinensis* | SEQ ID NO: 28 |
| *L. mucosae* | SEQ ID NO: 29 |
| *L. pentosus* | SEQ ID NO: 30 |
| *L. plantarum* | SEQ ID NO: 31 |
| *L. reuteri* | SEQ ID NO: 32 |
| *L rhamnosus* | SEQ ID NO: 33 |
| *L. sakei* | SEQ ID NO: 34 |
| *L. salivarius* | SEQ ID NO: 35 |
| *L. paracasei* | SEQ ID NO: 36 |
| *L. kisonensis* | SEQ ID NO: 37 |
| *L. paralimentarius* | SEQ ID NO: 38 |
| *L. perolens* | SEQ ID NO: 39 |
| *L. apis* | SEQ ID NO: 40 |
| *L. ghanensis* | SEQ ID NO: 41 |
| *L. dextrinicus* | SEQ ID NO: 42 |
| *Lactococcus lactis* | SEQ ID NO: 43 |
| *Bacteroides vulgatus* | SEQ ID NO: 44 |
| *Bacteroides fragilis* | SEQ ID NO: 45 |
| *Faecalibacterium prausnitzii* | SEQ ID NO: 46 |
| *E. rectale* | SEQ ID NO: 47 |
| *S. thermophilus* | SEQ ID NO: 48 |
| *P. parvulus* | SEQ ID NO: 49 |
| *P. lolii* or *P. acidilactci* | SEQ ID NO: 50 or 51 |
| *P. argentinicus* | SEQ ID NO: 52 |
| *P. claussenii* | SEQ ID NO: 53 |
| *P. pentosaceus* | SEQ ID NO: 54 |
| *P. stilesii* | SEQ ID NO: 55 |

In certain embodiments, the at least one probiotic strain has or includes a nucleic acid sequence with at least 97%, at least 98%, at least 99%, or at least 99.5% identity to a nucleic acid sequence set forth in any of SEQ ID NOS: 1-55. In particular embodiments, the at least one probiotic strain has or includes a nucleic acid sequence with at least 97%, at least 98%, at least 99%, or at least 99.5% identity to a nucleic acid sequence set forth in any of SEQ ID NOS: 1-16 or 43-46. In certain embodiments, the at least one probiotic strain has or includes a nucleic acid sequence with at least 97%, at least 98%, at least 99%, or at least 99.5% identity to a nucleic acid sequence set forth in any of SEQ ID NOS: 1-7, 11, 12, 17, 24, or 43-47. In some embodiments, the at least one probiotic strain has or includes a nucleic acid sequence with at least 97%, at least 98%, at least 99%, or at least 99.5% identity to a nucleic acid sequence set forth in any of SEQ ID NOS: 1-7, 11, 44, or 45. In certain embodiments, the at least one probiotic strain has or includes a nucleic acid sequence with at least 97%, at least 98%, at least 99%, or at least 99.5% identity to a nucleic acid sequence set forth in any of SEQ ID NOS: 1-16. In particular embodiments, the at least one probiotic strain has or includes a nucleic acid sequence with at least 97%, at least 98%, at least 99%, or at least 99.5% identity to a nucleic acid sequence set forth in any of SEQ ID NOS: 1-7.

In particular embodiments, the at least one probiotic strain is or includes a strain of *B. longum* subsp. *infantis*. In particular embodiments, the strain of *B. longum* subsp. *infantis* has or includes a nucleic acid sequence with at least 97%, at least 98%, at least 99%, or at least 99.5% identity to a nucleic acid sequence set forth in any of SEQ ID NOS: 1-7. In particular embodiments, the strain of *B. longum* subsp. *infantis* has or includes a nucleic acid sequence of at least 200, 300, 400, 500, 600, 700, 800, 900, 1,000, 1,200, or 1,500 nucleotides in length with at least 60%, 70%, 80%, 90%, 95%, 99%, or 99.9% sequence identity to a nucleic acid sequence set forth in SEQ ID NOS: 59-78. In some embodiments, the strain of *B. longum* subsp. *infantis* has or includes a nucleic acid sequence having at least 60%, 70%, 80%, 90%, 95%, 99%, or 99.9% sequence identity to a nucleic acid sequence set forth in SEQ ID NOS: 59-78. In certain embodiments, the strain of *B. longum* subsp. *infantis* has or includes a nucleic acid sequence having at least 70%, 80%, or 90%, sequence identity to a nucleic acid sequence set forth in SEQ ID NOS: 59-69. In some embodiments, the strain of *B. longum* subsp. *infantis* has or includes a nucleic acid sequence having at least 80%, 85%, or 90% sequence identity to a nucleic acid sequence set forth in SEQ ID NOS: 70-74. In particular embodiments, the strain of *B. longum* subsp. *infantis* has or includes a nucleic acid sequence having at least 90%, 95%, or 99% sequence identity to a nucleic acid sequence set forth in SEQ ID NOS: 75-78. In some embodiments, the strain of *B. longum* subsp. *infantis* has or includes nucleic acid sequences having at least 90%, 95%, or 99% sequence identity to one or more of the nucleic acid sequences set forth in SEQ ID NOS: 59-78. In some embodiments, the strain of *B. longum* subsp. *infantis* has or includes the nucleic acid sequences set forth in one or more of SEQ ID NOS: 59-78. In particular embodiments, the strain of *B. longum* subsp. *infantis* has or includes nucleic acid sequences having at least 90%, 95%, or 99% sequence identity to all of the nucleic acid sequences set forth in SEQ ID NOS: 59-78. In various embodiments, the strain of *B. longum* subsp. *infantis* has or includes the nucleic acid sequences set forth in SEQ ID NOS: 59-78.

In some embodiments, the at least one probiotic strain is or includes a strain of *Bifidobacterium* or a *Bacteroides* capable of consuming, metabolizing, and/or internalizing HMOs. In some aspects, HMO cannot be metabolized by the host, e.g., mammals such as humans, or most bacteria, including many species of pathogenic bacteria and most bacteria commonly found in the microbiome of adult humans. In particular aspects, some strains, species, or subspecies of *Bifidobacterium*, such as *B. longum* subsp. *infantis*, or *Bacteroides* have enzymatic activity able to degrade specific alpha and beta bonds of HMOs. Five monosaccharides can be found in different HMO structures, glucose, galactose, N-acetyl glucosamine, fucose, and sialic acid (also referred to herein as N-acetyl neuraminic acid). Some strains, species, or subspecies of *Bifidobacterium* are able to fully degrade HMO intracellularly. Such *Bifidobacterium* possess genes encoding specific transporters (e.g., ABC transporters such as those described in Sela et al. PNAS (2008) 105 (48) 18964-18969; Schell, et al. PNAS. (2002) 99(22):14422-14427 and LoCascio et al. Appl Environ Microbiol. (2010) 76(22):7373-81), incorporated by reference herein, that selectively transport or import HMO and enzymes necessary for HMO degradation (alpha-fucosidase, alpha-sialidase, beta-galactosidase, and beta-N-hexosaminidase). Other *Bifidobacterium* strains, such as for example *B. bifidum* degrades HMO externally or extracellularly, such as for example by lacto-N-biosidase, which cleaves lacto-N-biose I (LNB) from HMO. The LNB is then internalized by a transporter and degraded by LNB-phosphorylase. In some embodiments, the at least one probiotic strain is a at least one strain of bacterium having one or more genes encoding all or a portion of a transporter, e.g., an ABC transporter, capable of internalizing an oligosaccharide such as an HMO. In particular embodiments, the at least one probiotic strain is a bacterium having one or more genes encoding one or more enzymes, e.g., alpha-fucosidase, alpha-sialidase, beta-galactosidase, and beta-N-hexosaminidase, capable degrading an oligosaccharide such as an HMO. In certain embodiments, the at least one probiotic strain is at least one strain of *Bifidobacterium* or *Bacteroides* having one or more genes encoding all or a portion of a transporter, e.g., an ABC transporter, capable of internalizing an oligosaccharide, e.g., an HMO.

In some embodiments, the at least one probiotic strain is *B. longum* subsp. *infantis*. Particular embodiments contemplate that *B. longum* subsp. *infantis* is known and readily identifiable by those of skill in the art using routine techniques. In some embodiments, *B. longum* subsp. *infantis*, including its genome and biology, are known and for example have been described, including in Sela et al. PNAS (2008) 105 (48) 18964-18969; Underwood et al., Pediatr Res. (2015) 77(0): 229-235, incorporated by reference herein. In certain embodiments, *Bifidobacterium*, e.g., *B. longum* subsp. *infantis*, may be isolated using known selective microbiological media, e.g., De Man, Rogosa and Sharpe agar (MRS), optionally in combination with mupirocin, or those described in O'Sullivan et al., J Appl Microbiol. 2011 August; 111(2):467-73, incorporated by reference herein. In some embodiments, suitable sources for isolating *Bifidobacterium*, e.g., *B. infantis*, are known, and include stool samples obtained from breast fed infants. In certain embodiments, bacterial colonies may be identified or characterized by routine biochemical techniques, such as PCR. In some embodiments, *B. longum* subsp. *infantis* is identified by taqman qPCR, such as described in Lawley et al., PeerJ. 2017 May 25; 5: e3375. e.g., as performed with forward primer sequence ATACAGCAGAACCTTGGCCT (SEQ ID NO: 56), reverse primer sequence GCGATCACATGGACGAGAAC (SEQ ID NO: 57) and probe sequence [FAM dye]-TTTCACGGA-[ZEN quencher]-TCACCGGACCATACG-[3IABkFQ quencher] (SEQ ID NO: 58). In some aspects, a strain may be confirmed as *B. longum* subsp. *infantis* by observing growth when HMOs are provided as the sole carbon source, such as with an assay described in Gotoh et al. Sci Rep. 2018 Sep. 18; 8(1):13958, incorporated by reference herein.

C.) Proton Pump Inhibitors

In particular embodiments, the provided compositions, kits, or articles of manufacture contain a probiotic strain and a prebiotic mixture that are administered to a subject in need thereof. In some such embodiments, the subject in need thereof has a condition, disease, or disorder, e.g., graft versus host disease, with symptoms that may include, relate to, or resemble stomach discomfort, heartburn, or gastroesophageal reflux disease. In particular embodiments, the subject may take one or more agents that reduces or prevents stomach acid production.

In some embodiments, compositions, kits, or articles of manufacture that contain the at least one probiotic strain also includes an agent that reduces or prevents stomach acid production and/or increases or neutralized gastric pH. In certain embodiments, the agent improves, increases, or enhances the probably that the at least one probiotic strain will successfully engraft or colonize in a subject's gut or within the subject's intestinal microbiome, e.g., as compared to administration of the probiotic strain in the absence of the agent. In particular embodiments, the agent is not omeprazole or a derivative thereof.

In certain embodiments, the agent is administered in an amount sufficient to reduce or prevent $H^+$—$K^+$ ATPase activity of gastric parietal cells. In certain embodiments, the agent is administered in an amount sufficient to reduce acidity of gastric fluid and/or raise or neutralize gastric pH.

Particular embodiments contemplate that administration of an agent that raises or neutralizes gastric pH prevents or reduces death, inactivation, or degradation of an orally administered probiotic strain. In certain embodiments, the agent may be a proton pump inhibitor (PPI). Exemplary PPI compounds and methods for their synthesis include those described in U.S. Pat. Nos. 4,544,750; 4,758,579; 5,045,552; 5,374,730 and 5,386,032, incorporated by reference herein.

In particular embodiments, the agent is not a proton pump inhibitor (PPI), e.g., omeprazole or derivative a thereof.

In certain embodiments, the agent is or includes one or more a $H_2$ histamine receptor antagonist (also referred to herein as an $H_2$-receptor antagonist or "H2 antagonist"). In some embodiments, the $H_2$-receptor antagonist is or includes a compound capable of blocking the action of histamine on parietal cells in the stomach and thereby decrease acid production by these cells. $H_2$-receptor antagonists include, but are not limited to, cimetidine (TAGAMET®), famotidine (PEPCID®), nizatidine (ACCID®) and ranitidine (ZANTAC®), as well as their pharmaceutically acceptable salts, various crystal forms, and prodrug forms. In certain embodiments, the agent is or includes ranitidine, cimetidine, nizatidine, famotidine, pharmaceutically acceptable salts, isomers, and derivatives thereof, single enantiomers thereof and combinations thereof. In certain preferred embodiments of the invention, the H2-receptor antagonist is famotidine, or a pharmaceutically acceptable salt thereof. In particular embodiments, the agent is or includes famotidine.

In particular embodiments, the agent is not a benzimidazole derivative. Benzimidazole derivatives (also referred to herein as benzimidazoles or substituted benzimidazoles) include, but are not limited to, omeprazole, lansoprazole, dexlansoprazole, esomeprazole, timoprazole, picoprazole, pantoprazole, rabeprazole, thiadiazole and thiazole and imidazopyridine derivatives. In some embodiments, the agent is not dontoprazole, esomeprazole, habeprazole, hydroxyomeprazole, omeprazole, lansoprazole, leminoprazole, pantoprazole, pariprazole, periprazole, ransoprazole, rabeprazole, tenatoprazole, or tenatoprazole; or a free base, free acid, salt, hydrate, ester, amide, enantiomer, isomer, tautomer, polymorph, prodrug, or active metabolite of any or all of the foregoing. Active metabolites may include, but are not limited to, hydroxy-omeprazole, hydroxylansoprazole, omeprazole carboxylic acid, desmethyl pantoprazole and optically pure isomers thereof. In particular embodiments, the agent is not omeprazole.

In particular embodiments, the compositions, kits, or articles of manufacture that contain the at least one probiotic strain include an agent that reduces or prevents stomach acid production and/or raises or neutralizes gastric pH. Particular embodiments contemplate that omeprazole or benzimidazole derivatives in general may inhibit growth, viability, expansion, or engraftment of the one or more probiotic strains. Thus, in some embodiments, the compositions, kits, or articles of manufacture that contain the at least one probiotic strain include an agent for raising or neutralizing gastric pH that is not or does not include omeprazole or a benzimidazole derivative.

D.) Exemplary Compositions, Kits, and Articles of Manufacture

In some embodiments, provided herein are compositions, kits, or articles of manufacture that are or include a combination of prebiotics, e.g., prebiotic mixtures of non-digestible carbohydrates such as human milk oligosaccharides, and at least one probiotic, e.g., a strain of Bifidobacteria such as *B. longum* subsp. *infantis*. In certain aspects, the prebiotic mixture and/or the probiotic strain may be formulated as a pharmaceutical composition or a nutritional composition. In some embodiments, provided herein is a composition that includes the prebiotic mixture and the probiotic. In particular embodiments, the probiotic strain may be formulated as a pharmaceutical composition or a nutritional composition. In certain embodiments, the prebiotic mixture and the at least one probiotic are contained within separate compositions. In some embodiments, provided herein are kits or articles of manufacture that are or include separate prebiotic and probiotic compositions.

In some embodiments, provided herein are kits or articles of manufacture that are or include a composition that is a prebiotic mixture, e.g., of human milk oligosaccharides, and a composition that is or includes at least one strain of probiotic bacteria. In certain embodiments, the probiotic strain is capable of consuming (e.g., hydrolyzing) the prebiotics contained in the prebiotic mixture. In particular embodiments, the probiotic strain is capable of internalizing and consuming (e.g., hydrolyzing) the prebiotics of the prebiotic mixture. In various embodiments, the probiotic strain is capable of internalizing and consuming (e.g., hydrolyzing) human milk oligosaccharides, e.g., the human milk oligosaccharides of the prebiotic mixture. In particular embodiments, the probiotic strain is capable of consuming, internalizing, and/or hydrolyzing a prebiotic in vivo such within the human gut.

In particular embodiments, formulations for use in accordance with the invention are or include (i) a prebiotic mixture and (ii) a probiotic strain for administration to the subject simultaneously, separately or sequentially. In certain embodiments, the prebiotic mixture is or includes one or more human milk oligosaccharides and the at least one probiotic strain is or includes any of the probiotic strains listed in Table 1. In various embodiments, the at least one probiotic is or includes a strain of Bifidobacteria and the prebiotic is or includes a mixture of human milk oligosaccharides. In particular embodiments, the strain of Bifidobacteria is or includes *B. longum* subsp. *infantis* and the prebiotic mixture is or includes a mixture of at least 5, 10, 25, 50, or 100 human milk oligosaccharides and/or is or includes a concentrated ultra-filtered permeate from ultra-filtered human skim milk, such as described herein or produced by a method described herein, e.g., in Section-I-A-(i).

In certain embodiments, the prebiotic mixture is or includes one or more human milk oligosaccharides and the at least one probiotic strain is or includes any of the probiotic strains listed in Table 1. In various embodiments, the at least one probiotic is or includes a strain of Bifidobacteria and the prebiotic is or includes a mixture of human milk oligosaccharides. In certain embodiments, the strain of Bifidobacteria is or includes a strain of *B. breve, B. bifidum, B. longum* subsp. *infantis*, or *B. longum* subsp. *longum*. In particular embodiments, the prebiotic mixture is or includes a mixture of at least 5, 10, 25, 50, 100, 125, or 150 human milk oligosaccharides. In some embodiments, the prebiotic mixture is or includes one or more synthetic human milk oligosaccharides. In particular embodiments, the prebiotic mixture is or includes a concentrated human milk permeate, e.g., a concentrated human milk permeate described herein and/or produced by a method described herein such as in Section I-A-(i).

II. METHODS OF TREATMENT

In particular embodiments, provided herein are methods for treating, preventing, or ameliorating one or more diseases, disorders, or conditions in a subject in need thereof. In some embodiments, the method is or includes steps for administering to the subject a prebiotic mixture, such as any described herein, e.g., in Section I-A, and at least one probiotic strain, such as a probiotic strain described herein, e.g., in Section I-B or listed in Table 1.

In certain embodiments, provided herein are methods for treating, preventing, or ameliorating one or more diseases, disorders, or conditions that are or may be associated with dysbiosis, e.g., of the intestinal microbiome, in a subject in need thereof. In some aspects, the intestinal microbiome is involved in or associated with a number of physiological functions including digestion, metabolism, extraction of nutrients, synthesis of vitamins, prevention of pathogen colonization, and immune modulation. In some such aspects, alterations or changes in composition and biodiversity of the intestinal microbiome may be associated with or exacerbate various metabolic states, gastrointestinal disorders, and other pathophysiological conditions. In some aspects, conditions, diseases, or disorders with inflammatory components or components relating to infection, allergy, or immune dysfunction may be exacerbated by dysbiosis or may have an underlying contribution of dysbiosis to the pathology. Thus, in certain aspects, targeting the microbiome with the provided prebiotic and probiotic compositions may successfully treat, alleviate, or prevent a wide range of conditions, diseases, and disorders.

In some embodiments, provided herein is a method for treating, reducing, ameliorating, or preventing dysbiosis. In particular embodiments method is or includes steps for administering to the subject a prebiotic mixture, such as any described herein e.g., in Section I-A, and at least one probiotic strain, such as a probiotic strain described herein, e.g., in Section I-B or listed in Table 1. In some embodiments, the one or more diseases or conditions is, includes, or is associated with dysbiosis, e.g., of the intestinal microbiome. In certain embodiments, the microbiome is an intestinal microbiome of a human. In certain embodiments, the microbiome is an intestinal microbiome of an adult human.

In some embodiments, the method is or includes steps for administering to the subject a prebiotic mixture, such as any described herein, e.g., in Section I-A, and at least one probiotic strain, such as a probiotic strain described herein, e.g., in Section I-B or listed in Table 1. In certain embodiments, the one or more diseases or conditions is, includes, or is associated with inflammation, infection, allergy, immune dysfunction, or dysbiosis of the intestinal microbiome. In certain embodiments, the one or more diseases or conditions is, includes, or is associated with dysbiosis. In certain embodiments, the one or more diseases or conditions is, includes, or is associated with inflammation. In particular embodiments, the one or more diseases or conditions is, includes, or is associated with an autoimmune disease. In particular embodiments, the one or more diseases is or is associated with an allergy. In certain embodiments, the prebiotic mixture, e.g., of human milk oligosaccharides, and the probiotic strain, e.g., *B. longum* subsp. *infantis*, are administered to prevent a disease, disorder, or condition. In some embodiments, the prebiotic mixture and the probiotic strain prevents a condition described herein, e.g., in Section II-B. In particular embodiments, the prebiotic mixture and the probiotic strain reduce the risk, likelihood, or probability of the disease, disorder, or condition, and/or of experiencing one or more symptoms associated with the disease, disorder, or condition. In some embodiments, the risk, likelihood, or probability is reduced by at least 10%, 20%, 25%, 30%, 40%, 50%, 60%, 70%, 75%, 80%, 90%, 99%, or 99.9% as compared to alternative treatments or no treatments, or as compared to administration of the probiotic strain or prebiotic mixture alone.

As used herein, "subject" and "subject in need thereof" are used interchangeably. In particular embodiments, the subject is a human. In some embodiments, the subject is an infant, a child, a juvenile, or an adult. In certain embodiments, the subject is at least 1 month, 3 months, 6 months, 12 months, 18 months, or 24 months of age. In certain embodiments, the subject is at least 1 year, 2 years, 5 years, 10 years, 12 years, 16 years, or at least 18 years of age. In some embodiments, the subject is at least 12 years old. In certain embodiments, the subject is at least 18 years old. In some embodiments, the subject is an adult. In certain embodiments, the subject is elderly, e.g., at least 65 or 75 years of age.

A.) Treatment Regimens

In some embodiments, the prebiotic mixture, e.g., of HMOs, and the at least one probiotic strain, e.g., *B. longum* subsp. *infantis*, are administered together to the subject. In certain embodiments, the prebiotic mixture and the at least one probiotic strain are administered together once to the subject. In particular embodiments, the mixture and the at least one probiotic are administered together multiple times to the subject. In some embodiments, the prebiotic mixture and the at least one probiotic strain are administered once, twice, three times, four times, five times or more than five times per month; once, twice, three times, four times, five times, six times, seven times, or more than seven times per week; or once, twice, or more than twice daily. In some embodiments, the mixture and the at least one probiotic strain are administered multiple times during a regimen lasting for, for about, or for at least, one week, two weeks, three weeks, four weeks, five weeks, ten weeks, one month, two months, three months, six months twelve months, eighteen months, one year, two years, three years, four years, five years, or more than five years. In particular embodiments, the prebiotic mixture, e.g., of HMOs, and the at least one probiotic strain, e.g., *B. longum* subsp. *infantis*, are administered to a subject in need thereof after the subject has underwent an allogenic transplant, e.g., an allogenic BMT or HSCT. In some embodiments, the subject undergoes a treatment with antibiotics, and the prebiotic mixture, e.g., of HMOs, and the at least one probiotic strain, e.g., *B. longum* subsp. *infantis*, are administered to a subject immediately after the treatment with antibiotics is completed.

In particular embodiments, the prebiotic mixture, e.g., of HMOs, and the at least one probiotic strain, e.g., *B. longum* subsp. *infantis*, are administered separately to the subject. In certain embodiments, the at least one probiotic strain and the prebiotic mixture, e.g., of non-digestible carbohydrates, are administered both together and separately during the same treatment regimen. For example, in some embodiments the at least one probiotic strain and the prebiotic mixture are administered together initially over one or more treatment days, and then one or both of the at least one probiotic strain and the prebiotic mixture are administered alone over one or more subsequent treatment days. In some instances, the at least one probiotic strain is administered with the prebiotic mixture initially during the treatment regimen (such as during an initial or first treatment phase), and later in the regimen the mixture is administered in the absence of the at least one probiotic strain (such as during a second or subsequent treatment phase).

In certain embodiments, the prebiotic mixture and the probiotic strain are administered together or separately for a period of time, such as in a treatment regimen. In some embodiments, the administration of the prebiotic mixture, e.g., of HMOs, allows for the engraftment and expansion of the probiotic strain, e.g., *B. longum* subsp. *infantis*. In certain embodiments, the probiotic strain is exogenous to the subject's microbiome, e.g., intestinal microbiome. In particular embodiments, the probiotic strain is not present within the subject's microbiome prior to administration. In certain embodiments, the prebiotic mixture is administered concurrently with and/or subsequently to administration of the at least one probiotic strain. In some embodiments, the at least one probiotic strain is present and/or expands within the subject's microbiome during a time period in which the prebiotic mixture is administered. In certain embodiments, the present or amount of the at least one probiotic strain within the microbiome is reduced when administration of the prebiotic mixture ends, is ceased or is terminated. In particular embodiments, the probiotic strain is absent and/or undetectable following the termination or end of administration of the prebiotic mixture. In certain embodiments, the presence of the probiotic strain, e.g., *B. infantis*, is transient and is regulated by administration of the prebiotic mixture.

In some embodiments, the prebiotic mixture, e.g., of HMOs, provides an energy and/or a carbon source selectively or exclusively to the probiotic strain, e.g., *B. longum* subsp. *infantis*, such that it promotes growth or expansion of the probiotic strain, e.g., in vivo in the gut or within the microbiome. In certain embodiments, the mixture of non-digestible carbohydrates and the at least one probiotic strain are administered in a manner sufficient for the probiotic strain to grow, expand, or establish itself within the microbiome of the subject. In particular embodiments, the administration of the mixture and the probiotic strain results in an increase of lactate or short chain fatty acid (SCFA) levels in the gut that is synergistic, e.g., greater than what would be expected based on administration of the mixture or probiotic strain alone.

In certain embodiments, the expansion, level, or amount of the probiotic strain, e.g., *B. longum* subsp. *infantis*, may be regulated by the administration of the prebiotic mixture. Thus, in some aspects, the probiotic strain is administered to the subject, and the concurrent or subsequent administration of the prebiotic mixture may be adjusted to provide a therapeutic response, e.g., to promote growth or expansion of beneficial microbiota. In some embodiments, the dosage and/or duration of treatment with the prebiotic mixture, e.g., of HMOs, can depend on several factors, including severity and responsiveness of the disease, route of administration, time course of treatment (days to months to years), and time to amelioration of the disease.

In certain embodiments, the prebiotic mixture and the probiotic strain are administered during one or more treatment phases, such as during a treatment regimen. In some embodiments, the method or treatment regimen is or includes a treatment phase during which time both the prebiotic mixture and the at least one probiotic are administered. In some embodiments, the prebiotic mixture and the probiotic strain are administered during the treatment phase separately, e.g., in separate doses. In certain embodiments, a treatment phase includes administration of one but not both of the at least one probiotic strain or the prebiotic mixture. In some embodiments, the prebiotic mixture is administered at least once, twice, or three times daily during a treatment phase. In certain embodiments, the at least one probiotic is administered at least once, twice, or three times daily during a treatment phase. In some embodiments, the prebiotic mixture is administered twice daily and the probiotic strain is administered once daily during a treatment phase. In some embodiments, a treatment phase where both the probiotic strain and prebiotic mixture are administered is immediately followed by a treatment phase where only the prebiotic mixture is administered, e.g., to extend the duration of time the probiotic strain remains colonized within the subject's gut and/or intestinal microbiome.

In some embodiments, the method or treatment regimen is or includes more than one treatment phase. For example, in some embodiments, the method or treatment regimen includes a first or initial treatment phase that includes the administration of the probiotic strain or both the prebiotic mixture and the probiotic strain, and a second or subsequent treatment phase that includes the administration of the prebiotic mixture. In some embodiments, an additional treatment phase occurs before the first or initial treatment phase, whereby the prebiotic mixture is administered prior to any administration of the at least one probiotic strain. In some embodiments, the first or initial treatment phase lasts for at least one day, or for at least two, three, four, five, seven, ten, twelve, fourteen days, or for at least one, two, three, four, six, eight, ten, twelve weeks, or for at least one, two, three, six, or twelve months. In certain embodiments, the second or subsequent treatment phase lasts for at least one day, or for at least two, three, four, five, seven, ten, twelve, fourteen days, or for at least one, two, three, four, six, eight, ten, twelve weeks, or for at least one, two, three, six, or twelve months. In particular embodiments, the first or initial treatment phase lasts for at least about seven days, and the second or subsequent treatment phase lasts for about seven days. In certain embodiments, the method or treatment regimen includes additional treatment phases, e.g., a third or fourth treatment phase, where one or both of the prebiotic mixture and the at least one probiotic strain is administered. Treatment phases may in some embodiments be consecutive, e.g., so that the next treatment phase begins on the day after the earlier treatment phase ends, or may be spaced apart, e.g., by one or more days or weeks.

In certain embodiments, the prebiotic mixture is administered daily for at least 2, 3, 4, 5, 7, 10, 14, 21, or 28 days, e.g., consecutive days. In certain embodiments, the prebiotic mixture is administered in an amount of at least 0.001 g, 0.01 g, 0.1 g, 1 g, 2 g, 3 g, 4 g, 5 g, 6 g, 7.5 g, 8 g, 9 g, 10 g, 12 g, 16 g, 18 g, 20 g, 25 g, or 50 g per day, e.g., total weight of the probiotics such as non-digestible carbohydrates such as human milk oligosaccharides. In particular embodiments, the prebiotic mixture is administered in an amount of at least 0.001 g, 0.01 g, 0.1 g, 1 g, 2 g, 3 g, 4 g, 5 g, 6 g, 7.5 g, 8 g, 9 g, 10 g, 12 g, 16 g, 18 g, 20 g, 25 g, or 50 g total human milk oligosaccharides per day. In some embodiments, the prebiotic mixture is administered in an amount of between 0.1 g and 50 g; 0.5 g and 25 g, 1 g and 20 g, 2 g and 18 g, 1 g and 5 g, 2 g and 3 g, 3 g and 6 g, 4 g and 5 g, 5 g and 10 g, 8 g and 10 g, 10 g and 20 g, 15 g and 20 g, or 17 g and 19 g total human milk oligosaccharides per day. In some embodiments, the prebiotic mixture is administered in an amount of, of about, or of at least 2 g, 4.5 g, 6 g, 9 g, 12 g, 16 g, or 18 g total human milk oligosaccharides per day.

In particular embodiments, the probiotic strain is administered daily for at least 2, 3, 4, 5, 7, 10, 14, 21, or 28 days, e.g., consecutive days. In some embodiments, the at least one probiotic strain is administered in an amount of at least $1\times10^1$, $1\times10^2$, $1\times10^3$, $1\times10^4$, $1\times10^5$, $1\times10^6$, $5\times10^6$, $1\times10^7$, $1\times10^7$, $5\times10^7$, $1\times10^8$, or $5\times10^8$ colony forming units (CFU) per day. In various embodiments, the at least one probiotic strain is administered in an amount of at least $1\times10^1$, $1\times10^1$, $1\times10^2$, $1\times10^3$, $1\times10^4$, $1\times10^5$, $1\times10^6$, $5\times10^6$, $1\times10^7$, $1\times10^7$, $5\times10^7$, $1\times10^8$, or $5\times10^8$ colony forming units (CFU) per dose. In certain embodiments, the at least one probiotic strain is administered in an amount of between $1\times10^6$ and $1\times10^{12}$, $5\times10^6$ and $1\times10^{10}$, $1\times10^7$ and $1\times10^9$, or $1\times10^7$ and $1\times10^8$ CFU per day. In some embodiments, the at least one probiotic strain is administered in an amount of, of about, or at least $5\times10^6$ colony forming units (CFU) per dose or per day. In some embodiments, the at least one probiotic strain is administered in an amount of, of about, or at least $8\times10^7$ colony forming units (CFU) per dose or per day.

In certain embodiments, each dose of the at least one probiotic strain is enterally coated, e.g., to prevent damage or death of the probiotic by stomach acid. In some embodiments, a dose of the at least one probiotic is administered with or after an agent to reduce stomach acid production or neutralize stomach acid.

In some embodiments, the agent is a proton pump inhibitor (PPI). In certain embodiments, the PPI is administered in an amount sufficient to reduce or prevent $H^+$—$K^+$ ATPase activity of gastric parietal cells. Particular embodiments contemplate that administration of a PPI prevents or reduces death, inactivation, or degradation of an orally administered probiotic strain, e.g., *B. longum* subsp. *infantis*.

Particular embodiments contemplate that some PPIs may reduce engraftment, growth, viability, or expansion of the at least one probiotic strain. Certain embodiments contemplate that PPIs that are benzimidazole derivatives (also referred to herein as substituted benzimidazoles) may inhibit or reduce engraftment, growth, expansion, or viability of the at least one probiotic strain. Various embodiments contemplate that PPIs that are or include omeprazole may inhibit or reduce engraftment, growth, expansion, or viability of the at least one probiotic strain.

In certain embodiments, the subject has a condition, disease, or disorder, e.g., graft versus host disease, with symptoms that may include, relate to, or resemble stomach discomfort, heartburn, or gastroesophageal reflux disease. In particular embodiments, the subject may take one or more agents that reduces or prevents stomach acid production and/or increases or neutralizes gastric pH. In certain such embodiments, the subject is treated with an agent that is not or does not include a PPI prior to, during, or after treatment with the at least one probiotic strain. In some such embodiments, the subject is treated with an agent that is not or does not include a benzimidazole derivative prior to, during, or after treatment with the at least one probiotic strain. In some embodiments, the subject is treated with an agent that is not or does not include omeprazole prior to, during, or after treatment with the at least one probiotic strain. In certain embodiments, the subject is not administered a benzimidazole derivative or omeprazole at least 4 weeks, 3 weeks, 2 weeks, 1 week, 10 days, 7 days, 5 days, 3 days, 2 days, 1 day, 48 hours, 36 hours, 24 hours, 18 hours, 12 hours, or 6 hours prior to the initiation of a treatment with the at least one probiotic strain. In some embodiments, the subject is not administered a benzimidazole derivative or omeprazole for at least 24 hours, 36 hours, 48 hours, 1 day, 2 days, 3 days, 5 days, 7 days, 10 days, 1 week, 2 weeks, 3 weeks, 4 weeks, 6 weeks, 8 weeks, 1 month, 2 months, or 3 months after a final dose of a treatment regimen with the probiotic strain In some embodiments, one or more doses of the probiotic strain is administered without a PPI. In particular embodiments, one or more doses of the probiotic strain are administered with an agent that is not omeprazole. In some embodiments, a dose of the at least one probiotic strain is not administered within or within about 1 hour, 2 hours, 4 hours, 6 hours, 12 hours, 24 hours, 36 hours, 48 hours, 60 hours, 2 days, 3 days, 4 days, 5 days, 7 days, 10 days, 2 weeks, 3 weeks, 4 weeks, 6 weeks, 8 weeks, 10 weeks, or 12 weeks of an administration of or all of (i) a PPI; (ii) a benzimidazole derivative; and/or (iii) omeprazole.

In certain embodiments, one or more doses of the probiotic strain are administered with an agent that increases or neutralizes gastric pH, e.g., an $H_2$ histamine receptor antagonist, that is not a benzimidazole derivative. In certain embodiments, an $H_2$ histamine receptor antagonist, e.g., famotidine, is administered at least 48 hours, 36 hours, 24 hours, 18 hours, 12 hours, 8 hours, 6 hours, 3 hours, 2 hours, 1 hours, 60 minutes, 30 minutes, or 15 minutes prior to administering the probiotic strain. In particular embodiments, an $H_2$ histamine receptor antagonist, e.g., famotidine, is administered at least about 1 hour prior to administering the probiotic strain.

In some embodiments, at least one probiotic strain that is capable of consuming or metabolizing some or all of the oligosaccharides, e.g., HMOs, of the prebiotic mixture is administered to a subject. In particular embodiments, the at least one probiotic strain is capable of internalizing some or all of the oligosaccharides in the mixture. In some embodiments, the timing or dosing for administering the at least one probiotic strain and the prebiotic mixture, e.g., of HMOs, achieves a growth or expansion of the probiotic strain in vivo, e.g., within the microbiome of the subject. In certain embodiments, the administered oligosaccharides, e.g., HMOs, selectively or exclusively serve as a carbon source for the at least one probiotic strain, e.g., as opposed to other bacterial strains present in the gut or microbiome. In some embodiments, the oligosaccharides of the mixture selectively or exclusively serve as an energy source for the at least one probiotic strain e.g., as opposed to other bacterial strains present in the gut or microbiome.

In certain embodiments, subjects are administered (e.g., at least once daily) both the at least one probiotic strain, e.g., *B. longum* subsp. *infantis*, and the prebiotic mixture, e.g., of human milk oligosaccharides, during a first or initial treatment phase, e.g., for at least 1, 3, 7, or 14 days, and then are administered the prebiotic mixture alone during a subsequent treatment phase, e.g., such that occurs immediately the first or initial treatment phase. In some embodiments, administration of the prebiotic mixture extends the duration of the colonization of the probiotic strain within the subject's gut and/or microbiome.

In some embodiments, the methods are or include administering the mixture of non-digestible carbohydrates to a subject, e.g., a subject in need thereof such as a subject who will or who has undergone an allogenic transplant, e.g., an allogenic BMT or HSCT, to expand or maintain the amount, growth, or presence of a probiotic strain in the gut or microbiome of the subject. In some embodiments, the probiotic strain has been administered to the subject. In some embodiments, the probiotic strain is or will be administered to the subject. In certain embodiments, the probiotic strain is exogenous to the subject's microbiome, e.g., the probiotic strain is not present or detectable in the subject's gut or microbiome prior to an initial administration of the probiotic strain.

B.) Conditions, Diseases, and Disorders

In certain embodiments, provided herein are methods for treating, preventing, or ameliorating one or more diseases, disorders, or conditions that are or may be associated with dysbiosis, e.g., of the intestinal microbiome, in a subject in need thereof. In certain embodiments, administration of the prebiotic mixture, e.g., of HMOs, and the probiotic strain, e.g., *B. longum* subsp. *infantis*, are useful to treat, ameliorate, remedy, or prevent diseases, disorders, or conditions such as obesity, inflammatory bowel disease (IBD), celiac disease, irritable bowel syndrome (IBS), colon cancer, diabetes, liver disorders, cystic fibrosis, and allergies.

In certain embodiments, the prebiotic mixture, e.g., of human milk oligosaccharides, and the at least one probiotic strain, e.g., *B. longum* subsp. *infantis*, are administered to a subject to treat, ameliorate, remedy, or prevent a gastrointestinal condition, disease, or disorder associated with, related to, or caused by dysbiosis, e.g., of the intestinal microbiome. In certain embodiments, the gastrointestinal condition, disease, or disorder is or includes one or more of a chronic inflammatory disease, an autoimmune disease, an infection, bowel resection, and/or a condition associated with chronic diarrhea. In certain embodiments, the gastrointestinal condition, disease, or disorder is or includes one or more of irritable bowel syndrome (IBS), inflammatory bowel disease (IBD) including Crohn's Disease and colitis, short bowel syndrome (SBS), celiac disease, small intestinal bacterial overgrowth (SIBO), gastroenteritis, leaky gut syndrome, and gastric lymphoma. In certain embodiments, the gastrointestinal condition, disease, or disorder is associated with a bacterial, viral or parasitic infection or overgrowth. In a particular embodiment, the disease or disorder is associated with infection by drug-resistant bacteria, e.g., vancomycin-resistant enterococcus (VRE). In particular embodiments, administration of the at least one prebiotic mixture, e.g., of human milk oligosaccharides, and the at least one probiotic strain, e.g., *B. longum* subsp. *infantis*, prevents, reduces, or ameliorates one or more symptoms of the gastrointestinal condition.

In some embodiments, the prebiotic mixture, e.g., of human milk oligosaccharides, and the at least one probiotic strain, e.g., *B. longum* subsp. *infantis*, are administered to a subject with an immune dysfunction. In some embodiments, the subject is immunocompromised. In certain embodiments, the administration prevents, reduces, treats, or ameliorates an infection in the immunocompromised subject. In some embodiments, the administration prevents, reduces, treats, or ameliorates overgrowth or domination of pathogenic bacteria. In some embodiments, the immunocompromised subject has undergone one or more treatments for cancer. In some embodiments, the treatments are or include chemotherapy. In certain embodiments, the treatment is or includes an allogenic transplant, e.g., a hematopoietic stem cell transplant or bone marrow transplant. In certain embodiments, the immunocompromised subject is in an ICU, has received an organ transplant, is elderly (e.g., at least 65 or 75 years old) and/or has been on prolonged antibiotic treatment (e.g., for at least 2, 3, 4, 6, 8, 10, or 12 weeks, or at least 1, 2, 3, 6, 12, 18, or 24 months). In certain embodiments, the administration prevents or reduces the probability or likelihood of a systemic infection by, by about, or by at least 10%, 20%, 30%, 40%, 50%, 60%, 70%, 75%, 80%, 90%, or 95%, e.g., as compared to a subject administered an alternative treatment and/or not administered the at least one probiotic strain and/or the prebiotic mixture.

In particular embodiments, the prebiotic mixture, e.g., of human milk oligosaccharides, and the probiotic strain, are administered to treat or prevent overgrowth or domination of pathogenic bacteria (also referred to herein as gut domination). In some aspects, domination of pathogenic bacteria refers to the presence of a species of bacteria (e.g., a pathogenic species), of at least 1%, 5%, 10%, 20%, or 30%, relative to the bacteria present in the subject's gut or intestinal microbiome. Particular embodiments contemplate that overgrowth or domination may be determined by routine techniques in the art, such as including but not limited to PCR or high throughput sequencing.

In certain embodiments, the prebiotic mixture, e.g., of HMOs, and the at least one probiotic strain, e.g., *B. longum* subsp. *infantis*, are administered to a subject having, suspected of having, or at risk of having dysbiosis, e.g., of the intestinal microbiome. In certain embodiments, the transient presence, engraftment, or expansion of the probiotic strain, e.g., *B. longum* subsp. *infantis*, reduces, decreases, or ameliorates the dysbiosis. Particular embodiments contemplate that the presence, engraftment, or expansion of the probiotic strain, e.g., *B. longum* subsp. *infantis*, creates, promotes, or generates an environment and/or one or more conditions that (i) promotes the presence, growth, or expansion of beneficial microbiota; (ii) decreases the presence, growth, or expansion of pathogenic microbiota; (iii) promotes diversity of microbiota present within the microbiome; or (iv) any or all of (i) through (iii).

In certain embodiments, administration of the prebiotic mixture, e.g., of HMOs, and at least one probiotic strain of bacterium, e.g., *B. longum* subsp. *infantis*, reduces the presence or abundance of pathogenic bacteria in the subject's gut. In certain embodiments, administration of the prebiotic mixture, e.g., of HMOs, and at least one probiotic strain of bacterium, e.g., *B. longum* subsp. *infantis*, reduces gut domination by pathogenic taxa (e.g., Enterobacteriaceae, *Enterococcus, Staphylococcus*). In particular embodiments, the growth of the at least one probiotic strain, e.g., *B. longum* subsp. *infantis*, within the gut or microbiome reduces the abundance, level, activity, or presence of pathogenic taxa. In certain embodiments, administration of the prebiotic mixture, e.g., of HMOs, and the probiotic strain, e.g., *B. longum* subsp. *infantis*, reduces the abundance, level, activity, or presence of pathogenic bacteria and/or taxa by, by about, or by at least 10%, 20%, 30%, 40%, 50%, 60%, 70%, 75%, 80%, 90%, 95%, or 100%, e.g., as compared to prior to the administration or as compared to the gut or microbiome of a subject not administered the at least one probiotic strain and/or the prebiotic mixture. In particular embodiments, the growth of the at least one probiotic strain, e.g., *B. longum* subsp. *infantis*, within the gut or microbiome increases the amount, level, presence, or concentration of at least one short chain fatty acid, e.g., acetate or butyrate, within the gut.

In certain embodiments, the prebiotic mixture, e.g., of human milk oligosaccharides, and the probiotic strain, e.g., *B. longum* subsp. *infantis*, are administered to a subject who is at risk of an infection or gut domination, e.g., by pathogenic bacteria. In some embodiments, the subject has an increased risk of infection or gut domination, e.g., as compared to the general population. In certain embodiments the subject is immunocompromised, undergoing an extended antibiotic treatment regimen (e.g., lasting at least 2, 3, 4, 5, 6, 8 10, or 12 weeks or 2, 3, 6, 12, 18, or 24 months), is elderly, is hospitalized e.g., in an intensive care unit (ICU, has received an organ transplant, and/or is immunosuppressed. In certain aspects, the subject will undergo or has received a medical procedure such a surgery or a chemotherapy that may increase the risk, likelihood, or probability of infection.

In certain embodiments, administration of the prebiotic strain and probiotic mixture reduces the risk, likelihood, or probability of infection, e.g., by pathogenic bacteria, is reduced by at least 10%, 20%, 25%, 30%, 40%, 50%, 60%, 70%, 75%, 80%, 90%, 99%, or 99.9% as compared to alternative treatments or no treatments, or as compared to administration of the probiotic strain or prebiotic mixture alone. In some embodiments, the prebiotic mixture and the probiotic strain are administered at least once at least 1 hour, 2 hours, 3 hours, 4 hours, 6 hours, 8 hours, 12 hours, 18 hours, 24 hours, 1 day, 2 days, 3 days, 4 days, 5 days, 7 days, 10 days, 1 week, 2 weeks, 4 weeks, 6 weeks, one month, or two months prior to the medical procedure, e.g., surgery or chemotherapy. In particular embodiments, the prebiotic mixture and the probiotic strain are administered at least once during the medical procedure, e.g., surgery or chemotherapy. In certain embodiments, the prebiotic mixture and the probiotic strain are administered at least once at least 1 hour, 2 hours, 3 hours, 4 hours, 6 hours, 8 hours, 12 hours, 18 hours, 24 hours, 1 day, 2 days, 3 days, 4 days, 5 days, 7 days, 10 days, 1 week, 2 weeks, 4 weeks, 6 weeks, one month, or two months after to the medical procedure, e.g., surgery or chemotherapy.

Pathogenic bacteria may include known microbes with pathogenicity for the gastrointestinal tract, e.g., from esophagus down to rectum. In some embodiments, pathogenic bacteria are or include one or more species, subspecies, or strains of Proteobacteria. In certain embodiments, the pathogenic bacteria may include, but are not limited to strains, species, subspecies, or strains of one or more of *Firmicutes, Clostridium, Enterobacteriaceae, Enterococcus, Staphylococcus, Corynebacteria, Salmonella, Shigella, Staphylococcus, Campylobacter* (e.g., *Campylobacter jejuni*), *Clostridia, Escherichia coli, Yersinia, Vibrio cholerae, Mycobacterium avium* subspecies *paratuberculosis, Brachyspira hyodysenteriae*, or *Lawsonia intracellularis*. In particular embodiments, administration of the prebiotic mixture and the at least one probiotic strain reduces or decreases the presence, growth, or abundance of pathogenic bacteria within the gut.

In some embodiments, administration of the prebiotic mixture and the at least one probiotic strain impairs the growth of one or more pathogens. Such pathogens treated by the provided methods include, but are not limited to, *Aeromonas hydrophila, Bacillus*, e.g., *Bacillus cereus, Bifidobacterium, Bordetella, Borrelia, Brucella, Burkholderia, C. difficile, Campylobacter*, e.g., *Campylobacter fetus* and *Campylobacter jejuni, Chlamydia, Chlamydophila, Clostridium*, e.g., *Clostridium botulinum, Clostridium difficile*, and *Clostridium perfringens, Corynebacterium, Coxiella, Ehrlichia, Enterobacteriaceae*, e.g., Carbapenem-resistant Enterobacteriaceae (CRE) and Extended Spectrum Beta-Lactamase producing Enterobacteriaceae (ESBL-E), fluoroquinolone-resistant Enterobacteriaceae, Enterococcus, e.g., vancomycin-resistant enterococcus spp., extended spectrum beta-lactam resistant Enterococci (ESBL), and vancomycin-resistant Enterococci (VRE), *Escherichia*, e.g., enteroaggregative *Escherichia coli*, enterohemorrhagic *Escherichia coli*, enteroinvasive *Escherichia coli*, enteropathogenic *E. coli*, enterotoxigenic *Escherichia coli* (such as but not limited to LT and/or ST), *Escherichia coli* 0157:H7, and multi-drug resistant bacteria *E. coli, Francisella, Haemophilus, Helicobacter*, e.g., *Helicobacter pylori, Klebsiella*, e.g., *Klebsiellia pneumonia* and multi-drug resistant bacteria *Klebsiella, Legionella, Leptospira, Listeria*, e.g., *Lysteria monocytogenes, Morganella, Mycobacterium, Mycoplasma, Neisseria, Orientia, Plesiomonas shigelloides*, Antibiotic-resistant *Proteobacteria, Proteus, Pseudomonas, Rickettsia, Salmonella*, e.g., *Salmonella paratyphi, Salmonella* spp., and *Salmonella typhi, Shigella*, e.g., *Shigella* spp., *Staphylococcus*, e.g., *Staphylococcus aureus* and *Staphylococcus* spp., *Streptococcus, Treponema, Vibrio*, e.g., *Vibrio cholerae, Vibrio parahaemolyticus, Vibrio* spp., and *Vibrio vulnificus*, and *Yersinia*, e.g., *Yersinia enterocolitica*. At least one of the one or more pathogens can be an antibiotic-resistant bacterium (ARB), e.g., Antibiotic-resistant Proteobacteria, Vancomycin Resistant Enterococcus (VRE), Carbapenem Resistant Enterobacteriaceae (CRE), fluoroquinolone-resistant Enterobacteriaceae, or Extended Spectrum Beta-Lactamase producing Enterobacteriaceae (ESBL-E).

In some embodiments, the condition, disease, or disorder is an immune dysfunction that is an autoimmune disorder. In some embodiments, the autoimmune disorder includes, but is not limited to, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert- Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & Ill autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis.

In some embodiments, the condition, disease, or disorder is a diarrheal disease including, but not limited to, acute bloody diarrhea (e.g., dysentery), acute watery diarrhea (e.g., cholera), checkpoint inhibitor-associated colitis, diarrhea due to food poisoning, persistent diarrhea, and traveler's diarrhea.

In some embodiments, administration of the at least one probiotic strain and the prebiotic mixture treats or prevents various GI disorders known to result from or be associated or accompanied with dysbiosis of the intestinal microbiome. In certain embodiments, administration of the at least on probiotic strain and prebiotic mixture reduces GI immunoactivation and/or inflammation. In some embodiments, GI immunoactivation and inflammation may be assessed by known methods that are routine in the art. In some embodiments, the condition, disease, or disorder is an inflammatory bowel disease (IBD) or related disease including, but not limited to, Behcet's disease, collagenous colitis, Crohn's disease, diversion colitis, fulminant colitis, intermediate colitis, left-sided colitis, lymphocytic colitis, pancolitis, pouchitis, proctosigmoiditis, short bowel syndrome, ulcerative colitis, and ulcerative proctitis.

In various embodiments, administration of the at least one probiotic strain and the prebiotic mixture treats or prevents various bloodstream infections (BSI). In certain embodiments, administration of the probiotic strain and the prebiotic mixture treats or prevents catheter or intravascular-line infections (e.g., central-line infections). In some embodiments, administration of the probiotic strain and the prebiotic mixture treats or prevents chronic inflammatory diseases.

In particular embodiments, administration of the at least one probiotic strain and the prebiotic mixture treats or prevents meningitis; pneumonia, e.g., ventilator-associated pneumonia; skin and soft tissue infections; surgical-site infections; urinary tract infections (e.g., antibiotic-resistant urinary tract infections and catheter-associated urinary tract infections); wound infections; and/or antibiotic-resistant infections and antibiotic-sensitive infections.

In certain embodiments, administration of the at least one probiotic strain and the prebiotic mixture treats or prevents diseases or disorders relating to the "gut-brain axis", including neurodegenerative, neurodevelopmental, and neurocognitive disorders, such as anorexia, anxiety, autism-spectrum disorder, depression, Parkinson's, and Schizophrenia. In certain embodiments, administration of the at least one probiotic strain and the prebiotic mixture reduces one or more symptoms associated with anorexia, anxiety, autism-spectrum disorder, depression, Parkinson's, and/or Schizophrenia.

In some embodiments, administration of the at least one probiotic strain and the prebiotic mixture treats or prevents a side effect of an anti-cancer therapy and/or increases efficacy of an anti-cancer therapeutic agent and/or anti-cancer therapy. In some embodiments, the anti-cancer therapy is surgery, radiation therapy, chemotherapy (including hormonal therapy) and/or targeted therapy (including an immunotherapy). Illustrative chemotherapeutics agents are provided elsewhere herein. In particular embodiments, the immunotherapy binds to and/or recognizes a tumor-cell antigen and/or a cancer-cell antigen, e.g., CTLA-4, PD-1, PD-L1, or PD-L2. In some embodiments, the immunotherapy comprises administration of Keytruda (Pembrolizumab), Opdivo (Nivolumab), Yervoy (Ipilimumab), Tecentriq (atezolizumab), Bavencio (avelumab), and Imfinzi (durvalumab).

In some embodiments, the subject is refractory and/or non-responsive to an anti-cancer therapy. In certain embodiments, the probiotic strain and prebiotic mixture treats a subject that presents a non-curative response, a limited response, or no response to the anti-cancer therapy, or even progress, after 12 weeks or so of receiving the anti-cancer therapy. Thus, in some aspects, the provided probiotic strain and prebiotic mixture of the present invention can rescue subjects that are refractory and/or non-responsive to the anti-cancer therapy. In certain embodiments, the subject is refractory and/or non-responsive to a treatment directed to a checkpoint molecule, e.g., CTLA-4, PD-1, PD-L1, and/or PD-L2. In particular embodiments, the treatment directed to a checkpoint molecule comprises administration of Keytruda (Pembrolizumab), Opdivo (Nivolumab), Yervoy (Ipilimumab), Tecentriq (atezolizumab), Bavencio (avelumab), or lmfinzi (durvalumab).

In some embodiments, the prebiotic mixture, e.g., of human milk oligosaccharides, and the at least one probiotic strain, e.g., *B. longum* subsp. *infantis*, are administered to an immunocompromised subject. In certain embodiments, the administration prevents, reduces, treats, or ameliorates an infection in the immunocompromised subject. In some embodiments, the administration prevents, reduces, treats, or ameliorates overgrowth or domination of pathogenic bacteria. In some embodiments, the immunocompromised subject has undergone one or more treatments for cancer. In some embodiments, the treatments are or include chemotherapy. In certain embodiments, the treatment is or includes an allogenic transplant, e.g., a hematopoietic stem cell transplant or bone marrow transplant. In certain embodiments, the administration prevents or reduces the probability or likelihood of a systemic infection by, by about, or by at least 10%, 20%, 30%, 40%, 50%, 60%, 70%, 75%, 80%, 90%, or 95%, e.g., as compared to an alternative treatment or treatment with either the probiotic strain or prebiotic mixture alone.

In certain embodiments, the prebiotic mixture, e.g., of human milk oligosaccharides, and the at least one probiotic strain, e.g., *B. longum* subsp. *infantis*, are administered to a subject who has or is at risk of sepsis. In some embodiments, the probability or likelihood of sepsis is reduced or decreased by at least 10%, 20%, 30%, 40%, 50%, 60%, 70%, 80%, 90%, 95%, or 99%, e.g., as compared to a subject (e.g., who has or is at risk for sepsis) not administered the prebiotic mixture or the at least one probiotic. In certain embodiments, the administration of the prebiotic mixture and the at least one probiotic improves or increases the survival of the subject over 6 months, 12 months, 18 months, 1 year, 2 years, 5 years, 10 years, and/or 20 years or more by, by about, or by at least 5%, 10%, 20%, 25%, 30%, 40%, 50%, 60%, 70%, 75%, 80%, 90%, 95%, 100%, or 1-fold, 2-fold, 3-fold, 4-fold, or 5-fold greater than in subjects (e.g., who have or are at risk for sepsis) not administered the prebiotic mixture and the at least one probiotic strain.

In particular embodiments, administration of the prebiotic mixture and the at least one probiotic strain prevents, reduces, decreases, remedies, or ameliorates one or more symptoms associated with a gastrointestinal condition, disease, or disorder. In certain embodiments, the one or more symptoms associated with gastrointestinal condition, disease, or disorder may include, but are not limited to, diarrhea, fever, fatigue, abdominal pain and cramping, blood in stool, mouth sores, weight loss, fistula, inflammation (of skin, eyes, or joints), inflamed liver or bile ducts, delayed growth (in children). In particular embodiments, administration of the prebiotic mixture and the at least one probiotic strain reduces the risk or probability for the subject of experiencing one or more symptoms associated with the gastrointestinal condition, disease, or disorder by, by about, or by at least 10%, 20%, 30%, 40%, 50%, 60%, 70%, 75%, 80%, 90%, or 95%, e.g., as compared to a subject not administered the at least one probiotic strain and/or the prebiotic mixture. In certain embodiments, administration of the prebiotic mixture and the at least one probiotic strain increases probability or likelihood for remission by, by about, or by at least 10%, 20%, 30%, 40%, 50%, 60%, 70%, 75%, 80%, 90%, 100%, or 1-fold, 2-fold, 5-fold, 10-fold, 20-fold, 50-fold, or 100-fold e.g., as compared to a subject not administered the at least one probiotic strain and/or the prebiotic mixture. In some embodiments, administration of the prebiotic mixture and the at least one probiotic strain increases probability or likelihood for remission within 12 weeks, 10 weeks, 8 weeks, 6 weeks, 4 weeks, or less than 4 weeks, e.g., from the initiation or termination of the administration.

In various embodiments, the prebiotic mixture, e.g., of human milk oligosaccharides, and the at least one probiotic strain, e.g., *B. longum* subsp. *infantis*, are administered to a subject to treat, ameliorate, remedy, or prevent a chronic inflammatory disease, an autoimmune disease, an infection, bowel resection, and/or a condition associated with chronic diarrhea. According to particular embodiments, the pathology is selected from the group consisting of: irritable bowel syndrome (IBS), inflammatory bowel disease (IBD), short bowel syndrome (SBS), celiac disease, small intestinal bacterial overgrowth (SIBO), gastroenteritis, leaky gut syndrome, and gastric lymphoma. In another embodiment the disease or disorder is associated with a bacterial, viral, or parasitic infection or overgrowth, e.g. by drug-resistant bacteria. In some embodiments, administration of the prebiotic mixture and the at least one probiotic strain increases probability or likelihood for cure or remission of the chronic inflammatory disease, autoimmune disease, infection, bowel resection, and/or chronic diarrhea for by, by about, or by at least 10%, 20%, 30%, 40%, 50%, 60%, 70%, 75%, 80%, 90%, 100%, or 1-fold, 2-fold, 5-fold, 10-fold, 20-fold, 50-fold, or 100-fold e.g., as compared to a subject not administered the at least one probiotic strain and/or the prebiotic mixture. In some embodiments, administration of the prebiotic mixture and the at least one probiotic strain increases probability or likelihood for the cure or remission within 12 weeks, 10 weeks, 8 weeks, 6 weeks, 4 weeks, or less than 4 weeks, e.g., from the initiation or termination of the administration.

In certain embodiments, the probiotic strain and the prebiotic mixture are administered to a subject to treat, prevent, or ameliorate an allergy. In some embodiments, the allergy is a food allergy. In certain embodiments, the food allergy is or includes a chronic or acute immunological hypersensitivity reaction (e.g. a type I hypersensitivity reaction) elicited in a mammal in response to an ingested material or food antigen (also referred to in the art as a "food allergen"). Identification and diagnosis of food allergy is routine among persons of ordinary skill in the art. Food allergies may include, but are not limited to, allergies to nuts, peanuts, shellfish, fish, milk, eggs, wheat, or soybeans.

In some embodiments, the probiotic strain and the prebiotic mixture are administered to treat or ameliorate an allergy, e.g., a food allergy. In certain embodiments, the probiotic strain and the prebiotic mixture reduce or decrease the severity of the allergic response to the allergen, e.g., as compared to the allergic response prior to any treatment with the probiotic strain and prebiotic mixture. In certain embodiments, the probiotic strain and the prebiotic mixture attenuates or reduces the severity or intensity of one or more symptoms or clinical manifestations of the allergy, e.g., food allergy, to subsequent exposures to the allergen, e.g., as compared to symptoms or clinical manifestations observed prior to treatment with the probiotic strain and prebiotic mixture. In some embodiments, the symptoms or clinical manifestations of the allergy may include, but are not limited to rash, eczema, atopic dermatitis, hives, urticaria, angiodema, asthma, rhinitis, wheezing, sneezing, dyspnea, swelling of the airways, shortness of breath, other respiratory symptoms, abdominal pain, cramping, nausea, vomiting, diarrhea, melena, tachycardia, hypotension, syncope, seizures, and anaphylactic shock.

In particular embodiments, the probiotic strain and the prebiotic mixture are administered to a subject, e.g., a subject at risk of having or developing an allergy, to prevent or reduce or decrease the probability or likelihood experiencing an allergic response. In certain embodiments, administration of the probiotic strain and prebiotic mixture reduce the likelihood or probability of having an allergic response within the next month, 3 months, 6 months, 12 months, 18 months, year, 2 years, 3 years, 5 years, 10 years, or 20 years. In some embodiments, the probability or likelihood of developing the allergy is reduced by at least 10%, 20%, 30%, 40%, 50%, 60%, 70%, 75%, 80%, 90%, or 99% as compared to a subject with a similar risk profile who is not administered the probiotic strain and the prebiotic mixture. In some embodiments, administration of the probiotic strain and prebiotic mixture reduces the severity of one or more symptoms or clinical manifestations of an allergic response following exposure to the allergen over the next month, 3 months, 6 months, 12 months, 18 months, year, 2 years, 3 years, 5 years, 10 years, or 20 years, e.g., as compared to exposure of the allergen to a subject with the same or similar allergy who was not administered the probiotic strain and the prebiotic mixture.

In some embodiments, the prebiotic mixture, e.g., of human milk oligosaccharides, and the at least one probiotic strain, e.g., *B. longum* subsp. *infantis*, are administered to a subject to treat, ameliorate, remedy, or prevent pouchitis. In certain aspects, pouchitis is inflammation that occurs in the lining of a pouch created during surgery to treat ulcerative colitis or certain other diseases. In some embodiments, the surgery is or includes removal of a diseased colon or portion thereof. In certain embodiments, the surgery is a J pouch surgery (ileoanal anastomosis—IPAA).

In some embodiments, the prebiotic mixture, e.g., of human milk oligosaccharides, and the at least one probiotic strain, e.g., *B. longum* subsp. *infantis*, are administered to a subject to treat, ameliorate, remedy, or prevent pouchitis in a subject in need thereof, e.g., a subject who has undergone an IPAA surgery. In particular embodiments, administration of the prebiotic mixture and the at least one probiotic strain prevents, reduces, decreases, remedies, or ameliorates one or more symptoms associated with pouchitis. In certain embodiments, the one or more symptoms associated with pouchitis may include, but are not limited to, increased stool frequency, tenesmus, straining during defecation, blood in the stool, incontinence, seepage of waste matter during sleep, abdominal cramps, pelvic or abdominal discomfort, or tail bone pain. In certain embodiments, symptoms associated with more severe pouchitis include, but are not limited to, fever, dehydration, malnutrition, fatigue, iron-deficiency anemia, or joint pain. In particular embodiments, administration of the prebiotic mixture and the at least one probiotic strain reduces the risk or probability for the subject of experiencing pouchitis by, by about, or by at least 10%, 20%, 30%, 40%, 50%, 60%, 70%, 75%, 80%, 90%, or 95%, e.g., as compared to a subject not administered the at least one probiotic strain and/or the prebiotic mixture.

In various embodiments, the prebiotic mixture, e.g., of human milk oligosaccharides, and the at least one probiotic strain, e.g., *B. longum* subsp. *infantis*, are administered to a subject to treat, ameliorate, remedy, or prevent a chronic inflammatory disease, an autoimmune disease, an infection, bowel resection, and/or a condition associated with chronic diarrhea. Such pathology includes, but is not limited to: irritable bowel syndrome (IBS), inflammatory bowel disease (IBD), short bowel syndrome (SBS), celiac disease, small intestinal bacterial overgrowth (SIBO), gastroenteritis, leaky gut syndrome, and gastric lymphoma. In some embodiments the disease or disorder is associated with a bacterial, viral, or parasitic infection or overgrowth, e.g. by drug-resistant bacteria. In some embodiments, administration of the prebiotic mixture and the probiotic strain increases probability or likelihood for cure or remission of the chronic inflammatory disease, autoimmune disease, infection, bowel resection, and/or chronic diarrhea for by, by about, or by at least 10%, 20%, 30%, 40%, 50%, 60%, 70%, 75%, 80%, 90%, 100%, or 1-fold, 2-fold, 5-fold, 10-fold, 20-fold, 50-fold, or 100-fold e.g., as compared to a subject not administered the probiotic strain and prebiotic mixture and/or a subject administered an alternative therapy. In some embodiments, administration of the prebiotic mixture and the probiotic strain increases probability or likelihood for the cure or remission within 12 weeks, 10 weeks, 8 weeks, 6 weeks, 4 weeks, or less than 4 weeks, e.g., from the initiation or termination of the administration e.g., as compared to a subject not administered the probiotic strain and prebiotic mixture and/or a subject administered an alternative therapy.

In some embodiments, the prebiotic mixture, e.g., of human milk oligosaccharides, the probiotic strain, e.g., *B. longum* subsp. *infantis*, are administered to a subject to treat, ameliorate, remedy, or prevent pouchitis. In certain aspects, pouchitis is inflammation that occurs in the lining of a pouch created during surgery to treat ulcerative colitis or certain other diseases. In some embodiments, the surgery is or includes removal of a diseased colon or portion thereof. In certain embodiments, the surgery is a J pouch surgery (ileoanal anastomosis—IPAA).

In some embodiments, the prebiotic mixture, e.g., of human milk oligosaccharides, and the probiotic strain, e.g., *B. longum* subsp. are administered to a subject to treat, ameliorate, remedy, or prevent pouchitis in a subject in need thereof, e.g., a subject who has undergone an IPAA surgery. In particular embodiments, administration of the prebiotic mixture, and the probiotic strain prevents, reduces, decreases, remedies, or ameliorates one or more symptoms associated with pouchitis. In certain embodiments, the one or more symptoms associated with pouchitis may include, but are not limited to, increased stool frequency, tenesmus, straining during defecation, blood in the stool, incontinence, seepage of waste matter during sleep, abdominal cramps, pelvic or abdominal discomfort, or tail bone pain. In certain embodiments, symptoms associated with more severe pouchitis include, but are not limited to, fever, dehydration, malnutrition, fatigue, iron-deficiency anemia, or joint pain. In particular embodiments, administration of the prebiotic mixture, the probiotic strain, and the bacteriotherapy reduces the risk or probability for the subject of experiencing pouchitis by, by about, or by at least 10%, 20%, 30%, 40%, 50%, 60%, 70%, 75%, 80%, 90%, or 95%, e.g., as compared to a subject not administered the probiotic strain and/or the prebiotic mixture.

In some embodiments, the subject is a patient in an intensive care unit (ICU). In some embodiments, the subject is an organ transplant recipient. In some embodiments, the subject is a geriatric patient (e.g., at least 65, 70, 75, 80, or 85 years old). In some embodiments, the subject has received prolonged antibiotic treatment (e.g., at least 2, 3, 4, 5, 6, 8, 10, or 12 weeks, or at least 1, 2, 3, 6, 12, 18, or 24 months). In some embodiments, the subject is a recipient of a broad-spectrum antibiotic treatment. In some embodiments, the subject is a recipient, or recent recipient (e.g., within at least 1, 2, 3, 4, 5, 6, or 7 days, or within at least 1, 2, 3, or 4 weeks), of parenteral nutrition (e.g., total parenteral nutrition or partial parenteral nutrition). In some embodiments, the subject is a recipient of enteral nutrition.

i.) GVHD

In particular embodiments, provided herein are methods of preventing or reducing the incidence or severity of graft versus host disease (GVHD) in a subject in need thereof. In certain embodiments, the provided methods prevent or reduce incidence or severity of GVHD in a subject that has received or will receive an allogenic stem cell transplant. In some embodiments, the provided mixtures of HMOs are formulated to be administered to subjects who have, are, or will undergo an allogenic transplant, e.g., BMT or HSCT. In some embodiments, the at least one probiotic stain is formulated to be administered to subject who has underwent, is undergoing, or will undergo an allogenic transplant. In certain embodiments, the method is or includes steps for administering to the subject a prebiotic mixture, such as any described herein e.g., in Section I-A, and at least one probiotic strain, such as a probiotic strain described herein, e.g., in Section I-B or listed in Table 1.

In certain embodiments, the method is or includes administering a prebiotic mixture of non-digestible carbohydrates or HMOs, and at least one probiotic strain, e.g., *B. longum* subsp. *infantis*. In some embodiments, the method includes administering a prebiotic mixture of non-digestible carbohydrates or HMOs, such as any of those that are described herein, e.g., in Section I-A, and administering at least one probiotic strain, e.g., a *Bifidobacterium*, such as any one or more of those described herein, e.g., in Section I-B. In certain embodiments, the prebiotic mixture, e.g., HMOs, and the at least one probiotic strain, e.g., *B. longum* subsp. *infantis*, are administered separately, such as at different times or in separate compositions, formulations, or doses. In particular embodiments, the prebiotic mixture, e.g., of human milk oligosaccharides, and the at least one probiotic strain, e.g., *B. longum* subsp. *infantis*, are administered together, such as at the same time or in the same composition, formulation, or dose.

In certain embodiments, the prebiotic mixture of non-digestible carbohydrates is administered to treat, prevent, ameliorate, reduce, or decrease GVHD in a subject in need thereof. In some embodiments, the probiotic strain and the mixture of non-digestible carbohydrates are administered to treat, prevent, ameliorate, reduce, or decrease GVHD in a subject in need thereof. In certain embodiments, the subject is a mammal. In particular embodiments, the subject is a human. In certain embodiments, the subject is a human infant, child, adolescent, or adult. In particular embodiments, the subject is at risk or suspected of being at risk of having GVHD. In some embodiments, the GHVD is associated with, or accompanied by, an allogenic transplant, such as an allogenic bone marrow transplant (BMT) or an allogenic hematopoietic stem cell transplant (HSCT).

In some embodiments, the prebiotic mixture and the at least one probiotic strain is administered to a subject has undergone or will undergo an allogenic stem cell transplant. In certain embodiments, the allogenic transplant is a bone marrow transplant (BMT). In particular embodiments, the allogenic transplant is a hematopoietic stem cell transplantation (HSCT). In particular embodiments, the subject has undergone the allogenic stem cell transplant within 12 weeks, 8 weeks, 6 weeks, 4 weeks, 3 weeks, 2 weeks, 14 days, 12 days 10 days, 7 days, 5 days, 4 days, 3 days, 2 days, or 1 day prior to administration of a first dose of the prebiotic mixture or the at least one probiotic strain. In certain embodiments, the first dose of the prebiotic mixture or the at least one probiotic strain is administered within 12 weeks, 8 weeks, 6 weeks, 4 weeks, 3 weeks, 2 weeks, 14 days, 12 days 10 days, 7 days, 5 days, 4 days, 3 days, 2 days, or 1 day prior to receiving the allogenic stem cell transplant.

In some embodiments, provided herein are methods for treating, preventing, or ameliorating GVHD in a subject in need thereof. In certain embodiments, provided herein are methods for treating, preventing, or ameliorating a condition or disease associated or accompanied with GVHD in a subject in need thereof. In certain embodiments, provided herein are methods for treating, preventing, reducing, decreasing, or ameliorating the severity or presence of one or more symptoms associated with GVHD or a disease or condition associated or accompanied with GVHD in a subject in need thereof.

In particular embodiments, administration of the prebiotic mixture and the at least one probiotic strain reduces or decreases the probability or likelihood of experiencing GVHD. In certain embodiments, the probability or likelihood is reduced or decreased by at least 10%, 20%, 30%, 40%, 50%, 60%, 70%, 80%, 90%, 95%, or 99%, e.g., as compared to a subject not administered the prebiotic mixture or the at least one probiotic. In certain embodiments, the probability or likelihood of experiencing GVHD within 20 years, 10 years, 7 years, 5 years, 2 years or 1 year, or within the subject's lifetime, is reduced or decreased, e.g., as compared to a subject not administered the prebiotic mixture or the at least one probiotic.

In certain embodiments, the prebiotic mixture, e.g., HMOs, and the at least one probiotic strain, e.g., *B. longum* subsp. *infantis*, are administered to decrease or reduce mortality associated with an allogenic transplant, e.g., BMT or HSCT, or with GVHD. In some embodiments, the prebiotic mixture, e.g., HMOs, and the probiotic strain, e.g., *B. longum* subsp. *infantis*, are administered to increase survival of subjects who undergo an allogenic transplant, e.g., BMT or HSCT. In particular embodiments, administration of the prebiotic mixture, e.g., HMOs, and the probiotic strain, e.g., *B. longum* subsp. *infantis*, improves or increases the survival of the subject over 6 months, 12 months, 18 months, 1 year, 2 years, 5 years, 10 years, and/or 20 years or more by, by about, or by at least 5%, 10%, 20%, 25%, 30%, 40%, 50%, 60%, 70%, 75%, 80%, 90%, 95%, 100%, or 1-fold, 2-fold, 3-fold, 4-fold, or 5-fold greater than in subjects (e.g., subjects who received an allogenic transplant, e.g., BMT or HSCT) not administered the prebiotic mixture and the at least one probiotic strain.

In some embodiments, the prebiotic mixture, e.g., of human milk oligosaccharides, and the at least one probiotic strain, e.g., *B. longum* subsp. *infantis*, are administered to treat, prevent, ameliorate, reduce, or decrease the severity, occurrence, or likelihood of experiencing one or more symptoms, e.g., symptoms associated with or accompanying GHVD. In particular embodiments, the GVHD is acute GVHD. In some embodiments, the GVHD is chronic GVHD. In particular embodiments, the symptoms of GVHD are or include, but are not limited to, a rash, such as with burning or itching sensation; blistering, e.g., of the skin; flaking of the skin; nausea; vomiting; abdominal cramps; loss of appetite; diarrhea; and jaundice. In some embodiments, the symptoms of GVHD are or include, but are not limited to dry mouth, mouth ulcers, difficulty eating, gum disease, tooth decay, rash, itchy sensation, thickening and tightening of the skin, jaundice, changes in skin coloration, hair loss, premature gray hair, loss of body hair, loss of appetite, unexplained weight loss, nausea, vomiting diarrhea, stomach pain, shortness of breath, difficulty breathing, persistent or chronic cough, wheezing, impaired liver function, abdominal swelling, muscle weakness, muscle cramps, and joint stiffness. In particular embodiments, administration of the prebiotic mixture, e.g., HMOs, and the at least one probiotic strain, e.g., *B. longum* subsp. *infantis*, treats, prevents, ameliorates, reduces, or decreases the severity, occurrence, or likelihood of the one or more symptoms as compared to what is observed in subjects (e.g., subjects who have had or will undergo an allogeneic transplant) that are not administered the prebiotic mixture and the at least one probiotic strain. In some aspects, the presence, occurrence, and severity of a symptom may be recognized, identified, or scored by skilled person (e.g., a healthcare practitioner) as a matter of routine.

In certain embodiments, the provided methods are or include administering a prebiotic mixture and at least one probiotic strain to a subject who will undergo or who has undergone an allogenic transplant, e.g., a BMT or HSCT. In certain embodiments, the prebiotic mixture is a mixture of human milk oligosaccharides. In particular embodiments, the prebiotic mixture is a concentrated permeate, e.g., a concentrated permeate obtained from ultra-filtering skim from pooled human milk (such as described herein or produced by a method described herein, e.g., in Section I-A-(i). In certain embodiments, the prebiotic mixture is or incudes at least 10, 25, 50, or 80 different human milk oligosaccharides. In certain aspects, the at least one probiotic strain is a *Bifidobacterium*. In particular embodiments, the at least one probiotic strain is *B. longum* subsp. *infantis*. In certain embodiments, administration of a prebiotic mixture of human milk oligosaccharides and a probiotic strain of *B. longum* subsp. *infantis* reduces or decreases the probability or likelihood of experiencing GVHD. In some embodiments, administration of a prebiotic mixture of human milk oligosaccharides and a probiotic strain of *B. longum* subsp. *infantis* reduces the incidence or severity of one or more symptoms associated with GVHD.

C. Exemplary Methods and Features

In some embodiments, provided herein are methods of administering prebiotics, e.g., prebiotic mixtures of non-digestible carbohydrates such as human milk oligosaccharides, and at least one probiotic, e.g., a strain of *Bifidobacterium* such as *B. longum* subsp. *infantis*, to treat or prevent a disease, disorder, or condition associated with one or more of inflammation, infection, allergy, immune dysfunction, of dysbiosis of the intestinal microbiome in a subject in need thereof. In certain embodiments, the probiotic strain is capable of consuming (e.g., hydrolyzing) the prebiotics contained in the prebiotic mixture. In particular embodiments, the probiotic strain is capable of internalizing and consuming (e.g., hydrolyzing) the prebiotics of the prebiotic mixture. In various embodiments, the probiotic strain is capable of internalizing and consuming (e.g., hydrolyzing) human milk oligosaccharides, e.g., the human milk oligosaccharides of the prebiotic mixture. In particular embodiments, a probiotic strain that is capable of consuming, internalizing, and/or hydrolyzing a prebiotic is capable of consuming, internalizing, and/or hydrolyzing the prebiotic in vivo such within the human gut.

In certain embodiments, the provided methods are or include administering a prebiotic mixture that is or includes one or more human milk oligosaccharides and at least one probiotic strain that is or includes any of the probiotic strains listed in Table 1. In various embodiments, the method is or includes administering a probiotic strain of Bifidobacteria and a mixture of human milk oligosaccharides, such as to treat or prevent a disease, disorder, or condition associated with inflammation, infection, allergy, immune dysfunction, or dysbiosis of the intestinal microbiome. In certain embodiments, the method is or includes administering a probiotic strain of *B. breve, B. bifidum, B. longum* subsp. *infantis*, or *B. longum* subsp. *longum*. In particular embodiments, the prebiotic mixture is or includes a mixture of at least 5, 10, 25, 50, 100, 125, or 150 human milk oligosaccharides. In some embodiments, the prebiotic mixture is or includes synthetic human milk oligosaccharides. In particular embodiments, the prebiotic mixture is or includes a concentrated human milk permeate, e.g., a concentrated human milk permeate described herein such as in Section I-A-(i).

In some embodiments, provided herein is a method of treating or preventing a disease, disorder, or condition associated with one or more of inflammation, infection, allergy, immune dysfunction, of dysbiosis of the intestinal microbiome by administering a probiotic strain of *B. longum* subsp. *infantis* and a prebiotic mixture of at least 5, 10, 25, 50, or 100 human milk oligosaccharides. In certain embodiments, the prebiotic mixture is a concentrated human milk permeate described herein such as in Section I-A-(i), e.g., that comprises as least 50 or 100 human milk oligosaccharides. In certain embodiments, the disease, disorder, or condition is one or more of any of those described herein, e.g., in Section II-B.

In certain embodiments, the provided methods are or include administering a probiotic strain of *B. longum* subsp. *infantis* and a prebiotic mixture of at least 10, 25, 50, or 100 human milk oligosaccharides. In certain embodiments, the prebiotic mixture is a concentrated human milk permeate described herein such as in Section I-A-(i), e.g., that comprises as least 50 or 100 human milk oligosaccharides. In certain embodiments, the disease, disorder, or condition is one or more of any of those described herein, e.g., in Section II-B.

Particular embodiments contemplate that the probiotic strain and the prebiotic mixture treat or ameliorate dysbiosis. In certain embodiments, it is contemplated that correcting or restoring a healthy microbiome of a subject with a condition, disorder, or disease related to, associated with, or accompanied by dysbiosis will improve one or more symptoms of the condition, disease, or disorder and/or cure or trigger the remission of the condition, disease, or disorder. In some embodiments, treating or ameliorating dysbiosis includes one or more of increasing microbial diversity (e.g., alpha diversity) of the subject's microbiome, eliminating overgrowth or gut domination of one or more pathogens or pathobionts, reducing the presence or colonization of one or more pathogens within the subject's gut or microbiome, enhancement of the gut mucosal barrier, or suppression of GI inflammation. Certain embodiments contemplate that features associated with treated or ameliorated dysbiosis can be assessed by those of skill as a matter of routine.

In some embodiments, the prebiotic mixture and the probiotic strain may be administered over the course of a treatment regimen that may have more than one treatment phases. In some embodiments, an initial or first treatment phase is or includes one or more days where the probiotic strain, e.g., *B. longum* subsp. *infantis*, is administered. In some embodiments, the prebiotic mixture, e.g., of human milk oligosaccharides, is administered on the same days as the probiotic strain during the initial or first treatment phase. In certain embodiments, one or more subsequent treatment phases are or include one or more days where the prebiotic mixture but not the probiotic strain is administered. In particular embodiments, a prebiotic mixture of over 10, 25, or 50 human milk oligosaccharides, e.g., a concentrated human milk permeate (such as described herein or produced by a method described herein, e.g., in Section I-A-(i), are administered on the same days as a probiotic strain of *B. longum* subsp. *infantis* during the initial or first treatment phase. In certain embodiments, one or more subsequent treatment phases are or include one or more days where the prebiotic mixture but not *B. longum* subsp. *infantis* is administered.

Particular embodiments contemplate that the effectiveness of the provided methods relate, at least in part, to interactions, e.g., synergistic interactions, among the different compositions. For example, in some aspects, the provided methods more successfully correct or ameliorate dysbiosis and related disorders to a much greater extent than what would be expected from treatment with an alternative treatment, e.g., alternative medicaments, alternative probiotics, or alternative prebiotics, or from treatment with the prebiotic mixture or the probiotic strain alone. In certain embodiments, administration of a probiotic strain of *B.*

*longum* subsp. *infantis* and mixture of human milk oligosaccharides more successfully correct or ameliorate dysbiosis and related or disorders to a much greater extent than what would be expected from treatment with an alternative treatment, e.g., alternative medicaments, alternative probiotics, or alternative prebiotics, or from treatment with *B. longum* subsp. *infantis* or human milk oligosaccharides alone.

Certain embodiments contemplate that the prebiotic mixture, e.g., of human milk oligosaccharides, is selectively consumed in vivo by the probiotic, e.g., *B. longum* subsp. *infantis*. In some such embodiments, the prebiotic mixture directly promotes the growth and expansion of the probiotic while minimally promoting growth or expansion of other microbiota present in the host's microbiome or gut. In certain embodiments, the timing or dosage of the prebiotic mixture may be adjusted to affect the abundance of the probiotic strain in vivo. In particular embodiments, the mixture of human oligosaccharides directly promotes the growth and expansion of the *B. longum* subsp. *infantis* probiotic strain while minimally promoting growth or expansion of other microbiota present in the host's microbiome or gut. In certain embodiments, the timing or dosage of the human milk oligosaccharides may be adjusted to affect the abundance of the *B. longum* subsp. *infantis* probiotic strain in vivo.

In particular aspects, the probiotic strain, e.g., *B. longum* subsp. *infantis*, is capable of producing factors, such as acetate and lactate, which influence the intestinal environment in a manner that suppresses growth of pathogenic bacteria and favors the growth of beneficial bacteria. In some aspects, the consumption of these factors by microbiota present within the host's microbiome, e.g., butyrate producers, can result in production of other factors, e.g., butyrate, that will further influence the environment surrounding the microbiome, such as by promoting the health of the gut epithelium, improving host immune function, and inhibiting pathogenic taxa. Thus, in some aspects, timing or administration of the prebiotic mixture. In certain aspects, dosage and/or timing of administration of the prebiotic mixture, e.g., of human milk oligosaccharides, can influence, control, or tailor the production of factors produced within the subject's microbiome. Thus, in some aspects, the interplay between the prebiotic mixture, e.g., of human milk oligosaccharides, the probiotic strain, e.g., *B. longum* subsp. *infantis*, and microbiota within the subject's microbiome maximize the potential to correct dysbiosis within the host's microbiome.

In some embodiments, the probiotic strain is capable of consuming or metabolizing some or all of the prebiotic mixture, e.g., of HMOs, and furthermore, the prebiotic mixture is selectively utilized by the probiotic strain in vivo, e.g., as opposed to other bacteria present within the microbiome. Thus, in some aspects, an advantage of the provided methods is that the prebiotic mixture selectively feeds the probiotic strain, and thus minimizes the utilization of the prebiotics by other bacteria, allowing for a controlled interaction between the prebiotics and the probiotic strain. For example, in certain embodiments, the prebiotic mixture contains human milk oligosaccharides, which are not typically present in an adult diet and therefore not typically supplied to an adult human microbiome, and, in particular embodiments, the probiotic strain is *B. longum* subsp. *infantis*, which is capable of consuming HMO and is not typically detectable in an adult human microbiome. Thus, in particular aspects, the combination of the prebiotic mixture and probiotic strain greatly reduce the risk of unwanted or adverse effects by unintentionally promoting the growth of pathogenic bacteria.

In some aspects, the combination of the prebiotic mixture and the probiotic strain, e.g., the combination of human milk oligosaccharides and *B. longum* subsp. *infantis*, indirectly results in butyrate production through cross-feeding (e.g., by acetate and lactate production) to other members of the gut microbiota. In certain aspects, butyrate production within the microbiome benefits the subject. However, to maximize the benefits of this treatment, then butyrate producers would have to be present in the subject's microbiome. In certain aspects, this may not be the case with a dysbiotic microbiome. Thus, in some aspects, the bacteriotherapy serves, at least in part, to provide butyrate producing bacteria from a healthy microbiome, thus maximizing the benefits of the prebiotic/probiotic combination. Therefore, in certain aspects, the combination of all three of the prebiotic mixture, the probiotic strain, and the bacteriotherapy improve the clinical outcomes, consistency, and safety of the methods.

III. Compositions and Methods for Treating or Preventing Hyperammonemia

Also provided herein are compositions, methods, kits, and articles of manufacture that are useful, inter alia, in the treatment or prevention of hyperammonemia or related conditions and disorders in subjects in need thereof. In some aspects, provided herein is a prebiotic mixture with a low nitrogen content. In some embodiments, some, most, or all of the non-digestible carbohydrates or oligosaccharides of the prebiotic mixture lack or do not incorporate one or more nitrogen containing residues e.g., an N-acetyl glucosamine residue, or chemical groups, e.g., an N-acetyl group. In certain aspects, the low nitrogen containing prebiotic mixture is administered with or in addition to a probiotic strain of bacterium described herein, e.g., a *Bifidobacterium* such as *B. longum* subsp. *infantis*, capable of consuming or metabolizing oligosaccharides. In certain embodiments, one or both of the at least one probiotic strain of bacterium and the oligosaccharides are administered to a subject to treat, mend, remedy, ameliorate, or prevent hyperammonemia or one or more symptoms associated with hyperammonemia. In certain embodiments, the at least one probiotic strain is capable of consuming or metabolizing one or more of the oligosaccharides present in the mixture.

Ammonia is highly toxic and generated during metabolism. In mammals, the healthy liver protects the body from accumulating excess ammonia by converting it to non-toxic molecules, e.g., urea or glutamine, and preventing excess amounts of ammonia from entering the systemic circulation. Hyperammonemia is characterized by the decreased detoxification and/or increased production of ammonia. In healthy individuals, the urea cycle detoxifies ammonia by enzymatically converting ammonia into urea, which is then removed in the urine. Decreased ammonia detoxification may be caused by urea cycle disorders (UCDs) in which urea cycle enzymes are defective, such as argininosuccinic aciduria, arginase deficiency, carbamoylphosphate synthetase deficiency, citrullinemia, N-acetylglutamate synthetase deficiency, and ornithine transcarbamylase deficiency. In addition, several non-UCD disorders, such as hepatic encephalopathy, portosystemic shunting, and organic acid disorders, can also cause hyperammonemia. Hyperammonemia can produce neurological manifestations, e.g., seizures, ataxia, stroke-like lesions, coma, psychosis, vision loss, acute encephalopathy, cerebral edema, as well as vomiting, respiratory alkalosis, hypothermia, or death.

Current therapies for hyperammonemia, and associated conditions or diseases such as hepatic encephalopathy and UCDs, aim to reduce excess ammonia, but are widely regarded as suboptimal. For example, hepatic encephalopathy is associated with impairment of normal cognitive function due to confusion and memory loss, which can make it extremely difficult for individuals with hepatic encephalopathy to carry out repeated complex tasks such as preparing and timely taking their therapeutic agent regimen. Thus, it can be extremely difficult for individuals suffering from hepatic encephalopathy to carry out the various tasks required of compliance including preparing the therapeutic agents (i.e. mixing solutions) and remembering to take the therapeutic agents. Furthermore, the currently available treatments such as lactulose and Rifaximin can have side effects which patients may find unbearable, such as including but not limited to diarrhea, nausea, vomiting, gas, stomach pain and abdominal discomfort. In addition, lactulose, a traditional therapeutic, is unpalatable to most individuals. As such, compliance of hepatic encephalopathy patients with therapeutic regiment is relatively poor. Thus, there is significant unmet need for effective, reliable, and/or long-term treatment for disorders associated with hyperammonemia, including hepatic encephalopathy.

In some embodiments, compositions, methods, techniques, kits, and articles of manufacture are provided that address these needs. In some aspects, administration of one or both of a low nitrogen prebiotic mixture, e.g., human milk oligosaccharides lacking or containing low nitrogen, and the probiotic strain, e.g., *B. longum* subsp. *infantis*, efficiently reduces the levels of ammonia, and in particular aspects demonstrate an improved reduction of ammonia as compared to known existing treatments. In certain aspects, the low nitrogen prebiotic mixture, e.g., of human milk oligosaccharides lacking or containing low nitrogen, reduces the amount or level of ammonia in a subject with less or even none of the unwanted side effects that may accompany the known alternative treatments. Thus, the compositions, methods, techniques, kits, and articles of manufacture of the invention provide improved treatments for hyperammonemia and associated conditions such as hepatic encephalopathy or UCD.

In some aspects, ammonia is a major metabolic product of the gut microbiome. Much of the ammonia production is due to the breakdown of urea or the fermentative metabolism of amino acids. Thus, in some aspects, the microbiome may be considered a major source of ammonia, including in cases of hyperammonemia or associated conditions and disorders. In particular aspects, the low nitrogen prebiotic mixture, e.g., of human milk oligosaccharides lacking or containing low nitrogen, and the probiotic strain, e.g., a probiotic strain described herein, such as in Section I-B, reduces the presence, production, amount, and/or accumulation of ammonia by altering the composition and/or the metabolic activity of the microbiome. In some aspects, the low nitrogen prebiotic mixture and the probiotic strain reduce the production of ammonia by the microbiome. In certain aspects, the low nitrogen prebiotic mixture e.g., of human milk oligosaccharides lacking or containing low nitrogen, and the probiotic strain, e.g., *B. longum* subsp. *infantis*, increase the consumption of ammonia within the microbiome. In particular aspects, the low nitrogen prebiotic mixture and the probiotic strain increase the consumption of nitrogen sources such as amino acids, e.g., glutamine, within the microbiome. In some cases, the low nitrogen prebiotic mixture and the probiotic strain reduce levels of glutamine and therefore prevents catabolism of glutamine into glutamate and ammonia.

In particular embodiments, the low nitrogen prebiotic mixture, e.g., of human milk oligosaccharides lacking or containing low nitrogen, is or is capable of being utilized as the carbon source, but not as a nitrogen source, for commensal organisms in the gut. In certain embodiments, at least a portion of the oligosaccharides or non-digestible carbohydrates of the low nitrogen prebiotic mixture lack nitrogen or certain nitrogen containing residues, e.g., N-acetyl glucosamine residues or N-acetyl-neuraminic acid residues. In particular aspects, the low nitrogen prebiotic mixture, e.g., of human milk oligosaccharides lacking or containing low nitrogen, promotes the growth or expansion of microbes or bacteria that consume ammonia. In some aspects, the low nitrogen prebiotic mixture, e.g., of human milk oligosaccharides lacking or containing low nitrogen, promotes the growth or expansion of microbes or bacteria that consume nitrogen sources such as amino acids (e.g., glutamine) without or essentially without generating ammonia. In particular embodiments, administration of the low nitrogen prebiotic mixture reduces the amount, level, or presence of bacteria that produce ammonia, such as Enterobacteriaceae and other strains with urease activity.

In particular embodiments, the low nitrogen prebiotic mixture is administered to a subject that has been, is being, or will be administered at least one probiotic strain of bacterium. In some embodiments, the low nitrogen prebiotic mixture, e.g., of human milk oligosaccharides lacking or containing low nitrogen, is or is capable of being utilized as the carbon source, but not as a nitrogen source, for the at least one probiotic strain of bacterium, e.g., in the gut or microbiome. In certain embodiments, at least a portion of the non-digestible carbohydrates or oligosaccharides of the low nitrogen prebiotic mixture lack nitrogen or certain nitrogen containing residues, e.g., N-acetyl glucosamine residues or N-acetyl-neuraminic acid residues. In certain aspects, when administered to the same subject as the probiotic strain, the low nitrogen prebiotic mixture promotes the growth or expansion of the probiotic strain(s), e.g., *B. longum* subsp. *infantis*. In some aspects, this growth is accompanied with a nitrogen scavenging activity of the probiotic strain. In some embodiments, the probiotic strain reduces the levels of ammonia or amino acids, e.g., in the gut, directly by utilizing the ammonia as a nitrogen source, or indirectly, such as by depleting available amino acids or alternative nitrogen sources thereby increasing the utilization of ammonia or nitrogen sources by other bacteria of the microbiome.

In some embodiments, the engraftment, growth, or expansion of the probiotic strain, e.g., *B. longum* subsp. *infantis*, reduces the amount, level, or presence of bacteria that produce ammonia, such as Enterobacteriaceae and other species, subspecies, or strains of bacteria with urease activity. In certain embodiments, the probiotic strain is any one or more of the probiotic strains described herein, such as in Section I-B. In certain embodiments, the probiotic strain is or includes *B. longum* subsp. *infantis*.

In some aspects, an advantage of the provided mixture is that the non-digestible carbohydrates or oligosaccharides of the low nitrogen prebiotic mixture selectively promote the growth and expansion of the at least one probiotic strain in the human gut or human microbiome in vivo. Particular embodiments contemplate that, in some cases, the at least one probiotic strain may consume or internalize certain oligosaccharides in some environments, such as in vitro assays or in the gut or microbiome of non-human animals in vivo, but not in a human gut or microbiome. Thus, in some embodiments, while many kinds of oligosaccharides may promote the growth of the provided at least one probiotic strain, e.g., *B. longum* subsp. *infantis*, in vitro, the provided low nitrogen prebiotic mixture promotes the growth and expansion in the human gut in vivo.

In some embodiments, provided herein are compositions, methods, kits, and articles of manufacture that are useful, inter alia, in the treatment or prevention of hyperammonemia or related conditions and disorders. In some aspects, the provided compositions, methods, kits, or articles of manufacture are or include a low nitrogen prebiotic mixture of oligosaccharides and at least one strain of probiotic bacteria. In some aspects, the probiotic bacteria strain is capable of internalizing and metabolizing the oligosaccharides. In certain aspects, the oligosaccharides contain low amounts of nitrogen, e.g., lower than what would be a sufficient amount to serve as the sole source of nitrogen for the probiotic bacteria. In particular embodiments, administration of the at least one probiotic strain and oligosaccharides to a subject in need thereof reduces or prevents an increase of the amount or level of ammonia, e.g., in the gut.

In certain embodiments, provided herein is a composition or kit comprising a low nitrogen prebiotic mixture of oligosaccharides; wherein (i) the prebiotic mixture is free or essentially free of oligosaccharides that incorporate an N-acetyl glucosamine residue or (ii) the percentage by weight of oligosaccharides comprising nitrogen in the mixture is less than 50%. In certain embodiments, the composition or kit further comprises at least one probiotic strain of bacterium capable of consuming each oligosaccharide of the mixture. In particular embodiments, the at least one probiotic strain is capable of internalizing each oligosaccharide of the mixture.

In some embodiments, provided herein is a composition or kit comprising a low nitrogen prebiotic mixture of oligosaccharides, wherein: (i) each oligosaccharide of the mixture is a human oligosaccharide (HMO); (ii) each oligosaccharide of the mixture comprises two or fewer nitrogen atoms; and (iii) the percentage by weight of oligosaccharides in the mixture comprising one or two nitrogen atoms is less than 25%, 20%, 10%, 5%, or 1%.

In certain embodiments, provided herein is a composition or kit comprising 2'-fucosyllactose, 3-fucosyllactose, difucosyllactose, 3'-sialyllactose, and 6'-sialyllactose and a strain of *B. longum* subsp. *infantis*. In particular embodiments, provided herein is a composition comprising 2'-fucosyllactose, 3-fucosyllactose, and difucosyllactose, and at least one strain of *B. longum* subsp. *infantis*.

In some embodiments, the composition or the compositions within the kit are used in the manufacture of a medicament for the treatment or prevention of hyperammonemia or to reduce ammonia in a subject in need thereof.

In particular embodiments, provided herein is a method of treating hyperammonemia, comprising administering to a subject in need thereof a composition described herein or one or more of the compositions of a kit described herein. In some embodiments, provided herein is a method of treating hyperammonemia, comprising administering to a subject in need thereof a low nitrogen prebiotic mixture of oligosaccharides, wherein (i) the mixture is free or essentially free of oligosaccharides that incorporate an N-acetyl glucosamine residue or (ii) the percentage by weight of oligosaccharides comprising nitrogen in the mixture is less than 50%. In certain embodiments, provided herein is a method of decreasing the level or amount of ammonia in a subject in need thereof, comprising administering to a subject a low nitrogen prebiotic mixture of oligosaccharides, wherein (i) the mixture is free or essentially free of oligosaccharides that incorporate an N-acetyl glucosamine residue or (ii) the percentage by weight of oligosaccharides in the mixture comprising nitrogen is less than 50%. In certain embodiments, the method further comprises administering at least one probiotic strain of bacterium capable of consuming each oligosaccharide of the prebiotic mixture.

In certain embodiments, provided herein is a method of treating hyperammonemia, comprising administering to a subject in need thereof (i) a low nitrogen prebiotic mixture of oligosaccharides, wherein all or essentially all of the oligosaccharides of the mixture are human milk oligosaccharides (HMOs) that do not incorporate an N-acetyl glucosamine residue, and (ii) at least one probiotic strain of bacterium, wherein the at least one probiotic bacterium strain is at least one *Bifidobacterium* strain capable of consuming HMOs. In particular embodiments, provided herein is a method of treating hyperammonemia, comprising administering to a subject in need thereof (i) a low nitrogen prebiotic mixture of oligosaccharides, wherein all or essentially all of the oligosaccharides of the mixture are human milk oligosaccharides (HMOs) that do not incorporate an N-acetyl glucosamine residue, and (ii) at least one probiotic strain of bacterium, wherein the at least one probiotic bacterium strain is at least one *Bifidobacterium* strain capable of internalizing HMOs.

In some embodiments, provided herein is a method of reducing ammonia in a subject in need thereof, comprising administering to a subject (i) a low nitrogen prebiotic mixture of oligosaccharides, wherein all or essentially all of the oligosaccharides of the mixture are human milk oligosaccharides (HMOs) that do not incorporate an N-acetyl glucosamine residue, and (ii) at least one probiotic strain of bacterium, wherein the at least one probiotic bacterium strain is at least one *Bifidobacterium* strain capable of internalizing HMOs.

In certain embodiments, one or both of the at least one probiotic bacteria strain and the low nitrogen prebiotic mixture are enterically coated.

In certain embodiments, provided herein is a method of treating hyperammonemia comprising administering to a subject in need thereof a low nitrogen prebiotic mixture comprising 2'-fucosyllactose, 3-fucosyllactose, difucosyllactose, 3'-sialyllactose, and 6'-sialyllactose and at least one strain of *B. longum* subsp. *infantis*.

In certain embodiments, provided herein is a method of treating hyperammonemia comprising administering to a subject in need thereof a low nitrogen prebiotic mixture comprising 2'-fucosyllactose, 3-fucosyllactose, and difucosyllactose and at least one strain of *B. longum* subsp. *infantis*.

In particular embodiments, provided herein is an article of manufacture comprising any of the compositions or kits described herein and instructions for use. In certain embodiments, the instructions describe any of the methods described herein.

In particular embodiments, the low nitrogen prebiotic mixture comprises one or more human milk oligosaccharides (HMOs). In some embodiments, all or essentially all of the oligosaccharides of the mixture are HMOs. In certain embodiments, the mixture is free or essentially free of oligosaccharides that incorporate an N-acetyl glucosamine residue. In particular embodiments, the mixture is free or essentially free of oligosaccharides that incorporate an N-acetyl glucosamine residue or an N-acetyl-neuraminic acid residue. In some embodiments, the percentage by weight of oligosaccharides in the mixture comprising nitrogen is less than 50%. In certain embodiments, the percentage by weight of oligosaccharides in the mixture comprising nitrogen is less than 40%, 30%, 25%, 20%, 10%, 5%, or 1%. In particular embodiments, the mixture is free or essentially free of oligosaccharides that comprise nitrogen.

In some embodiments, the low nitrogen prebiotic mixture comprises at least 2, at least 3, at least 4, at least 5, at least 6, or at least 7 different oligosaccharides, e.g., that lack or contain low nitrogen. In certain embodiments, the percentage by weight of oligosaccharides in the mixture comprising more than five monosaccharide residues is less than 50%. In particular embodiments, the percentage by weight of oligosaccharides in the mixture comprising five or more monosaccharide residues is less than 40%, 30%, 25%, 20%, 10%, 5%, or 1%. In some embodiments, the mixture is free or essentially free of oligosaccharides that comprise nitrogen. In certain embodiments, the composition is free or essentially free of oligosaccharides comprising five or more monosaccharide residues.

In particular embodiments, the molecular weight of each oligosaccharide of the prebiotic mixture is below or below about 1,000 g/mol. In some embodiments, the molecular weight of each oligosaccharide of the mixture is below or below about 750 g/mol.

In particular embodiments, the at least one probiotic strain is a *Bifidobacterium* strain, optionally a strain of *B. breve, B. bifidum*, or *B. longum*. In certain embodiments, the at least one probiotic strain is at least one strain of *B. longum* subsp. *infantis*.

In particular embodiments, the low nitrogen prebiotic mixture comprises one or more of 2'-fucosyllactose (2'-FL), 3-fucosyllactose (3-FL), 3'-sialyllactose (3'-SL), 6'-sialyllactose (6'-SL), difucosyllactose, lacto-N-tetraose (LNT), and Lacto-N-Neotetraose (LNnT). In some embodiments, the low nitrogen prebiotic mixture comprises one or more of 2'-fucosyllactose, 3-fucosyllactose, difucosyllactose, 3'-sialyllactose, or 6'-sialyllactose. In certain embodiments, the prebiotic mixture comprises 2'-fucosyllactose, 3-fucosyllactose, difucosyllactose, 3'-sialyllactose, and 6'-sialyllactose.

In particular embodiments, the low nitrogen prebiotic mixture consists or consists essentially of 2'-fucosyllactose, 3-fucosyllactose, difucosyllactose, 3'-sialyllactose, and 6'-sialyllactose. In some embodiments, the low nitrogen prebiotic mixture comprises one or more of 2'-fucosyllactose, 3-fucosyllactose, or difucosyllactose. In certain embodiments, the prebiotic mixture comprises 2'-fucosyllactose, 3-fucosyllactose, and difucosyllactose. In particular embodiments, the oligosaccharides of the mixture consist or consist essentially of 2'-fucosyllactose, 3-fucosyllactose, and difucosyllactose.

In particular embodiments, the rate of ammonia/nitrogen depletion in a culture comprising the at least one probiotic strain and the prebiotic low nitrogen mixture of oligosaccharides is at least 10% greater than in a cell culture comprising the probiotic strain and a combination of at least 50, 100, or 150 HMOs derived from pooled human milk or from a concentrated ultra-filtered human milk permeate, and wherein the percentage by weight of nitrogen in the mixture is less than that of the combination.

In some embodiments, the subject in need thereof has, is at risk of having, or is suspected of having hyperammonemia. In certain embodiments, the subject in need thereof has, is suspected of having, or is at risk of having hepatic encephalopathy. In particular embodiments, the subject in need thereof has, is suspected of having, or is at risk of having a urea cycle disorder.

A.) Low Nitrogen Prebiotic Mixtures

In particular embodiments, the low nitrogen prebiotic mixture contains little or no nitrogen, and therefore, in certain aspects, is not a significant nitrogen source for a probiotic strain or an intestinal microbiome. In some embodiments, the low nitrogen prebiotic mixture, e.g., of human milk oligosaccharides lacking or containing low nitrogen, promotes the growth or expansion of the probiotic strain, e.g., in vivo such as in the human gut. In certain embodiments, the low nitrogen prebiotic mixture promotes, e.g., selectively or exclusively, the colonization, expansion, extension, or increased presence of the probiotic strain within the microbiome. In some embodiments, the low nitrogen prebiotic mixture selectively provides a carbon source, but not a nitrogen source, for the probiotic strain. In particular embodiments, low nitrogen prebiotic mixture promotes the growth or expansion of a probiotic strain of bacterium described herein, e.g., in Table 1, and/or a *Bifidobacterium* such as *B. longum* subsp. *infantis*, in vivo such as in the human gut. In certain embodiments, the low nitrogen prebiotic mixture promotes, e.g., selectively or exclusively, the colonization, engraftment, expansion, extension, or increased presence of the probiotic strain, e.g., of a probiotic strain of bacterium described herein, e.g., in Table 1, and/or a *Bifidobacterium* such as *B. longum* subsp. *infantis*, within the microbiome.

In particular embodiments, the low nitrogen prebiotic mixture is a mixture of at least two, at least three, at least four, at least five, at least six, at least seven, at least eight, at least nine, at least ten, at least twenty, at least fifty, or at least one hundred non-digestible carbohydrates, e.g., that contain no or low nitrogen content. In certain embodiments, the low nitrogen prebiotic mixture is a mixture of at least two, at least three, at least four, at least five, at least six, at least seven, at least eight, at least nine, at least ten, at least twenty, at least fifty, or at least one hundred oligosaccharides, e.g., that contain no or low nitrogen content. In certain embodiments, the low nitrogen prebiotic mixture is or includes one or more oligosaccharides, e.g., that contain no or low nitrogen content, that are obtained from milk, e.g., human milk. In certain embodiments, the mixture is or includes one or more oligosaccharides, e.g., that contain no or low nitrogen content, that are synthesized, e.g., chemically or through fermentation. In particular embodiments, the mixture is or includes one or more synthetic human milk oligosaccharides.

In some embodiments, the oligosaccharides or non-digestible carbohydrates of the low nitrogen prebiotic mixture are capable of being internalized and metabolized by the probiotic strain. In certain embodiments, the oligosaccharides or non-digestible carbohydrates of the low nitrogen prebiotic mixture are capable of being internalized and metabolized by one or more strains, species, or subspecies of *Bifidobacterium*. In some embodiments, the oligosaccharides or non-digestible carbohydrates of the low nitrogen prebiotic mixture are capable of being internalized and metabolized by one or more strains, species, or subspecies listed in Table 1. In certain embodiments, all or a portion of the oligosaccharides or non-digestible carbohydrates of the mixture lack or do not incorporate one or more nitrogen containing residues, such as an N-acetyl glucosamine residue. In some embodiments, all or a portion of the oligosaccharides or non-digestible carbohydrates of the mixture do not incorporate N-acetyllactoseamine, lacto-N-biose, or sialic acid. In certain embodiments, all or a portion of the oligosaccharides or non-digestible carbohydrates of the mixture lack an N-acetyl group. In particular embodiments, all or a portion of the oligosaccharides or non-digestible carbohydrates of the mixture lack nitrogen. In certain embodiments, all or a portion of the oligosaccharides or non-digestible carbohydrates of the mixture (i) are capable of being internalized and metabolized by a strain, species, or subspecies of *Bifidobacterium*, e.g., *B. longum* subsp. *infantis*, and (ii) lack or do not incorporate or contain N-acetyl glucosamine residues, N-acetyl groups, or nitrogen.

In some embodiments, the low nitrogen prebiotic mixture is or includes one or more oligosaccharides. In some embodiments, the oligosaccharides may be internalized by a probiotic strain, e.g., of a probiotic strain of bacterium described herein, e.g., in Table 1, and/or a *Bifidobacterium* such as *B. longum* subsp. *infantis*. In some embodiments, the oligosaccharides may include one or more of a fructo-oligosacharide (FOS), galactooligosaccharide (GOS), trans-galactooligosaccharide (TOS), gluco-oligosaccharide, xylo-oligosaccharide (XOS), chitosan oligosaccharide (COS), soy oligosaccharide (SOS), isomalto-oligosaccharide (IMOS), or derivatives thereof. In certain embodiments, such derivatives include those with modifications that may increase the likelihood or probability of consumption, metabolism, and/or internalization (such as by transport or import) of the oligosaccharide by the at least one probiotic strain, e.g., *B. longum* subsp. *infantis*. Such modifications may include but are not limited to fucosylation or sialylation. In some embodiments, the oligosaccharides of the mixture may include one or more of a FOS, GOS, TOS, gluco-oligosaccharide, XOS, COS, SOS, IMOS, or derivatives or any or all of the foregoing, that are capable of being metabolized, consumed, and/or internalized by one or more strains, species, or subspecies of *Bifidobacterium*, e.g., *B. longum* subsp. *infantis*. In certain embodiments, the oligosaccharides of the mixture include one or more oligosaccharides that are obtained or derived from a resistant starch, pectin, psyllium, arabinogalactan, glucomannan, galactomannan, xylan, lactosucrose, lactulose, lactitol and various other types of gums such as tara gum, acacia, carob, oat, bamboo, citrus fibers, such as by treatment with enzymes that hydrolyze fiber or polysaccharides. In some embodiments, the one or more oligosaccharides of the mixture that are obtained by these means are capable of being consumed, metabolized, and/or internalized by the probiotic strain, at least one strain of *Bifidobacterium* such as *B. longum* subsp. *infantis*.

In certain embodiments, the low nitrogen prebiotic mixture is or includes one or more oligosaccharides found in a mammalian milk. In certain embodiments, the mammalian milk oligosaccharides are derived from or found milk that includes but is not limited to milk from camel, goat, cow, yak, buffalo, horse, donkey, zebu, sheep, reindeer, giraffe, elephant, non-human primate, or human. In some embodiments, all or a portion of the oligosaccharides of the low nitrogen prebiotic mixture are human milk oligosaccharides, e.g., at least 25%, 50%, 75%, 90%, 95%, or 99% of the oligosaccharide by either i) the percentage of oligosaccharide species present in the mixture or ii) by total weight of the oligosaccharides in the mixture. In certain embodiments, all or essentially all of the oligosaccharides of the mixture are human milk oligosaccharides.

In certain embodiments, the oligosaccharides, e.g., human milk oligosaccharides, of the low nitrogen prebiotic mixture are between three and twenty monosaccharide residues in length. In particular embodiments, all or a portion of the oligosaccharides of the mixture are less than twenty, eighteen, sixteen, fourteen, twelve, ten, nine, eight, seven, six, five, or four monosaccharide residues in length. In particular embodiments, all or a portion of the oligosaccharides are between three and twenty, three and fifteen, three and ten, three and eight, three and five, or three and four monosaccharide residues in length, each inclusive. In particular embodiments, all of the oligosaccharides of the mixture are between three and five monosaccharide residues in length. In certain embodiments, all of the oligosaccharides are between three and four monosaccharide residues in length.

In particular embodiments, the oligosaccharides, e.g., human milk oligosaccharides of the low nitrogen prebiotic mixture have a molecular weight of between or between about 300 kDa and 5,000 kDa. In certain embodiments, all or a portion (e.g., at least 50%, 60%, 70%, 80%, 90%, 95%, 99%, or 99.9%) of the oligosaccharides have a molecular weight of, of about, or of less than 5,000 kDa, 4,000 kDa, 3,000 kDa, 2,500 kDa, 2,000 kDa, 1,800 kDa, 1,600 kDa, 1,500 kDa, 1,400 kDa, 1,200 kDa, 1,000 kDa, 900 kDa, 800 kDa, 750 kDa, 600 kDa, or 500 kDa. In particular embodiments, all or a portion of the oligosaccharides have a molecular weight of, of about, or of less than 2,500 kDa. In certain embodiments, all or a portion of the oligosaccharides of the mixture have a molecular weight of, of about, or of less than 1,500 kDa. In some embodiments, all or a portion of the oligosaccharides have a molecular weight of, of about, or of less than 1,000 kDa. In particular embodiments, all or a portion of the oligosaccharides have a molecular weight of, of about, or of less than 750 kDa. In particular embodiments, the or a portion of the oligosaccharides are between or between about 300 kDa and 5,000 kDa, 400 kDa and 1,500 kDa, 450 and 1,000 kDa, or 450 kDa and 750 kDa.

In particular embodiments, the low nitrogen prebiotic mixture does not provide a sufficient amount of nitrogen to the probiotic strain, e.g., *B. longum* subsp. *infantis*, to serve as a nitrogen source for the probiotic strain in vivo, e.g., in the human gut. In particular embodiments, one or more of the oligosaccharides of the mixture lack an N-acetyl glucosamine residue. In some embodiments, all or substantially all of the oligosaccharides lack an N-acetyl glucosamine residue. In certain embodiments, one or more of the oligosaccharides lack an N-acetyl group. In some embodiments, all or substantially all of the oligosaccharides lack an N-acetyl group. In certain embodiments, one or more of the oligosaccharides lack nitrogen. In some embodiments, all or substantially all of the oligosaccharides lack nitrogen.

In particular embodiments, the low nitrogen prebiotic mixture has a low nitrogen content. In some embodiments, the low nitrogen content is, is about, or is less than 0.1 g, 0.01 g, 0.001 g, 0.1 mg, 0.01 mg, 0.001 mg, 0.1 ng, 0.01 ng, 0.001 ng, 0.1 pg, 0.01 pg, 0.001 pg, 0.1 fg, 0.01 fg, or 0.001 fg, of nitrogen per gram of the mixture. In certain embodiments, the low nitrogen content is less than 0.01 g of nitrogen per gram of the mixture. In some embodiments, the low nitrogen content is less than 1 mg per gram of the mixture. In particular embodiments, the low nitrogen content is less than 1 ng per gram of the mixture.

In some embodiments, the low nitrogen prebiotic mixture includes less than 0.1 g, 0.01 g, 0.001 g, 0.1 mg, 0.01 mg, 0.001 mg, 0.1 ng, 0.01 ng, 0.001 ng, 0.1 pg, 0.01 pg, 0.001 pg, 0.1 fg, 0.01 fg, or 0.001 fg, of nitrogen per gram of oligosaccharides, e.g., human milk oligosaccharides. In certain embodiments, low nitrogen prebiotic mixture includes less than 0.01 g of nitrogen per gram of oligosaccharides. In some embodiments, low nitrogen prebiotic mixture includes less than 25 mg of nitrogen per gram of oligosaccharides. In some embodiments, low nitrogen prebiotic mixture includes less than 5 mg of nitrogen per gram of oligosaccharides.

In certain embodiments, the low nitrogen content is or includes a weight or mass of nitrogen that is, is about, or is less than 5%, 1%, 0.5%, 0.1%, 0.05%, 0.01%, 0.005%, 0.0001%, 0.00005%, or 0.00001% of the total weight or mass of the low nitrogen prebiotic mixture. In some embodiments, the low nitrogen content is a weight or mass of nitrogen that is, is about, or is less than 0.05% of the total weight or mass of the mixture. In particular embodiments, the low nitrogen content is a weight or mass of nitrogen that is, is about, or is less than 0.05% of the total weight or mass of the mixture. In particular embodiments, the low nitrogen content is a weight or mass of nitrogen that is, is about, or is less than 0.01% of the total weight or mass of the mixture. In some embodiments, the low nitrogen content is a weight or mass of nitrogen that is, is about, or is less than 0.001% of the total weight or mass of the mixture.

In certain embodiments, the low nitrogen content is less than 50, less than 25, less than 10, less than 9, less than 8, less than 7, less than 6, less than 5, less than 4, less than 3, less than 2, less than 1, or less than 0.5, 0.1, 0.01, 0.001, 0.0001, or 0.00001 moles of nitrogen per mole of oligosaccharides, e.g., human milk oligosaccharides, of the mixture. In certain embodiments, the low nitrogen content is less than one mole nitrogen per mole of oligosaccharides in the mixture. In particular embodiments, the low nitrogen content is less than 0.1 moles nitrogen per mole of oligosaccharides in the mixture. In some embodiments, the nitrogen content is less than 0.01 moles nitrogen per mole of oligosaccharides in the mixture. In some embodiments, low nitrogen prebiotic mixture includes less than 50, less than 25, less than 10, less than 9, less than 8, less than7, less than 6, less than 5, less than 4, less than 3, less than 2, less than 1, or less than 0.5, 0.1, 0.01, 0.001, 0.0001, or 0.00001 moles of nitrogen per mole of oligosaccharides of the mixture. In certain embodiments, the low nitrogen prebiotic mixture includes less than one mole nitrogen per mole of oligosaccharides in the mixture. In particular embodiments, the low nitrogen prebiotic mixture includes less than 0.1 moles nitrogen per mole of oligosaccharides in the mixture. In some embodiments, the low nitrogen prebiotic mixture includes less than 0.01 moles nitrogen per mole of oligosaccharides in the mixture.

In certain embodiments, the low nitrogen prebiotic mixture is or includes one or more oligosaccharides, e.g., human milk oligosaccharides, that lack an N-acetyl glucosamine residue, an N-acetyl group, or nitrogen. In some embodiments, the portion of oligosaccharides in the mixture that lack an N-acetyl glucosamine residue is, is about, or is at least 25%, 40%, 50%, 60%, 70%, 75%, 80%, 85%, 90%, 95%, 98%, 99%, 99.9%, or 99.99% of the mixture, e.g., by weight. In certain embodiments, the portion of oligosaccharides in the mixture that lack an N-acetyl group is, is about, or is at least 25%, 40%, 50%, 60%, 70%, 75%, 80%, 85%, 90%, 95%, 98%, 99%, 99.9%, or 99.99% of the mixture, e.g., by weight. In particular embodiments, the portion of oligosaccharides in the mixture that lack nitrogen is, is about, or is at least 25%, 40%, 50%, 60%, 70%, 75%, 80%, 85%, 90%, 95%, 98%, 99%, 99.9%, or 99.99% of the mixture, e.g., by weight.

In some embodiments, the low nitrogen prebiotic mixture is or includes one or more oligosaccharides, e.g., human milk oligosaccharides, that do not contain or incorporate an N-acetyl glucosamine residue, N-acetyl groups, or nitrogen. In some embodiments, the portion of oligosaccharides in the mixture that contains or includes an N-acetyl glucosamine residue is, is about, or is less than 60%, 50%, 40%, 30% 25%, 20%, 10%, 5%, 1%, 0.1%, or 0.01% of the mixture, e.g., by weight. In some embodiments, the oligosaccharides of the mixture that contain or incorporate an N-acetyl glucosamine residue contain or incorporate less than seven, six, five, four, three, or two N-acetyl glucosamine residues. In certain embodiments, the oligosaccharides of the mixture that contain or incorporate an N-acetyl glucosamine residue contain two or fewer N-acetyl glucosamine residues. In certain embodiments, the oligosaccharides in the mixture that contain an N-acetyl glucosamine residue contain only a single N-acetyl glucosamine residue.

In particular embodiments, the portion of oligosaccharides, e.g., human milk oligosaccharides, in the mixture that contains an N-acetyl group is, is about, or is less than 60%, 50%, 40%, 30% 25%, 20%, 10%, 5%, 1%, 0.1%, or 0.01% of the mixture, e.g., by weight. In some embodiments, the oligosaccharides in the mixture that contain an N-acetyl group contain or contain less than seven, six, five, four, three, two, or one an N-acetyl groups. In certain embodiments, the oligosaccharides in the mixture that contain an N-acetyl group contain two or fewer an N-acetyl groups. In certain embodiments, the oligosaccharides in the mixture that contain an N-acetyl group contain a single an N-acetyl group.

In certain embodiments, the portion of oligosaccharides, e.g., human milk oligosaccharides, in the mixture that contains nitrogen is, is about, or is less than 60%, 50%, 40%, 30% 25%, 20%, 10%, 5%, 1%, 0.1%, or 0.01% of the mixture, e.g., by weight. In some embodiments, the oligosaccharides in the mixture that contain nitrogen contain or contain less than seven, six, five, four, three, two, or one nitrogen atoms. In certain embodiments, the oligosaccharides in the mixture that contain nitrogen contain two or fewer nitrogen atoms. In certain embodiments, the oligosaccharides in the mixture that contain nitrogen contain a single nitrogen atom.

In particular embodiments, low nitrogen prebiotic mixture, e.g., of non-digestible carbohydrates such as human milk oligosaccharides with no or low nitrogen, is free or essentially free of N-acetyl glucosamine residues. In certain embodiments, the low nitrogen prebiotic mixture is free or essentially free of N-acetyl groups. In certain embodiments, the low nitrogen prebiotic mixture, e.g., HMOs, is free or essentially free of nitrogen. In certain embodiments, all or substantially all of the oligosaccharides of the mixture lack N-acetyl glucosamine residues. In certain embodiments, all or substantially all of the oligosaccharides lack N-acetyl groups. In certain embodiments, all or substantially all of the oligosaccharides lack nitrogen. In certain embodiments, all or substantially all of the oligosaccharides of the mixture are human milk oligosaccharides that lack N-acetyl glucosamine residues. In certain embodiments, all or substantially all of the oligosaccharides of the mixture are human milk oligosaccharides that lack N-acetyl groups. In certain embodiments, all or substantially all of the oligosaccharides of the mixture are human milk oligosaccharides that lack nitrogen.

In certain embodiments, all or a portion of the non-digestible carbohydrates or oligosaccharides of the mixture are human milk oligosaccharides or derivatives thereof. In certain embodiments, the human milk oligosaccharide derivatives are or include human milk oligosaccharides that have been modified to remove a nitrogen or nitrogen containing group, e.g., an N-acetyl group. In certain embodiments, all or a portion of the oligosaccharides or non-digestible carbohydrates of the mixture are human milk oligosaccharides, or derivatives thereof, that contain no more than 20, 15, 10, 9, 8, 7, 6, 5, 4, 3, 2, or 1 nitrogen atoms, e.g., per molecule. In particular embodiments, all of the oligosaccharides or non-digestible carbohydrates of the mixture are human milk oligosaccharides, or derivatives thereof, that contain no more than 5 nitrogen atoms. In some embodiments, all of the non-digestible carbohydrates or oligosaccharides of the mixture are human milk oligosaccharides, or derivatives thereof, that have no more than 2 nitrogen atoms. In some embodiments, all of the non-digestible carbohydrates or oligosaccharides of the mixture are human milk oligosaccharides, or derivatives thereof, that have either one or no nitrogen atoms. In particular embodiments, all of the non-digestible carbohydrates or oligosaccharides of the mixture are human milk oligosaccharides that lack nitrogen.

In some embodiments, all or a portion of the oligosaccharides of the mixture have a molar percentage of nitrogen of less than 20%, 15%, 10%, 5%, 2.5%, 1%, 0.1% or 0.01%. In certain embodiments, all or essentially all of the oligosaccharides of the mixture have a molar percentage of nitrogen of less than 20%, 15%, 10%, 5%, 2.5%, 1%, 0.1% or 0.01%. In certain embodiments, all or essentially all of the oligosaccharides of the mixture have a molar percentage of nitrogen of less than 5%. In some embodiments, all or essentially all of the oligosaccharides of the mixture have a molar percentage of nitrogen of less than 2.5%. In particular embodiments, all or essentially all of the oligosaccharides of the mixture have a molar percentage of nitrogen of less than 1%.

In certain embodiments, the low nitrogen prebiotic mixture has a molar percentage of nitrogen of less than 20%, 10%, 5%, 2.5%, 1%, 0.1%, 0.01%, 0.001%, or 0.0001%. In some embodiments, the low nitrogen prebiotic mixture has a molar percentage of nitrogen of less than 2.5%. In certain embodiments, the low nitrogen prebiotic mixture has a molar percentage of nitrogen of less than 1%. In certain embodiments, the low nitrogen prebiotic mixture has a molar percentage of nitrogen of less than 0.1%.

In certain embodiments, all or a portion of the non-digestible carbohydrates or oligosaccharides of the mixture are human milk oligosaccharides, or derivatives thereof, that have no more than 20, no more than 10, no more than 8, no more than 6, no more than 5, no more than 4, or no more than 3 monosaccharide residues. In particular embodiments, all of the non-digestible carbohydrates or oligosaccharides of the mixture are human milk oligosaccharides, or derivatives thereof, that have no more than five monosaccharide residues. In some embodiments, all of the non-digestible carbohydrates or oligosaccharides of the mixture are human milk oligosaccharides, or derivatives thereof, that have no more than four monosaccharide residues. In some embodiments, all of the non-digestible carbohydrates or oligosaccharides of the mixture are human milk oligosaccharides, or derivatives thereof, that have between three and five monosaccharide residues.

In certain embodiments, the low nitrogen prebiotic mixture is or includes one or more human milk oligosaccharides that contain two or fewer nitrogen atoms. In particular embodiments, the low nitrogen prebiotic mixture is or includes one or more human milk oligosaccharides with between three and five monosaccharide residues. In some embodiments, the non-digestible carbohydrates or oligosaccharides of the mixture are all human milk oligosaccharides that contain between zero and two nitrogen atoms. In some embodiments, the non-digestible carbohydrates or oligosaccharides of the mixture are all human milk oligosaccharides that contain between zero and one nitrogen atoms. In certain embodiments, the non-digestible carbohydrates or oligosaccharides of the mixture are all human milk oligosaccharides that contain between three and five monosaccharide residues. In particular embodiments, all of the non-digestible carbohydrates or oligosaccharides of the mixture are human milk oligosaccharides that contain between zero and two nitrogen atoms and between three and five saccharide residues.

In certain embodiments, the low nitrogen prebiotic mixture is or includes one or more of 2'-Fucosyllactose (2'-FL), 3-fucosyllactose (3-FL), 3'-sialyllactose (3'-SL), 6'-sialyllactose (6'-SL), 6'-Sialyl-N-acetyllactosamine (6'-SLN), Difucosyllacto-N-hexaose (DFLNH(a)), Difucosyl-Lacto-N-hexaose b (DFLNH(b))difucosyllactose (DFL), Disialyllacto-N-tetraose (DSLNT), Fucosyl-p-lacto-N-hexaose (FpLNH), Lactodifucotetraose (LDFT), Lacto-N-difucohexaose I (LNDFH I), Lacto-N-difucohexaose II (LNDFH II), Lacto-N-fucopentaose I (LNFP I), Lacto-N-fucopentaose II (LNFP II), Lacto-N-fucopentaose III (LNFP III), Lacto-N-fucopentaose V (LNFP V), lacto-N-hexaose (LNH), Lacto-N-neohexaose (LNnH), Lacto-N-Neotetraose (LNnT), lacto-N-tetraose (LNT), Fucosyl-lacto-N-hexaose (FLNH), LS-Tetrasaccharide a (LST a), LS-Tetrasaccharide b (LST b), LS-Tetrasaccharide c (LST c), Monofucosyllacto-N-hexaose III (MFLNH-III), Sialyl-3-fucosyllactose (3'-S, 3-FL), Sialyl-N-acetyllactosamine (3'-SLN), or Trifucosyllacto-N-hexaose (TFLNH).

In some embodiments, the non-digestible carbohydrates or oligosaccharides of the mixture are all of or are selected from 2'-Fucosyllactose (2'-FL), 3-fucosyllactose (3-FL), 3'-sialyllactose (3'-SL), 6'-sialyllactose (6'-SL), 6'-Sialyl-N-acetyllactosamine (6'-SLN), Difucosyllacto-N-hexaose (DFLNH(a)), Difucosyl-Lacto-N-hexaose b (DFLNH(b))difucosyllactose (DFL), Disialyllacto-N-tetraose (DSLNT), Fucosyl-p-lacto-N-hexaose (FpLNH), Lactodifucotetraose (LDFT), Lacto-N-difucohexaose I (LNDFH I), Lacto-N-difucohexaose II (LNDFH II), Lacto-N-fucopentaose I (LNFP I), Lacto-N-fucopentaose II (LNFP II), Lacto-N-fucopentaose III (LNFP III), Lacto-N-fucopentaose V (LNFP V), lacto-N-hexaose (LNH), Lacto-N-neohexaose (LNnH), Lacto-N-Neotetraose (LNnT), lacto-N-tetraose (LNT), Fucosyl-lacto-N-hexaose (FLNH), LS-Tetrasaccharide a (LST a), LS-Tetrasaccharide b (LST b), LS-Tetrasaccharide c (LST c), Monofucosyllacto-N-hexaose III (MFLNH-III), Sialyl-3-fucosyllactose (3'-S,3-FL), Sialyl-N-acetyllactosamine (3'-SLN), or Trifucosyllacto-N-hexaose (TFLNH).

In certain embodiments, the low nitrogen prebiotic mixture is or includes one or more of 2'-Fucosyllactose (2'-FL), Lacto-N-Neotetraose (LNnT). In some embodiments, the non-digestible carbohydrates or oligosaccharides of the mixture are 2'-Fucosyllactose (2'-FL) and Lacto-N-Neotetraose (LNnT). In certain embodiments, the low nitrogen prebiotic mixture is or includes one or more of 2'-Fucosyllactose (2'-FL), 3-fucosyllactose (3-FL), 3'-sialyllactose (3'-SL), 6'-sialyllactose (6'-SL), lacto-N-tetraose (LNT). In particular embodiments, the non-digestible carbohydrates or oligosaccharides of the mixture are all of or are selected from 2'-Fucosyllactose (2'-FL), 3-fucosyllactose (3-FL), 3'-sialyllactose (3'-SL), 6'-sialyllactose (6'-SL), lacto-N-tetraose (LNT).

In certain embodiments, the low nitrogen prebiotic mixture is or includes one or more of 2'-Fucosyllactose (2'-FL), 3-fucosyllactose (3-FL), 3'-sialyllactose (3'-SL), 6'-sialyllactose (6'-SL), difucosyllactose, lacto-N-tetraose (LNT), or Lacto-N-Neotetraose (LNnT). In particular embodiments, the non-digestible carbohydrates or oligosaccharides of the mixture are all of or are selected from 2'-Fucosyllactose (2'-FL), 3-fucosyllactose (3-FL), 3'-sialyllactose (3'-SL), 6'-sialyllactose (6'-SL), difucosyllactose, lacto-N-tetraose (LNT), and lacto-N-Neotetraose (LNnT).

In certain embodiments, the low nitrogen prebiotic mixture is or includes one or more of 2'-fucosyllactose (2'-FL), 3-fucosyllactose (3-FL), 3'-sialyllactose (3'-SL), 6'-sialyllactose (6'-SL), LS-Tetrasaccharide a (LST a), LS-Tetrasaccharide b (LST b), or LS-Tetrasaccharide c (LST c). In certain embodiments, the non-digestible carbohydrates or oligosaccharides of the mixture are all of or are selected from 2'-Fucosyllactose (2'-FL), 3-fucosyllactose (3-FL), 3'-sialyllactose (3'-SL), 6'-sialyllactose (6'-SL), LS-tetrasaccharide a (LST a), LS-tetrasaccharide b (LST b), and LS-tetrasaccharide c (LST c).

In some embodiments, low nitrogen prebiotic mixture is or includes one or more of 2'-fucosyllactose, 3-fucosyllactose, difucosyllactose, 3'-sialyllactose, or 6'-sialyllactose. In certain embodiments, the all of the oligosaccharides of the mixture are selected from 2'-fucosyllactose, 3-fucosyllactose, difucosyllactose, 3'-sialyllactose, and 6'-sialyllactose. In particular embodiments, low nitrogen prebiotic mixture is or includes one or more of 2'-fucosyllactose, 3-fucosyllactose, or difucosyllactose. In certain embodiments, the all of the oligosaccharides of the mixture are selected from 2'-fucosyllactose, 3-fucosyllactose, or difucosyllactose.

In certain embodiments, low nitrogen prebiotic mixture is a mixture of, e.g., consisting essentially of, 2'-fucosyllactose, 3-fucosyllactose, difucosyllactose, 3'-sialyllactose, and 6'-sialyllactose. In particular embodiments, low nitrogen prebiotic mixture is a mixture of, e.g., consisting essentially of, 2'-fucosyllactose, 3-fucosyllactose, and difucosyllactose.

B.) Probiotic Strains Useful for the Treatment of Hyperammonemia

In particular embodiments, the probiotic strain is a probiotic strain described herein, such as in Section I-B. In certain embodiments, a probiotic strain useful for the treatment of hyperammonemia or a related disorder or condition is or includes any of the probiotic strains described herein, e.g., in Section I-B. In some embodiments, *B. longum* subsp. *infantis* and the low nitrogen prebiotic mixture are useful for treating or preventing hyperammonemia in a subject in need thereof.

C.) Exemplary Compositions, Kits, and Articles of Manufacture

In some embodiments, the provided compositions, kits, or articles of manufacture include a low-nitrogen prebiotic mixture, e.g., as described herein such as in Section III-A. In some embodiments, the low nitrogen content may be due, at least in part, to (i) a low portion, e.g., less than 50%, 25%, 10%, or 1%, by weight or number, oligosaccharides containing nitrogen or functional groups or monosaccharide residues containing nitrogen atoms, (ii) a relatively small size of the oligosaccharides, e.g., such that the mixture contains only oligosaccharides that have five or fewer monosaccharide residues, (iii) a low molar ratio of nitrogen atoms within the oligosaccharides of the mixture to the total number of oligosaccharides, e.g., below 1, 0.1, or 0.01 moles of nitrogen per mole of total oligosaccharides, or (iv) a combination of any or all of the foregoing. In particular embodiments, the low nitrogen prebiotic mixture is free or essentially free of oligosaccharides that contain nitrogen. In certain embodiments, the low nitrogen prebiotic mixture is or includes a mixture of 2'-fucosyllactose, 3-fucosyllactose, difucosyllactose, 3'-sialyllactose, and 6'-sialyllactose. In certain embodiments, the composition is or includes a mixture of 2'-fucosyllactose, 3-fucosyllactose, and difucosyllactose. In certain aspects, the low nitrogen prebiotic mixture may be formulated as a pharmaceutical composition or a nutritional composition.

In certain embodiments, provided herein are kits that include a low nitrogen prebiotic mixture. In some embodiments, the kit includes a low nitrogen prebiotic mixture described herein, e.g., in Section III-A. In certain embodiments, the kit includes human milk oligosaccharides with no or low nitrogen content. In some embodiments, the kit includes a mixture of 2'-fucosyllactose, 3-fucosyllactose, difucosyllactose, 3'-sialyllactose, and 6'-sialyllactose. In particular embodiments, the kit includes a mixture of 2'-fucosyllactose, 3-fucosyllactose, and difucosyllactose.

In some embodiments, the provided composition is or includes a low nitrogen prebiotic mixture described herein, e.g., in Section III-A, and at least one probiotic strain of bacterium described herein, e.g., in Section I-B or III-B. In some embodiments, the probiotic strain includes at least one strain, species, or subspecies of *Bifidobacterium* capable of consuming or metabolizing human milk oligosaccharides, e.g., *B. longum* subsp. *infantis*. The probiotic strain may be formulated as a pharmaceutical composition or a nutritional composition.

In particular embodiments, provided herein are kits that include a low nitrogen prebiotic mixture and at least one strain of probiotic bacterium. In some embodiments, the kit includes a low nitrogen prebiotic mixture described herein, e.g., in Section III-A, and the probiotic strain of described herein, e.g., in Section I-B or III-B. In some embodiments, the probiotic strain and the low nitrogen prebiotic mixture are contained or formulated together within the same composition. In particular embodiments, the at least one probiotic strain and the low nitrogen prebiotic mixture are separate, e.g., have been formulated or prepared into separate compositions, such that for example the mixture and the probiotic strain may be administered to a subject separately, e.g., at different times or days. In some embodiments, the kit includes at least one strain, species, or subspecies of *Bifidobacterium* capable of internalizing HMOs and a mixture of HMOs with a low nitrogen content. In particular embodiments, the kit includes at least one strain of *B. longum* subsp. *infantis* and a mixture of 2'-fucosyllactose, 3-fucosyllactose, difucosyllactose, 3'-sialyllactose, and 6'-sialyllactose. In certain embodiments, the kit includes at least one strain of *B. longum* subsp. *infantis* and a mixture of 2'-fucosyllactose, 3-fucosyllactose, and difucosyllactose.

In some embodiments, a composition or a kit described herein is included in an article of manufacture. In certain embodiments, the article of manufacture includes a label or instructions for use that provide instructions, e.g., to a skilled medical practitioner and/or a subject or patient, for administering the low nitrogen prebiotic mixture, e.g., of human milk oligosaccharides containing no or low nitrogen, and the probiotic strain, e.g., *B. longum* subsp. *infantis*. In some embodiments, the label or instructions provide instructions for performing any of the methods described herein, e.g., in Section III-D.

D.) Method for Treating Hyperammonemia

In some embodiments, provided herein are methods for treating, preventing, or ameliorating hyperammonemia in a subject in need thereof. In certain embodiments, provided herein are methods for treating, preventing, or ameliorating a condition or disease associated or accompanied with hyperammonemia in a subject in need thereof. In certain embodiments, provided herein are methods for treating, preventing, reducing, decreasing, or ameliorating the severity or presence of one or more symptoms associated with hyperammonemia or a disease or condition associated or accompanied with hyperammonemia in a subject in need thereof. In particular embodiments, provided herein are methods for decreasing or reducing ammonia in a subject in need thereof.

In certain embodiments, the method is or includes administering a low nitrogen prebiotic mixture, e.g., of human milk oligosaccharides containing no or low nitrogen, to a subject. In particular embodiments, the method includes administering a low nitrogen prebiotic mixture, such as any of those that are described herein, e.g., in Section III-A. In some embodiments, the administration of the low nitrogen prebiotic mixture achieves a growth or expansion of commensal bacteria in vivo, e.g., within the microbiome of a subject. In particular embodiments, the oligosaccharides of the mixture selectively or exclusively serve as a carbon or energy source for commensal bacteria that consume ammonia or consume other nitrogen sources such as amino acids, without or essentially without producing ammonia.

In certain embodiments, a prebiotic mixture, e.g., of human milk oligosaccharides, having a low nitrogen content is administered to a subject, e.g., a subject having or suspected of having hyperammonemia. In particular embodiments, the oligosaccharides of the mixture do not provide a sufficient source of nitrogen to the subject's microbiome.

In some embodiments, administration of the low nitrogen prebiotic mixture, e.g., of human milk oligosaccharides containing no or low nitrogen, reduces or decreases plasma ammonia concentrations in a subject. In certain embodiments, the low nitrogen prebiotic mixture and the probiotic strain, e.g., *B. longum* subsp. *infantis*, are administered to treat, prevent, ameliorate, reduce, or decrease the severity, occurrence, or likelihood of experiencing one or more symptoms, e.g., symptoms associated with or accompanying hyperammonemia. In some embodiments, the mixture of oligosaccharides, e.g., HMOs, is administered to decrease or reduce mortality associated with hyperammonemia. In particular embodiments, the low nitrogen prebiotic mixture is administered to increase survival of subjects (e.g., subjects having hyperammonemia, a UCD, or hepatic encephalopathy).

In certain embodiments, administration of the low nitrogen prebiotic mixture, e.g., of human milk oligosaccharides containing no or low nitrogen, reduces or decreases the level, amount, activity (e.g., ammonia production or urease activity), or number of bacteria present in the microbiome that generate or are capable of generating ammonia. In particular embodiments, administration of the low nitrogen prebiotic mixture increases the level, amount, activity, or number of bacteria in the microbiome that scavenge, utilize, metabolize, absorb, consume, and/or deplete ammonia. In some embodiments, administration of the low nitrogen prebiotic mixture increases, promotes, raises, or accelerates the activity of the microbiome to scavenge, utilize, metabolize, absorb, consume, and/or deplete ammonia.

In particular embodiments, the low nitrogen prebiotic mixture is administered to treat, prevent, ameliorate, reduce, or decrease the severity of one or more symptom(s) associated with diseases or disorders associated with or accompanied by hyperammonemia.

In some embodiments, the method is or includes administering a low nitrogen prebiotic mixture, e.g., of human milk oligosaccharides containing no or low nitrogen, and a probiotic strain described herein such as in Section I-B or III-B, e.g., *B. longum* subsp. *infantis*. In some embodiments, the method includes administering a low nitrogen prebiotic mixture, such as any of those that are described herein, e.g., in Section III-A, and administering the probiotic strain, e.g., *B. longum* subsp. *infantis*. In certain embodiments, the low nitrogen prebiotic mixture and the probiotic strain are administered separately, such as at different times or in separate compositions, formulations, or doses. In particular embodiments, the low nitrogen prebiotic mixture and the probiotic strain are administered together, such as at the same time or in the same composition, formulation, or dose.

In some embodiments, administration of the low nitrogen prebiotic mixture and the probiotic strain is synergistic. In particular embodiments, growth or expansion of the probiotic strain is not observed or is not detectable when the low nitrogen prebiotic mixture is administered without any administration of the probiotic strain. In certain embodiments, growth or expansion of the probiotic strain is not observed or is not detectable when the probiotic strain is administered without any administration of the low nitrogen prebiotic mixture. In certain embodiments, administration of the low nitrogen prebiotic mixture and the probiotic strain reduces the level or amount of ammonia in a subject to a greater degree than what would be expected based on the reduction observed when the at least one probiotic or the mixture are administered alone.

In particular embodiments, the low nitrogen prebiotic mixture does not provide a sufficient source of nitrogen to the probiotic strain, e.g., in vivo such as in the human microbiome or gut. In certain embodiments, administration of the low nitrogen prebiotic mixture and the probiotic strain, e.g., *B. longum* subsp. *infantis*, result in the growth or expansion of the probiotic strain in vivo, such as in the human gut. In some embodiments, the growth or expansion of the probiotic strain in vivo reduces the amount or level of ammonia, e.g., in the human gut or microbiome. In certain aspects, the probiotic strain utilizes ammonia as a nitrogen source. In particular embodiments, the probiotic strain utilizes available nitrogen sources alternative to ammonia, such as amino acids, thereby reducing available nitrogen resources for other bacteria and, in certain embodiments, increasing ammonia consumption by the other bacteria present in the gut or microbiome.

In certain embodiments, the low nitrogen prebiotic mixture is administered to treat, prevent, ameliorate, reduce, or decrease hyperammonemia in a subject in need thereof. In some embodiments, the probiotic strain and the low nitrogen prebiotic mixture are administered to treat, prevent, ameliorate, reduce, or decrease hyperammonemia in a subject in need thereof. In certain embodiments, the subject is a mammal. In particular embodiments, the subject is a human. In certain embodiments, the subject is a human infant, child, adolescent, or adult. In particular embodiments, the subject is a human having, suspected of having, or at risk of having hyperammonemia. In some embodiments, the hyperammonemia is caused by, associated with, or accompanied by decreased detoxification and/or increased production of ammonia.

In some embodiments, the methods are or include administering the low nitrogen prebiotic mixture to a subject, e.g., a subject in need thereof such as a subject having or suspected of having hyperammonemia or a related condition or disorder, to expand or maintain the amount, growth, or presence of a probiotic strain in the gut or microbiome of the subject. In some embodiments, the probiotic strain has been administered to the subject. In some embodiments, the probiotic strain is or will be administered to the subject. In certain embodiments, the probiotic strain is exogenous to the subject's microbiome, e.g., the probiotic strain is not present in the subject's gut or microbiome prior to an initial administration of the probiotic strain.

In some embodiments, the subject has, is suspected of having, or is at risk of having hepatic encephalopathy. In some embodiments, the subject has, is suspected of having, or is at risk of having Hepatitis A, Hepatitis B, Hepatitis C, Alcohol-related Liver Disease, Non-alcoholic Fatty Liver Disease (NAFLD), Non-alcoholic Steatohepatitis (NASH), Autoimmune Hepatitis, bile duct disease, e.g., Primary Biliary Cirrhosis (PBC) or Primary Sclerosing Cholangitis (PSC), Metabolic diseases such as Hemochromatosis, or Wilson disease and Alpha-1 antitrypsin deficiency. In certain embodiments, the subject has or is at risk of having hyperammonemia or hepatic encephalopathy associated with or accompanying one or more of Hepatitis B, Hepatitis C, Alcohol-related Liver Disease, NAFLD, NASH, Autoimmune Hepatitis, bile duct disease (e.g., PBC or PSC), or a Metabolic disease (e.g., Hemochromatosis, or Wilson disease and Alpha-1 antitrypsin deficiency).

In some embodiments, the subject has or is at risk of having hyperammonemia that is associated with or caused or accompanied by decreased detoxification of ammonia. In some embodiments, the decreased detoxification is caused or accompanied by or is associated with urea cycle disorders (UCDs). In certain embodiments, the decreased detoxification is caused or accompanied by or is associated with a decreased activity of the liver, such as from bypass of the liver, e.g., open ductus hepaticus; and/or deficiencies in glutamine synthetase. In some embodiments, the hyperammonemia is associated with or caused or accompanied by a liver disorder such as hepatic encephalopathy, acute liver failure, or chronic liver failure. In some embodiments, the hyperammonemia is associated with or caused or accompanied by neurodegenerative disorders such as Huntington's Disease.

In particular embodiments, the subject has, is at risk of having, or is suspected of having a UCD. In some aspects, current treatment for subjects with UCD require substantially modified diets consisting of protein restriction that must be carefully monitored. Treatments for subjects with a UCD may require supplementation with ammonia scavenging drugs, such as sodium phenylbutyrate, sodium benzoate, and glycerol phenylbutyrate, which in some cases must be administered three to four times per day. Side effects of these drugs include nausea, vomiting, irritability, lack of appetite and anorexia. In children, the delivery of food and medication may require a gastrostomy tube surgically implanted in the stomach or a nasogastric tube manually inserted through the nose into the stomach. When these treatment options fail, a liver transplant may be required.

In some embodiments, one or both of the low nitrogen prebiotic mixture and the probiotic strain, e.g., *B. longum* subsp. *infantis*, is administered to a subject without the need for a diet with restricted or reduced protein. In some embodiments, administration of one or both of the low nitrogen prebiotic mixture and the probiotic strain, e.g., *B. longum* subsp. *infantis*, reduces ammonia, e.g., plasma ammonia levels, in a subject not undergoing a restricted diet, e.g. with restricted or reduced protein.

In certain embodiments, the UCD is argininosuccinic aciduria, arginase deficiency, carbamoylphosphate synthetase deficiency, citrullinemia, N-acetylglutamate synthetase deficiency, or ornithine transcarbamylase deficiency. In some embodiments, the low nitrogen prebiotic mixture is administered to treat, prevent, ameliorate, reduce, or decrease hyperammonemia in a subject having or suspected of having a UCD. In particular embodiments, the low nitrogen prebiotic mixture is administered to lower ammonia levels, e.g., plasma ammonia levels and/or ammonia present in the gut of a subject having or suspected of having a UCD. In certain embodiments, the low nitrogen prebiotic mixture and the probiotic strain, e.g., *B. longum* subsp. *infantis*, are administered to treat, prevent, ameliorate, reduce, or decrease hyperammonemia in a subject having or suspected of having a UCD. In particular embodiments, the low nitrogen prebiotic mixture and the probiotic strain, e.g., *B. longum* subsp. *infantis*, are administered to lower ammonia levels, e.g., plasma ammonia levels and/or ammonia present in the gut of a subject having or suspected of having a UCD.

In some embodiments, the low nitrogen prebiotic mixture and the probiotic strain, e.g., *B. longum* subsp. *infantis*, are administered to a subject having or suspected of having increased production of ammonia. In some embodiments, the increased production of ammonia is caused by or is associated or accompanied by an infection, effects of a drug or medication, neurogenic bladder, or intestinal bacterial overgrowth.

In some embodiments, the subject has or is suspected of having a disease, disorder, or condition associated with hyperammonemia. In some embodiments, the disease, disorder, or condition is a liver disorders such as hepatic encephalopathy, acute liver failure, or chronic liver failure; an organic acid disorder; isovaleric aciduria; 3-methylcrotonylglycinuria; methylmalonic acidemia; propionic aciduria; a fatty acid oxidation defect; a carnitine cycle defect; a carnitine deficiency; a β-oxidation deficiency; a lysinuric protein intolerance; a pyrroline-5-carboxylate synthetase deficiency; a pyruvate carboxylase deficiency; an ornithine aminotransferase deficiency; a carbonic anhydrase deficiency; a hyperinsulinism-hyperammonemia syndrome; a mitochondrial disorder; valproate therapy; asparaginase therapy; total parenteral nutrition; cystoscopy with glycine-containing solutions; post-lung/bone marrow transplantation; portosystemic shunting; a urinary tract infection; ureter dilation; multiple myeloma; or chemotherapy.

In some embodiments, a diagnostic signal of hyperammonemia is a plasma ammonia concentration of at least or at least about 50 pmol/L, 80 pmol/L, 150 pmol/L, 180 pmol/L, or 200 pmol/L. In some aspects, healthy subjects, e.g., human subjects not having or suspected of having hyperammonemia, have a plasma ammonia concentration of less than or less than about 50 pmol/L. In particular embodiments, one or both of the low nitrogen prebiotic mixture and the probiotic strain, e.g., *B. longum* subsp. *infantis*, are administered to a subject having a plasma ammonia level of, of about, or greater than 50 pmol/L. In some embodiments, the low nitrogen prebiotic mixture and the probiotic strain, e.g., *B. longum* subsp. *infantis*, are administered to a subject having a plasma ammonia level of, of about, or greater than 50 pmol/L. In particular embodiments, one or both of the low nitrogen prebiotic mixture and the probiotic strain, e.g., *B. longum* subsp. *infantis*, are administered to a subject to reduce the plasma level to less than or less than about 50 pmol/L. In certain embodiments, the low nitrogen prebiotic mixture and the probiotic strain, e.g., *B. longum* subsp. *infantis*, are administered to a subject to reduce the plasma level to less than or less than about 50 pmol/L.

In some embodiments, administration of one or both of the low nitrogen prebiotic mixture and the one or more probiotic strain, e.g., *B. longum* subsp. *infantis*, reduces or decreases plasma ammonia concentrations in a subject. In certain embodiments, administration of the low nitrogen prebiotic mixture and the one or more probiotic strain, e.g.,

*B. longum* subsp. *infantis*, reduces or decreases plasma ammonia concentrations in a subject. In certain embodiments, the plasma ammonia concentration is reduced or decreased by, by about, or by at least 1 pmol/L, 5 pmol/L, 10 pmol/L, 20 pmol/L, 30 pmol/L, 40 pmol/L, 50 pmol/L, 100 pmol/L, or at least 200 pmol/L.

In some embodiments, administration of one or both of the provided low nitrogen prebiotic mixture and one or more probiotic strain of bacterium reduce the ammonia concentration in a subject by at least or at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the ammonia concentration in a subject before and after administration of the pharmaceutical composition. In some embodiments, the method of treating or ameliorating hyperammonemia allows one or more symptoms of the condition or disorder to improve by at least about 10%, 20%, 30%, 40%, 50%, 60%, 70%, 80%, 90%, 95%, or more. In some embodiments, administration of one or both of the low nitrogen prebiotic mixture and the probiotic strain, e.g., *B. longum* subsp. *infantis*, reduces or decreases plasma ammonia concentrations in a subject.

In some embodiments, the low nitrogen prebiotic mixture and the probiotic strain, e.g., *B. longum* subsp. *infantis*, are administered to treat, prevent, ameliorate, reduce, or decrease the severity, occurrence, or likelihood of experiencing one or more symptoms, e.g., symptoms associated with or accompanying hyperammonemia, a UCD, or hepatic encephalopathy. In particular embodiments, the symptoms are or include confusion, decreased attention span, memory impairments, mood swings, changes in personality, inappropriate behavior, difficultly with simple mental tasks (e.g., simple or basic arithmetic), altered sleep patterns, impaired fine motor skills (e.g., difficulty writing), slurred speech, confusion, anxiety, disorientation (e.g., regarding time and place), shaking or arms or hands (flapping), or impaired speech. In certain embodiments, the symptoms include severe symptoms such as unresponsiveness or coma. In particular embodiments, administration of the low nitrogen prebiotic mixture and the probiotic strain, e.g., *B. longum* subsp. *infantis*, treats, prevents, ameliorates, reduces, or decreases the severity, occurrence, or likelihood of the one or more symptoms as compared to what is observed in subjects (e.g., subjects having hyperammonemia, a UCD, or hepatic encephalopathy) that are not administered the low nitrogen prebiotic mixture and/or the probiotic strain. In certain embodiments, administration of the low nitrogen prebiotic mixture and the probiotic strain, e.g., *B. longum* subsp. *infantis*, treats, prevents, ameliorates, reduces, or decreases the severity, occurrence, or likelihood of the one or more symptoms as compared to what was observed in the subject prior to the administration. In some aspects, the presence, occurrence, and severity of a symptom may be recognized, identified, or scored by skilled person (e.g., a healthcare practitioner) as a matter of routine.

In certain embodiments, the low nitrogen prebiotic mixture and the probiotic strain, e.g., *B. longum* subsp. *infantis*, are administered to decrease or reduce mortality associated with hyperammonemia, a UCD, or hepatic encephalopathy. In some embodiments, the low nitrogen prebiotic mixture and the probiotic strain, e.g., *B. longum* subsp. *infantis*, are administered to increase survival of subjects (e.g., subjects having hyperammonemia, a UCD, or hepatic encephalopathy). In particular embodiments, administration of the low nitrogen prebiotic mixture and the probiotic strain, e.g., *B. longum* subsp. *infantis*, improves or increases the survival of the subject over 6 months, 12 months, 18 months, 1 year, 2 years, 3 years, 4 years, or 5 years by, by about, or by at least 5%, 10%, 20%, 25%, 30%, 40%, 50%, 60%, 70%, 75%, 80%, 90%, 95%, 100%, or 1-fold, 2-fold, 3-fold, 4-fold, or 5-fold greater than in subjects (e.g., subjects having hyperammonemia, a UCD, or hepatic encephalopathy) not administered the low nitrogen prebiotic mixture and/or the probiotic strain.

In certain embodiments, administration of the low nitrogen prebiotic mixture and probiotic strain of bacterium, e.g., *B. longum* subsp. *infantis*, reduces the level, amount, or number of bacteria present in the microbiome that generates or is capable of generating ammonia. In particular embodiments, the growth of the probiotic strain, e.g., *B. longum* subsp. *infantis*, within the gut or microbiome reduces the amount, level, activity, or presence of bacteria that produce ammonia, such as Enterobacteriaceae and other strains with urease activity. In certain embodiments, administration of the low nitrogen prebiotic mixture and the probiotic strain, e.g., *B. longum* subsp. *infantis*, reduces the amount, level, activity, or presence of Enterobacteriaceae by, by about, or by at least 10%, 20%, 30%, 40%, 50%, 60%, 70%, 75%, 80%, 90%, 95%, or 100%, e.g., as compared to prior to the administration or as compared to the gut or microbiome of a subject not administered the probiotic strain and/or the mixture of oligosaccharides. In particular embodiments, administration of the low nitrogen prebiotic mixture and the probiotic strain, e.g., *B. longum* subsp. *infantis*, reduces the amount, level, or presence of urease activity or ammonia production by, by about, or by at least 10%, 20%, 30%, 40%, 50%, 60%, 70%, 75%, 80%, 90%, 95%, or 100%, e.g., as compared to prior to the administration or as compared to the gut or microbiome of a subject not administered the probiotic strain and/or the mixture of oligosaccharides.

In certain embodiments, subjects administered one or both of the low nitrogen prebiotic mixture and the probiotic strain, e.g., *B. longum* subsp. *infantis*, experience fewer side effects or experience less severe side effects than a subject administered lactulose or Rifaximin. In particular embodiments, a subject administered one or both of the low nitrogen prebiotic mixture and one or both of the low nitrogen prebiotic mixture and the probiotic strain, does not experience one or more of diarrhea, nausea, vomiting, gas, stomach pain, or abdominal discomfort. In particular embodiments, a subject administered one or both of the low nitrogen prebiotic mixture and the probiotic strain, e.g., *B. longum* subsp. *infantis*, experiences less frequent or less severe episodes of diarrhea, nausea, vomiting, gas, stomach pain, or abdominal discomfort, e.g., as compared to a subject administered lactulose or Rifaximin.

In some embodiments, subjects, e.g., subjects having, suspected of having, or at risk of having hyperammonemia or related condition, are administered one or both of the low nitrogen prebiotic mixture and the probiotic strain, e.g., *B. longum* subsp. *infantis*, and experience fewer infections or less severe infections than subjects administered an alternative treatment, e.g., lactulose or Rifaximin. In particular embodiments, a subject administered one or both of the low nitrogen prebiotic mixture and the probiotic strain, e.g., *B. longum* subsp. *infantis*, have an increased diversity of microbes in the microbiome as compared to subjects administered an alternative treatment, e.g., lactulose or Rifaximin. In some embodiments, a subject administered one or both of the low nitrogen prebiotic mixture and the probiotic strain, e.g., *B. longum* subsp. *infantis*, have an increased or improved barrier function, e.g., gut barrier function, as compared to subjects administered an alternative treatment, e.g., lactulose or Rifaximin. Particular embodiments contemplate that barrier function may be assessed as a matter of routine by those of skill in the art, such as but not limited to health care providers. In some aspects, improved microbial diversity of the microbiome or increased or improved barrier function may reduce the incidence, frequency, or severity of infections associated with hyperammonemia and other liver disorders.

In some embodiments, the low nitrogen prebiotic mixture has a low nitrogen content, such as compared to the HMOs present in human milk. Compositions containing the HMOs present in human milk, e.g., concentrated human milk permeate, are known and have been described, e.g., in U.S. Pat. No. 8,927,027 and PCT Application No. WO 2018053535, incorporated by reference. In some aspects, the low nitrogen content of the mixture, e.g., in relation to the HMOs found in human milk, contributes to a reduction of ammonia production within the gut or microbiome. In particular embodiments, administration of the probiotic strain, e.g., *B. longum* subsp. *infantis*, and the low nitrogen prebiotic mixture results in at least a 5%, 10%, 20%, 25%, 30%, 40%, 50%, 60%, 70%, 75%, 80%, 90%, or 95% reduction of ammonia production in the gut or microbiome, e.g., as compared to prior to administration or as compared to administration of the probiotic strain and the HMOs found in human milk. In certain embodiments, administration of the probiotic strain, e.g., *B. longum* subsp. *infantis*, and the low nitrogen prebiotic mixture results in a reduction of at least or at least about 5%, 10%, 20%, 25%, 30%, 40%, 50%, 60%, 70%, 75%, 80%, 90%, or 95% of the rate of ammonia production, e.g., as compared to prior to administration or as compared to administration of the probiotic strain and the HMOs found in human milk.

In certain aspects, the production of ammonia in the microbiome can be modeled in cell culture as a matter of routine, e.g., such as the in vitro cell culture models described in Jacobson et al. Cell Host and Microbe (2018); 24(2): 296-307; Sorbara et al., Journal of Experimental Medicine (2018); DOI: 10.1084/jem.20181639). In some embodiments, the cell culture is performed in a bioreactor that models all or a portion of the human GI tract. In some embodiments, the cell culture contains bacteria from microbiome samples of healthy subjects. In certain embodiments, the cell culture contains microbiome samples from subjects having hyperammonemia, UCD, or hepatic encephalopathy. In certain embodiments, the presence of the one or more probiotic strain, e.g., *B. longum* subsp. *infantis*, and low nitrogen prebiotic mixture in such cultures is accompanied by less ammonia production or a reduced rate of ammonia production as compared to the presence of the probiotic strain and the HMOs found in human milk. In particular embodiments, the presence of the one or more probiotic strain, e.g., *B. longum* subsp. *infantis*, and low nitrogen prebiotic mixture in such cultures shows at least or at least about a 5%, 10%, 20%, 25%, 30%, 40%, 50%, 60%, 70%, 75%, 80%, 90%, or 95% less ammonia production as compared to the presence of the probiotic strain and the HMOs found in human milk. In some embodiments, the presence of the probiotic strain, e.g., *B. longum* subsp. *infantis*, and low nitrogen prebiotic mixture in such cultures shows a reduction of at least or at least about 5%, 10%, 20%, 25%, 30%, 40%, 50%, 60%, 70%, 75%, 80%, 90%, or 95% of the rate of ammonia.

In particular embodiments, administration of the provided low nitrogen prebiotic mixture and probiotic strain of bacterium increases the level, amount, or number of bacteria in the microbiome that scavenge, utilize, metabolize, absorb, consume, and/or deplete ammonia. In some embodiments, administration of the provided low nitrogen prebiotic mixture and probiotic strain, e.g., *B. longum* subsp. *infantis*, increases, promotes, raises, or accelerates the activity of the microbiome to scavenge, utilize, metabolize, absorb, consume, and/or deplete ammonia.

In particular embodiments, the low nitrogen prebiotic mixture and probiotic strain of bacterium, e.g., *B. longum* subsp. *infantis*, are administered to treat, prevent, ameliorate, reduce, or decrease the severity of one or more symptom(s) associated with diseases or disorders associated with or accompanied by hyperammonemia. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine transcarbamylase deficiency. In alternate embodiments, the disorder is a liver disorder such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the symptoms may include, but are not limited to, seizures, ataxia, stroke-like lesions, coma, psychosis, vision loss, acute encephalopathy, cerebral edema, vomiting, respiratory alkalosis, and hypothermia.

In some embodiments, before, during, and after the administration of the provided oligosaccharides and probiotic strain, ammonia concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce ammonia concentrations in a subject to undetectable levels, or to less than about 1%, 2%, 5%, 10%, 20%, 25%, 30%, 40%, 50%, 60%, 70%, 75%, or 80% of the subject's ammonia concentrations prior to treatment.

In certain embodiments, the probiotic strain, when administered within the same treatment regimen as the mixture of oligosaccharide, grows, expands, or is established within the microbiome without prior treatment or administration of antibiotics.

In some embodiments, the low nitrogen prebiotic mixture and the probiotic strain, e.g., *B. longum* subsp. *infantis*, are administered together to the subject. In certain embodiments, the mixture and the probiotic strain are administered together once to the subject. In particular embodiments, the mixture and the at least one probiotic are administered together multiple times to the subject. In some embodiments, the mixture and the probiotic strain are administered once, twice, three times, four times, five times or more than five times per month; once, twice, three times, four times, five times, six times, seven times, or more than seven times per week; or once, twice, or more than twice daily. In some embodiments, the mixture and the probiotic strain are administered multiple times during a regimen lasting for, for about, or for at least, one week, two weeks, three weeks, four weeks, five weeks, ten weeks, one month, two months, three months, six months twelve months, eighteen months, one year, two years, three years, four years, five years, or more than five years.

In particular embodiments, the low nitrogen prebiotic mixture and the probiotic strain, e.g., *B. longum* subsp. *infantis*, are administered separately to the subject. In certain embodiments, the probiotic strain and the low nitrogen prebiotic mixture are administered both together and separately during the same treatment regimen. For example, in some embodiments the probiotic strain and the low nitrogen prebiotic mixture are administered together initially, and then one or both of the probiotic strain and the mixture are administered separately. In some instances, the probiotic strain is administered with the low nitrogen prebiotic mixture initially during the treatment regimen, and later in the regiment the mixture is administered in the absence of the probiotic strain.

In some embodiments, the probiotic strain, e.g., *B. longum* subsp. *infantis*, is administered once to the subject. In particular embodiments, and the probiotic strain is administered multiple times to the subject. In some embodiments, and the probiotic strain is administered once, twice, three times, four times, five times or more than five times per month; once, twice, three times, four times, five times, six times, seven times, or more than seven times per week; or once, twice, or more than twice daily. In some embodiments, the prebiotic mixture and the probiotic strain are administered multiple times during a regimen lasting for, for about, or for at least, one week, two weeks, three weeks, four weeks, five weeks, ten weeks, one month, two months, three months, six months twelve months, eighteen months, one year, two years, three years, four years, five years, or more than five years.

In certain embodiments, the low nitrogen prebiotic mixture is administered once to the subject. In particular embodiments, the low nitrogen prebiotic mixture is administered multiple times to the subject. In some embodiments, the low nitrogen prebiotic mixture is administered once, twice, three times, four times, five times, or more than five times per month; once, twice, three times, four times, five times, six times, seven times, or more than seven times per week; or once, twice, or more than twice daily. In some embodiments, the low nitrogen prebiotic mixture is administered multiple times during a regimen lasting for, for about, or for at least, one week, two weeks, three weeks, four weeks, five weeks, ten weeks, one month, two months, three months, six months twelve months, eighteen months, one year, two years, three years, four years, five years, or more than five years.

In certain embodiments, provided herein are methods for treating, preventing, eliminating, ameliorating, decreasing, or reducing hyperammonemia in a subject in need thereof by administering a low nitrogen prebiotic mixture described herein, e.g., in Section III-A, and at least one strain of probiotic bacterium described herein, e.g., in Section I-B. In some embodiments, provided herein are methods for treating, preventing, eliminating, ameliorating, decreasing, or reducing a condition or disorder, or one or more symptoms associated with the condition or disorder, that is associated with, accompanied by, or caused by hyperammonemia in a subject in need thereof, by administering a low nitrogen prebiotic mixture described herein and a strain of probiotic bacterium described herein. In particular embodiments, provided herein are methods for reducing or decreasing the level or amount of ammonia in a subject in need thereof, e.g., plasma ammonia concentration.

In some embodiments, one or both of the probiotic strain and the low nitrogen prebiotic mixture are administered with an agent that reduces or prevents stomach acid production. In certain embodiments, the agent is a proton pump inhibitor (PPI). In certain embodiments, the PPI is administered in an amount sufficient to reduce or prevent $H^+$—$K^+$ ATPase activity of gastric parietal cells. Particular embodiments contemplate that administration of a PPI prevents or reduces death, inactivation, or degradation of an orally administered probiotic strain.

In some embodiments, the PPI is dontoprazole, esomeprazole, habeprazole, hydroxyomeprazole, omeprazole, lansoprazole, leminoprazole, pantoprazole, pariprazole, periprazole, ransoprazole, rabeprazole, tenatoprazole, or tenatoprazole; or a free base, free acid, salt, hydrate, ester, amide, enantiomer, isomer, tautomer, polymorph, prodrug, or active metabolite of any or all of the foregoing. Active metabolites may include, but are not limited to, hydroxyomeprazole, hydroxylansoprazole, omeprazole carboxylic acid, desmethyl pantoprazole and optically pure isomers thereof. Exemplary PPI compounds and methods for their synthesis include those described in U.S. Pat. Nos. 4,544,750; 4,758,579; 5,045,552; 5,374,730 and 5,386,032, incorporated by reference herein.

In some embodiments, the administered low nitrogen prebiotic mixture provides an energy and/or a carbon source selectively or exclusively to the probiotic strain, e.g., *B. longum* subsp. *infantis*, such that it promotes growth or expansion of the probiotic strain, e.g., in vivo in the gut or within the microbiome. In certain embodiments, the low nitrogen prebiotic mixture and the probiotic strain are administered in a manner sufficient for the probiotic strain to grow, expand, or establish itself within the microbiome of the subject.

In certain embodiments, the provided methods are or include administering a low nitrogen prebiotic mixture and at least one strain of *Bifidobacterium*, e.g., *B. longum* subsp. *infantis*, capable of internalizing the oligosaccharides, e.g., HMOs. In some embodiments, the at least one *Bifidobacterium* strain is administered with a low nitrogen prebiotic mixture having a low nitrogen content. Thus, in certain embodiments, the growth or expansion of the *Bifidobacterium* results in an increased utilization or consumption of ammonia, either by the *Bifidobacterium* itself or other bacteria of the microbiome. In particular embodiments, administration of the *Bifidobacterium*, e.g., *B. longum* subsp. *infantis*, and the low nitrogen prebiotic mixture reduces the level or amount of ammonia in the subject.

In some embodiments, a low nitrogen prebiotic mixture or HMOs having a low nitrogen content is administered to the subject to promote the growth, expansion, or establishment of the probiotic strain, e.g., *B. longum* subsp. *infantis*, and/or to reduce the level or amount of ammonia in the subject. In certain embodiments, The low nitrogen content may be due, at least in part, to (i) a low portion, e.g., less than 25%, 10%, or 1% by weight or number, of HMOs containing nitrogen or functional groups or monosaccharide residues containing nitrogen atoms, (ii) a relatively small size of the HMOs, e.g., such that the mixture contains only HMOs that have five or fewer monosaccharide residues, (iii) a low molar ratio of nitrogen atoms within the HMOs of the mixture to the total number of HMOs, e.g., below 1, 0.1, or 0.01 moles of nitrogen per mole of total oligosaccharides, or (iv) a combination of any or all of the foregoing.

In some embodiments, a strain of *B. longum* subsp. *infantis* and a mixture of HMOs that are or include 2'-fucosyllactose, 3-fucosyllactose, difucosyllactose, 3'-sialyllactose, and 6'-sialyllactose are administered to a subject, thereby reducing the amount or level of ammonia in the subject. In particular embodiments, the subject has hyperammonemia. In certain embodiments, the subject has a UCD. In certain embodiments, the subject has hepatic encephalopathy.

In particular embodiments, a strain of *B. longum* subsp. *infantis* and a mixture of HMOs that are or include 2'-fucosyllactose, 3-fucosyllactose, and difucosyllactose are administered to a subject, thereby reducing the amount or level of ammonia in the subject in need thereof. In particular embodiments, the subject has hyperammonemia. In certain embodiments, the subject has a UCD. In certain embodiments, the subject has hepatic encephalopathy.

IV. Formulations

In certain embodiments, the provided at least one probiotic bacteria, e.g., *B. longum* subsp. *infantis*, and the provided prebiotic mixtures, e.g., HMOs, are formulated together or separately, e.g., for administering to a human subject. In some embodiments, the at least one probiotic bacterium, e.g., *B. longum* subsp. *infantis*, and the prebiotic mixture, e.g., the prebiotic mixture of human milk oligosaccharides or a low nitrogen prebiotic mixture are formulated into the same or separate compositions, such as pharmaceutical or nutritional compositions. In certain embodiments, the provided at least one probiotic bacteria strain and oligosaccharides are formulated into the same pharmaceutical composition.

The compositions, e.g., one or both of prebiotic mixtures and probiotic strains, described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the compositions described herein are subjected to tableting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The probiotic strain and prebiotic mixture described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the provided at least one probiotic bacteria strain may range from about $10^5$ to $10^{12}$ bacteria, e.g., at, at about, or at least $10^5$ bacteria, $10^6$ bacteria, $10^7$ bacteria, $10^8$ bacteria, $10^9$ bacteria, $10^{10}$ bacteria, $10^{11}$ bacteria, or $10^{12}$ bacteria.

In some embodiments, the prebiotic mixture, e.g., prebiotic mixture of human milk oligosaccharides or a low nitrogen prebiotic mixture, is administered to the subject generally in the range of about 20 mg to about 20 g, e.g., total prebiotic weight (such as weight of total HMO) per dose. In certain embodiments, between or between about 50 mg and 10 g, 100 mg and 7.5 g, or 500 mg to 5 g, 1 g and 2.5 g, 50 mg and 20 g, 100 mg and 15 g, 500 mg and 10 g, or 1 g and 7.5 g prebiotic weight per dose. In some embodiments, during an initial treatment phase, the dosing can be higher; for example, 100 mg to 20 g, 100 mg to 30 g, 500 mg to 15 g, 1 g to 10 g, or 2.5 g to 7.5 g per dose. During a secondary treatment phase, the dosing can be reduced; for example, in certain embodiments, to 20 mg to 10 g per dose, 100 mg to 7.5 g per dose, 500 mg to 2.5 g per dose, 750 mg to 1.5 g per dose, 20 mg to 20 g per dose, 100 mg to 10 g per dose, 500 mg to 7.5 g per dose, or 750 mg to 5 g per dose. In certain embodiments, the prebiotic mixture is administered to the subject in an amount of or about 5 g per day. In some embodiments, a dose of the prebiotic mixture is administered at least once per month, once per week, or once per day. In some embodiments, a dose of the prebiotic mixture is administered at least once, twice, three times, four times, five times, six times, eight times, ten times, or twelve times daily.

In some embodiments, the pharmaceutical compositions, e.g., pharmaceutical compositions containing one or both of the at least one probiotic bacteria strain and prebiotic mixture, may be administered once or more daily, weekly, or monthly. The at least one probiotic bacteria strain and the prebiotic mixture may be formulated, together or separately, into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the probiotic strain may be formulated in a solution of sodium bicarbonate, e.g., 1 molar solution of sodium bicarbonate (to buffer an acidic cellular environment, such as the stomach, for example). The probiotic strain may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In some embodiments, the pharmaceutical compositions containing the provided at least one probiotic bacteria strain and the prebiotic mixture, e.g., together or as separate compositions, may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, methyl cellulose, hydroxypropylmethyl-cellulose, sodium carbomethylcellulose; and/or physiologically acceptable polymers such as) polyethylene glycol (PEG).

Disintegrating agents may also be added, such as cross-linked agar, alginic acid or a salt thereof such as sodium alginate.

Tablets or capsules can be prepared by conventional means with pharmaceutically acceptable excipients such as binding agents (e.g., pregelatinized maize starch, hydroxypropyl methylcellulose, carboxymethyl cellulose, polyethylene glycol, sucrose, glucose, sorbitol, starch, gum, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, such as with membrane selected from, but not limited to, polylactide, polyglycolic acid, polyanhydride, other biodegradable polymers, hydroymethylacrylate-methyl methacrylate (HEMA-MMA), multilayered HEMA-MMA-MAA, polyethylene glycol/poly pentamethylcyclopentasiloxane/polydimethylsiloxane (PEG/PD5/PDMS), siliceous encapsulates, cellulose acetate phthalate, calcium alginate, k-carrageenan-locust bean gum gel beads, poly(lactide-co-glycolides), carrageenan, starch polyanhydrides, starch polymethacrylates, and enteric coating polymers.

In some embodiments, the one or both of the at least one probiotic strain and the prebiotic mixture are enterically coated, such as in order to remain viable during transit through the stomach, reduce contact with bile acids in the small intestine, or for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

In some embodiments, one or both of the at least one probiotic bacteria strain and the prebiotic mixture are administered orally in conjunction with administration of an acid reducing agent such as a PPI or an $H_2$ receptor antagonist. In certain embodiments, a dose of the agent that is between about 10 mg to about 3000 mg of the PPI, such as, as about, or at least 5 mg, 10 mg, 15 mg, 20 mg, 30 mg, 40 mg, 50 mg, 60 mg, 80 mg, 160 mg, or 320 mg is administered in conjunction with oral administration of one or both of the probiotic strain and the mixture. In certain embodiments, a PPI is administered in conjunction with oral administration of the at least one probiotic strain. In particular embodiments, an $H_2$ receptor antagonist is administered in conjunction with oral administration of the at least one probiotic strain.

In certain embodiments, the pharmaceutical compositions are formulated as liquid preparations. Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the bacteria described herein.

In some embodiments, the one or both of the probiotic strain and prebiotic mixture may be formulated in a composition suitable for administration to pediatric subjects. As is well known in the art, children differ from adults in many aspects, including different rates of gastric emptying, pH, gastrointestinal permeability, etc. Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, taste blockers. or suitable to be mixed in a foodstuff, e.g., applesauce. In one embodiment, a composition suitable for administration to pediatric subjects may also be suitable for administration to adults.

In certain embodiments, the pharmaceutical composition, e.g., containing one or both of the probiotic strain and prebiotic mixture, that is suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In some embodiments, the pharmaceutical composition, e.g., composition suitable for administration to pediatric subjects, may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, cherry, and chocolate.

In particular embodiments, the probiotic strain and the prebiotic mixture may, together or separately, be orally administered, such as with an inert diluent or an assimilable edible carrier. In some aspects, the probiotic strain and the prebiotic mixture may also be enclosed in a hard or soft-shell gelatin capsule, a hydroxypropylmethyl cellulose (HPMC) capsule, compressed into tablets, or incorporated directly into the subject's diet. For oral therapeutic administration, the probiotic strain and prebiotic mixture may, together or separately, be incorporated with excipients and used in the form of ingestible tablets, buccal tablets, troches, capsules, elixirs, suspensions, syrups, wafers, and the like. In some aspects, it may be necessary to coat or co-administer the pharmaceutical composition with a material to prevent inactivation of the probiotic strain and/or the prebiotic mixture.

In some embodiments, the composition containing one or both of the probiotic strain and the prebiotic mixture may be a nutritional or a comestible product, e.g., a food product or nutritional composition. In some embodiments, the composition is nutritional composition such as food product. In certain embodiments, the food product or nutritional composition is or includes milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In some embodiments, the nutritional composition or food product is a fermented food, such as a fermented dairy product. In particular embodiments, the fermented dairy product is yogurt. In certain embodiments, the fermented dairy product is cheese, milk, cream, ice cream, milk shake, or kefir. In some embodiments, the probiotic strain of the invention, e.g., a *B. longum* subsp. *infantis* strain, is combined in a preparation containing other live bacterial cells intended to serve as probiotics. In some embodiments, the food product is a beverage. In one embodiment, the beverage is a fruit juice-based beverage or a beverage containing plant or herbal extracts. In certain embodiments, the food product or nutritional composition is a jelly or a pudding. Other food products suitable for administration of the probiotic strain and prebiotic mixtures provided herein are known, such as those described in U.S. Application Nos. 2015/0359894 and 2015/0238545. In yet another embodiment, the pharmaceutical composition of the invention is injected into, sprayed onto, or sprinkled onto a food product, such as bread, yogurt, or cheese.

In some embodiments, the composition, e.g., pharmaceutical composition, that includes one or both of the prebiotic mixture and the probiotic strain is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

In some embodiments, disclosed herein are pharmaceutically acceptable compositions continuing one or both of the probiotic strain and prebiotic mixture in single dosage forms. Single dosage forms may be in a liquid or a solid form. Single dosage forms may be administered directly to a subject without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition containing one or both of the probiotic strain and prebiotic mixture may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a subject.

In certain embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly((2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens of one or both of the prebiotic mixture or the probiotic strain may be adjusted to provide a therapeutic response, e.g., to improve or maintain SCFA or lactate production. Dosing can depend on several factors, including severity and responsiveness of the disease, route of administration, time course of treatment (days to months to years), and time to amelioration of the disease. For example, a single bolus or one or both of the mixture and the probiotic strain may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, LD50, ED50, EC50, and IC50 may be determined, and the dose ratio between toxic and therapeutic effects (LD50/ED50) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

In some embodiments, ingredients (e.g., probiotic strain, prebiotic mixture, and pharmaceutically acceptable excipients) are supplied either separately or mixed together in unit dosage form, for example, as a dry lyophilized powder or water-free concentrate in a hermetically sealed container such as an ampoule or sachet indicating the quantity of active agent.

The pharmaceutical compositions, e.g., containing one or both of the prebiotic mixture and probiotic strain, may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include polydextrose, dextrins (e.g., maltodextrin (e.g., a native maltodextrin or a resistant maltodextrin)), inulin, β-glucan, resistant starches (e.g., resistant maltodextrin), hydrocolloids (e.g., one or more of gum Arabic, pectin, guar gum, alginate, carrageenan, xanthan gum and cellulose gum), corn syrup solids and the like and polysorbate 80.-. Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

In some embodiments, the pharmaceutical compositions, e.g., containing one or both of the probiotic strain and prebiotic mixtures are administered with food. In alternate embodiments, the pharmaceutical composition is administered before or after eating food. The pharmaceutical compositions may be administered in combination with one or more dietary modifications, e.g., low-protein diet and amino acid supplementation. The dosage of the pharmaceutical compositions and the frequency of administration may be selected based on the severity of the symptoms and the progression of the disorder. The appropriate therapeutically effective dose and/or frequency of administration can be selected by a treating clinician.

V. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the described or claimed subject matter. This applies regardless of the breadth of the range.

Throughout this disclosure, ranges that are presented or expressed as "between" two endpoints, e.g., "between A and B" are understood to include the endpoints, e.g. "A" and "B", unless otherwise indicated.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". In some embodiments, "about" a value means within a range of ±25%, ±10%, ±5%, ±1%, ±0.1%, or ±0.01% of the value.

As used herein the term "pharmaceutical composition" means, for example, a mixture or formulation containing a specified amount, e.g., a therapeutically effective amount, of an active ingredient such as a human milk fraction, in a pharmaceutically acceptable carrier to be administered to a mammal, e.g., a human.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response, and other problem complications commensurate with a reasonable benefit/risk ratio. Such reasonable benefit/risk ratios may be determined by of skill as a matter of routine.

By "human milk oligosaccharide(s)" (also referred to herein as "HMO(s)") is meant a family of structurally diverse unconjugated glycans that are found in human breast milk. As used herein human milk oligosaccharides include oligosaccharides found in human milk that contain lactose at the reducing end and, typically, fucose, sialic acid or N-acetylglucosamine at the non-reducing end (Morrow et al., J. Nutri. 2005 135:1304-1307). Unless otherwise indicated, human milk oligosaccharides also encompass 3'-sialyllactose (3'-SL) and 6'-sialyllactose (6'-SL) oligosaccharides that are found in human milk.

Unless otherwise noted, a number of human milk oligosaccharides, e.g., "at least 5 human milk oligosaccharides," refers to the number of unique species of human milk oligosaccharides, e.g., human milk oligosaccharides having different chemical structures or formulas.

Glycans in milk are found as oligosaccharides or conjugated to milk proteins as glycoproteins, or lipid as glycolipids etc. HMO are free glycans that constitute the third most abundant component of human milk, after lactose and lipid (Morrow, 2005). The majority of HMO, however, are not metabolized by the infant and can be found in infant feces largely intact.

By "consisting essentially" of, as used herein refers to compositions containing particular recited components while excluding other major bioactive factors.

"Probiotic" as used herein, refers to any live, non-pathogenic microorganisms, e.g., bacteria, which can confer health benefits to a host organism, e.g., a mammal such as a human, that contains an appropriate amount of the microorganism. In some aspects, those of skill in the art may readily identify species, strains, and/or subtypes of non-pathogenic bacteria that are recognized as probiotic bacteria. Examples of probiotic bacteria may include, but are not limited to, Bifidobacteria, *Escherichia coli, Lactobacillus*, and *Saccharomyces*, e.g., *Bifidobacterium bifidum, Entero-*

*coccus faecium, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006).

"*Bifidobacterium*" or "Bifidobacteria" as used herein, refers to a genus of gram-positive, nonmotile, anaerobic bacteria. In some aspects, *Bifidobacterium* are ubiquitous inhabitants of the gastrointestinal tract, vagina, and mouth of mammals, including humans. In certain aspects, Bifidobacteria are one of the major genera of bacteria that make up the gastrointestinal tract microbiota in mammals. In certain aspects, some or all species, subspecies, or strains of *Bifidobacterium* are probiotics.

The term "dysbiosis" as used herein refers to a state of the microbiota of the gut or other body area in a subject, in which the normal diversity and/or function of the microbial populations is disrupted. This unhealthy state can be due to a decrease in diversity, the overgrowth of one or more pathogens or pathobionts, symbiotic organisms able to cause disease only when certain genetic and/or environmental conditions are present in a subject, or the shift to an ecological microbial network that no longer provides an essential function to the host subject, and therefore no longer promotes health. According to non-limitative examples, essential functions may include enhancement of the gut mucosal barrier, direct or indirect reduction and elimination of invading pathogens, enhancement of the absorption of specific substances, and suppression of GI inflammation.

As used herein, the terms "gut microbiome" and "intestinal microbiome" are used interchangeably unless otherwise noted.

As used herein, "non-digestible" as used in the term "non-digestible carbohydrate" refers to the fact that the carbohydrate is not digested by the host or human subject.

The term "essentially" such as when used in the phrase "essentially all" of a given substance may be used to infer that the substance, e.g., oligosaccharides, includes unavoidable impurities, e.g., no more impurities than what might be unavoidable with standard techniques for manufacture, formulation, transporting, and storage. Likewise, when used in the phrase "essentially free" of a given substance (or "essentially no" or "essentially none of" a given substance) may mean no more of the given substance than is unavoidable, e.g., as an impurity.

The term "internalization" such as in reference to an internalization of an oligosaccharide by a bacterial cell refers to the transfer of the oligosaccharide from the outside of the bacterial cell to the inside of the bacterial cell. Unless otherwise indicated, "internalization of an oligosaccharide" refers to the internalization of the intact oligosaccharide.

VI. EXAMPLES

The following examples are included for illustrative purposes only and are not intended to limit the scope of the invention.

Example 1: Manufacture of a Concentrated HMO Mixture

Human milk from previously screened and approved donors was tested to verify donor identity and then mixed together to generate a pooled bulk of donor milk. In a clean room environment, the pool of donor milk was further tested, including for specific pathogens and bovine proteins. After testing, the pooled donor milk was filtered through a 200 μm filter, heated to a temperature of at least 63° C. for 30 minutes, and then cooled to between 22° C. and 26° C. The pooled human milk was then transferred to a centrifuge to separate the cream from the skim. The resulting skim milk was processed through an ultra-filtration system with a 10 kDa membrane, and the material that was passed through the filter was collected as the permeate fraction. The permeate was frozen and stored at approximately −20° C. Each permeate lot was tested to confirm quality parameters, including a minimal HMO concentration of approximately 0.2 to 0.4 g/L total HMOs, prior to its release for further processing.

Multiple qualified lots of the permeate were thawed and pooled. The pH of the pooled permeate was adjusted to a target pH of 4.5±0.2. The permeate was then heated to approximately 50° C. Lactase enzyme was added to the permeate at a 0.1% w/w concentration and incubated at approximately 50° C. for 60 minutes. The permeate and lactase enzyme mixture then was cooled to between 20° C. and 30° C. and clarified by depth filtration (Filtrox CH113P). The resulting depth filter filtrate was processed through an ultra-filtration skid (Biomax-10K membrane) to remove the lactase. The ultra-filtered permeate was then concentrated by nanofiltration using membranes with an estimated 400 to 500 Dalton molecular weight cut-off (GE G-5 UF). The concentrated HMO composition was then pasteurized and clarified though 0.2 μm sterile filters. This final HMO composition was then filled into containers and stored at ≤−20° C. The final concentrations of HMO were targeted to between 84.5 to 105.4 g/L and quantified using high performance anion exchange chromatography with pulsed amperometry detection (HPAEC-PAD) with commercially available standards.

Example 2: Administration of *B. longum* Subsp. *infantis* and a Concentrated HMO Mixture to Healthy Adult Subjects Healthy adult men and women between the ages of 18 and 75 are enrolled as subjects in a study to evaluate administration of a *B. longum* subsp. *infantis* probiotic and the concentrated HMO mixture prepared as described in Example 1. Subjects receiving the *B. longum* subsp. *infantis* probiotic consume a dose of at least $8\times10^7$ CFU of a *B. longum* subsp. *infantis* probiotic daily for the first seven days (days 1-7) of the clinical study. Some of the subjects are assigned to take a single 20 mg dose of an over-the-counter proton pump inhibitor containing omeprazole with sodium bicarbonate (ZEGERID™) 1-2 hours prior to consuming the probiotic. Subjects assigned to receive the concentrated HMO mixture consume two doses daily for the first fourteen days of the study (days 1-14) for a total daily dose of 4.5 g/day, 9 g/day, or 18 g/day HMO. Subjects of an additional cohort consume the PPI and *B. longum* subsp. *infantis* probiotic on days 1-7 and 18 g/day HMO on days 1-14, and then this treatment regimen is repeated beginning on day 29 of the study. The experimental cohorts are summarize in Table E1.

TABLE E1

| Experimental Cohorts | | | |
|---|---|---|---|
| Cohort | Target HMO Amount (Days 1-14) | *B. infantis* (Day 1-7) | PPI (Day 1-7) |
| 1 | 0 g/day | Yes | Yes |
| 2 | 18 g/day | No | Yes |
| 3 | 4.5 g/day | Yes | Yes |
| 4 | 9 g/day | Yes | Yes |
| 5* | 18 g/day | Yes | Yes |
| 6 | 18 g/day | Yes | No |

*Cohort 5 undergoes the same dosing regimen of HMO, *B infantis*, and PPI twice. A first dosing regimen from days 1-14 and a second dosing regimen from days 29-43.

Biological samples (e.g., blood, urine, and stool samples) are collected from the subjects at various timepoints throughout the study. In particular, stool samples and blood samples are collected at screening (day 0) and various timepoints throughout the study.

Stool samples for microbiome analysis are prepared for DNA extraction. After DNA extraction, a sample will be analyzed using species- and strain-specific quantitative PCR analysis to evaluate *B. longum* subsp. *infantis* colonization both during and after HMO ingestion. Selected samples may also be analyzed by next generation DNA sequencing to determine the taxonomic composition, alpha- and beta-diversity and change of each subject's microbiome during the study. Methods may include 16S and/or whole metagenomic shotgun sequencing and culture-specific methods.

Aliquots of stool are refrigerated immediately after collection and then frozen at about −70° C. or colder within 24 hours Some samples are sent to a facility with metabolomic capabilities, such as to measure production of short chain fatty acids, levels of HMO, and/or other microbial metabolites.

Blood samples collected at screening (day 0) are be used to determine subject eligibility and baseline results. Blood samples will be collected and tested for the purpose of safety monitoring at various timepoints throughout the study. The following tests may be performed: CBC with differential and platelets; alkaline phosphatase, ALT, AST, LDH, total and conjugated bilirubin, albumin, and total protein for liver function; electrolytes Na, K, Cl, HCO3, and glucose; total calcium, magnesium, and phosphate; creatinine and BUN for renal function. Blood will also be tested for markers of immunological activity, including but not limited to, TGF beta.

The levels of *B. longum* subsp. *infantis* within the gut microbiome present at baseline and at subsequent study points are evaluated by quantitative PCR using primers for species and strain. Quantitation limits are demonstrated by qualification assays demonstrating the lower limit of detection in order to establish minimum log-fold change in *B. longum* subsp. *infantis*. Results from baseline samples may indicate that adults do not harbor detectable levels of *B. longum* subsp. *infantis*. Results may indicate that B. longum subsp. infantis is not detectable in samples from subjects administered *B. longum* subsp. *infantis* without a dose of the concentrated HMO mixture at study points after the *B. longum* subsp. *infantis* has been administered. Results may also indicate that *B. longum* subsp. *infantis* is not detectable in samples from subjects administered *B. longum* subsp. *infantis* without a PPI. Alternatively, results may indicate that administration of a PPI reduces the levels of *B. longum* subsp. *infantis*. Likewise, results may indicate that B. infants is not detectable in samples from subjects administered the concentrated HMO mixture but not the *B. longum* subsp. *infantis* probiotic.

Results will indicate that *B. longum* subsp. *infantis* is present in at least some of the samples from subjects administered the *B. longum* subsp. *infantis* probiotic and the concentrated HMO mixture and may indicate a synergy between probiotic and mixture with respect to the abundance of *B. longum* subsp. *infantis* the microbiome (e.g., the abundance of *B. longum* subsp. *infantis* at one or more timepoints will be greater than what would have been expected based on the administration of the probiotic or the mixture alone). Results may also indicate that the abundance of *B. longum* subsp. *infantis* increases during the HMO dosing regimen, and then decreases after day 14 once HMOs are no longer administered.

Changes in stool microbiota will be measured as well as dynamic changes in the gut community structure. These changes will be evaluated by next generation sequencing using proportions of key bacterial operational taxonomy units (OTUs), relative abundance of various taxa, diversity (alpha and beta) and stability of communities and functional metabolomic changes. Results may indicate that administration of the concentrated HMO mixture or both the concentrated HMO mixture and the *B. longum* subsp. *infantis* probiotic measurably changes the gut community structure. The results may indicate that the changes persist after the dosing regimens are completed. Results may also indicate that administration of the concentrated HMO mixture increases microbiome diversity, which may further be increased by administration of the *B. longum* subsp. *infantis* probiotic. Observations of increased microbiome diversity may persist at time points from after the dosing regimens are completed.

Changes in viability of proteobacteria and Enterococcus will be determined by plating on selective media. These measurements will predictive for success in suppressing pathogenic bacterial relatives in future trials. Results may indicate greater suppression of proteobacteria and Enterococcus in samples from subjects administered both the concentrated HMO mixture and the *B. longum* subsp. *infantis* probiotic as compared to samples from subjects administered either one alone and/or samples taken at baseline.

If higher levels of *B. longum* subsp. *infantis* is observed in stool from subjects administered a PPI than those from subjects not administered a PPI, such results may indicate a need for protection of *B. longum* subsp. *infantis* from stomach acid in order for engraftment of the organism into the gut microbiome to occur. Results may indicate that protection from exposure to stomach acid at a physiological pH, e.g., stomach acid at a pH of 1.5 to 3.5, is required for *B. longum* subsp. *infantis* engraftment. Alternatively, results may indicate that administration of a PPI does not influence the levels of *B. longum* subsp. *infantis* detected in stool samples. Results may even indicate that administration of a PPI reduces the levels of *B. longum* subsp. *infantis* detected in stool samples, which would be consistent with an inhibition, reduction, or prevention of *B. longum* subsp. *infantis* engraftment associated with the administration of the PPI.

Any adverse events are reported. Results may indicate that no major adverse events are reported, as *B. longum* subsp. *infantis*, HMOs, and PPIs are generally considered safe.

Example 3: Administration of *B. longum* Subsp. *infantis* and a Concentrated HMO Mixture to Healthy Adult Subjects A clinical study was performed similar to as described in Example 2. The study was performed with 12 total subjects, with two subjects each assigned to cohorts 1-6 shown in Table E1. Subjects were administered *B. longum* subsp. *infantis* from days 1-8 and/or one or both of a concentrated HMO mixture and a PPI from days 1-15. Stool samples were collected from the subjects as described in Example 2 at day 1 prior to administration of the *B. longum* subsp. *infantis* and/or the concentrated HMO mixture, and at days 5, 8, 15, 22, and 29.

The levels of *B. longum* subsp. *infantis* within the gut microbiome present at the study points were evaluated by quantitative PCR of stool samples using primers for *B. longum* subsp. *infantis* similar to as described in Example 2. Results are summarized in Table E2.

TABLE E2

Summary of *B. longum* subsp. *infantis* qPCR results in samples by subject

| | Treatment | | | Copy Number/Reaction | | | | | |
|---|---|---|---|---|---|---|---|---|---|
| Subject | B. inf | HMO | PPI | Day 1 | Day 5 | Day 8 | Day 15 | Day 22 | Day 29 |
| 1 | Yes | 0 g/day | Yes | – | + | + | – | – | – |
| 2 | Yes | 0 g/day | Yes | – | + | + | – | – | – |
| 3 | No | 18 g/day | Yes | – | – | – | – | – | – |
| 4 | No | 18 g/day | Yes | – | – | – | – | – | – |
| 5 | Yes | 4.5 g/day | Yes | – | + | + | + | – | – |
| 6 | Yes | 4.5 g/day | Yes | – | – | + | + | – | – |
| 7 | Yes | 9 g/day | Yes | – | + | + | – | – | – |
| 8 | Yes | 9 g/day | Yes | – | + | + | – | – | – |
| 9 | Yes | 18 g/day | Yes | – | + | – | – | – | – |
| 10 | Yes | 18 g/day | Yes | – | + | + | N/A | N/A | – |
| 11 | Yes | 18 g/day | No | – | ++ | ++ | ++ | + | – |
| 12 | Yes | 18 g/day | No | – | ++ | ++ | ++ | + | – |

Limit of detection = about 10 copies per reaction.
"–" indicates at or below limit of detection;
"+" indicates between 10 and 10,000 copies per reaction;
and "++" indicates above 10,000 copies per reaction.
"N/A" indicates unavailability due to subject non-compliance.

As shown in Table E2, *B. longum* subsp. *infantis* was not detectable by qPCR in any of the baseline samples collected at day 1, consistent with *B. longum* subsp. *infantis* not being present in a majority of adult intestinal microbiomes. Subjects administered *B. longum* subsp. *infantis* were administered the probiotic daily during days 1-8, and *B. longum* subsp. *infantis* was detectable in one or both of the stool samples collected at days 5 and 8 in all these subjects. *B. longum* subsp. *infantis* was not detected in any of the samples collected from subjects who were not administered the probiotic.

Day 15 was 7 days after the administration of the last doses of *B. longum* subsp. *infantis* and the last day that the concentrated HMO mixtures were administered, and day 22 was 14 days after the last doses of *B. longum* subsp. *infantis* and the 7 days after the last doses of concentrated HMO mixtures were administered. *B. longum* subsp. *infantis* was detected in stool samples collected at day 15 from four subjects, with the highest levels observed in the two subjects that received 18 g/day HMO and *B. longum* subsp. *infantis* without the PPI *B. longum* subsp. *infantis* was still detected in stool samples collected at day 22 from the subjects that received 18 g/day HMO and *B. longum* subsp. *infantis* without the PPI. These results are consistent with administration of the concentrated HMO mixture supporting engraftment and expansion of *B. longum* subsp. *infantis* that persists in the subject's intestinal microbiome beyond the daily administration of the probiotic. These results are also consistent with an impairment of *B. longum* subsp. *infantis* engraftment associated with the administration of the PPI.

Approximately 48 additional subjects are enrolled in this study. Subjects are assigned to the same cohorts described above, with the following changes. Subjects assigned to receive doses of *B. longum* subsp. *infantis* and the concentrated HMO mixture at doses of 4.5 and 9 g/day HMO are not administered a PPI. Subjects assigned to Cohort 5 undergo two dosing regimens of HMO and *B. longum* subsp. *infantis* similar to as described in Example 2 (the dosing regimens from days 1-14 and from days 29-43), in which they receive ZEGRID during the first dosing regimen at days 1-7, and then receive either no drug for reducing acid production or the H2 receptor antagonist famotidine during the second dosing regimen at days 29-35. Results may indicate that administration of *B. longum* subsp. *infantis* in conjunction with the concentrated HMO mixture at doses at or below 18 g HMO result in detection of *B. longum* subsp. *infantis* in stool samples collected at various timepoints, including timepoints occurring after day 8 of the study (e.g., at day 15 or later). Results may also indicate that administration of famotidine does not impair engraftment or expansion of *B. longum* subsp. *infantis*, or that administration of famotidine increases the engraftment, expansion, or abundance of *B. longum* subsp. *infantis*, e.g., as compared to subjects not administered a PPI.

Example 4: Treatment for Prevention of GVHD

Subjects who receive an allogenic hematopoietic stem cell transplantation (HSCT) receive a treatment that includes administration of a prebiotic mixture of non-digestible carbohydrates and a Bifidobacteria probiotic. The mixture of non-digestible carbohydrates is a mixture of human milk oligosaccharides (HMOs) obtained from pooled milk. The mixture may contain at least 10, at least 25, at least 50, at least 100, at least 150, or at least 200 different species of HMO. The *Bifidobacterium* probiotic may be a strain of *B. longum* subsp. *infantis*.

The mixture of non-digestible carbohydrates (HMOs) and the *Bifidobacterium* probiotic are administered at the time of neutrophil engraftment (immediately after completion of antibiotic regimen). Subjects are administered between 3.0 g/day and 18.0 g/day, such as 12.5 g/day, of non-digestible carbohydrates and $1\times10^9$ units of the *Bifidobacterium* probiotic. The treatment is orally administered twice daily.

At approximately 180 days post-transplant, subjects who receive the treatment experience (e.g., relative to subjects that did not receive the treatment following allogenic HSCT):

- reduction in bacterial bloodstream infections requiring antibiotics
- reduction in rate of acute grade 3 or grade 4 GI GVHD
- Reduction in viral reactivation in CMV+ and EBV+ patients
- Reduction in gut domination by pathogenic taxa (e.g., Enterobacteriaceae, *Enterococcus, Staphylococcus*)
- Preservation and restoration of gut microbiota diversity
- Enhancement in gut barrier function (measured by circulating LPS, soluble CD14, etc.)
- Increase in production of short chain fatty acids (e.g., acetate in serum, butyrate in stool)

The reduction in bacterial bloodstream infections requiring antibiotics may be observed or determined to be by about 35%. The reduction in the rate of acute grade 3 or 4 GVHD may be observed or determined to be by about 35%. The reduction in mortality due to infections and GI GVHD may be observed or determined to be by about 20%.

Overall, the treatment is observed to be well tolerated. No infections or bacteremia due to Bifidobacteria are observed (Bifidobacteria have a known safety profile in humans). Some subjects may report abdominal discomfort during or following the treatment that is transient, not severe. In some instances, abdominal discomfort during the treatment may be managed by dose-reduction of non-digestible carbohydrates (HMOs). The treatment is contraindicated for use during periods of antibiotic treatment The treatment does not alter anti-cancer efficacy of the allogenic HSCT.

Example 5: Treatment for Prevention of Pouchitis

Subjects with ulcerative colitis undergo IPAA surgery. Immediately after surgery, the subjects are administered the prebiotic mixture of non-digestible carbohydrates and the *Bifidobacterium* similar to as described in Example 3.

Following the treatment, subjects who receive the treatment experience (e.g., relative to subjects that did not receive the treatment following IPAA surgery):

- Reduction in pouchitis occurrence at 6 months (this reduction may be an approximate 50% reduction)
- Reduction in stool frequency and fluidity
- Remission of microscopic inflammation
- Reduction in urgency, incontinence, abdominal pain, and blood loss The reduction in bacterial bloodstream infections requiring antibiotics may be observed or determined to be by about 35%. The reduction in the rate of acute grade 3 or 4 GVHD may be observed or determined to be by about 35%. The reduction in mortality due to infections and GI GVHD may be observed or determined to be by about 20%.

Overall, the treatment is observed to be well tolerated. No infections or bacteremia due to Bifidobacteria are observed (Bifidobacteria have a known safety profile in humans). Some subjects may report abdominal discomfort during or following the treatment that is transient, not severe. In some instances, abdominal discomfort during the treatment may be managed by dose-reduction of non-digestible carbohydrates (HMOs). The treatment is contraindicated for use during periods of antibiotic treatment.

Example 6: HMO Stimulates Growth of *B. longum* Subsp. *infantis* In Vitro in the Presence of Microbiota Obtained from Healthy Adult Stool

*B. longum* subsp. *infantis* and microbiota obtained from the stool of a healthy adult subject were cultured separately or together in a carbon-depleted modified Reinforced Clostridial Media (RCM) base media. Cells were incubated in the presence or absence of a mixture of HMOs at a concentration of 2.5 mg/mL (weight of total HMO per mL). The HMO mixture was prepared from a human milk ultrafiltered permeate similar to as described in Example 1 with additional steps to remove monosaccharides.

The samples from each culture were assessed for growth at various timepoints. Optical density at 600 nm (OD600) was measured to assess total biomass in the cultures. Growth of *B. longum* subsp. *infantis* was assessed with a Taqman qPCR assay similar to as described in Lawley et al., PeerJ. 2017 May 25; 5:e3375. using the primer and probe sequences disclosed by SEQ ID NOS: 56-58.

Figure 2:
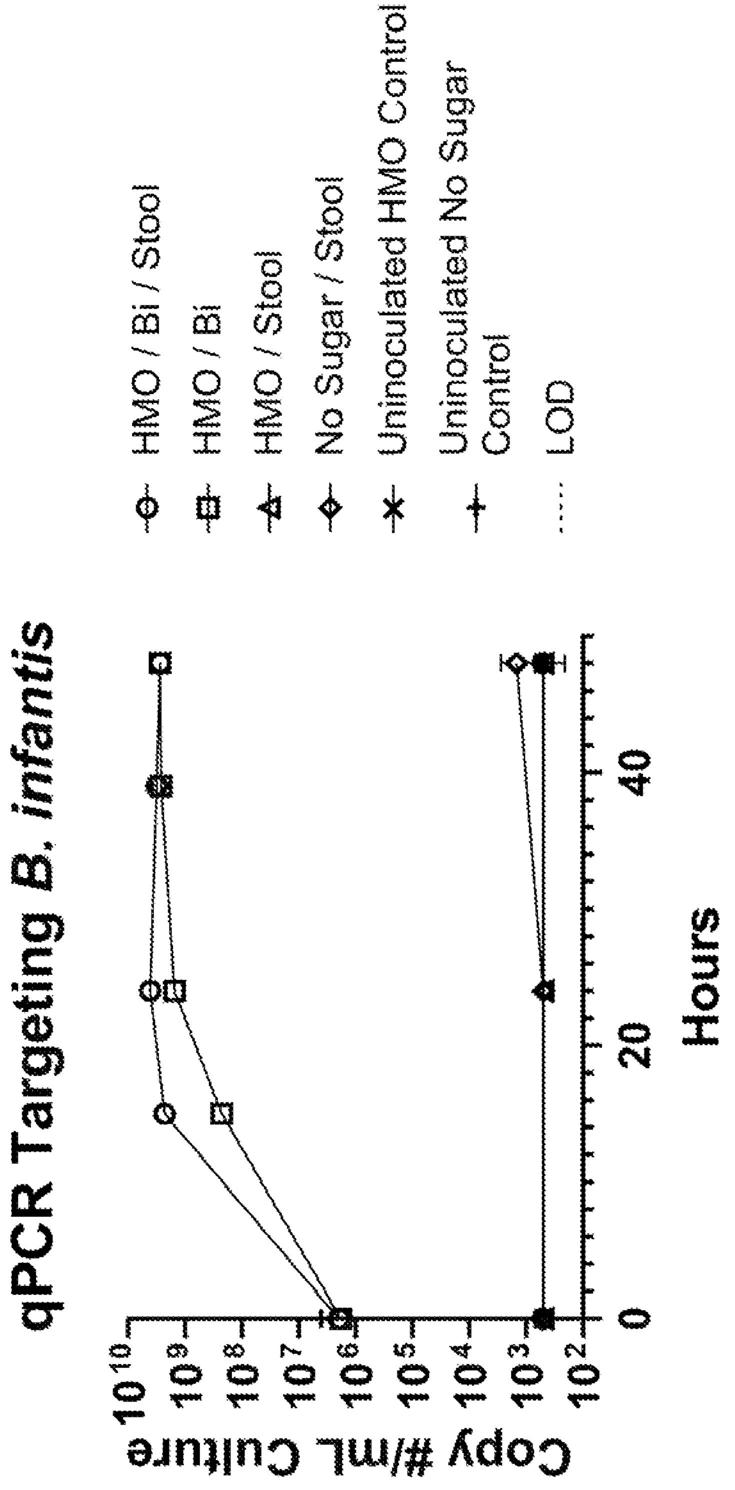
FIG. 2 provides a graph displaying results of qPCR targeting *B. longum* sub. sp. *infantis* at various time points for similar culture conditions as described in FIG. 1. The Limit of detection (LOD) was 502 copies/mL culture.

Results from exemplary experiments are shown in FIGS. 1 and 2. As shown in FIG. 1, OD600 values increased over time in cultures incubated with HMO to a greater degree than in controls, consistent with growth from utilization of HMOs as a carbon source. Co-cultures containing both *B. longum* subsp. *infantis* and stool microbiota displayed the largest increase in biomass as compared to cultures of *B. longum* subsp. *infantis* or stool microbiota alone, consistent with additive growth of *B. longum* subsp. *infantis* and the stool microbiota, or cooperative interactions between *B. longum* subsp. *infantis* and components of the stool microbiota in the presence of HMO.

As shown in FIG. 2, *B. longum* subsp. *infantis* could be detected by qPCR in *B. longum* subsp. *infantis* cultures and in co-cultures with stool microbiota that were incubated with HMO. Growth of *B. longum* subsp. *infantis* was observed when cultured alone and when cultured with stool microbiota, consistent with an ability of *B. longum* subsp. *infantis* to compete with intestinal microbiota to utilize HMO as a carbon source. *B. longum* subsp. *infantis* was not detectable in uninoculated control cultures or in cultures containing only stool microbiota.

Example 7: Effects of Acid Reducing Compounds on Viability of *B. longum* Subsp. *Infantis*

Viability of *B. longum* subsp. *infantis* following exposure to various acid reducing compounds was examined. The benzimidazole derivative compounds omeprazole, esomeprazole, lansoprazole, pantoprazole, and rabeprazole and the $H_2$ receptor antagonist famotidine were suspended in citrate buffer (pH 5) to concentrations of 1 μg/ml and 0.5 μg/ml. An amount of $2.4\times10^8$ colony forming units (CFU) *B. longum* subsp. *infantis* was pelleted and resuspended in each of the citrate buffer and drug solutions. Controls included $2.4\times10^8$ CFU *B. longum* subsp. *infantis* added to citrate buffer alone. Cells were incubated for 3 hours at 37° C. and then plated under anaerobic conditions. Anaerobic CFU were quantified to assess viability.

Figure 3A:
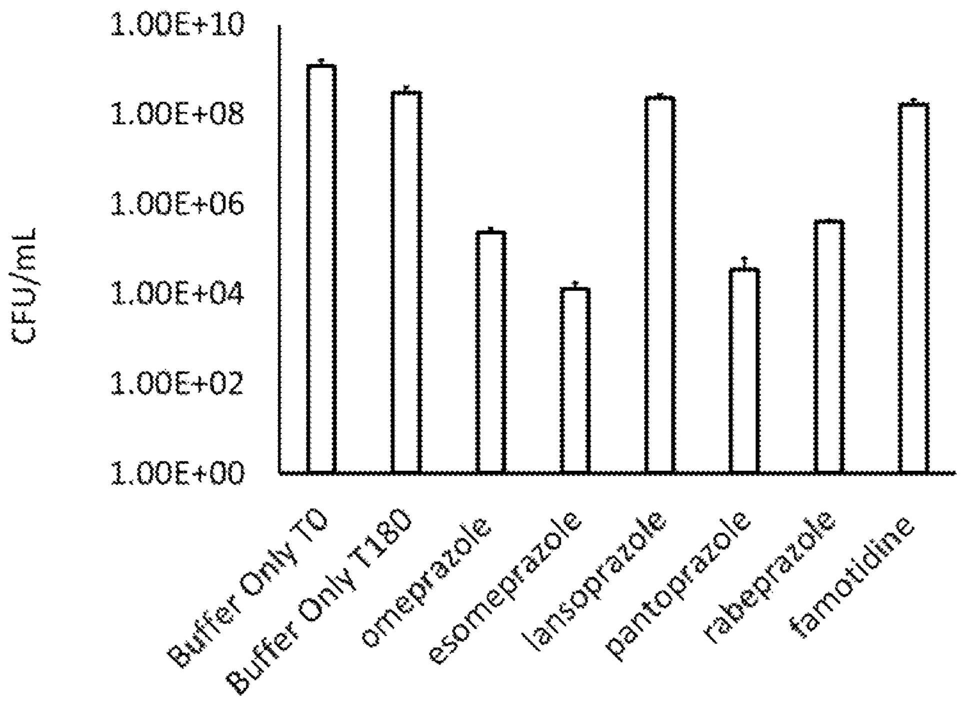
FIGS. 3A and 3B show graphs displaying anaerobic colony forming unit (CFU) counts following a three-hour incubation of *B. longum* subsp. *infantis* with various acid reducing compounds at concentrations of 1 μg/mL (FIG. 3A) or 0.5 μg/mL (FIG. 3B) and prior to (Buffer Only T0) or after (Buffer Only T180) a three-hour incubation in buffer alone.
Figure 3B:
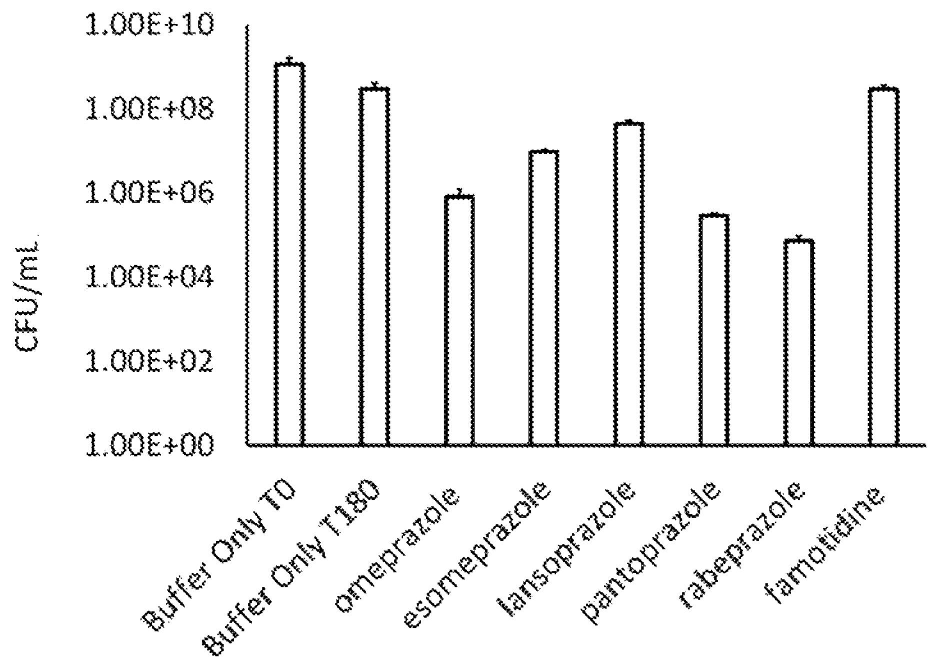

Exemplary results are shown in FIGS. 3A and 3B. Generally, anaerobic CFU counts were reduced following incubation with omeprazole and other substituted benzimidazole compounds with respect to buffer only controls, although CFU counts following incubation with lansoprazole were generally higher. Incubation with famotidine resulted in similar CFU counts as buffer only controls. Taken together, these results are consistent with impaired viability of *B. longum* subsp. *infantis* following exposure to omeprazole and other benzimidazole compounds.

Example 8: Effects of Acid Reducing Compounds on *B. longum* Subsp. *infantis* Growth Growth of *B. longum* subsp. *infantis* was assessed in the presence of various acid-reducing compounds, including proton pump inhibitor (PPI) compounds and an $H_2$ receptor antagonist. Stock solutions were prepared by adding 10 mg/mL omeprazole, esomeprazole, lansoprazole, pantoprazole, rabeprazole, and famotidine to DMSO. The stock solutions were diluted 1:4 in PBS and then added in 2-fold serial dilutions to Reinforced Clostridial Media (RCM). The media was then inoculated with $5\times10^5$ colony forming units (CFU) of *B. longum* subsp. *infantis* and incubated under anaerobic conditions at 37° C. Vehicle only control groups consisted of $5\times10^5$ CFU *B. longum* subsp. *infantis* incubated in RCM with the same amounts of PBS and DMSO as the PPI conditions for each dose. Samples were collected from the cell cultures at various time points and assessed for optical density at 600 nm (OD600) and for *B. longum* subsp. *infantis* levels by qPCR similar to as described in Example 2.

Figure 4A:
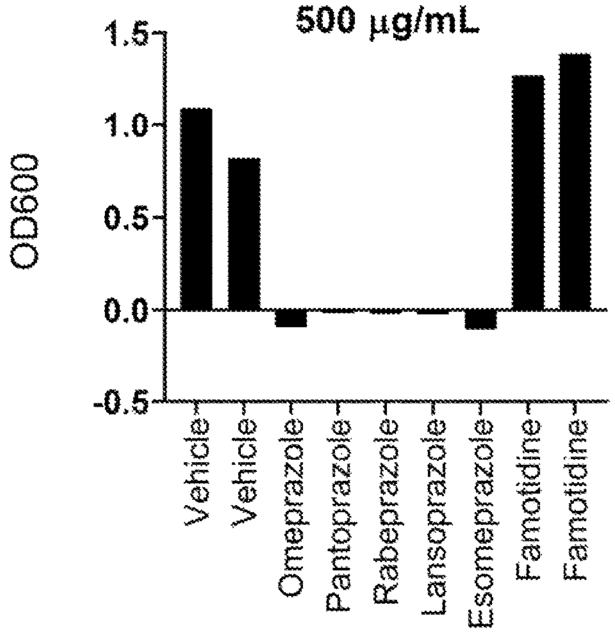
FIGS. 4A-4H show graphs displaying results of OD600 measurements (FIGS. 4A-4D) or qPCR targeting *B. longum* subsp. *infantis* following a 24-hour incubation with various acid reducing compounds at concentrations of 500 μg/mL (FIGS. 4A and 4E), 250 μg/mL (FIGS. 4B and 4F), 125 μg/mL (FIGS. 4C and 4G), 62.5 μg/mL (FIGS. 4D and 4H) or with vehicle controls.
Figure 4B:
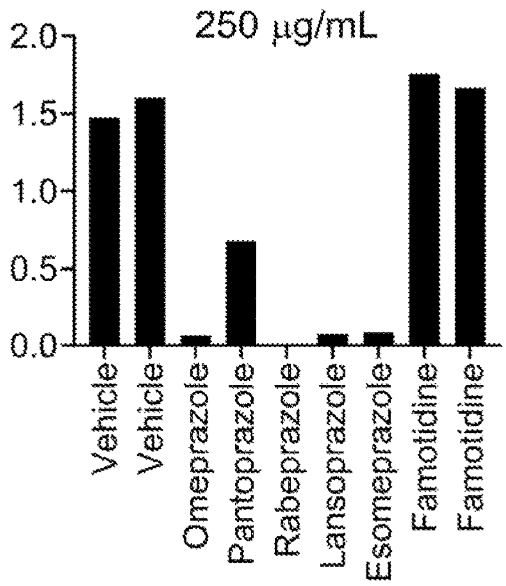
Figure 4C:
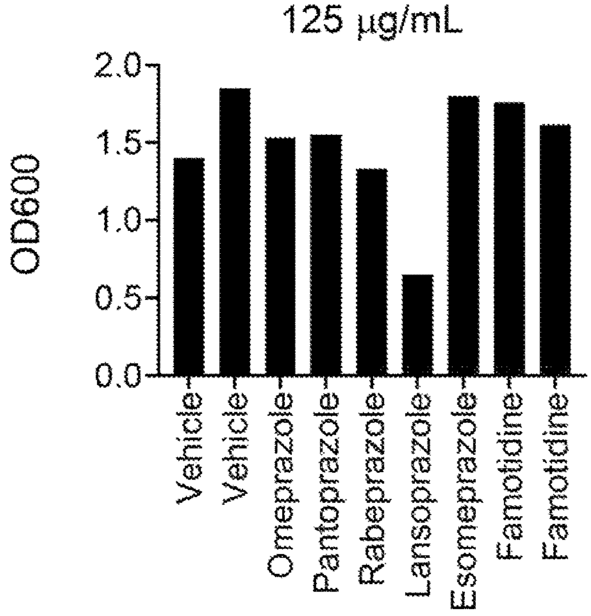
Figure 4D:
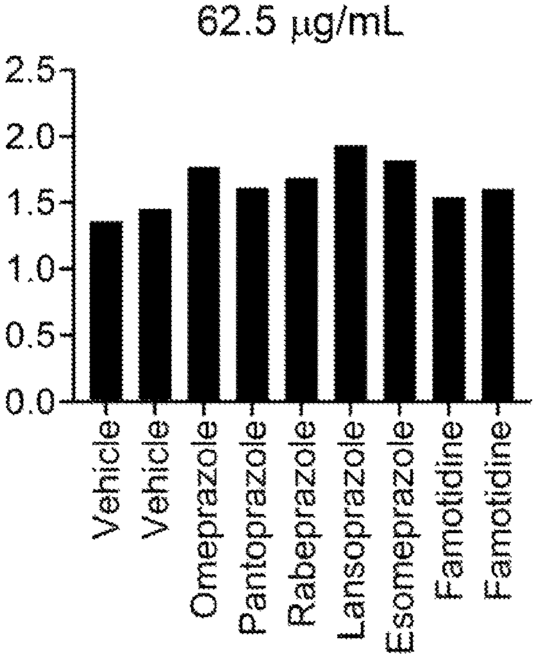
Figure 4E:
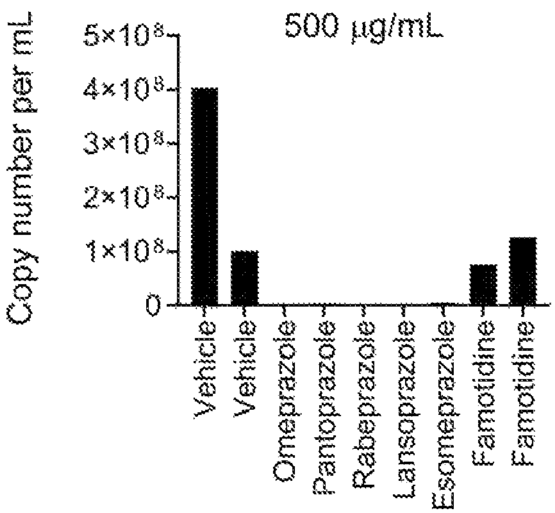
Figure 4F:
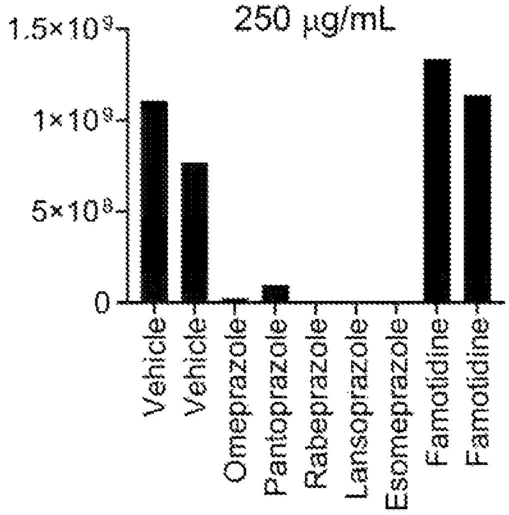
Figure 4G:
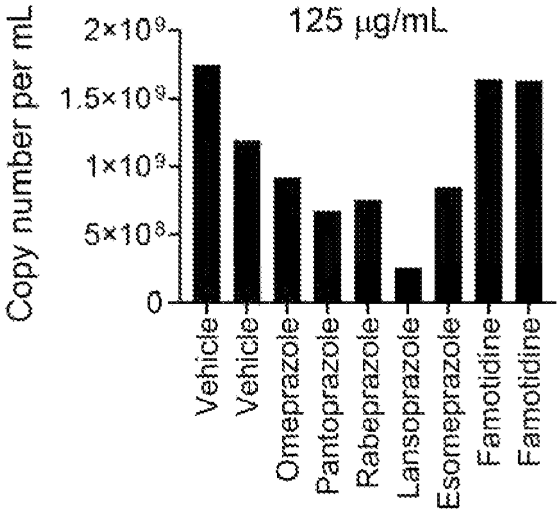

Exemplary results are shown in FIGS. 4A-4H. At 24 hours following incubation, cell cultures incubated with famotidine had similar OD600 values to vehicle controls at all doses tested (FIGS. 4A-4D). In contrast, cell cultures incubated with 500 μg/mL or 250 μg/mL of omeprazole or other substituted benzimidazole compounds had reduced OD600 values compared to vehicle controls (FIGS. 4A and 4B). For samples collected from cell cultures with 125 μg/mL PPI compounds, only lansoprazole was observed to have reduced OD600 values with respect to vehicle controls (FIG. 4C). No differences in OD600 values were observed among any of the samples collected from cultures incubated with PPIs at 62.5 μg/mL as compared to vehicle controls (FIG. 4D).

Figure 4H:
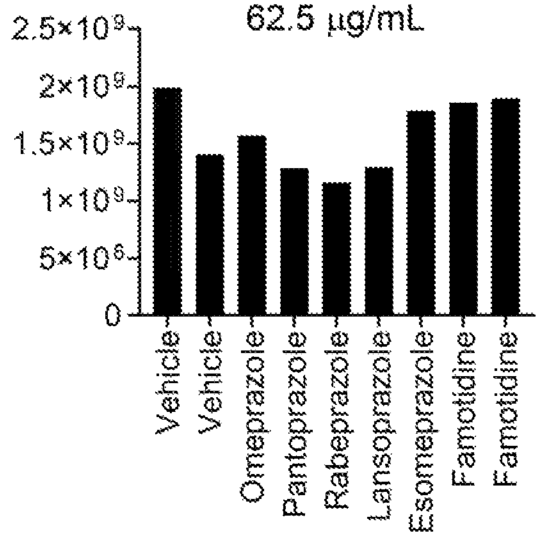

Similar results were observed with *B. longum* subsp. *infantis* levels as measured by qPCR in samples collected after 24 hours of incubation (FIGS. 4E-4H). Cell cultures incubated with famotidine had similar copy numbers corresponding to *B. longum* subsp. *infantis* DNA as compared to vehicle controls at all doses tested, consistent with similar growth under these conditions. Samples from cell cultures incubated with 500 μg/mL, 250 μg/mL, or 125 μg/mL of omeprazole or other substituted benzimidazole compounds displayed trends of reduced of *B. longum* subsp. *infantis* copy number compared to vehicle controls (FIGS. 4E-4G), consistent with impaired growth under these conditions. Incubation with 62.5 μg/mL substituted benzimidazoles resulted in similar copy numbers of *B. longum* subsp. *infantis* as was observed from vehicle controls (FIG. 4H).

Taken together, these data are consistent with impaired growth of *B. longum* subsp. *infantis* with exposure to high levels of omeprazole and other benzimidazole derivatives.

Example 9: *B. longum* Subsp. *infantis* Colonizes Mice Inoculated with a Humanized Intestinal Microbiome A mouse model of a humanized intestinal microbiome was generated to assess *B. longum* subsp. *infantis* engraftment under different conditions. Germ free mice each received a single fecal microbiota transplant (FMT) from a healthy human adult or infant donor (day −3). FMTs were prepared from human stool samples that were processed into a 10% slurry in a saline buffer with glucose added for stability and stored at −80° C. Prior to inoculation, the stool samples were thawed under anaerobic conditions, centrifuged to remove buffer and glycerol, and resuspended in saline buffer alone. FMTs were administered in a 100 μl volume to germ free mice by oral gavage.

Beginning three days after the FMT (day 0), mice were administered doses of $1\times10^8$ colony forming units (CFU) of *B. longum* subsp. *infantis* and 20 mg of total HMO from an HMO mixture (prepared as described in Example 1) twice daily for three days (day 0 to day 2). A group of germ free mice that did not receive an FMT also received treatment with *B. longum* subsp. *infantis* and HMO. A negative control group consisted of mice that received FMT from a healthy human adult donor but received a PBS vehicle in place of *B. longum* subsp. *infantis* and HMO. Fecal pellets were collected from mice in all experimental groups the day of the FMT (day −3) and then daily beginning on day 0 through day 5. DNA was isolated from the fecal pellets, and levels of *B. longum* subsp. *infantis* were assessed by qPCR performed similar to as described in Example 6.

Figure 5:
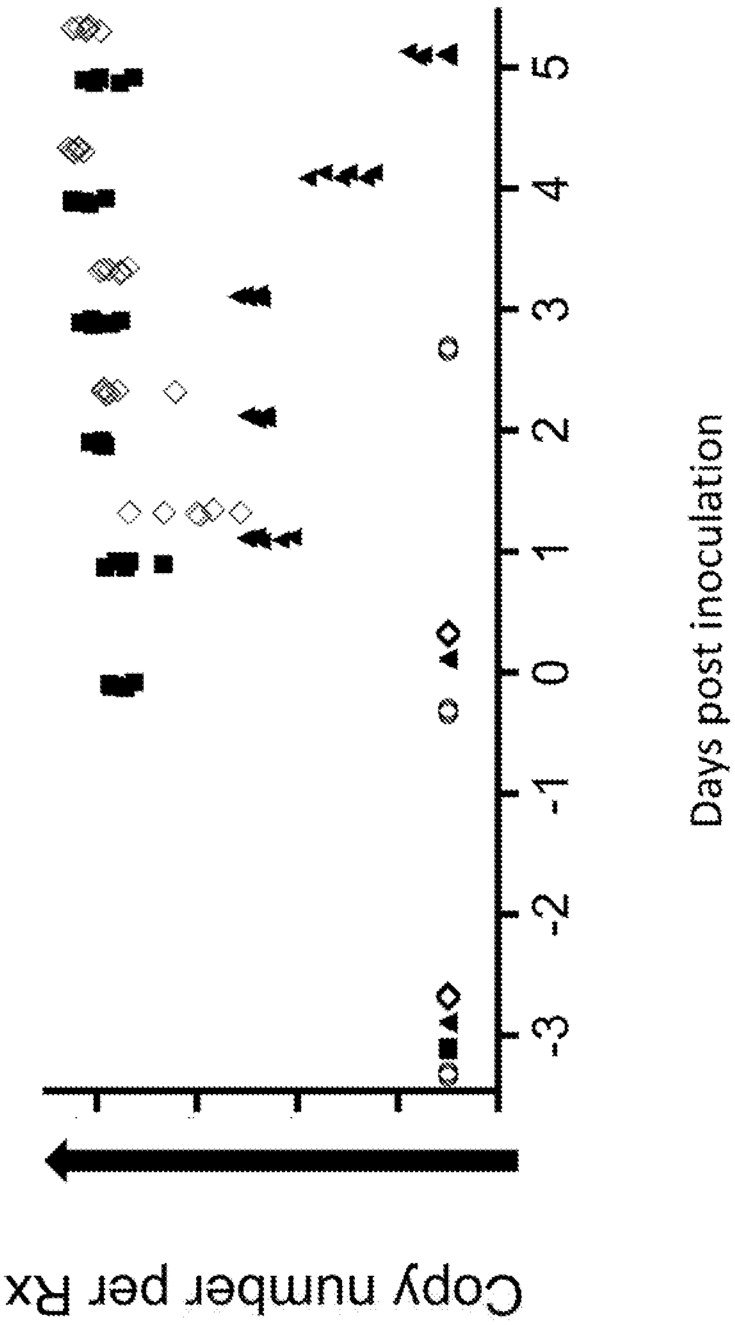
FIG. 5 shows a graph displaying results of qPCR targeting *B. longum* subsp. *infantis* from fecal pellets of individual germ-free mice at various timepoints. Experimental groups of germ free mice included germ free mice that received FMT from the stool of a healthy human adult donor and treatment with HMO (open circles); germ free mice that received FMT from the stool of a healthy human adult donor and treatment with *B. longum* subsp. *infantis* and HMO (solid triangles); germ free mice that received FMT from the stool of a healthy human infant donor and treatment with *B. longum* subsp. *infantis* and HMO (open diamonds); and germ free mice received treatment with *B. longum* subsp. *infantis* and HMO but not FMT (solid squares).

As shown in FIG. 5, *B. longum* subsp. *infantis* was detected in fecal pellets from mice inoculated with *B. longum* subsp. *infantis* but not in stool collected from mice in the negative control group. Consistent with colonization of *B. longum* subsp. *infantis*, this detection persisted to day 5, three days after the final *B. longum* subsp. *infantis* and HMO treatment was administered. Higher levels of *B. longum* subsp. *infantis* were detected in stool from the monocolonized mice (germ free mice that received *B. longum* subsp. *infantis* but not an FMT) and mice that received FMT from healthy infant donors than in mice that received an FMT from healthy adult donors. This trend is consistent with general observations that probiotic strains typically have greater expansion within microbiomes having lower microbial diversity (such as infant or dysbiotic microbiomes) than in healthy adult microbiomes which typically have high microbial diversity.

VII. SEQUENCES

| SEQ ID NO: | Description |
|---|---|
| 1 | *B. longum* subsp. *infantis* partial 16S sequence-GenBank: LC071820.1 |
| 2 | *B. longum* subsp. *infantis* partial 16S sequence-GenBank: KP326372.1 |
| 3 | *B. longum* subsp. *infantis* partial 16S sequence-AB116305.1 |
| 4 | *B. longum* subsp. *infantis* partial 16S sequence-GenBank: X70974.1 |
| 5 | *B. longum* subsp. *infantis* partial 16S sequence-GenBank: D86184.1 |
| 6 | *B. longum* subsp. *infantis* partial 16S sequence-GenBank: AB507102.1 |
| 7 | *B. longum* subsp. *infantis* strain FC13644 16S, partial sequence-MK962475.1 |
| 8 | *B. adolescentis* 16S sequence-NCBI Reference Sequence: NR_074802.2 |
| 9 | *B. animalis* subsp. *animalis* 16S sequence-NCBI Reference Sequence: NR_119007.1 |
| 10 | *B. animalis* subsp. *lactis* partial 16S sequence-GenBank: KU821112 |
| 11 | *B. bifidum* partial 16S sequence |
| 12 | *B. breve* partial 16S sequence-NCBI Reference Sequence: NR_040783.1 |
| 13 | *B. catenulatum* partial 16S sequence |
| 14 | *B. longum* partial 16S sequence-GenBank: LC306854.1 |
| 15 | *B. pseudocatanulatum* partial 16S sequence |
| 16 | *B. pseudolongum* partial 16S sequence-GenBank: M58742.1 |
| 17 | *L. acidophilus* partial 16S sequence-NCBI Reference Sequence: NR_043182.1 |
| 18 | *L. antri* partial 16S sequence-NCBI Reference Sequence: NR_027206.1 |
| 19 | *L. brevis* partial 16S sequence-NCBI Reference Sequence: NR_044704.2 |
| 20 | *L. casei* partial 16S sequence-NR041893.1 |
| 21 | *L. coleohominis* partial 16S sequence-NCBI Reference Sequence: NR_042436.1 |
| 22 | *L. crispatus* partial 16S sequence-NCBI Reference Sequence: NR_041800.1 |

-continued

| SEQ ID NO: | Description |
|---|---|
| 23 | *L. curvatus* partial 16S sequence |
| 24 | *L. delbrueckii* partial 16S sequence-NCBI Reference Sequence: NR_029106.1 |
| 25 | *L. fermentum* partial 16S sequence-NCBI Reference Sequence: NR_104927.1 |
| 26 | *L. gasseri* 16S sequence-NCBI Reference Sequence: NR_075051.2 |
| 27 | *L. johnsonii* partial 16S sequence-NCBI Reference Sequence: NR_025273.1 |
| 28 | *L. harbinensis* partial 16S sequence-NCBI Reference Sequence: NR_041263.1 |
| 29 | *L. mucosae* partial 16S sequence- NCBI Reference Sequence: NR_024994.1 |
| 30 | *L. pentosus* partial 16S sequence |
| 31 | *L. plantarum* partial 16S sequence-NCBI Reference Sequence: NR_042254.1 |
| 32 | *L. reuteri* partial 16S sequence-NCBI Reference Sequence: NR_025911.1 |
| 33 | *L. rhamnosus* partial 16S sequence-NCBI Reference Sequence: NR_043408.1 |
| 34 | *L. sakei* partial 16S sequence-NCBI Reference Sequence: NR_042443.1 |
| 35 | *L. salivarius* partial 16S sequence-NCBI Reference Sequence: NR_028725.2 |
| 36 | *L. paracasei* partial 16S sequence-NCBI Reference Sequence: NR_025880.1 |
| 37 | *L. kisonensis* partial 16S sequence-NCBI Reference Sequence: NR_041658.1 |
| 38 | *L. para-limentarius* partial 16S sequence-NCBI Reference Sequence: NR_025 045.1 |
| 39 | *L. perolens* partial 16S sequence-NCBI Reference Sequence: NR_029360.1 |
| 40 | *L. apis* partial 16S sequence-NCBI Reference Sequence: NR_125702.1 |
| 41 | *L. ghanensis* partial 16S sequence-NCBI Reference Sequence: NR_043896.1 |
| 42 | *L. dextrinicus* partial 16S sequence-NCBI Reference Sequence: NR_036861.1 |
| 43 | *Lactococcus lactis* Partial 16S Sequence-NCBI Reference Sequence: NR_040954.1 |
| 44 | *Bacteroides vulgatus* partial 16S sequence-NCBI Reference Sequence: NR_074515.1 |
| 45 | *Bacteroides fragilis* partial 16S sequence-NCBI Reference Sequence: NR_074784.2 |
| 46 | *Faecalibacterium prausnitzii* partial 16S sequence-NCBI Reference Sequence: NR_121697.2 |
| 47 | *E. rectale* partial 16S sequence-NCBI Reference Sequence: NR_074634.1 |
| 48 | *S. thermophilus* partial 16S sequence-NCBI Reference Sequence: NR_042778.1 |
| 49 | *P. parvulus* partial 16S sequence-NCBI Reference Sequence: NR_029136.1 |
| 50 | *P. lolii* partial 16S sequence-NCBI Reference Sequence: NR_041640.1 |
| 51 | *P. acidilactici* partial 16S sequence-NCBI Reference Sequence: NR_041640.1 |
| 52 | *P. argentinicus* partial 16S sequence-NCBI Reference Sequence: NR_042623.1 |
| 53 | *P. claussenii* partial 16S sequence-NCBI Reference Sequence: NR_042232.1 |
| 54 | *P. pentosaceus* partial 16S sequence-NCBI Reference Sequence: NR_042058.1 |
| 55 | *P. stilesii* partial 16S sequence-NCBI Reference Sequence: NR_042401.1 |
| 56 | forward primer sequence |
| 57 | reverse primer sequence |
| 58 | probe sequence |
| 59 | pksS; Polyketide_biosynthesis_cytochrome_P450_PksS-*B. longum* subsp. *infantis* |
| 60 | higB2; Putative_toxin_HigB2-*B. longum* subsp. *infantis* |
| 61 | putative Riboflavin biosynthesis gene-*B. longum* subsp. *infantis* |
| 62 | Endo-B-N-acetylglucosaminadase-*B. longum* subsp. *infantis* |
| 63 | HTH-type transcriptional activator RhaR-*B. longum* subsp. *infantis* |
| 64 | Putative N-acetylmannosamine-6-phosphate 2-epimerase-*B. longum* subsp. *infantis* |
| 65 | glucokinase-*B. longum* subsp. *infantis* |
| 66 | Lactose Transport Protein-*B. longum* subsp. *infantis* |
| 67 | Sialidase gene-*B. longum* subsp. *infantis* |
| 68 | L-fucose mutarotase-*B. longum* subsp. *infantis* |
| 69 | Hypothetical gene-*B. longum* subsp. *infantis* |
| 70 | ureC: Urease subunit alpha-*B. longum* subsp. *infantis* |
| 71 | LacG Lactose Transport System-*B. longum* subsp. *infantis* |
| 72 | putative multiple-sugar transport system permease YteP-*B. longum* subsp. *infantis* |
| 73 | por; PolyolNADP_oxidoreductase-*B. longum* subsp. *infantis* |
| 74 | UxaC: urinate-*B. longum* subsp. *infantis* |
| 75 | epsK; putative_membrane_protein_EpsK-*B. longum* subsp. *infantis* |
| 76 | putative 2-dehydro-3-deoxy-D-pentonate aldolase YjhH-*B. longum* subsp. *infantis* |
| 77 | Fucosidase-*B. longum* subsp. *infantis* |
| 78 | Hypothetical gene-*B. longum* subsp. *infantis* |

The invention claimed is:

1. A method of treatment, comprising:

administering a prebiotic mixture and at least one probiotic strain to treat or prevent graft versus host disease in a subject in need thereof, wherein:

the prebiotic mixture comprises a plurality of human milk oligosaccharides that comprise 2'-fucosyl-lactose, 3'-fucosyl-lactose, 3'-sialyl-lactose, 6'-sialyl-lactose, lacto-N-tetraose, lacto-N-difucohexaose I, lactodifucotetraose, lacto-N-fucopentaose I, sialylacto-N-tetraose c, sialylacto-N-tetraose b, and disialyllacto-N-tetraose; and the least one probiotic strain comprises *Bifidobacterium longum* subsp. *infantis*.

2. The method of claim 1, wherein the plurality of human milk oligosaccharides comprises at least 25 human milk oligosaccharides.

3. The method of claim 1, wherein the plurality of human milk oligosaccharides comprises at least 50 human milk oligosaccharides.

4. The method of claim 1, wherein the prebiotic mixture is, is comprises a concentrated permeate from pooled human milk, wherein the permeate is obtained from the ultrafiltration of human skim milk, wherein the human skim milk is obtained by removing cream from pooled human milk, and wherein the pooled human milk is pooled from the milk of multiple human milk donors.

5. The method of claim 1, wherein the prebiotic mixture and the probiotic strain are administered orally.

6. The method of claim 1, wherein the method comprises at least a first treatment phase and a second treatment phase, wherein the first treatment phase comprises administering to the subject the prebiotic mixture and the probiotic strain on the same day for at least one day, and wherein the second treatment phase begins after the end of the first treatment phase, and comprises administering the prebiotic mixture for at least one day, wherein the probiotic strain is not administered during the second treatment phase.

7. The method of claim 6, wherein the first treatment phase is between 3 and 14 days in length and wherein the second treatment phase is between 3 and 14 days in length.

8. The method of claim 1, wherein the probiotic strain is administered in an amount of at least $5\times10^6$ colony forming units (CFU) per day.

9. The method of claim 1, wherein the prebiotic mixture is administered in an amount of at least 500 mg of total human milk oligosaccharides per day.

10. The method of claim 9, wherein the prebiotic mixture is administered in an amount of between 0.5 g and 25 g, 1 g and 5 g, 2 g and 3 g, 3 g and 6 g, 4 g and 5 g, 5 g and 10 g, 8 g and 10 g, 10 g and 20 g, 15 g and 25 g, 15 g and 20 g, or 17 g and 19 g of total human milk oligosaccharides per day.

11. The method of claim 1, wherein the subject is a human subject that is a child, an adolescent, or an adult.

* * * * *

SEQUENCE LISTING

<160> NUMBER OF SEQ ID NOS: 78

<210> SEQ ID NO 1
<211> LENGTH: 1452
<212> TYPE: DNA
<213> ORGANISM: Bifidobacterium longum subsp. infantis

<400> SEQUENCE: 1
tggctcagga tgaacgctgg cggcgtgctt aacacatgca agtcgaacgg gatccatcgg 60
gctttgcttg gtggtgagag tggcgaacgg gtgagtaatg cgtgaccgac ctgccccata 120
caccggaata gctcctggaa acgggtggta atgccggatg ttccagttga tcgcatggtc 180
ttctgggaaa gctttcgcgg tatgggatgg ggtcgcgtcc tatcagcttg acggcggggt 240
aacggcccac cgtggcttcg acgggtagcc ggcctgagag ggcgaccggc cacattggga 300
ctgagatacg gcccagactc ctacgggagg cagcagtggg gaatattgca caatgggcgc 360
aagcctgatg cagcgacgcc gcgtgaggga tggaggcctt cgggttgtaa acctctttta 420
tcggggagca agcgtgagtg agtttacccg ttgaataagc accggctaac tacgtgccag 480
cagccgcggt aatacgtagg gtgcaagcgt tatccggaat tattgggcgt aaagggctcg 540
taggcggttc gtcgcgtccg gtgtgaaagt ccatcgctta acggtggatc cgcgccgggt 600
acgggcgggc ttgagtgcgg taggggagac tggaattccc ggtgtaacgg tggaatgtgt 660
agatatcggg aagaacacca atggcgaagg caggtctctg ggccgttact gacgctgagg 720
agcgaaagcg tggggagcga acaggattag ataccctggt agtccacgcc gtaaacggtg 780
gatgctggat gtggggcccg ttccacgggt tccgtgtcgg agctaacgcg ttaagcatcc 840
cgcctgggga gtacggccgc aaggctaaaa ctcaaagaaa ttgacggggg cccgcacaag 900
cggcggagca tgcggattaa ttcgatgcaa cgcgaagaac cttacctggg cttgacatgt 960
tcccgacgat cccagagatg gggtttccct tcggggcggg ttcacaggtg gtgcatggtc 1020
gtcgtcagct cgtgtcgtga gatgttgggt taagtcccgc aacgagcgca accctcgccc 1080
cgtgttgcca gcggattgtg ccgggaactc acgggggacc gccggggtta actcggagga 1140
aggtggggat gacgtcagat catcatgccc cttacgtcca gggcttcacg catgctacaa 1200
tggccggtac aacgggatgc gacgcggcga cgcggagcgg atccctgaaa accggtctca 1260
gttcggatcg cagtctgcaa ctcgactgcg tgaaggcgga gtcgctagta atcgcgaatc 1320
agcaacgtcg cggtgaatgc gttcccgggc cttgtacaca ccgcccgtca agtcatgaaa 1380
gtgggcagca cccgaagccg gtggcctaac cccttgtggg atggagccgt ctaaggtgag 1440
gctcgtgatt gg 1452

<210> SEQ ID NO 2
<211> LENGTH: 1537
<212> TYPE: DNA
<213> ORGANISM: Bifidobacterium longum subsp. infantis

<400> SEQUENCE: 2
tttttgtgga gggttcgatt ctggctcagg atgaacgctg gcggcgtgct taacacatgc 60
aagtcgaacg ggatccatcg ggctttgctt ggtggtgaga gtggcgaacg ggtgagtaat 120
gcgtgaccga cctgccccat acaccggaat agctcctgga aacgggtggt aatgccggat 180
gttccagttg atcgcatggt cttctgggaa agctttcgcg gtatgggatg gggtcgcgtc 240
ctatcagctt gacggcgggg taacggccca ccgtggcttc gacgggtagc cggcctgaga 300
gggcgaccgg ccacattggg actgagatac ggcccagact cctacgggag gcagcagtgg 360
ggaatattgc acaatgggcg caagcctgat gcagcgacgc cgcgtgaggg atggaggcct 420
tcgggttgta aacctctttt atcggggagc aagcgtgagt gagtttaccc gttgaataag 480
caccggctaa ctacgtgcca gcagccgcgg taatacgtag ggtgcaagcg ttatccggaa 540
ttattgggcg taaagggctc gtaggcggtt cgtcgcgtcc ggtgtgaaag tccatcgctt 600
aacggtggat ccgcgccggg tacgggcggg cttgagtgcg gtaggggaga ctggaattcc 660
cggtgtaacg gtggaatgtg tagatatcgg gaagaacacc aatggcgaag gcaggtctct 720
gggccgttac tgacgctgag gagcgaaagc gtggggagcg aacaggatta gataccctgg 780
tagtccacgc cgtaaacggt ggatgctgga tgtggggccc gttccacggg ttccgtgtcg 840
gagctaacgc gttaagcatc ccgcctgggg agtacggccg caaggctaaa actcaaagaa 900
attgacgggg gcccgcacaa gcggcggagc atgcggatta attcgatgca acgcgaagaa 960
ccttacctgg gcttgacatg ttcccgacga tcccagagat ggggtttccc ttcggggcgg 1020
gttcacaggt ggtgcatggt cgtcgtcagc tcgtgtcgtg agatgttggg ttaagtcccg 1080
caacgagcgc aaccctcgcc ccgtgttgcc agcggattgt gccgggaact cacgggggac 1140
cgccggggtt aactcggagg aaggtgggga tgacgtcaga tcatcatgcc ccttacgtcc 1200
agggcttcac gcatgctaca atggccggta caacgggatg cgacgcggcg acgcggagcg 1260
gatccctgaa aaccggtctc agttcggatc gcagtctgca actcgactgc gtgaaggcgg 1320
agtcgctagt aatcgcgaat cagcaacgtc gcggtgaatg cgttcccggg ccttgtacac 1380
accgcccgtc aagtcatgaa agtgggcagc acccgaagcc ggtggcctaa ccccttgtgg 1440
gatggagccg tctaaggtga ggctcgtgat tgggactaag tcgtaacaag gtagccgtac 1500
cggaaggtgc ggctggatca cctcctttct acggaga 1537

<210> SEQ ID NO 3
<211> LENGTH: 472
<212> TYPE: DNA
<213> ORGANISM: Bifidobacterium longum subsp. infantis

<400> SEQUENCE: 3
cgctggcggc gtgcttacac atgcaagtcg aacgggatcc atcgggcttt gcttggtggt 60
gagagtggcg aacgggtgaa taatgcgtga ccgacctgcc ccatacaccg gaatagctcc 120
tggaaacggg tggtaatgcc ggatgttcca gttgatcgca tggtcttctg ggaaagcttt 180
cgcggtatgg gatggggtcg cgtcctatca gcttgacggc ggggtaacgg cccaccgtgg 240
cttcgacggg tagccggcct gagagggcga ccggccacat tgggactgag atacggccca 300
gactcctacg ggaggcagca gtggggaata ttgcacaatg ggcgcaagcc tgatgcagcg 360
acgccgcgtg agggatggag gccttcgggt tgtaaacctc ttttatcggg gagcaagcgt 420
gagtagtgta cccgttgaat aagcaccggt taactcgtgc cagcagccgc gg 472

<210> SEQ ID NO 4
<211> LENGTH: 1458
<212> TYPE: DNA
<213> ORGANISM: Bifidobacterium longum subsp. infantis
<220> FEATURE:
<221> NAME/KEY: misc_feature
<223> OTHER INFORMATION: n = any nucleotide
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (353)..(353)

<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (813)..(817)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (868)..(950)
<223> OTHER INFORMATION: n is a, c, g, or t
<220> FEATURE:
<221> NAME/KEY: misc_feature
<222> LOCATION: (997)..(1009)
<223> OTHER INFORMATION: n is a, c, g, or t
<220> FEATURE:
<221> NAME/KEY: misc_feature
<222> LOCATION: (1013)..(1014)
<223> OTHER INFORMATION: n is a, c, g, or t
<220> FEATURE:
<221> NAME/KEY: misc_feature
<222> LOCATION: (1018)..(1019)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1046)..(1047)
<223> OTHER INFORMATION: n is a, c, g, or t
<220> FEATURE:
<221> NAME/KEY: misc_feature
<222> LOCATION: (1051)..(1051)
<223> OTHER INFORMATION: n is a, c, g, or t
<220> FEATURE:
<221> NAME/KEY: misc_feature
<222> LOCATION: (1054)..(1054)
<223> OTHER INFORMATION: n is a, c, g, or t
<220> FEATURE:
<221> NAME/KEY: misc_feature
<222> LOCATION: (1056)..(1068)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1097)..(1097)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1113)..(1114)
<223> OTHER INFORMATION: n is a, c, g, or t
<220> FEATURE:
<221> NAME/KEY: misc_feature
<222> LOCATION: (1121)..(1122)
<223> OTHER INFORMATION: n is a, c, g, or t
<220> FEATURE:
<221> NAME/KEY: misc_feature
<222> LOCATION: (1132)..(1133)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1187)..(1187)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:

<221> NAME/KEY: misc_feature
<222> LOCATION: (1276)..(1276)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1337)..(1337)
<223> OTHER INFORMATION: n is a, c, g, or t
<220> FEATURE:
<221> NAME/KEY: misc_feature
<222> LOCATION: (1340)..(1340)
<223> OTHER INFORMATION: n is a, c, g, or t
<220> FEATURE:
<221> NAME/KEY: misc_feature
<222> LOCATION: (1382)..(1383)
<223> OTHER INFORMATION: n is a, c, g, or t
<220> FEATURE:
<221> NAME/KEY: misc_feature
<222> LOCATION: (1393)..(1393)
<223> OTHER INFORMATION: n is a, c, g, or t
<220> FEATURE:
<221> NAME/KEY: misc_feature
<222> LOCATION: (1406)..(1406)
<223> OTHER INFORMATION: n is a, c, g, or t
<220> FEATURE:
<221> NAME/KEY: misc_feature
<222> LOCATION: (1423)..(1423)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1439)..(1439)
<223> OTHER INFORMATION: n is a, c, g, or t

<400> SEQUENCE: 4

```
tttgtggagg gttcgattct ggctcaggat gaacgctggc ggcgtgcttn acacatgcaa     60

gtcgaacggg atccatcggg ctttgcttgg tggtgagagt ggcgaacggg tgagtaatgc    120

gtgaccgacc tgccccatac accggaatag ctcctggaaa cgggtggtaa tgccgnatgt    180

tccagttgat cgcatggtct tctgggaaac tttcgcggta tgggatgggg tcgngtccta    240

tcagcttgac ggcggggtaa cggccnaccg tggcttcgac gggtagccgg cctgagaggg    300

cgaccggcca cattgggact gagatacggc ccagactcct acgggaggca gcngtgggga    360

atnttgcacn atgggcgcaa gcctgatgca gcgacgcngc gtgagggatg gaggcttcgg    420

gttgtaaacc tcttttntcg gggagcaagc ntnagtgagt tnacccnttg aatnagcacc    480

ggctaactac gtgccagcag ccgcggtaat acgtagggtg cnagcgtnat ccggaattat    540

tgggcgtnaa gggctcgtag gcggttcgtc gcgtccggtg tgaaagtcca tcgcttaacg    600

gtggatccgc gccgggtacg ggcgggcttg agtgcggtag gggagactgg aattcccggt    660

gtaacggtgg aatgtgtaga tatcgggaag aacaccaatg gcgaaggcag gtctctgggc    720

ngttactgac gcttaggagc taaagcgttg ggagcgaaca ggattagata ccctggtagt    780

ccacgccgta aacggtggat gctggangng ggnnnnnttc cacgggnncc gtgtcggacg    840

aacgcgttaa gcatccngcc tngggagnnn nnnnnnnnnn nnnnnnnnnn nnnnnnnnnn    900

nnnnnnnnnn nnnnnnnnnn nnnnnnnnnn nnnnnnnnnn nnnnnnnnnn aagaacctta    960

cctgggcttg acatgttccc gacgatccca gaggggnnnn nnnnnnnnng ggnnggtnna   1020

caggtggngc anggtcgtcg tcagcnngtg ncgngnnnnn nnnnnnnnag tcccgcaacg   1080

agcgcaacnc tcgcccngtg ttgccagcgg ntnntgccgg nnactcacgg gnnaccgccg   1140
```

-continued

```
gggttnactc ggaggaaggt ggggatgacg tcagatcatc atgcccntta cgtccagggc   1200

ttcacgcatg ctacaatggc cggtacaacg ggatgcgacg cggcgacgcg gagcggatcc   1260

ctgaaaaccn gnctcngttc ggatcgcagt ctgcnactcg actgcgtgaa ggcggagtcg   1320

ctagtaatcg cgaatcngcn gcgtcgcggt gaatgcgttc ccgggccttg tacacaccgc   1380

cnntcaagtc atnaaagtgg gcagcncccg aagccggtgg ccnaacccct ngtgggatng   1440

agccgtctaa ggtgaggc                                                 1458
```

<210> SEQ ID NO 5
<211> LENGTH: 1515
<212> TYPE: DNA
<213> ORGANISM: Bifidobacterium longum subsp. infantis

<400> SEQUENCE: 5

```
tttgatcatg gctcaggatg aacgctggcg gcgtgcttaa cacatgcaag tcgaacggga     60

tccatcgggc tttgcttggt ggtgagagtg gcgaacgggt gagtaatgcg tgaccgacct    120

gccccataca ccggaatagc tcctggaaac gggtggtaat gccggatgtt ccagttgatc    180

gcatggtctt ctgggaaagc tttcgcggta tgggatgggg tcgcgtccta tcagcttgac    240

ggcggggtaa cggcccaccg tggcttcgac gggtagccgg cctgagaggg cgaccggcca    300

cattgggact gagatacggc ccagactcct acgggaggca gcagtgggga atattgcaca    360

atgggcgcaa gcctgatgca gcgacgccgc gtgagggatg gaggccttcg ggttgtaaac    420

ctcttttatc ggggagcaag cgtgagtgag tttacccgtt gaataagcac cggctaacta    480

cgtgccagca gccgcggtaa tacgtagggt gcaagcgtta tccggaatta ttgggcgtaa    540

agggctcgta ggcggttcgt cgcgtccggt gtgaaagtcc atcgcttaac ggtggatccg    600

cgccgggtac gggcgggctt gagtgcggta ggggagactg gaattcccgg tgtaacggtg    660

gaatgtgtag atatcgggaa gaacaccaat ggcgaaggca ggtctctggg ccgttactga    720

cgctgaggag cgaaagcgtg gggagcgaac aggattagat accctggtag tccacgccgt    780

aaacggtgga tgctggatgt ggggcccgtt ccacgggttc cgtgtcggag ctaacgcgtt    840

aagcatcccg cctggggagt acggccgcaa ggctaaaact caaagaaatt gacgggggcc    900

cgcacaagcg gcggagcatg cggattaatt cgatgcaacg cgaagaacct tacctgggct    960

tgacatgttc ccgacgatcc cagagatggg gtttcccttc ggggcgggtt cacaggtggt   1020

gcatggtcgt cgtcagctcg tgtcgtgaga tgttgggtta agtcccgcaa cgagcgcaac   1080

cctcgccccg tgttgccagc ggattgtgcc gggaactcac gggggaccgc cggggttaac   1140

tcggaggaag gtggggatga cgtcagatca tcatgcccct tacgtccagg gcttcacgca   1200

tgctacaatg gccggtacaa cgggatgcga cgcggcgacg cggagcggat ccctgaaaac   1260

cggtctcagt tcggatcgca gtctgcaact cgactgcgtg aaggcggagt cgctagtaat   1320

cgcgaatcag caacgtcgcg gtgaatgcgt tcccgggcct tgtacacacc gcccgtcaag   1380

tcatgaaagt gggcagcacc cgaagccggt ggcctaaccc cttgtgggat ggagccgtct   1440

aaggtgaggc tcgtgattgg gactaagtcg taacaaggta gccgtaccgg aaggtgcggc   1500

tggatcacct cctta                                                    1515
```

<210> SEQ ID NO 6
<211> LENGTH: 658
<212> TYPE: DNA
<213> ORGANISM: Bifidobacterium longum subsp. infantis

<400> SEQUENCE: 6
ccatcgggct ttgcttggtg gtgagagtgg cgaacgggtg agtaatgcgt gaccgacctg 60
ccccatacac cggaatagct cctggaaacg ggtggtaatg ccggatgttc cagttgatcg 120
catggtcttc tgggaaagct ttcgcggtat gggatggggt cgcgtcctat cagcttgacg 180
gcggggtaac ggcccaccgt ggcttcgacg ggtagccggc ctgagagggc gaccggccac 240
attgggactg agatacggcc cagactccta cgggaggcag cagtggggaa tattgcacaa 300
tgggcgcaag cctgatgcag cgacgccgcg tgagggatgg aggccttcgg gttgtaaacc 360
tcttttatcg ggagcaagc gtgagtgagt ttacccgttg aataagcacc ggctaactac 420
gtgccagcag ccgcggtaat acgtagggtg caagcgttat ccggaattat tgggcgtaaa 480
gggctcgtag gcggttcgtc gcgtccggtg tgaaagtcca tcgcttaacg gtggatccgc 540
gccgggtacg ggcgggcttg agtgcggtag gggagactgg aattcccggt gtaacggtgg 600
aatgtgtaga tatcgggaag aacaccaatg gcgaaggcag gtctctgggc cgttactg 658

<210> SEQ ID NO 7
<211> LENGTH: 1447
<212> TYPE: DNA
<213> ORGANISM: Bifidobacterium longum subsp. infantis

<400> SEQUENCE: 7
gatgaacgct ggcggcgtgc ttaacacatg caagtcgaac gggatccatc aagcttgctt 60
ggtggtgaga gtggcgaacg ggtgagtaat gcgtgaccga cctgccccat acaccggaat 120
agctcctgga aacgggtggt aatgccggat gttccagttg atcgcatggt cttctgggaa 180
agctttcgcg gtatgggatg gggtcgcgtc ctatcagctt gacggcgggg taacggccca 240
ccgtggcttc gacgggtagc cggcctgaga gggcgaccgg ccacattggg actgagatac 300
ggcccagact cctacgggag gcagcagtgg ggaatattgc acaatgggcg caagcctgat 360
gcagcgacgc cgcgtgaggg atggaggcct tcgggttgta aacctctttt atcggggagc 420
aagcgtgagt gagtttaccc gttgaataag caccggctaa ctacgtgcca gcagccgcgg 480
taatacgtag ggtgcaagcg ttatccggaa ttattgggcg taaagggctc gtaggcggtt 540
cgtcgcgtcc ggtgtgaaag tccatcgctt aacggtggat ccgcgccggg tacgggcggg 600
cttgagtgcg gtaggggaga ctggaattcc cggtgtaacg gtggaatgtg tagatatcgg 660
gaagaacacc aatggcgaag gcaggtctct gggccgttac tgacgctgag gagcgaaagc 720
gtggggagcg aacaggatta gataccctgg tagtccacgc cgtaaacggt ggatgctgga 780
tgtggggccc gttccacggg ttccgtgtcg gagctaacgc gttaagcatc ccgcctgggg 840
agtacggccg caaggctaaa actcaaagaa attgacgggg gcccgcacaa gcggcggagc 900
atgcggatta attcgatgca acgcgaagaa ccttacctgg gcttgacatg ttcccgacga 960
tcccagagat ggggtttccc ttcggggcgg gttcacaggt ggtgcatggt cgtcgtcagc 1020
tcgtgtcgtg agatgttggg ttaagtcccg caacgagcgc aaccctcgcc ccgtgttgcc 1080
agcggattgt gccgggaact cacgggggac cgccggggtt aactcggagg aaggtgggga 1140
tgacgtcaga tcatcatgcc ccttacgtcc agggcttcac gcatgctaca atggccggta 1200
caacgggatg cgacgcggcg acgcggagcg gatccctgaa aaccggtctc agttcggatc 1260
gcagtctgca actcgactgc gtgaaggcgg agtcgctagt aatcgcgaat cagcaacgtc 1320
gcggtgaatg cgttcccggg ccttgtacac accgcccgtc aagtcatgaa agtgggcagc 1380
acccgaagcc ggtggcctaa ccccttgtgg gatggagccg tctaaggtga ggctcgtgat 1440

-continued tgggact 1447

<210> SEQ ID NO 8
<211> LENGTH: 1530
<212> TYPE: DNA
<213> ORGANISM: Bifidobacterium adolescentis

<400> SEQUENCE: 8
tttgtggagg gttcgattct ggctcaggat gaacgctggc ggcgtgctta acacatgcaa 60
gtcgaacggg atcggctgga gcttgctccg gccgtgagag tggcgaacgg gtgagtaatg 120
cgtgaccgac ctgccccata caccggaata gctcctggaa acgggtggta atgccggatg 180
ctccagttgg atgcatgtcc ttctgggaaa gattctatcg gtatgggatg gggtcgcgtc 240
ctatcagctt gatggcgggg taacggccca ccatggcttc gacgggtagc cggcctgaga 300
gggcgaccgg ccacattggg actgagatac ggcccagact cctacgggag gcagcagtgg 360
ggaatattgc acaatgggcg caagcctgat gcagcgacgc cgcgtgcggg atgacggcct 420
tcgggttgta aaccgctttt gactgggagc aagcccttcg ggtgagtgt acctttcgaa 480 taagcaccgg ctaactacgt gccagcagcc gcggtaatac gtagggtgca agcgttatcc 540
ggaattattg ggcgtaaagg gctcgtaggc ggttcgtcgc gtccggtgtg aaagtccatc 600
gcttaacggt ggatccgcgc cgggtacggg cgggcttgag tgcggtaggg gagactggaa 660
ttcccggtgt aacggtggaa tgtgtagata tcgggaagaa caccaatggc gaaggcaggt 720
ctctgggccg tcactgacgc tgaggagcga aagcgtgggg agcgaacagg attagatacc 780
ctggtagtcc acgccgtaaa cggtggatgc tggatgtggg gaccattcca cggtctccgt 840
gtcggagcca acgcgttaag catcccgcct ggggagtacg gccgcaaggc taaaactcaa 900
agaaattgac gggggcccgc acaagcggcg gagcatgcgg attaattcga tgcaacgcga 960
agaaccttac ctgggcttga catgttcccg acagccccag agatggggcc tcccttcggg 1020
gcgggttcac aggtggtgca tggtcgtcgt cagctcgtgt cgtgagatgt tgggttaagt 1080
cccgcaacga gcgcaaccct cgccctgtgt tgccagcacg tcgtggtggg aactcacggg 1140
ggaccgccgg ggtcaactcg gaggaaggtg gggatgacgt cagatcatca tgccccttac 1200
gtccagggct tcacgcatgc tacaatggcc ggtacaacgg gatgcgacct cgtgaggggg 1260
agcggatccc ttaaaaccgg tctcagttcg gattggagtc tgcaacccga ctccatgaag 1320
gcggagtcgc tagtaatcgc ggatcagcaa cgccgcggtg aatgcgttcc cgggccttgt 1380
acacaccgcc cgtcaagtca tgaaagtggg tagcacccga agccggtggc ccaacctttt 1440 tgggggggagc cgtctaaggt gagactcgtg attgggacta agtcgtaaca aggtagccgt 1500
accggaaggt gcggctggat cacctccttt 1530

<210> SEQ ID NO 9
<211> LENGTH: 1459
<212> TYPE: DNA
<213> ORGANISM: Bifidobacterium animalis subsp. animalis
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(64)

-continued

<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (325)..(328)
<223> OTHER INFORMATION: n is a, c, g, or t
<220> FEATURE:
<221> NAME/KEY: misc_feature
<222> LOCATION: (346)..(347)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (889)..(889)
<223> OTHER INFORMATION: n is a, c, g, or t
<220> FEATURE:
<221> NAME/KEY: misc_feature
<222> LOCATION: (895)..(897)
<223> OTHER INFORMATION: n is a, c, g, or t
<220> FEATURE:
<221> NAME/KEY: misc_feature
<222> LOCATION: (900)..(901)
<223> OTHER INFORMATION: n is a, c, g, or t
<220> FEATURE:
<221> NAME/KEY: misc_feature
<222> LOCATION: (911)..(911)
<223> OTHER INFORMATION: n is a, c, g, or t
<220> FEATURE:
<221> NAME/KEY: misc_feature
<222> LOCATION: (919)..(919)
<223> OTHER INFORMATION: n is a, c, g, or t
<220> FEATURE:
<221> NAME/KEY: misc_feature
<222> LOCATION: (925)..(926)
<223> OTHER INFORMATION: n is a, c, g, or t
<220> FEATURE:
<221> NAME/KEY: misc_feature
<222> LOCATION: (940)..(940)
<223> OTHER INFORMATION: n is a, c, g, or t
<220> FEATURE:

```
<221> NAME/KEY: misc_feature
<222> LOCATION: (949)..(951)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (1004)..(1005)
<223> OTHER INFORMATION: n is a, c, g, or t
<220> FEATURE:
<221> NAME/KEY: misc_feature
<222> LOCATION: (1009)..(1009)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1073)..(1073)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1091)..(1091)
<223> OTHER INFORMATION: n is a, c, g, or t
<220> FEATURE:
<221> NAME/KEY: misc_feature
<222> LOCATION: (1118)..(1119)
<223> OTHER INFORMATION: n is a, c, g, or t
<220> FEATURE:
<221> NAME/KEY: misc_feature
<222> LOCATION: (1126)..(1127)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1195)..(1195)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1220)..(1220)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1277)..(1277)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t
<220> FEATURE:
<221> NAME/KEY: misc_feature
<222> LOCATION: (1328)..(1328)
<223> OTHER INFORMATION: n is a, c, g, or t
```

<220> FEATURE:
<221> NAME/KEY: misc_feature
<222> LOCATION: (1331)..(1331)
<223> OTHER INFORMATION: n is a, c, g, or t
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1388)..(1388)
<223> OTHER INFORMATION: n is a, c, g, or t
<220> FEATURE:
<221> NAME/KEY: misc_feature
<222> LOCATION: (1390)..(1391)
<223> OTHER INFORMATION: n is a, c, g, or t
<220> FEATURE:
<221> NAME/KEY: misc_feature
<222> LOCATION: (1394)..(1396)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1411)..(1411)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1429)..(1429)
<223> OTHER INFORMATION: n is a, c, g, or t
<220> FEATURE:
<221> NAME/KEY: misc_feature
<222> LOCATION: (1452)..(1452)
<223> OTHER INFORMATION: n is a, c, g, or t

<400> SEQUENCE: 9
ggttcgattc tggctcagga tgaacgctng cggcgtgctt aacacatgca agtcgaacgg 60
natnctggnn gcctnnctgc cnggnngaga gtggcgaacg ggtgagtnat gcgtgaccaa 120
cctgccctgt gcaccggaat agctcctgga aacgngtggt aataccnnat ctccnccnac 180
cgcatggtgg nntgggaaat gctttttgcg gcatgggatg gngtcgcgtc ctatcagctt 240
gttggcgggg tgatggccca ccaaggcgtt gacgggnagc cggcctgaga gggtgaccgg 300
ccacnttggg actgagatac ggccnnnnct cctacgggag gcagcnntgg ggaatattgc 360
acaatgggcg caagcctgat gcagcgacgc cgcgtgcggg atggaggctt cgggttgtna 420
accgcntttg ttcnagggcn aggcacggct tcgggccgng ttgagtggat tgttcgaata 480
agcaccggct aactacgtgc cagcagccgc ggtnatacgt agggtgcnag cgttatccgg 540
atttnttggg cgtnaagggc tcgtaggcgg ttcgtcgcgt ccggtgtgaa agtccatcgc 600
taacggtgga tctgcgccgg gtacgggcgg gctggagtgc ggtaggggag actggaattc 660
ccggtgtaac ggtggaatgt gtagatatcg ggaagaacac caatggcgaa ggcaggtctc 720
tgggcngnta ctgacgctga ggagcnaaag cgtggggagc gaacaggatt ngatnccctg 780
gtngtccacg ccgtaaacgg tggatgctgg atgtggggcc ntttccacgg gtcctgtgtc 840
ggagccaacg cgttaagcat ccngcctggg gagtacggcc gcaaggctna aactnnnagn 900
nattgacggg ngccgcacna gcggnngagc atgcggattn attcgatgnn ncgcgaagna 960

-continued

```
ccttacctgg gcttgacatg tgccggatcg ccccggaaac gggnngtgnc ttcggggccg   1020

gttcacaggt ggngcatggt cgtcgtcagc tcgtgtcgtg agatgttggg ttnagtcccg   1080

caacgngcgc naccctcgcc gcatgttgcc agcgggtnnt gccggnnact catgtgggac   1140

cgccggggtc nactcggagg aaggtgggga tgacgtcaga tcatcatgcc ccttncgtcc   1200

agggcttcnc gcatgctncn atggccggta caacgcgatg cgacacggtg acgtggggcg   1260

gatcgctgaa aaccngnctc ngttcggatc gcagtctgcn actcgactgc gtgaaggcgg   1320

agtcgctngt natcgcggat cagcaacgcc gcggtgaatg cgttcccggg ccttgtacnc   1380

accgcncntn nagnnntnaa agtgggtagc ncccgnagcc ggtggcccna ccctcgtggg   1440

gggagccgtc tnaggtgag                                                1459
```

<210> SEQ ID NO 10
<211> LENGTH: 1420
<212> TYPE: DNA
<213> ORGANISM: Bifidobacterium animalis subsp. animalis

<400> SEQUENCE: 10

```
caggatgaac gctggcggcg tgcttaacac atgcaagtcg aacgggatcc ctggcagctt     60

gctgtcgggg tgagagtggc gaacgggtga gtaatgcgtg accaacctgc cctgtgcacc    120

ggaatagctc ctggaaacgg gtggtaatac cggatgctcc gctccatcgc atggtggggt    180

gggaaatgct tttgcggcat gggatggggt cgcgtcctat cagcttgttg gcggggtgat    240

ggcccaccaa ggcgttgacg ggtagccggc ctgagagggt gaccggccac attgggactg    300

agatacggcc cagactccta cgggaggcag cagtggggaa tattgcacaa tgggcgcaag    360

cctgatgcag cgacgccgcg tgcgggatgg aggccttcgg gttgtaaacc gcttttgttc    420

aagggcaagg cacggtttcg gccgtgttga gtggattgtt cgaataagca ccggctaact    480

acgtgccagc agccgcggta atacgtaggg tgcgagcgtt atccggattt attgggcgta    540

aagggctcgt aggcggttcg tcgcgtccgg tgtgaaagtc catcgcctaa cggtggatct    600

gcgccgggta cgggcgggct ggagtgcggt aggggagact ggaattcccg gtgtaacggt    660

ggaatgtgta gatatcggga agaacaccaa tggcgaaggc aggtctctgg gccgtcactg    720

acgctgagga gcgaaagcgt ggggagcgaa caggattaga taccctggta gtccacgccg    780

taaacggtgg atgctggatg tggggccctt tccacgggtc ccgtgtcgga gccaacgcgt    840

taagcatccc gcctggggag tacggccgca aggctaaaac tcaaagaaat tgacgggggc    900

ccgcacaagc ggcggagcat gcggattaat tcgatgcaac gcgaagaacc ttacctgggc    960

ttgacatgtg ccggatcgcc gtggagacgc ggtttccctt cggggccggt tcacaggtgg   1020

tgcatggtcg tcgtcagctc gtgtcgtgag atgttgggtt aagtcccgca acgagcgcaa   1080

ccctcgccgc atgttgccag cgggtgatgc cgggaactca tgtgggaccg ccggggtcaa   1140

ctcggaggaa ggtggggatg acgtcagatc atcatgcccc ttacgtccag ggcttcacgc   1200

atgctacaat ggccggtaca acgcggtgcg acacggtgac gtggggcgga tcgctgaaaa   1260

ccggtctcag ttcggatcgc agtctgcaac tcgactgcgt gaaggcggag tcgctagtaa   1320

tcgcggatca gcaacgccgc ggtgaatgcg ttcccgggcc ttgtacacac cgcccgtcaa   1380

gtcatgaaag tgggtagcac ccgaagccgg tggcccgacc                         1420
```

<210> SEQ ID NO 11
<211> LENGTH: 1488
<212> TYPE: DNA
<213> ORGANISM: Bifidobacterium bifidum

<400> SEQUENCE: 11
gatgaacgct ggcggcgtgc ttaacacatg caagtcgaac gggatccatc aagcttgctt 60
ggtggtgaga gtggcgaacg ggtgagtaat gcgtgaccga cctgccccat gctccggaat 120
agctcctgga aacgggtggt aatgccggat gttccacatg atcgcatgtg attgtgggaa 180
agattctatc ggcgtgggat ggggtcgcgt cctatcagct tgttggtgag gtaacggctc 240
accaaggctt cgacgggtag ccggcctgag agggcgaccg gccacattgg gactgagata 300
cggcccagac tcctacggga ggcagcagtg gggaatattg cacaatgggc gcaagcctga 360
tgcagcgacg ccgcgtgagg gatggaggcc ttcgggttgt aaacctcttt tgtttgggag 420
caagccttcg ggtgagtgta cctttcgaat aagcgccggc taactacgtg ccagcagccg 480
cggtaatacg tagggcgcaa gcgttatccg gatttattgg gcgtaaaggg ctcgtaggcg 540
gctcgtcgcg tccggtgtga aagtccatcg cttaacggtg gatctgcgcc gggtacgggc 600
gggctggagt gcggtagggg agactggaat tcccggtgta acggtggaat gtgtagatat 660
cgggaagaac accgatggcg aaggcaggtc tctgggccgt cactgacgct gaggagcgaa 720
agcgtgggga gcgaacagga ttagataccc tggtagtcca cgccgtaaac ggtggacgct 780
ggatgtgggg cacgttccac gtgttccgtg tcggagctaa cgcgttaagc gtcccgcctg 840
gggagtacgg ccgcaaggct aaaactcaaa gaaattgacg gggcccgca caagcggcgg 900 agcatgcgga ttaattcgat gcaacgcgaa gaaccttacc tgggcttgac atgttcccga 960
cgacgccaga gatggcgttt cccttcgggg cgggttcaca ggtggtgcat ggtcgtcgtc 1020
agctcgtgtc gtgagatgtt gggttaagtc ccgcaacgag cgcaaccctc gccccgtgtt 1080
gccagcacgt tatggtggga actcacgggg gaccgccggg gttaactcgg aggaaggtgg 1140
ggatgacgtc agatcatcat gccccttacg tccagggctt cacgcatgct acaatggccg 1200
gtacagcggg atgcgacatg gcgacatgga gcggatccct gaaaaccggt ctcagttcgg 1260
atcggagcct gcaacccggc tccgtgaagg cggagtcgct agtaatcgcg gatcagcaac 1320
gccgcggtga atgcgttccc gggccttgta cacaccgccc gtcaagtcat gaaagtgggc 1380
agcacccgaa gccggtggcc taacccttg tgggatggag ccgtctaagg tgaggctcgt 1440
gattgggact aagtcgtaac aaggtagccg taccggaagg tgcggctg 1488

<210> SEQ ID NO 12
<211> LENGTH: 1520
<212> TYPE: DNA
<213> ORGANISM: Bifidobacterium breve

<400> SEQUENCE: 12
ttcgattctg gctcaggatg aacgctggcg gcgtgcttaa cacatgcaag tcgaacggga 60
tccatcgggc tttgcttggt ggtgagagtg gcgaacgggt gagtaatgcg tgaccgacct 120
gccccatgca ccggaatagc tcctggaaac gggtggtaat gccggatgct ccatcacacc 180
gcatggtgtg ttgggaaagc ctttgcggca tgggatgggg tcgcgtccta tcagcttgat 240
ggcggggtaa cggcccacca tggcttcgac gggtagccgg cctgagaggg cgaccggcca 300
cattgggact gagatacggc ccagactcct acgggaggca gcagtgggga atattgcaca 360
atgggcgcaa gcctgatgca gcgacgccgc gtgagggatg gaggccttcg ggttgtaaac 420
ctcttttgtt agggagcaag gcactttgtg ttgagtgtac ctttcgaata agcaccggct 480
aactacgtgc cagcagccgc ggtaatacgt agggtgcaag cgttatccgg aattattggg 540

```
cgtaaagggc tcgtaggcgg ttcgtcgcgt ccggtgtgaa agtccatcgc ttaacggtgg    600

atccgcgccg ggtacgggcg ggcttgagtg cggtagggga gactggaatt cccggtgtaa    660

cggtggaatg tgtagatatc gggaagaaca ccaatggcga aggcaggtct ctgggccgtt    720

actgacgctg aggagcgaaa gcgtggggag cgaacaggat tagataccct ggtagtccac    780

gccgtaaacg gtggatgctg gatgtggggc ccgttccacg ggttccgtgt cggagctaac    840

gcgttaagca tcccgcctgg ggagtacggc cgcaaggcta aaactcaaag aaattgacgg    900

gggcccgcac aagcggcgga gcatgcggat taattcgatg caacgcgaag aaccttacct    960

gggcttgaca tgttcccgac gatcccagag atggggtttc ccttcggggc gggttcacag   1020

gtggtgcatg gtcgtcgtca gctcgtgtcg tgagatgttg ggttaagtcc cgcaacgagc   1080

gcaaccctcg ccccgtgttg ccagcggatt gtgccgggaa ctcacggggg accgccgggg   1140

ttaactcgga ggaaggtggg gatgacgtca gatcatcatg ccccttacgt ccagggcttc   1200

acgcatgcta caatggccgg tacaacggga tgcgacagtg cgagctggag cggatccctg   1260

aaaaccggtc tcagttcgga tcgcagtctg caactcgact gcgtgaaggc ggagtcgcta   1320

gtaatcgcga atcagcaacg tcgcggtgaa tgcgttcccg ggccttgtac acaccgcccg   1380

tcaagtcatg aaagtgggca gcacccgaag ccggtggcct aaccccttgc gggagggagc   1440

cgtctaaggt gaggctcgtg attgggacta agtcgtaaca aggtagccgt accggaaggt   1500

gcggctggat cacctcctta                                               1520
```

<210> SEQ ID NO 13
<211> LENGTH: 1445
<212> TYPE: DNA
<213> ORGANISM: Bifidobacterium catenulatum

<400> SEQUENCE: 13

```
tgaacgctgg cggcgtgctt aacacatgca agtcgaacgg gatccaggca gcttgctgcc     60

tggtgagagt ggcgaacggg tgagtaatgc gtgaccgacc tgccccatac accggaatag    120

ctcctggaaa cgggtggtaa tgccggatgc tccgactcct cgcatggggt gtcgggaaag    180

atttcatcgg tatgggatgg ggtcgcgtcc tatcaggtag tcggcggggt aacggcccac    240

cgagcctacg acgggtagcc ggcctgagag ggcgaccggc cacattggga ctgagatacg    300

gcccagactc ctacgggagg cagcagtggg gaatattgca caatgggcgc aagcctgatg    360

cagcgacgcc gcgtgcggga tgacggcctt cgggttgtaa accgcttttg atcgggagca    420

agccttcggg tgagtgtacc tttcgaataa gcaccggcta actacgtgcc agcagccgcg    480

gtaatacgta gggtgcaagc gttatccgga attattgggc gtaaagggct cgtaggcggt    540

tcgtcgcgtc cggtgtgaaa gtccatcgct taacggtgga tctgcgccgg gtacgggcgg    600

gctggagtgc ggtaggggag actggaattc ccggtgtaac ggtggaatgt gtagatatcg    660

ggaagaacac caatggcgaa ggcaggtctc tgggccgtta ctgacgctga ggagcgaaag    720

cgtggggagc gaacaggatt agataccctg gtagtccacg ccgtaaacgg tggatgctgg    780

atgtggggcc cgttccacgg gttccgtgtc ggagctaacg cgttaagcat cccgcctggg    840

gagtacggcc gcaaggctaa aactcaaaga aattgacggg ggcccgcaca agcggcggag    900

catgcggatt aattcgatgc aacgcgaaga accttacctg ggcttgacat gttcccgaca    960

gccgtagaga tacggtctcc cttcggggcg ggttcacagg tggtgcatgg tcgtcgtcag   1020

ctcgtgtcgt gagatgttgg gttaagtccc gcaacgagcg caaccctcgc cctgtgttgc   1080

cagcacgtca tggtgggaac tcacggggga ccgccggggt caactcggag gaaggtgggg   1140
```

-continued atgacgtcag atcatcatgc cccttacgtc cagggcttca cgcatgctac aatggccggt 1200
acaacgggat gcgacatggc gacatggagc ggatccctga aaaccggtct cagttcggat 1260
tggagtctgc aacccgactc catgaaggcg gagtcgctag taatcgcgga tcagcaacgc 1320
cgcggtgaat gcgttcccgg gccttgtaca caccgcccgt caagtcatga aagtgggtag 1380
cacccgaagc cggtggccta accccttgtg ggatggagcc gtctaaggtg agactcgtga 1440
ttggg 1445

<210> SEQ ID NO 14
<211> LENGTH: 1464
<212> TYPE: DNA
<213> ORGANISM: Bifidobacterium longum subsp. longum

<400> SEQUENCE: 14
tggctcagga tgaacgctgg cggcgtgctt aacacatgca agtcgaacgg gatccatcag 60
gctttgcttg gtggtgagag tggcgaacgg gtgagtaatg cgtgaccgac ctgccccata 120
caccggaata gctcctggaa acgggtggta atgccggatg ctccagttga tcgcatggtc 180
ttctgggaaa gctttcgcgg tatgggatgg ggtcgcgtcc tatcagcttg acggcggggt 240
aacggcccac cgtggcttcg acgggtagcc ggcctgagag ggcgaccggc cacattggga 300
ctgagatacg gcccagactc ctacgggagg cagcagtggg gaatattgca caatgggcgc 360
aagcctgatg cagcgacgcc gcgtgaggga tggaggcctt cgggttgtaa acctctttta 420
tcggggagca agcgagagtg agtttacccg ttgaataagc accggctaac tacgtgccag 480
cagccgcggt aatacgtagg gtgcaagcgt tatccggaat tattgggcgt aaagggctcg 540
taggcggttc gtcgcgtccg gtgtgaaagt ccatcgctta acggtggatc cgcgccgggt 600
acgggcgggc ttgagtgcgg taggggagac tggaattccc ggtgtaacgg tggaatgtgt 660
agatatcggg aagaacacca atggcgaagg caggtctctg ggccgttact gacgctgagg 720
agcgaaagcg tggggagcga acaggattag ataccctggt agtccacgcc gtaaacggtg 780
gatgctggat gtggggcccg ttccacgggt tccgtgtcgg agctaacgcg ttaagcatcc 840
cgcctgggga gtacggccgc aaggctaaaa ctcaaagaaa ttgacggggg cccgcacaag 900
cggcggagca tgcggattaa ttcgatgcaa cgcgaagaac cttacctggg cttgacatgt 960
tcccgacggt cgtagagata cggcttccct tcggggcggg ttcacaggtg gtgcatggtc 1020
gtcgtcagct cgtgtcgtga gatgttgggt taagtcccgc aacgagcgca accctcgccc 1080
cgtgttgcca gcggattatg ccgggaactc acgggggacc gccggggtta actcggagga 1140
aggtggggat gacgtcagat catcatgccc cttacgtcca gggcttcacg catgctacaa 1200
tggccggtac aacgggatgc gacgcggcga cgcggagcgg atccctgaaa accggtctca 1260
gttcggatcg cagtctgcaa ctcgactgcg tgaaggcgga gtcgctagta atcgcgaatc 1320
agcaacgtcg cggtgaatgc gttcccgggc cttgtacaca ccgcccgtca agtcatgaaa 1380
gtgggcagca cccgaagccg gtggcctaac cccttgtggg atggagccgt ctaaggtgag 1440
gctcgtgatt gggactaagt cgta 1464

<210> SEQ ID NO 15
<211> LENGTH: 1513
<212> TYPE: DNA
<213> ORGANISM: Bifidobacterium pseudocatenulatum

<400> SEQUENCE: 15

```
gtttcgattc tggctcagga tgaacgctgg cggcgtgctt aacacatgca agtcgaacgg      60

gatccatcag gctttgcttg gtggtgagag tggcgaacgg gtgagtaatg cgtgaccgac     120

ctgccccata caccggaata gctcctggaa acgggtggta atgccggatg ctccgactcc     180

tcgcatgggg tgtcgggaaa gatttcatcg gtatgggatg gggtcgcgtc ctatcaggta     240

gtcggcgggg taacggccca ccgagcctac gacgggtagc cggcctgaga gggcgaccgg     300

ccacattggg actgagatac ggcccagact cctacgggag gcagcagtgg ggaatattgc     360

acaatgggcg caagcctgat gcagcgacgc cgcgtgcggg atgacggcct tcgggttgta     420

aaccgctttt gatcgggagc aagccttcgg gtgagtgtac ctttcgaata agcaccggct     480

aactacgtgc cagcagccgc ggtaatacgt agggtgcaag cgttatccgg aattattggg     540

cgtaaagggc tcgtaggcgg ttcgtcgcgt ccggtgtgaa agtccatcgc ttaacggtgg     600

atctgcgccg ggtacgggcg ggctggagtg cggtagggga gactggaatt cccggtgtaa     660

cggtggaatg tgtagatatc gggaagaaca ccaatggcga aggcaggtct ctgggccgtt     720

actgacgctg aggagcgaaa gcgtggggag cgaacaggat tagataccct ggtagtccac     780

gccgtaaacg gtggatgctg gatgtggggc ccgttccacg ggttccgtgt cggagctaac     840

gcgttaagca tcccgcctgg ggagtacggc cgcaaggcta aaactcaaag aaattgacgg     900

gggcccgcac aagcggcgga gcatgcggat taattcgatg caacgcgaag aaccttacct     960

gggcttgaca tgttcccgac agccgtagag atatggcctc ccttcggggc gggttcacag    1020

gtggtgcatg gtcgtcgtca gctcgtgtcg tgagatgttg ggttaagtcc cgcaacgagc    1080

gcaaccctcg ccctgtgttg ccagcacgtc atggtgggaa ctcacggggg accgccgggg    1140

tcaactcgga ggaaggtggg gatgacgtca gatcatcatg ccccttacgt ccagggcttc    1200

acgcatgcta caatggccgg tacaacggga tgcgacacgg cgacgtggag cggatccctg    1260

aaaaccggtc tcagttcgga ttggagtctg caacccgact ccatgaaggc ggagtcgcta    1320

gtaatcgcgg atcagcaacg ccgcggtgaa tgcgttcccg ggccttgtac acaccgcccg    1380

tcaagtcatg aaagtgggta gcacccgaag ccggtggcct aaccctttgt ggatggagcc    1440

gtctaaggtg agactcgtga ttgggactaa gtcgtaacaa ggtagccgta ccggaaggtg    1500

cggctggatc acc                                                        1513
```

```
<210> SEQ ID NO 16
<211> LENGTH: 1475
<212> TYPE: DNA
<213> ORGANISM: Bifidobacterium pseudolongum
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
```

<222> LOCATION: (95)..(95)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (267)..(268)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (334)..(335)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (911)..(913)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:

<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1150)..(1150)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1276)..(1276)
<223> OTHER INFORMATION: n is a, c, g, or t
<220> FEATURE:
<221> NAME/KEY: misc_feature
<222> LOCATION: (1367)..(1367)
<223> OTHER INFORMATION: n is a, c, g, or t
<220> FEATURE:
<221> NAME/KEY: misc_feature
<222> LOCATION: (1386)..(1387)
<223> OTHER INFORMATION: n is a, c, g, or t
<220> FEATURE:
<221> NAME/KEY: misc_feature
<222> LOCATION: (1393)..(1393)
<223> OTHER INFORMATION: n is a, c, g, or t
<220> FEATURE:
<221> NAME/KEY: misc_feature
<222> LOCATION: (1428)..(1428)
<223> OTHER INFORMATION: n is a, c, g, or t
<220> FEATURE:
<221> NAME/KEY: misc_feature
<222> LOCATION: (1453)..(1453)
<223> OTHER INFORMATION: n is a, c, g, or t

<400> SEQUENCE: 16
nntttgtgga gggttcgatt ctggctcagg atgaacgctg gcggcgtgcn taacncntgc 60
nagtcgaacg ggatccatca agcttgcttg gtggngagag tggcgaacgg gtgagtaatg 120
cgtgaccgac ctgcccnata caccggaata gctcctggaa acgggtggta atgccggatg 180
ttccagttga tcgcatggtc ttctggnaaa gctttcgcgg tatgggatgg ggtcgngtcc 240
tatcagcttg acggcggggt aacggcnnac cgtggcttcg acgggtagcc ggcctgagag 300
ggngaccggc cacattggga ctgagatacg gccnngactc ctacgggagg cagcagtggg 360
gaatattgca caatgggcgc aagcctgatg cagcgacgcn gcgtgaggga tggaggcctt 420
cgggttgtaa acctctttta tcggggagca agcgagagtg agtttacccn ttgaataagc 480
accggctaac tacgtgccag cagccncggt aatacgtagg gtgcnagcgt tatccggaat 540
tattgggcgt aaagggctcg taggcggttc gtcgcgtccg gtgtgaaagt ccatcgctta 600
acggtggatc cgcgccgggt acgggcgggc ttgagtgcgg taggggagac tggaattccc 660
ggtgtaacgg tggaatgtgt agatatcggg aagaacacca atggcgaagg caggtctctg 720
ggcngttact gacgctgagg agcnaaagcg tggggagcga acaggattag ataccctggt 780
agtccacgcc gtaaacggtg gatgctggat gtggggccng ttccacgggt tccgtgtcgg 840
agctaacgcg ttaagcatcc cgccngggga gtacggncgc aaggctaaaa ctcaaagaaa 900
ttganggggg nnngcacaag cggcggagca tgcggattaa ttcgatgnaa cgcgaagaac 960
cttacctggg cttgacatgt tcccgacggt cgtagagata cggcntccct tcggggcggg 1020

-continued

```
ttcacaggtg gtgcatggtc gtcgtcagct cgtgtcgtga gatgttgggt taagtcccgc   1080

aacgagcgca accctcgccc cgtgttgcca gcggattntg ccgggaactc acnggncacc   1140

gccggggttn actcggagga aggtggggnt gacgtcagat catcatgccc cttacgtcca   1200

gggcttcacg catgctacaa tggccggtac aacgggatgc gacgcggcga cgcggagcgg   1260

atccctgaaa accggnctca gttcggatcg cagtctgcaa ctcgactgcg tgaaggcgga   1320

gtcgctagta atcgcgaatc agcaacgtcg cggtgaatgc gttcccnggc cttgtacaca   1380

ccgccnntca agncatgaaa gtgggcagca cccgaagccg gtggcctnac cccttgtggg   1440

atggagccgt ctnaggtgag gctcgtgatt gggtc                              1475
```

<210> SEQ ID NO 17
<211> LENGTH: 1478
<212> TYPE: DNA
<213> ORGANISM: Lactobacillus acidophilus

<400> SEQUENCE: 17

```
tcctggctca ggacgaacgc tggcggcgtg cctaatacat gcaagtcgag cgagctgaac     60

caacagattc acttcggtga tgacgttggg aacgcgagcg gcggatgggt gagtaacacg    120

tggggaacct gccccatagt ctgggatacc acttggaaac aggtgctaat accggataag    180

aaagcagatc gcatgatcag cttataaaag gcggcgtaag ctgtcgctat gggatggccc    240

cgcggtgcat tagctagttg gtagggtaac ggcctaccaa ggcaatgatg catagccgag    300

ttgagagact gatcggccac attgggactg agacacggcc caaactccta cgggaggcag    360

cagtagggaa tcttccacaa tggacgaaag tctgatggag caacgccgcg tgagtgaaga    420

aggttttcgg atcgtaaagc tctgttgttg gtgaagaagg atagaggtag taactggcct    480

ttatttgacg gtaatcaacc agaaagtcac ggctaactac gtgccagcag ccgcggtaat    540

acgtaggtgg caagcgttgt ccggatttat tgggcgtaaa gcgagcgcag gcggaagaat    600

aagtctgatg tgaaagccct cggcttaacc gaggaactgc atcggaaact gtttttcttg    660

agtgcagaag aggagagtgg aactccatgt gtagcggtgg aatgcgtaga tatatggaag    720

aacaccagtg gcgaaggcgg ctctctggtc tgcaactgac gctgaggctc gaaagcatgg    780

gtagcgaaca ggattagata ccctggtagt ccatgccgta aacgatgagt gctaagtgtt    840

gggaggtttc cgcctctcag tgctgcagct aacgcattaa gcactccgcc tggggagtac    900

gaccgcaagg ttgaaactca aaggaattga cgggggcccg cacaagcggt ggagcatgtg    960

gtttaattcg aagcaacgcg aagaacctta ccaggtcttg acatctagtg caatccgtag   1020

agatacggag ttcccttcgg ggacactaag acaggtggtg catggctgtc gtcagctcgt   1080

gtcgtgagat gttgggttaa gtcccgcaac gagcgcaacc cttgtcatta gttgccagca   1140

ttaagttggg cactctaatg agactgccgg tgacaaaccg gaggaaggtg gggatgacgt   1200

caagtcatca tgccccttat gacctgggct acacacgtgc tacaatggac agtacaacga   1260

ggagcaagcc tgcgaaggca agcgaatctc ttaaagctgt tctcagttcg gactgcagtc   1320

tgcaactcga ctgcacgaag ctggaatcgc tagtaatcgc ggatcagcac gccgcggtga   1380

atacgttccc gggccttgta cacaccgccc gtcacaccat gggagtctgc aatgcccaaa   1440

gccggtggcc taaccttcgg gaaggagccg tctaaggc                           1478
```

<210> SEQ ID NO 18
<211> LENGTH: 1520
<212> TYPE: DNA

<213> ORGANISM: Lactobacillus antri

<400> SEQUENCE: 18

```
ttgatcctgg ctcaggatga acgccggcgg tgtgcctaat acatgcaagt cgagcgcact     60
ggcccaactg aaatgacgtg cttgcacaga atggacgttg gattcccagt gagcggcgga    120
cgggtgagta acacgtgggc aacctgcccc aaagcggggg ataacatttg gaaacagatg    180
ctaataccgc ataagttgga aaaccacatg gttttcccat caaagatggt ttcggctatc    240
gctttgggat gggcccgcgg tgcattagct agttggtaag gtaacggctt accaaggcga    300
tgatgcatag ccgagttgag agactgatcg gccacaatgg aactgagaca cggtccatac    360
tcctacggga ggcagcagta gggaatcttc cacaatgggc gcaagcctga tggagcaaca    420
ccgcgtgagt gaagaagggt ttcggctcgt aaagctctgt tgttggagaa gaacgtgcgt    480
aagagtaact gtttacgcag tgacggtatc caaccagaaa gtcacggcta actacgtgcc    540
agcagccgcg gtaatacgta ggtggcaagc gttatccgga tttattgggc gtaaagcgag    600
cgcaggcggt tgcttaggtc tgatgtgaaa gccttcggct taaccgaaga agtgcatcgg    660
aaaccgggcg acttgagtgc agaagaggac agtggaactc catgtgtagc ggtggaatgc    720
gtagatatat ggaagaacac cagtggcgaa ggcggctgtc tggtctgcaa ctgacgctga    780
ggctcgaaag catgggtagc gaacaggatt agataccctg gtagtccatg ccgtwaacga    840
tgagtgctag gtgttggagg gtttccgccc ttcagtgccg aagctaacgc attaagcact    900
ccgcctgggg agtacgaccg caaggttgaa actcaaagga attgacgggg gcccgcacaa    960
gcggtggagc atgtggttta attcgaagct acgcgaagaa ccttaccagg tcttgacatc   1020
ttgcgccaac ctcagagatg aggcgttccc ttcggggacg caaagacagg tggtgcatgg   1080
tcgtcgtcag ctcgtgtcgt gagatgttgg gttaagtccc gcaacgagcg caacccttgt   1140
tactagttgc cagcattcag ttgggcactc tagtgagact gccggtgaca aaccggagga   1200
aggtggggac gacgtcagat catcatgccc cttatgacct gggctacaca cgtgctacaa   1260
tggccggtac aacgagcagc taacccgcga gggtgtgcaa atctcttaaa gccggtctca   1320
gttcggactg cagtctgcaa ctcgactgca cgaagtcgga atcgctagta atcgcggatc   1380
agcatgccgc ggtgaatacg ttcccgggcc ttgtacacac cgcccgtcac accatggaak   1440
tttgcaatgc ccaaagtcag tggcctaacc attatggagg gasctgccta aggcagggca   1500
gatgactggg gtgaagtcgt                                                1520
```

<210> SEQ ID NO 19
<211> LENGTH: 1513
<212> TYPE: DNA
<213> ORGANISM: Lactobacillus brevis
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t

<400> SEQUENCE: 19

```
taagatgaga gtttgatcct ggctcaggac gaacgctggc ggcatgccta atacatgcaa     60
gtcgaacgag cttccgttga atgacgtgct tgcactgatt tcaacaatga agctagtggc    120
gaactggtga gtaacacgtg ggaaatctgc ccagaagcag ggataacac ttggaaacag     180
gtgctaatac cgtataacaa caaaatccgc atggattttg tttgaaaggt ggcttcggct    240
atcacttctg gatgatcccg cggcgtatta gttagttggt gaggtaaagg cccaccaaga    300
cgatgatacg tagccgacct gagagggtaa tcggccacat tgggactgag acacggccca    360
aactcctacg ggaggcagca gtagggaatc ttccacaatg gacgaaagtc tgatggagca    420
atgccgcgtg agtgaagaag ggtttcggct cgtaaaactc tgttgttaaa gaagaacacc    480
tttgagagta actgttcaag ggttgacggt atttaaccag aaagccacgg ctaactacgt    540
gccagcagcc gcggtaatac gtaggtggcn agcgttgtcc ggatttattg ggcgtaaagc    600
gagcgcaggc ggttttttaa gtctgatgtg aaagccttcg gcttaaccgg agaagtgcat    660
cggaaactgg gagacttgag tgcagaagag gacagtggaa ctccatgtgt agcngtggaa    720
tgcgtagata tatggaagaa caccagtggc gaaggcggct gtctagtctg taactgacgc    780
tgaggctcna aagcatgggt agcgaacagg attagatacc ctggtagtcc atgccgtaaa    840
cgatgagtgc taagtgttgg agggtttccg cccttcagtg ctgcagctaa cgcattaagc    900
actccgcctg gggagtacga ccgcaaggtt gaaactcaaa ggaattgacg ggggccngca    960
caagcggtgg agcatgtggt ttaattcgaa gctacgcgaa gaaccttacc aggtcttgac   1020
atcttctgcc aatcttagag ataagacgtt ccccttcggg acagaatgac aggtggtgca   1080
tggttgtcgt cagctcgtgt cgtgagatgt tgggttaagt cccgcaacga gcgcaaccct   1140
tattatcagt tgccagcatt cagttgggca ctctggtgag actgccggtg acaaaccgga   1200
ggaaggtggg gatgacgtca aatcatcatg ccccttatga cctgggctac acacgtgcta   1260
caatggacgg tacaacgagt cgcgaagtcg tgaggctaag ctaatctctt aaagccgttc   1320
tcagttcgga ttgtaggctg caactcgcct acatgaagtt ggaatcgcta gtaatcgcgg   1380
atcagcatgc cgcggtgaat acgttcccgg gccttgtaca caccgcccgt cacaccatga   1440
gagtttgtaa cacccaaagc cggtgagata accttcggga gtcagccgtc taaggtggga   1500
cagatgatta ggg                                                      1513
```

```
<210> SEQ ID NO 20
<211> LENGTH: 1517
<212> TYPE: DNA
<213> ORGANISM: Lactobacillus casei

<400> SEQUENCE: 20

tcctggctca ggatgaacgc tggcggcgtg cctaatacat gcaagtcgaa cgagttttgg     60
tcgatgaacg gtgcttgcac tgagattcga cttaaaacga gtggcggacg ggtgagtaac    120
acgtgggtaa cctgccctta agtgggggat aacatttgga aacagatgct aataccgcat    180
aaatccaaga accgcatggt tcttggctga aagatggcgt caagctatcg cttttggatg    240
gacccgcggc gtattagcta gttggtgagg taacggctca ccaaggcgat gatacgtagc    300
cgaactgaga ggttgatcgg ccacattggg actgagacac ggcccaaact cctacgggag    360
gcagcagtag ggaatcttcc acaatggacg caagtctgat ggagcaacgc cgcgtgagtg    420
aagaaggctt tcgggtcgta aaactctgtt gttggagaag aatggtcggc agagtaactg    480
ttgtcggcgt gacggtatcc aaccagaaag ccacggctaa ctacgtgcca gcagccgcgg    540
```

-continued

```
taatacgtag gtggcaagcg ttatccggat ttattgggcg taaagcgagc gcaggcggtt    600
ttttaagtct gatgtgaaag ccctcggctt aaccgaggaa gcgcatcgga aactgggaaa    660
cttgagtgca gaagaggaca gtggaactcc atgtgtagcg gtgaaatgcg tagatatatg    720
gaagaacacc agtggcgaag gcggctgtct ggtctgtaac tgacgctgag gctcgaaagc    780
atgggtagcg aacaggatta gataccctgg tagtccatgc cgtaaacgat gaatgctagg    840
tgttggaggg tttccgccct tcagtgccgc agctaacgca ttaagcattc cgcctgggga    900
gtacgaccgc aaggttgaaa ctcaaaggaa ttgacggggg cccgcacaag cggtggagca    960
tgtggtttaa ttcgaagcaa cgcgaagaac cttaccaggt cttgacatct tttgatcacc   1020
tgagagatca ggtttcccct tcgggggcaa aatgacaggt ggtgcatggt tgtcgtcagc   1080
tcgtgtcgtg agatgttggg ttaagtcccg caacgagcgc aacccttatg actagttgcc   1140
agcattgagt tgggcactct agtaagactg ccggtgacaa accggaggaa ggtggggatg   1200
acgtcaaatc atcatgcccc ttatgacctg ggctacacac gtgctacaat ggatggtaca   1260
acgagttgcg agaccgcgag gtcaagctaa tctcttaaag ccattctcag ttcggactgt   1320
aggctgcaac tcgcctacac gaagtcggaa tcgctagtaa tcgcggatca gcacgccgcg   1380
gtgaatacgt tcccgggcct tgtacacacc gcccgtcaca ccatgagagt ttgtaacacc   1440
cgaagccggt ggcgtaaccc ttttagggag cgagccgtct aaggtgggac aaatgattag   1500
ggtgaagtcg taacaag                                                  1517
```

<210> SEQ ID NO 21
<211> LENGTH: 1564
<212> TYPE: DNA
<213> ORGANISM: Lactobacillus coleohominis

<400> SEQUENCE: 21

```
agtttgattc tggctcagga tgaacgccgg cggtgtgcct aatacatgca agtcgaacgc     60
gttggcccga ctgattgatg atgcttgcat cagattgacg acggtttact aacgagtggc    120
ggacgggtga gtaacacgta ggcaacctgc ccagaagcgg gggacaacat ttggaaacaa    180
gtgctaatac cgcataacaa cgaaaaccgc ctggttttcg tttaaaagat ggtttcggct    240
atcacttctg gatgggcctg cggcgcatta gctagttggt aaggtaacgg cttaccaagg    300
cagtgatgcg tagccgagtt gagagactga tcggccacaa tggaactgag acacgggcca    360
tactcctacg ggaggcagca gtagggaatc ttccacaatg ggcgcaagcc tgatggagca    420
acaccgcgtg agtgaagaag ggtttcggct cgtaaaactc tgttgttgaa gaagaacgtg    480
cgtgagagta actgttcacg cagtacggta ttcaaccaga aagtcacggc taactacgtg    540
ccagcagccg cggtaatacg taggtggcaa gcgttatccg gatttattgg gcgtaaagcg    600
agcgcaggcg gttttctaag tctgatgtga aagccttcgg cttaaccgga gaagggcatc    660
ggaaactgga taacttgagt gcaagagagg acagtggaac tccatgtgta gcggtggaat    720
gcgtagatat atggaagaac accagtggcg aaggcggctg tctagcttgc aactgacgct    780
gaggctcgaa agcatgggta gcgaacagga ttagataccc tggtagtcca tgccgtaaac    840
gatgagtgct aggtgttgga gggtttccgc ccttcagtgc cggagctaac gcattaagca    900
ctccgcctgg ggagtacgac cgcaaggttg aaactcaaag gaattgacgg gggcccgcac    960
aagcggtgga gcatgtggtt taattcgaag ctacgcgaag aaccttacca ggtcttgaca   1020
tcttgcgcca acctcagaga tgaggcgttc ccttcgggga cgcaatgaca ggtggtgcat   1080
ggtcgtcgtc agctcgtgtt gtgagatgtt gggttaagtc ccgcaacgag cgcaaccctt   1140
```

gttactagtt gccagcattc agttgggcac tctagtgaga ctgccggtga caaaccggag 1200
gaaggtgggg acgacgtcag atcatcatgc cccttatgac ctgggctaca cacgtgctac 1260
aatgggcggt acaacgagca gcgaactcgc gagggtaagc taatctctta aaaccgttct 1320
cagttcggac tgcagtctgc aactcgactg cacgaagtcg gaatcgctag taatcgcgga 1380
tcagcatgcc gcggtgaata cgttcccggg ccttgtacac accgcccgtc acaccatggg 1440
agtttgcaat gcccaaagcc ggtggcctaa ccttcgggaa ggagccgtct aaggcagggc 1500
agatgactgg ggtgaagtcg taacaaggta gccgtaggag aacctgcggc ttgatcacct 1560
tcat 1564

<210> SEQ ID NO 22
<211> LENGTH: 1518
<212> TYPE: DNA
<213> ORGANISM: Lactobacillus crispatus

<400> SEQUENCE: 22
gacgaacgct ggcggcgtgc ctaatacatg caagtcgagc gagcggaact aacagattta 60
cttcggtaat gacgttagga aagcgagcgg cggatgggtg agtaacacgt ggggaacctg 120
ccccatagtc tgggatacca cttggaaaca ggtgctaata ccggataaga aagcagatcg 180
catgatcagc ttttaaaagg cggcgtaagc tgtcgctatg ggatggcccc gcggtgcatt 240
agctagttgg taaggtaaag gcttaccaag gcgatgatgc atagccgagt tgagagactg 300
atcggccaca ttgggactga gacacggccc aaactcctac gggaggcagc agtagggaat 360
cttccacaat ggacgcaagt ctgatggagc aacgccgcgt gagtgaagaa ggttttcgga 420
tcgtaaagct ctgttgttgg tgaagaagga tagaggtagt aactggcctt tatttgacgg 480
taatcaacca gaaagtcacg gctaactacg tgccagcagc cgcggtaata cgtaggtggc 540
aagcgttgtc cggatttatt gggcgtaaag cgagcgcagg cggaagaata agtctgatgt 600
gaaagccctc ggcttaaccg aggaactgca tcggaaactg tttttcttga gtgcagaaga 660
ggagagtgga actccatgtg tagcggtgga atgcgtagat atatggaaga acaccagtgg 720
cgaaggcggc tctctggtct gcaactgacg ctgaggctcg aaagcatggg tagcgaacag 780
gattagatac cctggtagtc catgccgtaa acgatgagtg ctaagtgttg ggaggtttcc 840
gcctctcagt gctgcagcta acgcattaag cactccgcct ggggagtacg accgcaaggt 900
tgaaactcaa aggaattgac gggggcccgc acaagcggtg gagcatgtgg tttaattcga 960
agcaacgcga agaaccttac caggtcttga catctagtgc catttgtaga gatacaaagt 1020
tcccttcggg gacgctaaga caggtggtgc atggctgtcg tcagctcgtg tcgtgagatg 1080
ttgggttaag tcccgcaacg agcgcaaccc ttgttattag ttgccagcat taagttgggc 1140
actctaatga gactgccggt gacaaaccgg aggaaggtgg ggatgacgtc aagtcatcat 1200
gccccttatg acctgggcta cacacgtgct acaatgggca gtacaacgag aagcgagcct 1260
gcgaaggcaa gcgaatctct gaaagctgtt ctcagttcgg actgcagtct gcaactcgac 1320
tgcacgaagc tggaatcgct agtaatcgcg gatcagcacg ccgcggtgaa tacgttcccg 1380
ggccttgtac acaccgcccg tcacaccatg ggagtctgca atgcccaaag ccggtggcct 1440
aaccttcggg aaggagccgt ctaaggcagg gcagatgact ggggtgaagt cgtaacaagg 1500
tagccgtagg agaactgc 1518

<210> SEQ ID NO 23

<211> LENGTH: 1734
<212> TYPE: DNA
<213> ORGANISM: Lactobacillus curvatus

<400> SEQUENCE: 23
gacgaacgct ggcggcgtgc ctaatacatg caagtcgagc gagcggaact aacagattta 60
cttcggtaat gacgttagga aagcgagcgg cggatgggtg agtaacacgt ggggaacctg 120
ccccatagtc tgggatacca cttggaaaca ggtgctaata ccggataaga aagcagatcg 180
catgatcagc ttttaaaagg cggcgtaagc tgtcgctatg ggatggcccc gcggtgcatt 240
agctagttgg taaggtaaag gcttaccaag gcgatgatgc atagccgagt tgagagactg 300
atcggccaca ttgggactga gacacggccc aaactcctac gggaggcagc agtagggaat 360
cttccacaat ggacgcaagt ctgatggagc aacgccgcgt gagtgaagaa ggttttcgga 420
tcgtaaagct ctgttgttgg tgaagaagga tagaggtagt aactggcctt tatttgacgg 480
taatcaacca gaaagtcacg gctaactacg tgccagcagc cgcggtaata cgtaggtggc 540
aagcgttgtc cggatttatt gggcgtaaag cgagcgcagg cggaagaata agtctgatgt 600
gaaagccctc ggcttaaccg aggaactgca tcggaaactg tttttcttga gtgcagaaga 660
ggagagtgga actccatgtg tagcggtgga atgcgtagat atatggaaga acaccagtgg 720
cgaaggcggc tctctggtct gcaactgacg ctgaggctcg aaagcatggg tagcgaacag 780
gattagatac cctggtagtc catgccgtaa acgatgagtg ctaagtgttg ggaggtttcc 840
atggaagata ttgcaaatcc cgagcgtacc cggaaaattc tcaaacgtta cggctttaag 900
tttaaaaaga gcttaggcca aaacttctta accaacatcg ccattttgaa acaaattgtt 960
gaagctggtg atatcaccaa agatgacgat gtgattgaaa tcggccccgg aatcggttct 1020
ttaacggaac aaattgccag aaaagcgcac caggtcttga gttttgaaat tgatgaacgg 1080
ttaatgccgg tcttaaaaga tactttgaat cactaccata acgtcacgat tttaaaccaa 1140
gatattcttg aagcggattt aaaaacaatt atcgctgaac aattcgatgg taagcataat 1200
ctaaaaatcg ttgcgaactt accttattac attacgacgc caatcatgtt gcacttactt 1260
gaagcaggat tgccaattga ttgcatggtc ttaatgatgc aaaaggaagt ggcagaacgg 1320
atcaacgctg aacctggttc aaaggcttac ggctcattaa gtattgccgt tcaacttcat 1380
tcagaagtga acttagcctt tattgtgccc aagacagctt ttatgccaca accgaatgtt 1440
gattcagcga ttgttgaatt agtggggcgc aaagcaccgc ttgtaacagt tgctaatcaa 1500
accttatttg atcaattggt tcgtggcgca tttgcacaac gccgaaagac attatggaat 1560
aacttgcaaa atcaatttgg taaacaagat gaagtcaaag cagctttaac aacagcctta 1620
gaagcagtcg agattgcacc gagcgctcgt gctgaacaat tgagtatcca acaatttgcc 1680
caattaagcg atgtgctgaa taatcagcca attttttcta aaaaagctaa gtaa 1734

<210> SEQ ID NO 24
<211> LENGTH: 1515
<212> TYPE: DNA
<213> ORGANISM: Lactobacillus delbrueckii

<400> SEQUENCE: 24
gaacgctggc ggcgtgccta atacatgcaa gtcgagcgag ctgaattcaa agatcccttc 60
ggggtgattt gttggacgct agcggcggat gggtgagtaa cacgtgggca atctgcccta 120
aagactggga taccacttgg aaacaggtgc taataccgga taacaacatg aatcgcatga 180
ttcaagtttg aaaggcggcg caagctgtca ctttaggatg agcccgcggc gcattagcta 240

-continued gttggtgggg taaaggccta ccaaggcaat gatgcgtagc cgagttgaga gactgatcgg 300
ccacattggg actgagacac ggcccaaact cctacgggag gcagcagtag ggaatcttcc 360
acaatggacg caagtctgat ggagcaacgc cgcgtgagtg aagaaggttt tcggatcgta 420
aagctctgtt gttggtgaag aaggatagag gcagtaactg gtctttattt gacggtaatc 480
aaccagaaag tcacggctaa ctacgtgcca gcagccgcgg taatacgtag gtggcaagcg 540
ttgtccggat ttattgggcg taaagcgagc gcaggcggaa tgataagtct gatgtgaaag 600
cccacggctc aaccgtggaa ctgcatcgga aactgtcatt cttgagtgca gaagaggaga 660
gtggaactcc atgtgtagcg gtggaatgcg tagatatatg gaagaacacc agtggcgaag 720
gcggctctct ggtctgcaac tgacgctgag gctcgaaagc atgggtagcg aacaggatta 780
gataccctgg tagtccatgc cgtaaacgat gagcgctagg tgttggggac tttccggtcc 840
tcagtgccgc agcaaacgca ttaagcgctc cgcctgggga gtacgaccgc aaggttgaaa 900
ctcaaaggaa ttgacggggg cccgcacaag cggtggagca tgtggtttaa ttcgaagcaa 960
cgcgaagaac cttaccaggt cttgacatcc tgcgctacac ctagagatag gtggttccct 1020
tcggggacgc agagacaggt ggtgcatggc tgtcgtcagc tcgtgtcgtg agatgttggg 1080
ttaagtcccg caacgagcgc aacccttgtc tttagttgcc atcattaagt tgggcactct 1140
agagagactg ccggtgacaa accggaggaa ggtggggatg acgtcaagtc atcatgcccc 1200
ttatgacctg ggctacacac gtgctacaat gggcagtaca acgagaagcg aacccgcgag 1260
ggtaagcgga tctcttaaag ctgttctcag ttcggactgc aggctgcaac tcgcctgcac 1320
gaagctggaa tcgctagtaa tcgcggatca gcacgccgcg gtgaatacgt tcccgggcct 1380
tgtacacacc gcccgtcaca ccatggaagt ctgcaatgcc caaagtcggt gggataacct 1440
tttaggagtc agccgcctaa ggcagggcag atgactgggg tgaagtcgta acaaggtagc 1500
cgtaggagaa ctgcg 1515

<210> SEQ ID NO 25
<211> LENGTH: 1502
<212> TYPE: DNA
<213> ORGANISM: Lactobacillus fermentum

<400> SEQUENCE: 25
cggcggtgtg cctaatacat gcaagtcgaa cgcgttggcc caattgattg atggtgcttg 60
cacctgattg attttggtcg ccaacgagtg gcggacgggt gagtaacacg taggtaacct 120
gcccagaagc gggggacaac atttggaaac agatgctaat accgcataac aacgttgttc 180
gcatgaacaa cgcttaaaag atggcttctc gctatcactt ctggatggac ctgcggtgca 240
ttagcttgtt ggtggggtaa cggcctacca aggcgatgat gcatagccga gttgagagac 300
tgatcggcca caatgggact gagacacggc ccatactcct acgggaggca gcagtaggga 360
atcttccaca atgggcgcaa gcctgatgga gcaacaccgc gtgagtgaag aagggtttcg 420
gctcgtaaag ctctgttgtt aaagaagaac acgtatgaga gtaactgttc atacgttgac 480
ggtatttaac cagaaagtca cggctaacta cgtgccagca gccgcggtaa tacgtaggtg 540
gcaagcgtta tccggattta ttgggcgtaa agagagtgca ggcggttttc taagtctgat 600
gtgaaagcct tcggcttaac cggagaagtg catcggaaac tggataactt gagtgcagaa 660
gagggtagtg gaactccatg tgtagcggtg gaatgcgtag atatatggaa gaacaccagt 720
ggcgaaggcg gctacctggt ctgcaactga cgctgagact cgaaagcatg ggtagcgaac 780

```
aggattagat accctggtag tccatgccgt aaacgatgag tgctaggtgt tggagggttt    840

ccgcccttca gtgccggagc taacgcatta agcactccgc ctggggagta cgaccgcaag    900

gttgaaactc aaaggaattg acgggggccc gcacaagcgg tggagcatgt ggtttaattc    960

gaagctacgc gaagaacctt accaggtctt gacatcttgc gccaacccta gagatagggc   1020

gtttccttcg ggaacgcaat gacaggtggt gcatggtcgt cgtcagctcg tgtcgtgaga   1080

tgttgggtta agtcccgcaa cgagcgcaac ccttgttact agttgccagc attaagttgg   1140

gcactctagt gagactgccg gtgacaaacc ggaggaaggt ggggacgacg tcagatcatc   1200

atgcccctta tgacctgggc tacacacgtg ctacaatgga cggtacaacg agtcgcgaac   1260

tcgcgagggc aagcaaatct cttaaaaccg ttctcagttc ggactgcagg ctgcaactcg   1320

cctgcacgaa gtcggaatcg ctagtaatcg cggatcagca tgccgcggtg aatacgttcc   1380

cgggccttgt acacaccgcc cgtcacacca tgagagtttg taacacccaa agtcggtggg   1440

gtaacctttt aggagccagc cgcctaaggt gggacagatg attagggtga agtcgtaaca   1500

ag                                                                   1502
```

<210> SEQ ID NO 26
<211> LENGTH: 1573
<212> TYPE: DNA
<213> ORGANISM: Lactobacillus gasseri

<400> SEQUENCE: 26

```
gaaaatgaga gtttgatcct ggctcaggac gaacgctggc ggcgtgccta atacatgcaa     60

gtcgagcgag cttgcctaga tgaatttggt gcttgcacca gatgaaacta gatacaagcg    120

agcggcggac gggtgagtaa cacgtgggta acctgcccaa gagactggga taacacctgg    180

aaacagatgc taataccgga taacaacact agacgcatgt ctagagttta aaagatggtt    240

ctgctatcac tcttggatgg acctgcggtg cattagctag ttggtaaggt aacggcttac    300

caaggcaatg atgcatagcc gagttgagag actgatcggc cacattggga ctgagacacg    360

gcccaaactc ctacgggagg cagcagtagg gaatcttcca caatggacgc aagtctgatg    420

gagcaacgcc gcgtgagtga agaagggttt cggctcgtaa agctctgttg gtagtgaaga    480

aagatagagg tagtaactgg cctttatttg acggtaatta cttagaaagt cacggctaac    540

tacgtgccag cagccgcggt aatacgtagg tggcaagcgt tgtccggatt tattgggcgt    600

aaagcgagtg caggcggttc aataagtctg atgtgaaagc cttcggctca accggagaat    660

tgcatcagaa actgttgaac ttgagtgcag aagaggagag tggaactcca tgtgtagcgg    720

tggaatgcgt agatatatgg aagaacacca gtggcgaagg cggctctctg gtctgcaact    780

gacgctgagg ctcgaaagca tgggtagcga acaggattag ataccctggt agtccatgcc    840

gtaaacgatg agtgctaagt gttgggaggt ttccgcctct cagtgctgca gctaacgcat    900

taagcactcc gcctggggag tacgaccgca aggttgaaac tcaaaggaat tgacgggggc    960

ccgcacaagc ggtggagcat gtggtttaat tcgaagcaac gcgaagaacc ttaccaggtc   1020

ttgacatcca gtgcaaacct aagagattag gtgttccctt cggggacgct gagacaggtg   1080

gtgcatggct gtcgtcagct cgtgtcgtga gatgttgggt taagtcccgc aacgagcgca   1140

acccttgtca ttagttgcca tcattaagtt gggcactcta atgagactgc cggtgacaaa   1200

ccggaggaag gtggggatga cgtcaagtca tcatgcccct tatgacctgg gctacacacg   1260

tgctacaatg gacggtacaa cgagaagcga acctgcgaag gcaagcggat ctctgaaagc   1320

cgttctcagt tcggactgta ggctgcaact cgcctacacg aagctggaat cgctagtaat   1380
```

cgcggatcag cacgccgcgg tgaatacgtt cccgggcctt gtacacaccg cccgtcacac 1440
catgagagtc tgtaacaccc aaagccggtg ggataacctt tataggagtc agccgtctaa 1500
ggtaggacag atgattaggg tgaagtcgta acaaggtagc cgtaggagaa cctgcggctg 1560
gatcacctcc ttt 1573

<210> SEQ ID NO 27
<211> LENGTH: 1487
<212> TYPE: DNA
<213> ORGANISM: Lactobacillus johnsonii

<400> SEQUENCE: 27
ggcggcgtgc ctaatacatg caagtcgagc gagcttgcct agatgatttt agtgcttgca 60
ctaaatgaaa ctagatacaa gcgagcggcg gacgggtgag taacacgtgg gtaacctgcc 120
caagagactg ggataacacc tggaaacaga tgctaatacc ggataacaac actagacgca 180
tgtctagagt ttgaaagatg gttctgctat cactcttgga tggacctgcg gtgcattagc 240
tagttggtaa ggtaatggct taccaaggcg atgatgcata gccgagttga gagactgatc 300
ggccacattg ggactgagac acggcccaaa ctcctacggg aggcagcagt agggaatctt 360
ccacaatgga cgaaagtctg atggagcaac gccgcgtgag tgaagaaggg tttcggctcg 420
taaagctctg ttggtagtga agaaagatag aggtagtaac tggcctttat ttgacggtaa 480
ttacttagaa agtcacggct aactacgtgc cagcagccgc ggtaatacgt aggtggcaag 540
cgttgtccgg atttattggg cgtaaagcga gtgcaggcgg ttcaataagt ctgatgtgaa 600
acgcttcggc tcaaccggag aattgcatca gaaactgttg aacttgagtg cagaagagga 660
gagtggaact ccatgtgtag cggtggaatg cgtagatata tggaagaaca ccagtggcga 720
aggcggctct ctggtctgca actgacgctg aggctcgaaa gcatgggtag cgaacaggat 780
tagataccct ggtagtccat gccgtaaacg atgagtgcta agtgttggga ggtttccgcc 840
tctcagtgct gcagctaacg cattaagcac tccgcctggg gagtacgacc gcaaggttga 900
aactcaaagg aattgacggg ggcccgcaca agcggtggag catgtggttt aattcgaagc 960
aacgcgaaga accttaccag gtcttgacat ccagtgcaaa cctaagagat taggtgttcc 1020
cttcggggac gctgagacag gtggtgcatg gctgtcgtca gctcgtgtca tgagatgttg 1080
ggttaagtcc cgcaacgagc gcaacccttg tcattagttg ccatcattaa gttgggcact 1140
ctaatgagac tgccggtgac aaaccggagg aaggtgggga tgacgtcaag tcatcatgcc 1200
ccttatgacc tgggctacac acgtgctaca atggacggta caacgagaag cgaacctgcg 1260
aaggcaagcg gatctcttaa agccgttctc agttcggact gtaggctgca actcgcctac 1320
acgaagctgg aatcgctagt aatcgcggat cagcacgccg cggtgaatac gttcccgggc 1380
cttgtacaca ccgcccgtca caccatgaga gtctgtaaca cccaaagccg gtgggataac 1440
ctttatagga gtcagccgtc taaggtagga cagatgatta gggtgaa 1487

<210> SEQ ID NO 28
<211> LENGTH: 1507
<212> TYPE: DNA
<213> ORGANISM: Lactobacillus harbinensis

<400> SEQUENCE: 28
gctggcggcg tgcctaatac atgcaagtcg aacgaggttt ggtcagtttg cggtggtgct 60
tgcatcacca attaccgatc aaaccgagtg gcggacgggt gagtaacacg tgggtaacct 120

```
gcccttcagc aggggataac atttggaaac agatgctaat accgtataac cacggagacc    180
gcatggtctc cgggtaaaag atggcgcaag ctatcactga aggatggacc cgcggcgtat    240
tagccagttg gtggggtaac ggcctaccaa agcgatgata cgtagccgac ctgagagggt    300
aatcggccac attgggactg agacacggcc caaactccta cgggaggcag cagtagggaa    360
tcttccacaa tggacgcaag tctgatggag caacgccgcg tgagtgaaga aggctttcgg    420
gtcgtaaaac tctgttattg aagaagaacg tgtgtgacag taactggtca tgcagtgacg    480
gtattcaatc agaaagtcac ggctaactac gtgccagcag ccgcggtaat acgtaggtgg    540
caagcgttgt ccggatttat tgggcgtaaa gcgagtgcag gcggtctttt aagtctgatg    600
tgaaagcctt cggcttaacc gaagaagggc atcggaaact gggagacttg agtgcagaag    660
aggagagtgg aactccatgt gtagcggtga aatgcgtaga tatatggaag aacaccagtg    720
gcgaaggcgg ctctctggtc tgtaactgac gctgaggctc gaaagcgtgg gtagcaaaca    780
ggattagata ccctggtagt ccacgccgta aacgatgaat actaagtgtt ggagggtttc    840
cgcccttcag tgctgcagct aacgcattaa gtattccgcc tggggagtac gaccgcaagg    900
ttgaaactca aaggaattga cggggcccg cacaagcggt ggagcatgtg gtttaattcg    960
aagcaacgcg aagaacctta ccaggtcttg acatcttctg ccaggctgag agatcagctg   1020
ttcccttcgg ggacagaatg acaggtggtg catggttgtc gtcagctcgt gtcgtgagat   1080
gttgggttaa gtcccgcaac gagcgcaacc cttatgatca gttgccagca ttcagttggg   1140
cactctggtc agactgccgg tgacaaaccg gaggaaggcg gggatgacgt caaatcatca   1200
tgccccttat gacctgggct acacacgtgc tacaatgggt ggtacaacga gcagcgagac   1260
cgcgaggtca agcgaatctc taaaaaccat cctcagttcg gattgcaggc tgcaactcgc   1320
ctgcatgaag ctggaatcgc tagtaatcgc ggatcagcac gccgcggtga atacgttccc   1380
gggccttgta cacaccgccc gtcacaccat gagagtttgt aacacccaaa gccggtgaga   1440
caaccgcaag gagtcagccg tctaaggtgg gacaaatgat tagggtgaag tcgtaaacaa   1500
ggtaaca                                                             1507
```

<210> SEQ ID NO 29
<211> LENGTH: 1568
<212> TYPE: DNA
<213> ORGANISM: Lactobacillus mucosae

<400> SEQUENCE: 29

```
agagtttgat cctggctcag gatgaacgcc ggcggtgtgc ctaatacatg caagtcgaac     60
gcgttggccc aactgattga acgtgcttgc acggacttga cgttggttta ccagcgagtg    120
gcggacgggt gagtaacacg taggtaacct gccccaaagc gggggataac atttggaaac    180
agatgctaat accgcataac aatttgaatc gcatgattca aatttaaaag atggcttcgg    240
ctatcacttt gggatggacc tgcggcgcat tagcttgttg gtagggtaac ggcctaccaa    300
ggctgtgatg cgtagccgag ttgagagact gatcggccac aatggaactg agacacggtc    360
catactccta cgggaggcag cagtagggaa tcttccacaa tgggcgcaag cctgatggag    420
caacaccgcg tgagtgaaga agggtttcgg ctcgtaaagc tctgttgtta gagaagaacg    480
tgcgtgagag caactgttca cgcagtgacg gtatctaacc agaaagtcac ggctaactac    540
gtgccagcag ccgcggtaat acgtaggtgg caagcgttat ccggatttat tgggcgtaaa    600
gcgagcgcag gcggtttgat aagtctgatg tgaaagcctt tggcttaacc aaagaagtgc    660
atcggaaact gtcagacttg agtgcagaag aggacagtgg aactccatgt gtagcggtgg    720
```

```
aatgcgtaga tatatggaag aacaccagtg gcgaaggcgg ctgtctggtc tgcaactgac    780

gctgaggctc gaaagcatgg gtagcgaaca ggattagata ccctggtagt ccatgccgta    840

aacgatgagt gctaggtgtt ggagggtttc cgcccttcag tgccgcagct aacgcattaa    900

gcactccgcc tggggagtac gaccgcaagg ttgaaactca aaggaattga cgggggcccg    960

cacaagcggt ggagcatgtg gtttaattcg aagctacgcg aagaacctta ccaggtcttg   1020

acatcttgcg ccaaccctag agatagggcg tttccttcgg gaacgcaatg acaggtggtg   1080

catggtcgtc gtcagctcgt gtcgtgagat gttgggttaa gtcccgcaac gagcgcaacc   1140

cttgttacta gttgccagca ttcagttggg cactctagtg agactgccgg tgacaaaccg   1200

gaggaaggtg gggacgacgt cagatcatca tgccccttat gacctgggct acacacgtgc   1260

tacaatggac ggtacaacga gtcgcgaact cgcgagggca agctaatctc ttaaaaccgt   1320

tctcagttcg gactgcaggc tgcaactcgc ctgcacgaag tcggaatcgc tagtaatcgc   1380

ggatcagcat gccgcggtga atacgttccc gggccttgta cacaccgccc gtcacaccat   1440

gagagtttgc aacacccaaa gtcggtgggg taacccttcg ggagctagcc gcctaaggt    1500

ggggcagatg attagggtga agtcgtaaca aggtagccgt aggagaacct gcggctggat   1560

cacctcct                                                            1568
```

<210> SEQ ID NO 30
<211> LENGTH: 1519
<212> TYPE: DNA
<213> ORGANISM: Lactobacillus pentosus

<400> SEQUENCE: 30

```
gacgaacgct ggcggcgtgc ctaatacatg caagtcgaac gaactctggt attgattggt     60

gcttgcatca tgatttacat ttgagtgagt ggcgaactgg tgagtaacac gtgggaaacc    120

tgcccagaag cgggggataa cacctggaaa cagatgctaa taccgcataa caacttggac    180

cgcatggtcc gagtttgaaa gatggcttcg gctatcactt ttggatggtc ccgcggcgta    240

ttagctagat ggtggggtaa cggctcacca tggcaatgat acgtagccga cctgagaggg    300

taatcggcca cattgggact gagacacggc ccaaactcct acgggaggca gcagtaggga    360

atcttccaca atggacgaaa gtctgatgga gcaacgccgc gtgagtgaag aagggtttcg    420

gctcgtaaaa ctctgttgtt aaagaagaac atatctgaga gtaactgttc aggtattgac    480

ggtatttaac cagaaagcca cggctaacta cgtgccagca gccgcggtaa tacgtaggtg    540

gcaagcgttg tccggattta ttgggcgtaa agcgagcgca ggcggttttt taagtctgat    600

gtgaaagcct tcggctcaac cgaagaagtg catcggaaac tgggaaactt gagtgcagaa    660

gaggacagtg gaactccatg tgtagcggtg aaatgcgtag atatatggaa gaacaccagt    720

ggcgaaggcg gctgtctggt ctgtaactga cgctgaggct cgaaagtatg ggtagcaaac    780

aggattagat accctggtag tccataccgt aaacgatgaa tgctaagtgt tggagggttt    840

ccgcccttca gtgctgcagc taacgcatta agcattccgc ctggggagta cggccgcaag    900

gctgaaactc aaaggaattg acgggggccc gcacaagcgg tggagcatgt ggtttaattc    960

gaagctacgc gaagaacctt accaggtctt gacatactat gcaaatctaa gagattagac   1020

gttcccttcg ggacatggat acaggtggt gcatggttgt cgtcagctcg tgtcgtgaga    1080

tgttgggtta agtcccgcaa cgagcgcaac ccttattatc agttgccagc attaagttgg   1140

gcactctggt gagactgccg gtgacaaacc ggaggaaggt ggggatgacg tcaaatcatc   1200
```

-continued

```
atgcccctta tgacctgggc tacacacgtg ctacaatgga tggtacaacg agttgcgaac   1260

tcgcgagagt aagctaatct cttaaagcca ttctcagttc ggattgtagg ctgcaactcg   1320

cctacatgaa gtcggaatcg ctagtaatcg cggatcagca tgccgcggtg aatacgttcc   1380

cgggccttgt acacaccgcc cgtcacacca tgagagtttg taacacccaa agtcggtggg   1440

gtaacctttt aggaaccagc cgcctaaggt gggacagatg attagggtga agtcgtaaca   1500

aggtagccgt agggagaac                                                1519
```

<210> SEQ ID NO 31
<211> LENGTH: 1517
<212> TYPE: DNA
<213> ORGANISM: Lactobacillus plantarum

<400> SEQUENCE: 31

```
ckaacgcygg cggcgtgcct aatacatgca agtcgaacga actctggtat tgattggtgc     60

ttgcatcatg atttacattt gagtgagtgg cgaactggtg agtaacacgt gggaaacctg    120

cccaggaagc gggggataac acctggaaac akatgctaat accgcataac aacttggacc    180

gcatggtccg agtttgaaag atggcttcgg ctatcacttt tggatggycc cgcggcgtat    240

takctakatg gtggggtaac ggctcaccat ggcaatgata cgtacccgac ctgagagggt    300

aatcggccac attgggactg agacacggcc caaactccta cgggaggcag cagtagggaa    360

tcttccacaa tggacgaaag tctgatggag caacgccgcg tgagtgaaga agggtttcgg    420

ctcgtaaaac tctgttgtta aagaagaaca tatctgagag taactgttca ggtattgacg    480

gtatttaacc agaaagccac ggctaactac gtgccagcag ccgcggtaat acgtaggtgg    540

caagcgttgt ccggatttat tgggcgtaaa gcgagcgcag gcggtttttt aagtctgatg    600

tgaaagcctt cggctcaacc gaagaagtgc atcggaaact gggaaacttg agtgcagaag    660

aggacagtgg aactccatgt gtagcggtga aatgcgtata tatatggaas aacaccagtg    720

gcgaaggcgg ctgtctggtt ctgtaactga cgctgaggct cgaaagtatg ggtagcaaac    780

aggattagat accctggtag tccataccgt aaacgatgaa tgctaagtgt tggagggttt    840

ccgcccttca gtgctgcagc taacgcatta agcattccgc ctggggagta cggccgcaag    900

gctgaaactc aaaggaattg acgggggccc gcacaagcgg tggagcatgt ggtttaattc    960

gaagctacgc gaagaacctt accaggtctt gacatactat gcaaatctaa gagattagac   1020

gttcccttcg ggacatggat acaggtggt gcatggttgt cgtcagctcg tgtcgtgaga   1080

tgttgggtta agtcccgcaa cgagcgcaac ccttattatc agttgccagc attaagttgg   1140

gcactctggt gagactgccg gtgacaaacc ggaggaaggt ggggatgacg tcaaatcatc   1200

atgcccctta tgacctgggc tacacacgtg ctacaatgga tggtacaacg agttgcgaac   1260

tcgcgagagt aagctaatct cttaaagcca ttctcagttc ggattgtagg ctgcaactcg   1320

cctacatgaa gtcggaatcg ctagtaatcg cggatcagca tgccgcggtg aatacgttcc   1380

cgggccttgt acacaccgcc cgtcacacca tgagagtttg taacacccaa agtcggtggg   1440

gtaacctttt aggaaccagc cgcctaaggt gggacagatg attagggtga agtcgtaaca   1500

aggtagccgt aggagaa                                                  1517
```

<210> SEQ ID NO 32
<211> LENGTH: 1535
<212> TYPE: DNA
<213> ORGANISM: Lactobacillus reuteri

<400> SEQUENCE: 32

```
agagtttgat cctggctcag gatgaacgcc ggcagtgtgc ctaatacatg caagtcgtac     60

gcactggccc aactaattga tggtgcttgc tgaattgacg atggatcacc agtgagtggc    120

ggacgggtga gtaacacgta ggtaacctgc cccggagcgg ggaataacat ttggaaacag    180

atgctaatac cgcataacaa caaaagccgc atggtttttc tggaaagatg gctttggcta    240

tcactctggg atggacctgc ggtgcattta gctagttggt aaggtaacgg cttacccaag    300

gcgatgatgc atagccgagt tgagagactg atcggccaca atgggaactg agacacggtc    360

cataacttct acgggaggca gcagtaggga atcttccaca atgggcgcaa gctgatggag    420

caacaccgcg ttattaagaa agggtttcgg ccgcttaaac tctgttgttg gagaagaacg    480

tgcgttagag taactgttac gcagtgacgg tatccaacca gaaagtcacg gctaactacg    540

tgccagcagc cgcggtaata cgtaggtggc aagcgttatc cggatttatt gggcgtaaag    600

cgagcgcagg cggttgctta ggtctgatgt ggaaactcgg cttaaccgaa gaagtgcatc    660

ggaaaccggg cgacttgagt gcagaagagg acagtggaac tccatgtgta gcggtggaat    720

gcgtagatat atggaagaac accagtggcg aaggcggctg tctggtctgc aactgacgct    780

gaggctcgaa agcatgggta gcgaacagga ttagataccc tggtagtcca tgccgtaaac    840

gatgagtgct aggtgttgga gggtttccgc ccttcagtgc ctgttctaac gcattaatgc    900

actccgcctg gggagtacga ccgcaaggtt gaaactcaaa ggaattgacg ggggcccgca    960

caagcggtga agcatgtggt ttaattcgaa gctacgcgaa gaaccttacc aggtcttgac   1020

atcttgcgct aaccttagag ataaggcgtt cccttcgggg acgttaatga caggtggtgc   1080

atggtcgtcg tcagctcgtg tcgtgagatg ttgggttaag tcccgcaacg agcgcaaccc   1140

ttgttactag ttgccagcat taagttgggg actctagtga gactgccggt gacaaaccgg   1200

aggaaggtgg ggacgacgtc agatcatcat gccccttatg accctgggct acacacgtgc   1260

tacaatggac ggtacaacga gtcgcaaact cgcgagagta agctaatctc ttaaagccgt   1320

tctcagttcg gactgtaggc tgcaactcgc ctacacgaag tcggaatcgc tagtaatcgc   1380

ggatcagcat gccgcggtga atacgttccc gggccttgta cacaccgccc gtcacaccat   1440

gggagtttgt aacgcccaaa gttcggtggc ctaaccttta tggacgggta ccctaaggcg   1500

ggacagatga tctggggtga agtcgtaaca aggta                                1535
```

```
<210> SEQ ID NO 33
<211> LENGTH: 1521
<212> TYPE: DNA
<213> ORGANISM: Lactobacillus rhamnosus
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (1476)..(1476)
<223> OTHER INFORMATION: n is a, c, g, or t

<400> SEQUENCE: 33

grtsaacgct sgcggcgtgc ctaatacatg caagtcgaac gagttctgat tattgaaagg     60

tgcttgcatc ttgatttaat tttgaacgag tggcggacgg gtgagtaaca cgtgggtaac    120

ctgcccttaa gtgggggata acatttggaa acagatgcta ataccgcata aatccaagaa    180
```

ccgcatggtt cttggctgaa agatggcgta agctatcgct tttggatgga cccgcggcgt 240
attagctagt tggtgaggta acggctcacc aaggcaatga tacgtagccg aactgagagg 300
ttgatcggcc acattgggac tgagacacgg cccaaactct acgggaggca gcagtaggga 360
atcttccaca atggacgcaa gtctgatgga gcaacgccgc gtgagtnaag aaggctttcg 420
ggtcgtaaaa ctctgttgtt ggagaagaat ggtcggcaga gtaactgttg tcggcgtgac 480
ggtatccaac cagaaagcca cggctaacta cgtgccagca gccgcggtaa tacgtaggtg 540
gcaagcgtta tccggattta ttgggcgtaa agcgagcgca ggcggttttt taagtctgat 600
gtgaaagccc tcggcttaac cgaggaagtg catcggaaac tgggaaactt gagtncagaa 660
gaggacagtg gaactccatg tgtagcggtg aaatgcgtag atatatggaa gaacaccagt 720
ggcgaaggcg gctgtctggt ctgtaactga cgctgaggct cgaaagcatg ggtagcgaac 780
aggattagat accctggtag tccatgccgt aaacgatgaa tgctaggtgt tggagggttt 840
ccgcccttca gtgccgcagc taacgcatta agcattccgc ctggggagta cgaccgcaag 900
gttgaaactc aaaggaattg acgggggccc gcacaagcgg tggagcatgt ggtttaattc 960
gaagcaacgc gaagaacctt accaggtctt gacatctttt gatcacctga gagatcaggt 1020
ttccccttcg gggcaaaat gacaggtggt gcatggttgt cgtcagctcg tgtcgtgaga 1080
tgttgggtta agtcccgcaa cgagcgcaac ccttatgact agttgccagc atttagttgg 1140
gcactctagt aagactgccg gtgacaaacc ggaggaaggt ggggatgacg tcaaatcatc 1200
atgcccctta tgacctgggc tacacacgtg ctacaatgga tggtacaacg agttgcgaga 1260
ccgcgaggtc aagctaatct cttaaagcca ttctcagttc ggactgtagg ctgcaactcg 1320
cctacacgaa gtcggaatcg ctagtaatcg cggatcagca cgccgcggtg aatacgttcc 1380
cgggccttgt acacaccgcc cgtcacacca tgagagtttg taacacccga agccggtggc 1440
gtaacccttt tagggagcga gccgtctaag gtgggncaaa tgattagggt gaagtcgtaa 1500
caaggtagcc gtaggagaac c 1521

<210> SEQ ID NO 34
<211> LENGTH: 1561
<212> TYPE: DNA
<213> ORGANISM: Lactobacillus sake

<400> SEQUENCE: 34
aagtttgatt attgctcagg acgaacgctg gcggcgtgcc taatacatgc aagtcgaacg 60
cactctcgtt tagattgaag gagcttgctc ctgattgata aacatttgag tgagtggcgg 120
acgggtgagt aacacgtggg taacctgccc taaagtgggg gataacattt ggaaacagat 180
gctaataccg cataaaacct aacaccgcat ggtgtagggt tgaaagatgg tttcggctat 240
cactttagga tggacccgcg gtgcattagt tagttggtga ggtaaaggct caccaagacc 300
gtgatgcata gccgacctga gagggtaatc ggccacactg ggactgagac acggcccaga 360
ctcctacggg aggcagcagt agggaatctt ccacaatgga cgaaagtctg atggagcaac 420
gccgcgtgag tgaagaaggt tttcggatcg taaaactctg ttgttggaga agaatgtatc 480
tgatagtaac tgatcaggta gtgacggtat ccaaccagaa agccacggct aactacgtgc 540
cagcagccgc ggtaatacgt aggtggcaag cgttgtccgg atttattggg cgtaaagcga 600
gcgcaggcgg tttcttaagt ctgatgtgaa agccttcggc tcaaccgaag aagtgcatcg 660
gaaactggga aacttgagtg cagaagagga cagtggaact ccatgtgtag cggtgaaatg 720
cgtagatata tggaagaaca ccagtggcga aggcggatgt ctggtctgta actgacgctg 780

-continued aggctcgaaa gcatgggtag caaacaggat tagataccct ggtagtccat gccgtaaacg 840
atgagtgcta ggtgttggag ggtttccgcc cttcagtgcc gcagctaacg cattaagcac 900
tccgcctggg gagtacgacc gcaaggttga aactcaaagg aattgacggg ggcccgcaca 960
agcggtggag catgtggttt aattcgaagc aacgcgaaga accttaccag gtcttgacat 1020
cctttgacca ctctagagat agagctttcc cttcggggac aaagtgacag gtggtgcatg 1080
gttgtcgtca gctcgtgtcg tgagatgttg ggttaagtcc cgcaacgagc gcaaccctta 1140
ttactagttg ccagcattta gttgggcact ctagtgagac tgccggtgac aaaccggagg 1200
aaggtgggga cgacgtcaaa tcatcatgcc ccttatgacc tgggctacac acgtgctaca 1260
atggatggta caacgagttg cgagaccgcg aggtttagct aatctcttaa aaccattctc 1320
agttcggatt gtaggctgca actcgcctac atgaagccgg aatcgctagt aatcgcggat 1380
cagcatgccg cggtgaatac gttcccgggc cttgtacaca ccgcccgtca caccatgaga 1440
gtttgtaaca cccaaagccg gtgaggtaac ccttcgggga gccagccgtc taaggtggga 1500
cagatgatta gggtgaagtc gtaacaaggt agccgtagag aacctgcggc tggatcacct 1560
c 1561

<210> SEQ ID NO 35
<211> LENGTH: 1542
<212> TYPE: DNA
<213> ORGANISM: Lactobacillus salivarius

<400> SEQUENCE: 35
agagtttgat cctggctcag gacgaacgct ggcggcgtgc ctaatacatg caagtcgaac 60
gaaactttct tacaccgaat gcttgcrttc atcgtaagaa gttgagtggc ggacgggtga 120
gtaacacgtg ggtaacctgc ctaaaagaag ggataacac ttggaaacag gtgctaatac 180
cgtatatctc taaggatcgc atgatcctta gatgaaagat ggttctgcta tcgcttttag 240
atggacccgc ggcgtattaa ctagttggtg gggtaacggc ctaccaaggt gatgatacgt 300
agccgaactg agaggttgat cggccacatt gggactgaga cacggtccaa actcctacgg 360
gaggcagcag tagggaatct tccacaatgg acgcaagtct gatggagcaa cgccgcgtga 420
gtgaagaagg tcttcggatc gtaaaactct gttgttagag aagaacacga gtgagagtaa 480
ctgttcattc gatgacggta tctaaccagc aagtcacggc taactacgtg ccagcagccg 540
cggtaatacg taggtggcaa gcgttgtccg gatttattgg gcgtaaaggg aacgcaggcg 600
gtcttttaag tctgatgtga aagccttcgg cttaaccgga gtagtgcatt ggaaactgga 660
agacttgagt gcagaagagg agagtggaac tccatgtgta gcggtgaaat gcgtagatat 720
atggaagaac accagtggcg aaagcggctc tctggtctgt aactgacgct gaggttcgaa 780
agcgtgggta gcaaacagga ttagataccc tggtagtcca cgccgtaaac gatgaatgct 840
aggtgttgga gggtttccgc ccttcagtgc cgcagctaac gcaataagca ttccgcctgg 900
ggagtacgac cgcaaggttg aaactcaaag gaattgacgg gggcccgcac aagcggtgga 960
gcatgtggtt taattcgaag caacgcgaag aaccttacca ggtcttgaca tcctttgacc 1020
acctaagaga ttaggctttc ccttcgggga caaagtgaca ggtggtgcat ggctgtcgtc 1080
agctcgtgtc gtgagatgtt gggttaagtc ccgcaacgag cgcaaccctt gttgtcagtt 1140
gccagcatta agttgggcac tctggcgaga ctgccggtga caaaccggag gaaggtgggg 1200
acgacgtcaa gtcatcatgc cccttatgac ctgggctaca cacgtgctac aatggacggt 1260
acaacgagtc gcaagaccgc gaggtttagc taatctctta aagccgttct cagttcggat 1320
tgtaggctgc aactcgccta catgaagtcg gaatcgctag taatcgcgaa tcagcatgtc 1380
gcggtgaata cgttcccggg ccttgtacac accgcccgtc acaccatgag agtttgtaac 1440
acccaaagcc ggtggggtaa ccgcaaggag ccagccgtct aaggtgggac agatgattgg 1500
ggtgaagtcg taacaaggta gccgtaggag aacctgcggc tg 1542

<210> SEQ ID NO 36
<211> LENGTH: 1972
<212> TYPE: DNA
<213> ORGANISM: Lactobacillus paracasei

<400> SEQUENCE: 36
agagtttgat cctggctcag gacgaacgct ggcggcgtgc ctaatacatg caagtcgaac 60
gaaactttct tacaccgaat gcttgcrttc atcgtaagaa gttgagtggc ggacgggtga 120
gtaacacgtg ggtaacctgc ctaaaagaag gggataacac ttggaaacag gtgctaatac 180
cgtatatctc taaggatcgc atgatcctta gatgaaagat ggttctgcta tcgcttttag 240
atggacccgc ggcgtattaa ctagttggtg gggtaacggc ctaccaaggt gatgatacgt 300
agccgaactg agaggttgat cggccacatt gggactgaga cacggtccaa actcctacgg 360
gaggcagcag tagggaatct tccacaatgg acgcaagtct gatggagcaa cgccgcgtga 420
gtgaagaagg tcttcggatc gtaaaactct gatgaacgct ggcggcgtgc ctaatacatg 480
caagtcgaac gagttctcgt tgatgatcgg tgcttgcacc gagattcaac atggaacgag 540
tggcggacgg gtgagtaaca cgtgggtaac ctgcccttaa gtgggggata acatttggaa 600
acagatgcta ataccgcata gatccaagaa ccgcatggtt cttggctgaa agatggcgta 660
agctatcgct tttggatgga cccgcggcgt attagctagt tggtgaggta atggctcacc 720
aaggcgatga tacgtagccg aactgagagg ttgatcggcc acattgggac tgagacacgg 780
cccaaactcc tacgggaggc agcagtaggg aatcttccac aatggacgca agtctgatgg 840
agcaacgccg cgtgagtgaa gaaggctttc gggtcgtaaa actctgttgt tggagaagaa 900
tggtcggcag agtaactgtt gtcggcgtga cggtatccaa ccagaaagcc acggctaact 960
acgtgccagc agccgcggta atacgtaggt ggcaagcgtt atccggattt attgggcgta 1020
aagcgagcgc aggcggtttt ttaagtctga tgtgaaagcc ctcggcttaa ccgaggaagc 1080
gcatcggaaa ctgggaaact tgagtgcaga agaggacagt ggaactccat gtgtagcggt 1140
gaaatgcgta gatatatgga agaacaccag tggcgaaggc ggctgtctgg tctgtaactg 1200
acgctgaggc tcgaaagcat gggtagcgaa caggattaga taccctggta gtccatgccg 1260
taaacgatga atgctaggtg ttggagggtt tccgcccttc agtgccgcag ctaacgcatt 1320
aagcattccg cctggggagt acgaccgcaa ggttgaaact caaaggaatt gacgggggcc 1380
cgcacaagcg gtggagcatg tggtttaatt cgaagcaacg cgaagaacct taccaggtct 1440
tgacatcttt tgatcacctg agagatcagg tttccccttc gggggcaaaa tgacaggtgg 1500
tgcatggttg tcgtcagctc gtgtcgtgag atgttgggtt aagtcccgca acgagcgcaa 1560
cccttatgac tagttgccag catttagttg ggcactctag taagactgcc ggtgacaaac 1620
cggaggaagg tggggatgac gtcaaatcat catgcccctt atgacctggg ctacacacgt 1680
gctacaatgg atggtacaac gagttgcgag accgcgaggt caagctaatc tcttaaagcc 1740
attctcagtt cggactgtag gctgcaactc gcctacacga agtcggaatc gctagtaatc 1800
gcggatcagc acgccgcggt gaatacgttc ccgggccttg tacacaccgc ccgtcacacc 1860
atgagagttt gtaacacccg aagccggtgg cgtaaccctt ttagggagcg agccgtctaa 1920
ggtgggacaa atgattaggg tgaagtcgta acaaggtagc cgtaggagaa cc 1972

<210> SEQ ID NO 37
<211> LENGTH: 1565
<212> TYPE: DNA
<213> ORGANISM: Lactobacillus kisonensis

<400> SEQUENCE: 37
agagtttgat cctggctcag gacgaacgct ggcggcgtgc ctaatacatg caagtcgaac 60
gcgtcttggt tatcgaaggg aagtgcttgc atttccttga cttaacattg agacgagtgg 120
cgaactggtg agtaacacgt gggtaacctg cccttgaagt aggggataac acttggaaac 180
aggtgctaat accgtataac aaccaaagcc ccatgacttt ggtttaaaag atggcttcgg 240
ctatcacttt aggatggacc cgcggcgtat tagcttgttg gtgaggtaac ggctcaccaa 300
ggcaatgata cgtagccgac ctgagagggt aatcggccac attgggactg agacacggcc 360
caaactccta cgggaggcag cagtagggaa tcttccacaa tggacgaaag tctgatggag 420
caacgccgcg tgagtgatga agggtttcgg ctcgtaaaac tctgttgttg gagaagaacg 480
ggtgtgagag taactgttca catcgtgacg gtatccaacc agaaagccac ggctaactac 540
gtgccagcag ccgcggtaat acgtaggtgg caagcgttgt ccggatttat tgggcgtaaa 600
gcgagcgcag gcggtttttt aggtctgatg tgaaagcctt cggcttaacc ggagaagtgc 660
atcggaaacc gggagacttg agtgcagaag aggacagtgg aactccatgt gtagcggtga 720
aatgcgtaga tatatggaag aacaccagtg gcgaaggcgg ctgtctggtc tgtaactgac 780
gctgaggctc gaaagcatgg gtagcgaaca ggattagata ccctggtagt ccatgccgta 840
aacgatgagt gctaagtgtt ggagggtttc cgcccttcag tgctgcagct aacgcattaa 900
gcactccgcc tggggagtac gaccgcaagg ttgaaactca aaggaattga cgggggcccg 960
cacaagcggt ggagcatgtg gtttaattcg atgctacgcg aagaacctta ccaggtcttg 1020
acatcttctg ccaacctaag agattaggcg ttcccttcgg ggacagaatg acaggtggtg 1080
catggttgtc gtcagctcgt gtcgtgagat gttgggttaa gtcccgcaac gagcgcaacc 1140
cttattgtta gttgccagca tttagttggg cactctagca agactgccgg tgacaaaccg 1200
gaggaaggtg gggatgacgt caaatcatca tgccccttat gacctgggct acacacgtgc 1260
tacaatggac ggtacaacga gtcgcgaaac cgcgaggtca agctaatctc ttaaagccgt 1320
tctcagttcg gattgtaggc tgcaactcgc ctacatgaag ttggaatcgc tagtaatcgt 1380
ggatcagcat gccacggtga atacgttccc gggccttgta cacaccgccc gtcacaccat 1440
gagagtttgt aacacccaaa gccggtgagg taaccttcgg ggaccagccg tctaaggtgg 1500
gacagatgat tagggtgaag tcgtaacaag gtagccgtag gagaacctgc ggctggatca 1560
cctcc 1565

<210> SEQ ID NO 38
<211> LENGTH: 1522
<212> TYPE: DNA
<213> ORGANISM: Lactobacillus paralimentarius

<400> SEQUENCE: 38
gacgaacgct ggcggcatgc ctaatacatg caagtcgaac gaaccatcct gaagattgaa 60
gcttgcttca tgattcagac cttggtgagt ggcggacggg tgagtaacac gtgggtaacc 120

```
tgcccagaag tgggggataa catttggaaa caagtgctaa taccgcataa caacttagat    180
cacatgatct ttgtttaaaa gatggttttg ctatctcttc tggatggacc cgcggcgtat    240
tagctagttg gtgaggtaat agctcaccaa ggcgatgata cgtagccgac ctgagagggt    300
aatcggccac attgggactg agacacggcc caaactccta cgggaggcag cagtagggaa    360
tcttccacaa tggacgaaag tctgatggag caatgccgcg tgagtgaaga aggttttcgg    420
atcgtaaaac tctgttgttg aagaagaaca tatgtgagag taactgttca cgtactgacg    480
gtattcaacc agaaagccac ggctaactac gtgccagcag ccgcggtaat acgtaggtgg    540
caagcgttgt ccggatttat tgggcgtaaa gagaatgtag gcggtttatt aagtttgaag    600
tgaaagccct cggctcaacc gaggaagtgc ttcgaaaact ggtaaacttg agtgcagaag    660
aggaaagtgg aactccatgt gtagcggtgg aatgcgtaga tatatggaag aacaccagtg    720
gcgaaggcgg ctttctggtc tgtaactgac gctgagattc gaaagcatgg gtagcaaaca    780
ggattagata ccctggtagt ccatgccgta aacgatgagt gctaagtgtt ggagggtttc    840
cgcccttcag tgctgcagct aacgcattaa gcactccgcc tggggagtac gatcgcaaga    900
ttgaaactca aaggaattga cgggggcccg cacaagcggt ggagcatgtg gtttaattcg    960
aagcaacgcg aagaacctta ccaggtcttg acataccatg aaaagcttag agataagtct   1020
ttcccttcgg ggacatggat acaggtggtg catggttgtc gtcagctcgt gtcgtgagat   1080
gttgggttaa gtcccgcaac gagcgcaacc cttattatca gttgccagca ttcagttggg   1140
cactctggtg agactgccgg tgataaaccg gaggaaggtg gggacgacgt caaatcatca   1200
tgccccttat gacctgggct acacacgtgc tacaatggtc ggtacaacgt gctgcgaact   1260
cgcgagggca agcaaatcac ttaaaaccga tctcagttcg gattgtaggc tgcaactcgc   1320
ctacatgaag ctggaatcgc tagtaatcgc ggatcagcat gccgcggtga atacgttccc   1380
gggccttgta cacaccgccc gtcacaccat gagagtttgt aacacccaaa gtcggtgggg   1440
taacccttcg ggaactagc cgcctaaggt gggacaaatg attagggtga agtcgtaaca    1500
aggtagccgt aggagaacct gc                                            1522
```

```
<210> SEQ ID NO 39
<211> LENGTH: 1554
<212> TYPE: DNA
<213> ORGANISM: Lactobacillus perolens

<400> SEQUENCE: 39
```

```
tggctcagga cgaacgctgg cggcgtgcct aatacatgca agtcgaacga ggtttgatca     60
gtttgcggtg gtgcttgcat caccaattac cgattaaacc gagtggcgga cgggtgagta    120
acacgtgggt aacctgccct tcagcagggg ataacatttg gaaacagatg ctaataccgt    180
ataaccacgg agaccgcatg gtctccgggt aaaagatggc gaaagctatc actgagggat    240
ggacccgcgg cgtattagcc agttggtggg gtaatggcct accaaagcga tgatacgtag    300
ccgacctgag agggtaatcg gccacattgg gactgagaca cggcccaaac tcctacggga    360
ggcagcagta gggaatcttc cacaatggac gcaagtctga tggagcaacg ccgcgtgagt    420
gaagaaggct ttcgggtcgt aaaactctgt tattgaagaa gaacgtgtgt gagagtaact    480
gctcatgcag tgacggtatt caaccagaaa gtcacggcta actacgtgcc agcagccgcg    540
gtaatacgta ggtggcaagc gttgtccgga tttattgggc gtaaagcgag tgcaggcggt    600
tttttaagtc tgatgtgaaa gccttcggct taaccgaaga agtgcatcgg aaagtgggaa    660
acttgagtgc agaagaggag agtggaactc catgtgtagc ggtgaaatgc gtagatatat    720
```

-continued ggaagaacac cagtggcgaa ggcggctctc tggtctgtaa ctgacgctga ggctcgaaag 780
cgtgggtagc aaacaggatt agataccctg gtagtccacg ccgtaaacga tgaatactaa 840
gtgttggggg gtttccgccc ctcagtgctg cagctaacgc attaagtatt ccgcctgggg 900
agtacgaccg caaggttgaa actcaaagga attgacgggg gcccgcacaa gcggtggagc 960
atgtggttta attcgaagca acgcgaagaa ccttaccagg tcttgacatc ttctgccaag 1020
ctgagagatc agccgttcct tcggggacag aatgacaggt ggtgcatggt tgtcgtcagc 1080
tcgtgtcgtg agatgttggg ttaagtcccg caacgagcgc aacccttatg attagttgcc 1140
agcattcagt tgggcactct agtcagactg ccggtgacaa accggaggaa ggcggggatg 1200
acgtcaaatc atcatgcccc ttatgacctg ggctacacac gtgctacaat gggtggtaca 1260
acgagcagcg agaccgcgag gtcaagcgaa tctctaaaaa ccatcctcag ttcggattgt 1320
aggctgcaac tcgcctacat gaagctggaa tcgctagtaa tcgcggatca gcacgccgcg 1380
gtgaatacgt tcccgggcct tgtacacacc gcccgtcaca ccatgagagt ttgtaacacc 1440
caaagccggt aggacaaccg caaggagtca gccgtctaag gtgggacaaa tgattagggt 1500
gaagtcgtaa caaggtagcc gtaggagaac ctgcggctgg atcacctcct ttct 1554

<210> SEQ ID NO 40
<211> LENGTH: 1428
<212> TYPE: DNA
<213> ORGANISM: Lactobacillus apis

<400> SEQUENCE: 40
tgcagtcgag cgagcaagtt aaggaatact tcggtaggaa tttaatagcg cgagcggcgg 60
atgggtgagt aacacgtggg caacctgccc tttagcttgg gataccactt ggaaacaggt 120
gctaatacca aataagaagt aagagcgcat gctcaagcta tgaaaggcgg ctttcgagct 180
gtcactaaag gatgggcccg cggtgcatta gctagttggt aaggtaacgg cttaccaagg 240
caatgatgca tagccgagtt gagagactga tcggccacat tgggactgag acacggccca 300
aactcctacg ggaggcagca gtagggaatc ttccacaatg gacgcaagtc tgatggagca 360
acgccgcgtg agtgaagaag gttttcggat cgtaaagctc tgttgttggt gaagaaggac 420
atgggtagta actgatctat gtttgacggt aatcaaccag aaagtcacgg ctaactacgt 480
gccagcagcc gcggtaatac gtaggtggca agcgttgtcc ggatttattg ggcgtaaagc 540
gaacgcaggc gggagaacaa gtcagctgtg aaagccctcg gcttaaccga ggaacggcaa 600
ctgaaactgt ttttcttgag tgcagaagag gagagtggaa ctccatgtgt agcggtgaaa 660
tgcgtagata tatggaagaa caccagtggc gaaggcggct ctctggtctg taactgacgc 720
tgaggttcga aagcatgggt agcgaacagg attagatacc ctggtagtcc atgccgtaaa 780
cgatgagtgc taagtgttgg gaggtttccg cctctcagtg ctgcagctaa cgcattaagc 840
actccgcctg ggagtacga ccgcaaggtt aaaactcaaa ggaattgacg ggggcccgca 900
caagcggtgg agcatgtggt ttaattcgaa gcaacgcgaa gaaccttacc aggtcttgac 960
atctagtgcc aaccctagag atagggtgtt tccttcggga acactaagac aggtggtgca 1020
tggctgtcgt cagctcgtgt cgtgagatgt tgggttaagt cccgcaacga gcgcaaccct 1080
tattattagt tgccagcatt aagttgggca ctctaatgag actgccggtg acaaaccgga 1140
ggaaggtggg gacgacgtca agtcatcatg ccccttatga cctgggctac acacgtgcta 1200
caatggttag tacaacgagg agcgaacctg tgaaggcaag cgaatctctt aaagctaatc 1260

```
tcagttcgga ttgcactctg caactcgagt gcatgaagct ggaatcgcta gtaatcgcgg   1320

atcagcatgc cgcggtgaat acgttcccgg gccttgtaca caccgcccgt cacaccatga   1380

gagtttgtaa tacccaaagc cggtgagata acctgtaaag gagtcagc               1428


<210> SEQ ID NO 41
<211> LENGTH: 1460
<212> TYPE: DNA
<213> ORGANISM: Lactobacillus ghanensis

<400> SEQUENCE: 41

gcggcgtgcc taatacatgc aagtcgaacg aagttgtttt aactggtgct tgcaccgact     60

taaacaactg agtggcgaac gggtgagtaa cacgtgggta acctgcccca aagcggggga    120

taacatttgg aaacagatgc taataccgca taaccacaga aacctcatgg tttctgtgtc    180

aaagatggtt tcggctatca ctttgggatg gacccgcggc gtattagcta gttggtaagg    240

taacggctta ccaaggcaat gatacgtagc cgaactgaga ggttgatcgg ccacattggg    300

actgagacac ggcccaaact cctacgggag gcagcagtag ggaatcttcc acaatggacg    360

aaagtctgat ggagcaacgc cgcgtgagtg aagaaggttt tcggatcgta aaactctgtt    420

gtcagagaag aacgtgtgcg agagtaactg ttcgtgcagt gacggtatct gaccagaaag    480

ccacggctaa ctacgtgcca gcagccgcgg taatacgtag gtggcaagcg ttgtccggat    540

ttattgggcg taaagggaac gcaggcggtt ttttaagtct gatgtgaaag ccttcggctt    600

aaccgaagtc gtgcattgga aactggagaa cttgagtgca gaagaggaga gtggaactcc    660

atgtgtagcg gtgaaatgcg tagatatatg gaagaacacc agtggcgaaa gcggctctct    720

ggtctgtaac tgacgctgag gttcgaaagc gtgggtagca aacaggatta gataccctgg    780

tagtccacgc tgtaaacgat gaatgctaag tgttggaggg tttccgccct tcagtgccgc    840

agctaacgca ttaagcattc cgcctgggga gtacgaccgc aaggttgaaa ctcaaaggaa    900

ttgacggggg cccgcacaag cggtggagca tgtggtttaa ttcgaagcaa cgcgaagaac    960

cttaccaggt cttgacatct tctgcaagcc tgagagatca ggtgttccct tcggggacag   1020

aatgacaggt ggtgcatggt tgtcgtcagc tcgtgtcgtg agatgttggg ttaagtcccg   1080

caacgagcgc aacccttatt gccagttgcc agcattcagt tgggcactct gacaagactg   1140

ccggtgacaa accggaggaa ggtggggatg acgtcaaatc atcatgcccc ttatgacctg   1200

ggctacacac gtgctacaat ggacgataca acgagttgct agaccgcgag gttaagctaa   1260

tctcttaaag tcgttctcag ttcggattgc aggctgcaac tcgcctgcat gaagtcggaa   1320

tcgctagtaa tcgcggatca gcatgccgcg gtgaatacgt tcccgggcct tgtacacacc   1380

gcccgtcaca ccatgagagt ttgtaacacc caaagccggt ggggtaacca gtgggaacca   1440

gccgtctaag gtgggacaga                                                1460


<210> SEQ ID NO 42
<211> LENGTH: 1464
<212> TYPE: DNA
<213> ORGANISM: Lactobacillus dextrinicus
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
```

<222> LOCATION: (781)..(781)
<223> OTHER INFORMATION: n is a, c, g, or t

<400> SEQUENCE: 42
ctggcggcgt gcctaataca tgcaagtcga acgagtttgc ttttaatgaa ggcggtgctt 60
gcaccaactg atttaaaaat aaacgagtgg cggacgggtg agtaacacgt gggtaaccta 120
ccctaaagtg ggggataaca tttggaaaca gatgctaata ccgcataata tcaaaaacca 180
catggttttt aattgaaaga cggcgtaagc tgtcactttt ggatggaccc gcggcgtatt 240
agctagttgg tgaggtaacg gctcaccaag gcgatgatac gtagccgacc tgagagggtg 300
atcggccaca ttgggactga gacacggccc aaactcctac gggaggcagc agtagggaat 360
cttccacaat ggacgaaagt ctgatggagc aacnccncgt gagtgaagaa ggttttcgga 420
tcgtaaaact ctgttattgg agaagaacgt atttggtagt aactggccag atagtgacgg 480
tatccaatca gaaagccacg gctaactacg tgccagcagc cgcggtaata cgtaggtggc 540
aagcgttgtc cggatttatt gggcgtaaag cgagtgcagg cggtttttta agtctgatgt 600
gaaagccttc ggcttaaccg aagaaatgca ttggaaactg ggaaacttga gtgcagaaga 660
ggagagtgga actccatgtg tagcggtgaa atgcgtagat atatggaaga acaccagtgg 720
cgaaggcggc tctctggtct gtaactgacg ctgaggctcg aaagcgtggg tagcaaacag 780
nattagatac cctggtagtc cacgccgtaa acgatgagtg ctaagtgttg gagggtttcc 840
gcccttcagt gctgcagcta acgcattaag cactccgcct ggggagtacg accgcaaggt 900
tgaaactcaa aggaattgac gggggcccgc acaagcggtg gagcatgtgg tttaattcga 960
agcaacgcga agaaccttac caggtcttga catctagcgc caatcctaga gataggacgt 1020
tcccttcggg gacgctaaga caggtggtgc atggttgtcg tcagctcgtg tcgtgagatg 1080
ttgggttaag tcccgcaacg agcgcaaccc ttattatcag ttgccagcat ttagttgggc 1140
actctggtga gactgccggt gacaaaccgg aggaaggtgg ggatgacgtc aaatcatcat 1200
gccccttatg acctgggcta cacacgtgct acaatggcta gtacaacgag ttgcgagacc 1260
gcgaggtcaa gctaatctct aaaagctagt ctcagttcgg attgtaggct gcaactcgcc 1320
tacatgaagt tggaatcgct agtaatcgcg gatcagcacg ccgcggtgaa tacgttcccg 1380
ggccttgtac acaccgcccg tcacaccatg agagtttgta acacccgaag ccggtggagt 1440
aacccgtaag ggagctagcc gtct 1464

<210> SEQ ID NO 43
<211> LENGTH: 1499
<212> TYPE: DNA
<213> ORGANISM: Lactobacillus lactis

<400> SEQUENCE: 43
gacgaacgct ggcggcgtgc ctaatacatg caagttgagc gatgaagatt ggtgcttgca 60
ccaatttgaa gagcagcgaa cgggtgagta acgcgtgggg aatctgcctt tgagcggggg 120
acaacatttg gaaacgaatg ctaataccgc ataacaactt taaacataag ttttaagttt 180
gaaagatgca attgcatcac tcaaagatga tcccgcgttg tattagctag ttggtgaggt 240
aaaggctcac caaggcgatg atacatagcc gacctgagag ggtgatcggc cacattggga 300
ctgagacacg gcccaaactc ctacgggagg cagcagtagg gaatcttcgg caatggacga 360
aagtctgacc gagcaacgcc gcgtgagtga agaaggtttt cggatcgtaa aactctgttg 420
gtagagaaga acgttggtga gagtggaaag ctcatcaagt gacggtaact acccagaaag 480

-continued

```
ggacggctaa ctacgtgcca gcagccgcgg taatacgtag gtcccgagcg ttgtccggat    540

ttattgggcg taaagcgagc gcaggtggtt tattaagtct ggtgtaaaag gcagtggctc    600

aaccattgta tgcattggaa actggtagac ttgagtgcag gagaggagag tggaattcca    660

tgtgtagcgg tgaaatgcgt agatatatgg aggaacaccg gtggcgaaag cggctctctg    720

gcctgtaact gacactgagg ctcgaaagcg tggggagcaa acaggattag ataccctggt    780

agtccacgcc gtaaacgatg agtgctagat gtagggagct ataagttctc tgtatcgcag    840

ctaacgcaat aagcactccg cctggggagt acgaccgcaa ggttgaaact caaaggaatt    900

gacgggggcc cgcacaagcg gtggagcatg tggtttaatt cgaagcaacg cgaagaacct    960

taccaggtct tgacatactc gtgctattcc tagagatagg aagttccttc gggacacggg   1020

atacaggtgg tgcatggttg tcgtcagctc gtgtcgtgag atgttgggtt aagtcccgca   1080

acgagcgcaa cccctattgt tagttgccat cattaagttg ggcactctaa cgagactgcc   1140

ggtgataaac cggaggaagg tggggatgac gtcaaatcat catgcccctt atgacctggg   1200

ctacacacgt gctacaatgg atggtacaac gagtcgcgag acagtgatgt ttagctaatc   1260

tcttaaaacc attctcagtt cggattgtag gctgcaactc gcctacatga agtcggaatc   1320

gctagtaatc gcggatcagc acgccgcggt gaatacgttc ccgggccttg tacacaccgc   1380

ccgtcacacc acgggagttg ggagtacccg aagtaggttg cctaaccgca aggagggcgc   1440

ttcctaaggt aagaccgatg actggggtga agtcgtaaca aggtagccgt atcggaagg    1499


<210> SEQ ID NO 44
<211> LENGTH: 1510
<212> TYPE: DNA
<213> ORGANISM: Bacteroides vulgatus

<400> SEQUENCE: 44

tattacaatg aagagtttga tcctggctca ggatgaacgc tagctacagg cttaacacat     60

gcaagtcgag ggcagcatgg tcttagcttg ctaaggccga tggcgaccgg cgcacgggtg    120

agtaacacgt atccaacctg ccgtctactc ttggacagcc ttctgaaagg aagattaata    180

caagatggca tcatgagtcc gcatgttcac atgattaaag gtattccggt agacgatggg    240

gatgcgttcc attagatagt aggcggggta acggcccacc tagtcttcga tggataggg     300

gttctgagag gaaggtcccc cacattggaa ctgagacacg gtccaaactc ctacgggagg    360

cagcagtgag gaatattggt caatgggcga gagcctgaac cagccaagta gcgtgaagga    420

tgactgccct atgggttgta aacttctttt ataaaggaat aaagtcgggt atggataccc    480

gtttgcatgt actttatgaa taaggatcgg ctaactccgt gccagcagcc gcggtaatac    540

ggaggatccg agcgttatcc ggatttattg ggtttaaagg gagcgtagat ggatgtttaa    600

gtcagttgtg aaagtttgcg gctcaaccgt aaaattgcag ttgatactgg atatcttgag    660

tgcagttgag gcaggcggaa ttcgtggtgt agcggtgaaa tgcttagata tcacgaagaa    720

ctccgattgc gaaggcagcc tgctaagctg caactgacat tgaggctcga aagtgtgggt    780

atcaaacagg attagatacc ctggtagtcc acacggtaaa cgatgaatac tcgctgtttg    840

cgatatactg caagcggcca agcgaaagcg ttaagtattc cacctgggga gtacgccggc    900

aacggtgaaa ctcaaaggaa ttgacggggg cccgcacaag cggaggaaca tgtggtttaa    960

ttcgatgata cgcgaggaac cttacccggg cttaaattgc agatgaatta cggtgaaagc   1020

cgtaagccgc aaggcatctg tgaaggtgct gcatggttgt cgtcagctcg tgccgtgagg   1080

tgtcggctta agtgccataa cgagcgcaac ccttgttgtc agttactaac aggttccgct   1140
```

gaggactctg acaagactgc catcgtaaga tgtgaggaag gtggggatga cgtcaaatca 1200
gcacggccct tacgtccggg gctacacacg tgttacaatg gggggtacag agggccgcta 1260
ccacgcgagt ggatgccaat ccccaaaacc tctctcagtt cggactggag tctgcaaccc 1320
gactccacga agctggattc gctagtaatc gcgcatcagc cacggcgcgg tgaatacgtt 1380
cccgggcctt gtacacaccg cccgtcaagc catgggagcc gggggtacct gaagtgcgta 1440
accgcgagga gcgccctagg gtaaaactgg tgactggggc taagtcgtaa caaggtagcc 1500
gtaccggaag 1510

<210> SEQ ID NO 45
<211> LENGTH: 1529
<212> TYPE: DNA
<213> ORGANISM: Bacteroides fragilis

<400> SEQUENCE: 45
acaatgaaga gtttgatcct ggctcaggat gaacgctagc tacaggctta acacatgcaa 60
gtcgaggggc atcaggaaga aagcttgctt tctttgctgg cgaccggcgc acgggtgagt 120
aacacgtatc caacctgccc tttactcggg gatagccttt cgaaagaaag attaataccc 180
gatagcataa tgattccgca tggtttcatt attaaaggat tccggtaaag gatggggatg 240
cgttccatta ggttgttggt gaggtaacgg ctcaccaagc cttcgatgga taggggttct 300
gagaggaagg tcccccacat tggaactgag acacggtcca aactcctacg ggaggcagca 360
gtgaggaata ttggtcaatg ggcgctagcc tgaaccagcc aagtagcgtg aaggatgaag 420
gctctatggg tcgtaaactt cttttatata agaataaagt gcagtatgta tactgttttg 480
tatgtattat atgaataagg atcggctaac tccgtgccag cagccgcggt aatacggagg 540
atccgagcgt tatccggatt tattgggttt aaagggagcg taggtggact ggtaagtcag 600
ttgtgaaagt ttgcggctca accgtaaaat tgcagttgat actgtcagtc ttgagtacag 660
tagaggtggg cggaattcgt ggtgtagcgg tgaaatgctt agatatcacg aagaactccg 720
attgcgaagg cagctcactg gactgcaact gacactgatg ctcgaaagtg tgggtatcaa 780
acaggattag ataccctggt agtccacaca gtaaacgatg aatactcgct gtttgcgata 840
tacagtaagc ggccaagcga aagcattaag tattccacct ggggagtacg ccggcaacgg 900
tgaaactcaa aggaattgac gggggcccgc acaagcggag gaacatgtgg tttaattcga 960
tgatacgcga ggaaccttac ccgggcttaa attgcagtgg aatgatgtgg aaacatgtca 1020
gtgagcaatc accgctgtga aggtgctgca tggttgtcgt cagctcgtgc cgtgaggtgt 1080
cggcttaagt gccataacga gcgcaaccct tatctttagt tactaacagg ttatgctgag 1140
gactctagag agactgccgt cgtaagatgt gaggaaggtg gggatgacgt caaatcagca 1200
cggcccttac gtccggggct acacacgtgt tacaatgggg ggtacagaag gcagctagcg 1260
ggtgaccgta tgctaatccc aaaatcctct ctcagttcgg atcgaagtct gcaacccgac 1320
ttcgtgaagc tggattcgct agtaatcgcg catcagccac ggcgcggtga atacgttccc 1380
gggccttgta cacaccgccc gtcaagccat gggagccggg ggtacctgaa gtacgtaacc 1440
gcaaggatcg tcctagggta aaactggtga ctggggctaa gtcgtaacaa ggtagccgta 1500
ccggaaggtg cggctggaac acctcctttt 1529

<210> SEQ ID NO 46
<211> LENGTH: 1462
<212> TYPE: DNA

<213> ORGANISM: Faecalibacterium prausnitzii

<400> SEQUENCE: 46
gatcctggct caggcgaacg ctggcggcgc gcctaacaca tgcaagtcga acgagcgaga 60
gagagcttgc tttctcaagc gagtggcgaa cgggtgagta acgcgtgagg aacctgcctc 120
aaagaggggg acaacagttg gaaacgactg ctaataccgc ataagcccac gacccggcat 180
cgggtagagg gaaaaggagc aatccgcttt gagatggcct cgcgtccgat tagctagttg 240
gtgaggtaac ggcccaccaa ggcgacgatc ggtagccgga ctgagaggtt gaacggccac 300
attgggactg agacacggcc cagactccta cgggaggcag cagtggggaa tattgcacaa 360
tgggggaaac cctgatgcag cgacgccgcg tggaggaaga aggtcttcgg attgtaaact 420
cctgttgttg aggaagataa tgacggtact caacaaggaa gtgacggcta actacgtgcc 480
agcagccgcg gtaaaacgta ggtcacaagc gttgtccgga attactgggt gtaaagggag 540
cgcaggcggg aaggcaagtt ggaagtgaaa tccatgggct caacccatga actgctttca 600
aaactgtttt tcttgagtag tgcagaggta ggcggaattc ccggtgtagc ggtggaatgc 660
gtagatatcg ggaggaacac cagtggcgaa ggcggcctac tgggcaccaa ctgacgctga 720
ggctcgaaag tgtgggtagc aaacaggatt agataccctg gtagtccaca ctgtggccga 780
tgtttactag gtgttggagg attgacccct tcagtgccgc agttaacaca ataagtaatc 840
cacctgggga gtacgaccgc aaggttgaaa ctcaaaggaa ttgacggggg cccgcacaag 900
cagtggagta tgtggtttaa ttcgacgcaa cgcgaagaac cttaccaagt cttgacatcc 960
tgcgacgcac atagaaatat gtgtttcctt cgggacgcag agacaggtgg tgcatggttg 1020
tcgtcagctc gtgtcgtgag atgttgggtt aagtcccgca acgagcgcaa cccttatggt 1080
cagttactac gcaagaggac tctggccaga ctgccgttga caaaacggag gaaggtgggg 1140
atgacgtcaa atcatcatgc cctttatgac ttgggctaca cacgtactac aatggcgtta 1200
aacaaagaga agcaagaccg cgaggtggag caaaactcag aaacaacgtc ccagttcgga 1260
ctgcaggctg caactcgcct gcacgaagtc ggaattgcta gtaatcgcag atcagcatgc 1320
tgcggtgaat acgttcccgg gccttgtaca caccgcccgt cacaccatga gagccggggg 1380
gacccgaagt cggtagtcta accgcaagga ggacgccgcc gaaggtaaaa ctggtgattg 1440
gggtgaagtc gtaacaaggt ac 1462

<210> SEQ ID NO 47
<211> LENGTH: 1521
<212> TYPE: DNA
<213> ORGANISM: Eubacterium rectale

<400> SEQUENCE: 47
agagtttgat cctggctcag gatgaacgct ggcggcgtgc ttaacacatg caagtcgaac 60
gaagcacttt atttgatttc cttcgggact gattattttg tgactgagtg gcggacgggt 120
gagtaacgcg tgggtaacct gccttgtaca gggggataac agttggaaac ggctgctaat 180
accgcataag cgcacggcat cgcatgatgc agtgtgaaaa actccggtgg tataagatgg 240
acccgcgttg gattagctag ttggtgaggt aacggcccac caaggcgacg atccatagcc 300
gacctgagag ggtgaccggc cacattggga ctgagacacg gcccaaactc ctacgggagg 360
cagcagtggg gaatattgca caatgggcga aagcctgatg cagcgacgcc gcgtgagcga 420
agaagtattt cggtatgtaa agctctatca gcagggaaga taatgacggt acctgactaa 480
gaagcaccgg ctaaatacgt gccagcagcc gcggtaatac gtatggtgca agcgttatcc 540

-continued ggatttactg ggtgtaaagg gagcgcaggc ggtgcggcaa gtctgatgtg aaagcccggg 600
gctcaacccc ggtactgcat tggaaactgt cgtactagag tgtcggaggg gtaagcggaa 660
ttcctagtgt agcggtgaaa tgcgtagata ttaggaggaa caccagtggc gaaggcggct 720
tactggacga taactgacgc tgaggctcga aagcgtgggg agcaaacagg attagatacc 780
ctggtagtcc acgccgtaaa cgatgaatac taggtgttgg gaagcattgc ttctcggtgc 840
cgtcgcaaac gcagtaagta ttccacctgg ggagtacgtt cgcaagaatg aaactcaaag 900
gaattgacgg ggacccgcac aagcggtgga gcatgtggtt taattcgaag caacgcgaag 960
aaccttacca agtcttgaca tccttctgac cggtacttaa ccgtaccttc tcttcggagc 1020
aggagtgaca ggtggtgcat ggttgtcgtc agctcgtgtc gtgagatgtt gggttaagtc 1080
ccgcaacgag cgcaaccctt atctttagta gccagcggtt cggccgggca ctctagagag 1140
actgccaggg ataacctgga ggaaggcggg gatgacgtca aatcatcatg ccccttatga 1200
cttgggctac acacgtgcta caatggcgta aacaaaggga agcaaagctg tgaagccgag 1260
caaatctcaa aaataacgtc tcagttcgga ctgtagtctg caacccgact acacgaagct 1320
ggaatcgcta gtaatcgcag atcagaatgc tgcggtgaat acgttcccgg gtcttgtaca 1380
caccgcccgt cacaccatgg gagttgggaa tgcccgaagc cagtgaccta accgaaagga 1440
aggagctgtc gaaggcaggc tcgataactg ggtgaagtc gtaacaaggt agccgtatcg 1500
gaaggtgcgg ctggatcacc t 1521

<210> SEQ ID NO 48
<211> LENGTH: 1539
<212> TYPE: DNA
<213> ORGANISM: Streptococcus thermophilus

<400> SEQUENCE: 48
atgggagagt ttgatcctgg ctcaggacga acgctggcgg cgtgcctaat acatgcaagt 60
agaacgctga agagaggagc ttgctcttct tggatgagtt gcgaacgggt gagtaacgcg 120
taggtaacct gccttgtagc gggggataac tattggaaac gatagctaat accgcataac 180
aatggatgac acatgtcatt tatttgaaag gggcaattgc tccactacaa gatggacctg 240
cgttgtatta gctagtaggt gaggtaatgg ctcacctagg cgacgataca tagccgacct 300
gagagggtga tcggccacac tgggactgag acacggccca gactcctacg ggaggcagca 360
gtagggaatc ttcggcaatg gggcaaccc tgaccgagca acgccgcgtg agtgaagaag 420
gttttcggat cgtaaagctc tgttgtaagt caagaacggg tgtgagagtg gaaagttcac 480
actgtgacgg tagcttacca gaaagggacg gctaactacg tgccagcagc cgcggtaata 540
cgtaggtccc gagcgttgtc cggatttatt gggcgtaaag cgagcgcagg cggtttgata 600
agtctgaagt taaaggctgt ggctcaacca tagttcgctt tggaaactgt caaacttgag 660
tgcagaaggg gagagtggaa ttccatgtgt agcggtgaaa tgcgtagata tatggaggaa 720
caccggtggc gaaagcggct ctctggtctg taactgacgc tgaggctcga aagcgtgggg 780
agcgaacagg attagatacc ctggtagtcc acgccgtaaa cgatgagtgc taggtgttgg 840
atcctttccg ggattcagtg ccgcagctaa cgcattaagc actccgcctg gggagtacga 900
ccgcaaggtt gaaactcaaa ggaattgacg gggcccgca caagcggtgg agcatgtggt 960
ttaattcgaa gcaacgcgaa gaaccttacc aggtcttgac atcccgatgc tatttctaga 1020
gatagaaagt tacttcggta catcggtgac aggtggtgca tggttgtcgt cagctcgtgt 1080

-continued

```
cgtgagatgt tgggttaagt cccgcaacga gcgcaacccc tattgttagt tgccatcatt   1140

cagttgggca ctctagcgag actgccggta ataaaccgga ggaaggtggg gatgacgtca   1200

aatcatcatg ccccttatga cctgggctac acacgtgcta caatggttgg tacaacgagt   1260

tgcgagtcgg tgacggcgag ctaatctctt aaagccaatc tcagttcgga ttgtaggctg   1320

caactcgcct acatgaagtc ggaatcgcta gtaatcgcgg atcagcacgc cgcggtgaat   1380

acgttcccgg gccttgtaca caccgcccgt cacaccacga gagtttgtaa cacccgaagt   1440

cggtgaggta accttttgga gccagccgcc taaggtggga cagatgattg gggtgaagtc   1500

gtaacaaggt agccgtatcg gaaggtgcgg ctggatcac                          1539


<210> SEQ ID NO 49
<211> LENGTH: 1436
<212> TYPE: DNA
<213> ORGANISM: Pediococcus parvulus
<220> FEATURE:
<221> NAME/KEY: misc_feature
<222> LOCATION: (1345)..(1345)
<223> OTHER INFORMATION: n is a, c, g, or t

<400> SEQUENCE: 49

acatgcaagt cgaacgcact ttcgttgaat gaattagagg tgcttgcacc gaagatgatt     60

ttagctataa agtgagtggc gaacgggtga gtaacacgtg ggtaacctgc ccagaagtgg    120

gggataacac ctggaaacag atgctaatac cgcataacaa agtaaaccgc atggtttact    180

tttaaaagat ggcttcggct atcacttctg gatggacccg cggcgtatta gctagttggt    240

gagataaagg ctcaccaagg cagtgatacg tagccgacct gagagggtaa tcggccacat    300

tgggactgag acacggccca gactcctacg ggaggcagca gtagggaatc ttccacaatg    360

gacgaaagtc tgatggagca acgccgcgtg agtgatgaag gctttagggt cgtaaaactc    420

tgttgttgga gaagaacgtg tgtgagagta actgctcatg cagtgacggt atccaaccag    480

aaagccacgg ctaactacgt gccagcagcc gcggtaatac gtaggtggca agcgttatcc    540

ggatttattg ggcgtaaagc gagcgcaggc ggtcttttaa gtctaatgtg aaagccttcg    600

gcttaaccga agaagtgcat tggaaactgg aagacttgag tgcagaagag gacagtggaa    660

ctccatgtgt agcggtgaaa tgcgtagata tatggaagaa caccagtggc gaaggcggct    720

gtctggtctg taactgacgc tgaggctcga aagcatgggt agcgaacagg attagatacc    780

ctggtagtcc atgccgtaaa cgatgaatgc taagtgttgg agggtttccg cccttcagtg    840

ctgcagctaa cgcattaagc attccgcctg gggagtacga ccgcaaggtt gaaactcaaa    900

agaattgacg gggcccgca caagcggtgg agcatgtggt ttaattcgaa gctacgcgaa     960

gaaccttacc aggtcttgac atcttctgcc aatctaagag attagacgtt cccttcgggg   1020

acagaatgac aggtggtgca tggttgtcgt cagctcgtgt cgtgagatgt tgggttaagt   1080

cccgcaacga gcgcaaccct tattattagt tgccagcatt aagttgggca ctctagtgag   1140

actgccggtg acaaaccgga ggaaggtggg gacgacgtca aatcatcatg ccccttatga   1200

cctgggctac acacgtgcta caatggacgg tacaacgagt tgcgagaccg cgaggtttag   1260

ctaatctctt aaaaccgttc tcagttcgga ctgcaggctg caactcgcct gcacgaagtt   1320

ggaatcgcta gtaatcgcgg atcancatgc cgcggtgaat acgttcccgg gccttgtaca   1380

caccgcccgt cacaccatga gagtttgtaa cacccaaagc cggtggagta accttc       1436


<210> SEQ ID NO 50
<211> LENGTH: 1540
```

<212> TYPE: DNA
<213> ORGANISM: Pediococcus lolii

<400> SEQUENCE: 50
caagtcgaac gaacttccgt taattgatta tgacgtgctt gcactgaatg agattttaac 60
acgaagtgag tggcggacgg gtgagtaaca cgtgggtaac ctgcccagaa gcaggggata 120
acacctggaa acagatgcta ataccgtata acagagaaaa ccgcctggtt ttcttttaaa 180
agatggctct gctatcactt ctggatggac ccgcggcgca ttagctagtt ggtgaggtaa 240
cggctcacca aggcgatgat gcgtagccga cctgagaggg taatcggcca cattgggact 300
gagacacggc ccagactcct acgggaggca gcagtaggga atcttccaca atggacgcaa 360
gtctgatgga gcaacgccgc gtgagtgaag aagggtttcg gctcgtaaag ctctgttgtt 420
aaagaagaac gtgggtgaga gtaactgttc acccagtgac ggtatttaac cagaaagcca 480
cggctaacta cgtgccagca gccgcggtaa tagggtaggt ggcaagcgtt atccggattt 540
attgggcgta aagcgagcgc aggcggtctt ttaagtctaa tgtgaaagcc ttcggctcaa 600
ccgaagaagt gcattggaaa ctgggagact tgagtgcaga agaggacagt ggaactccat 660
gtgtagcggt gaaatgcgta gatatatgga agaacaccag tggcgaaggc ggctgtctgg 720
tctgtaactg acgctgaggc tcgaaagcat gggtagcgaa caggattaga taccctgtta 780
gtaccctgct gtcaacgata agagtgatta ctaagtgttg gagggtttcc gcccttcagt 840
gctgcagcta acgcattaag ttatccgcct ggggagtacg accgcaaggt tgaaactcaa 900
agaattgacg gggccgcac aagcgtggag catgtggtta attcgaagta cgcgaagaac 960
ttaccaggtc ttgacatctt tgccaaccta agagattagg cgttccttcg ggacagaat 1020 gacaggtggt gcatggttgt cgtcagctcg tgtcgtgaga tgttgggtta agtcccgcaa 1080
cgagcgcaac ccttattact agttgccagc attcagttgg gcactctagt gagactgccg 1140
gtgacaaacc ggaggaaggt ggggacgacg tcaaatcatc atgcccctta tgacctgggc 1200
tacacacgtg ctacaatgga tggtacaacg agtcgcgaaa ccgcgaggtt tagctaatct 1260
cttaaaacca ttctcagttc ggactgtagg ctgcaactcg cctacacgaa gtcggaatcg 1320
ctagtaatcg cggatcagca tgccgcggtg aatacgttcc cgggccttgt acacaccgcc 1380
cgtcacacca tgagagtttg taacacccaa agccggtggg gtaacctttt aggagctagc 1440
cgtctaaggt gggacagatg attagggtga agtcgtaaca aggtagccgt aggagaacct 1500
gcggctggat cacctccttt ctaaggaata atacggaacc 1540

<210> SEQ ID NO 51
<211> LENGTH: 1540
<212> TYPE: DNA
<213> ORGANISM: Pediococcus acidilactici

<400> SEQUENCE: 51
caagtcgaac gaacttccgt taattgatta tgacgtgctt gcactgaatg agattttaac 60
acgaagtgag tggcggacgg gtgagtaaca cgtgggtaac ctgcccagaa gcaggggata 120
acacctggaa acagatgcta ataccgtata acagagaaaa ccgcctggtt ttcttttaaa 180
agatggctct gctatcactt ctggatggac ccgcggcgca ttagctagtt ggtgaggtaa 240
cggctcacca aggcgatgat gcgtagccga cctgagaggg taatcggcca cattgggact 300
gagacacggc ccagactcct acgggaggca gcagtaggga atcttccaca atggacgcaa 360
gtctgatgga gcaacgccgc gtgagtgaag aagggtttcg gctcgtaaag ctctgttgtt 420

-continued

```
aaagaagaac gtgggtgaga gtaactgttc acccagtgac ggtatttaac cagaaagcca    480
cggctaacta cgtgccagca gccgcggtaa tagggtaggt ggcaagcgtt atccggattt    540
attgggcgta aagcgagcgc aggcggtctt ttaagtctaa tgtgaaagcc ttcggctcaa    600
ccgaagaagt gcattggaaa ctgggagact tgagtgcaga agaggacagt ggaactccat    660
gtgtagcggt gaaatgcgta gatatatgga agaacaccag tggcgaaggc ggctgtctgg    720
tctgtaactg acgctgaggc tcgaaagcat gggtagcgaa caggattaga taccctgtta    780
gtaccctgct gtcaacgata agagtgatta ctaagtgttg gagggtttcc gcccttcagt    840
gctgcagcta acgcattaag ttatccgcct ggggagtacg accgcaaggt tgaaactcaa    900
agaattgacg gggccgcac aagcgtggag catgtggtta attcgaagta cgcgaagaac     960
ttaccaggtc ttgacatctt tgccaaccta agagattagg cgttccttcg ggacagaat    1020
gacaggtggt gcatggttgt cgtcagctcg tgtcgtgaga tgttgggtta agtcccgcaa   1080
cgagcgcaac ccttattact agttgccagc attcagttgg gcactctagt gagactgccg   1140
gtgacaaacc ggaggaaggt ggggacgacg tcaaatcatc atgcccctta tgacctgggc   1200
tacacacgtg ctacaatgga tggtacaacg agtcgcgaaa ccgcgaggtt tagctaatct   1260
cttaaaacca ttctcagttc ggactgtagg ctgcaactcg cctacacgaa gtcggaatcg   1320
ctagtaatcg cggatcagca tgccgcggtg aatacgttcc cgggccttgt acacaccgcc   1380
cgtcacacca tgagagtttg taacacccaa agccggtggg gtaacctttt aggagctagc   1440
cgtctaaggt gggacagatg attagggtga agtcgtaaca aggtagccgt aggagaacct   1500
gcggctggat cacctccttt ctaaggaata atacggaacc                         1540


<210> SEQ ID NO 52
<211> LENGTH: 1492
<212> TYPE: DNA
<213> ORGANISM: Pediococcus argentinicus

<400> SEQUENCE: 52

gatgaacgct ggcggcgtgc ctaatacatg caagtcgaac gcacttccgt cgaatgattt     60
caaggtgctt gcaccgcgaa tgaaaatgac atgaagtgag tggcgaacgg gtgagtaaca    120
cgtgggtaac ctgcccagaa gtaggggata acacctggaa acagatgcta ataccgtata    180
atagagaaaa ccgcatggtt ttcttttgaa agatggctct gctatcactt ctggatggac    240
ccgcggcgta ttagctagtt ggtgaggtaa ckgctcacca aggcagtgat acgtagccga    300
cctgagaggg taatcggcca cattgggact gagacacggc ccagactcct acgggaggca    360
gcagtaggga atcttccaca atggacgaaa gtctgatgga gcaacgccgc gtgagtgaag    420
aagggtttcg gctcgtaaag ctctgttgtt aaagaagaac gtgggtaaga gtaactgttt    480
acccagtgac ggtatttaac cagaaagcca cggctaacta cgtgccagca gccgcggtaa    540
tacgtaggtg gcaagcgtta tccggattta ttgggcgtaa agcgagcgca ggcggtttct    600
taagtctaat gtgaaagcct tcggctcaac cgaagaagtg cattggaaac tgggaaactt    660
gagtgcagaa gaggatagtg gaactccatg tgtagcggtg aaatgcgtag atatatggaa    720
gaacaccagt ggcgaaggcg gctatctggt ctgcaactga cgctgaggct cgaaagcatg    780
ggtagcgaac aggattagat accctggtag tccatgccgt aaacgatgaa tgctaagtgt    840
tggagggttt ccgcccttca gtgctgcagc taacgcatta agcattccgc ctggggagta    900
cgaccgcaag gttgaaactc aaaagaattg acgggggccc gcacaagcgg tggagcatgt    960
ggtttaattc gaagctacgc gaagaacctt accaggtctt gacatcttct gccaatctaa   1020
```

```
gagattagac gttcccttcg gggacagaat gacaggtggt gcatggttgt cgtcagctcg   1080
tgtcgtgaga tgttgggtta agtcccgcaa cgagcgcaac ccttattact agttgccagc   1140
atttagttgg gcactctagt gagactgccg gtgacaaacc ggaggaaggt ggggacgacg   1200
tcaaatcatc atgcccctta tgacctgggc tacacacgtg ctacaatgga tggtacaacg   1260
agttgcgaga ccgcgaggtt tagctaatct cttaaaacca ttctcagttc ggattgtagg   1320
ctgcaactcg cctacatgaa gtcggaatcg ctagtaatcg cggatcagca tgccgcggtg   1380
aatacgttcc cgggccttgt acacaccgcc cgtcacacca tgagagtttg taacacccaa   1440
agccggtggg gtaacctttt aggagctagc cgtctaaggt gggacagatg at           1492
```

<210> SEQ ID NO 53
<211> LENGTH: 1472
<212> TYPE: DNA
<213> ORGANISM: Pediococcus claussenii

<400> SEQUENCE: 53

```
tgcaagtcga acgcatttcc gttaatagaa tcagaagtgc ttgcacggat agatgatttt     60
aacaatgaaa tgagtggcga acgggtgagt aacacgtggg taacctgccc agaagagggg    120
gataacactt ggaaacaggt gctaataccg cataataaag aaaaccgcat ggttttcctt    180
taaaagatgg tttcggctat cacttctgga tggacccgcg gcgtattagc tagttggtaa    240
ggtaaaggct taccaaggca gtgatacgta cccgacctga gagggtaatc ggccacattg    300
ggactgacac acggcccata ctcctacggg aggcagcaat agggaatctt ccacagtgga    360
cgaaagtctg atggagcaac gccgcgtgag tgaagaaggg tttcggctcg taaaactctg    420
ttgttaaaga agaacgtggg tgagagtaac tgttcaccca gtgacggtat ttaaccagaa    480
agccacggct aactacgtgc cagcagccgc ggtaatacgt aggtggcaag cgttatccgg    540
atttattggg cgtaaagcga gcgcaggcgg tcttttaagt ctaatgtgaa agccttcggc    600
tcaaccgaag aagtgcattg gaaactggga gacttgagtg cagaagagga cagtggaact    660
ccatgtgtag cggtgaaatg cgtagatata tggaagaaca ccagtggcga aggcggctgt    720
ctggtctgta actgacgctg aggctcgaaa gcatgggtag cgaacaggat tagataccct    780
ggtagtccat gccgtaaacg atgaatacta agtgttggag ggtttccgcc cttcagtgct    840
gcagctaacg cattaagtat tccgcctggg gagtacgacc gcaaggttga aactcaaaag    900
aattgacggg ggcccgcaca agcggtggag catgtggttt aattcgaagc tacgcgaaga    960
accttaccag gtcttgacat cttctgacat tctaagagat tagaagttcc cttcggggac   1020
agaatgacag gtggtgcatg gttgtcgtca gctcgtgtcg tgagatgttg ggttaagtcc   1080
cgcaacgagc gcaaccctta ttactagttg ccagcattaa gttgggcact ctagtgagac   1140
tgccggtgac aaaccggagg aaggtgggga cgacgtcaaa tcatcatgcc ccttatgacc   1200
tgggctacac acgtgctaca atggatggta caacgagtcg cgaaaccgcg aggtttagct   1260
aatctcttaa agccattctc agttcggact gtaggctgca actcgcctac acgaagtcgg   1320
aatcgctagt aatcgcggat cagcatgccg cggtgaatac gttcccgggc cttgtacaca   1380
ccgcccgtca caccatgaga gtttgtaaca cccaaagccg gtggggtaac cttttaggag   1440
ctagccgtct aaggtgggac agatgattag gg                                 1472
```

<210> SEQ ID NO 54
<211> LENGTH: 1569
<212> TYPE: DNA

<213> ORGANISM: Pediococcus pentosaceus
<220> FEATURE:
<221> NAME/KEY: misc_feature
<222> LOCATION: (120)..(120)
<223> OTHER INFORMATION: n is a, c, g, or t

<400> SEQUENCE: 54
agagtttgat catggctcag gatgaacgct ggcggcgtgc ctaatacatg caagtcgaac 60
gaacttccgt taattgatta tgacgtactt gtactgattg agattttaac acgaagtagn 120
tggcgaacgg gtgagtaaca cgtgggtaac ctgcccagaa gtaggggata acacctggaa 180
acagatgcta ataccgtata acagagaaaa ccgcatggtt ttcttttaaa agatggctct 240
gctatcactt ctggatggac ccgcggcgta ttagctagtt ggtgaggtaa aggcccacca 300
aggcagtgat acgtagccga cctgagaggg taatcggcca cattgggact gagacacggc 360
ccagactcct acgggaggca gcagtaggga atcttccaca atggacgcaa gtctgatgga 420
gcaacgccgc gtgagtgaag aagggtttcg gctcgtaaag ctctgttgtt aaagaagaac 480
gtgggtaaga gtaactgttt acccagtgac ggtatttaac cagaaagcca cggctaacta 540
cgtgccagca gccgcggtaa tacgtaggtg gcaagcgtta tccggattta ttgggcgtaa 600
agcgagcgca ggcggtcttt taagtctaat gtgaaagcct tcggctcaac cgaagaagtg 660
cattggaaac tgggagactt gagtgcagaa gaggacagtg gaactccatg tgtagcggtg 720
aaatgcgtag atatatggaa gaacaccagt ggcgaaggcg gctgtctggt ctgcaactga 780
cgctgaggct cgaaagcatg ggtagcgaac aggattagat accctggtag tccatgccgt 840
aaacgatgat tactaagtgt tggagggttt ccgcccttca gtgctgcagc taacgcatta 900
agtaatccgc ctggggagta cgaccgcaag gttgaaactc aaaagaattg acgggggccc 960
gcacaagcgg tggagcatgt ggtttaattc gaagctacgc gaagaacctt accaggtctt 1020
gacatcttct gacagtctaa gagattagag gttcccttcg ggacagaat gacaggtggt 1080 gcatggttgt cgtcagctcg tgtcgtgaga tgttgggtta agtcccgcaa cgagcgcaac 1140
ccttattact agttgccagc attaagttgg gcactctagt gagactgccg gtgacaaacc 1200
ggaggaaggt ggggacgacg tcaaatcatc atgcccctta tgacctgggc tacacacgtg 1260
ctacaatgga tggtacaacg agtcgcgaga ccgcgaggtt aagctaatct cttaaaacca 1320
ttctcagttc ggactgtagg ctgcaactcg cctacacgaa gtcggaatcg ctagtaatcg 1380
cggatcagca tgccgcggtg aatacgttcc cgggccttgt acacaccgcc cgtcacacca 1440
tgagagtttg taacacccaa agccggtggg gtaacctttt aggagctagc cgtctaaggt 1500
gggacagatg attagggtga agtcgtaaca aggtagccgt aggagaacct gcggctggat 1560
cacctcctt 1569

<210> SEQ ID NO 55
<211> LENGTH: 1529
<212> TYPE: DNA
<213> ORGANISM: Pediococcus stilesii

<400> SEQUENCE: 55
gatgaacgct ggcggcgtgc ctaatacatg caagtcgaac gaacttccgt taattgatta 60
agcggtactt gtaccaattg agattttaac acgaagtgag tggcgaacgg gtgagtaaca 120
cgtgggtaay ctgcccagaa gtaggggata acacctggaa acagatgcta ataccgtata 180
atagagaaaa ccgcatggtt ttcttttgaa agatggctct gctatcactt ctggatggac 240
ccgcggcgca ttagctagtt ggtaaggtaa aggcttacca aggcagtgat gcgtagccga 300
cctgagaggg taatcggcca cattgggact gagacacggc ccagactcct acgggaggca 360
gcagtaggga atcttccaca atggacgcaa gtctgatgga gcaacgccgc gtgagtgaag 420
aagggtttcg gctcgtaaag ctctgttgtt aaagaagaac gtgggtgaga gtaactgttc 480
acccagtgac ggtatttaac cagaaagcca cggctaacta cgtgccagca gccgcggtaa 540
tacgtaggtg gcaagcgtta tccggattta ttgggcgtaa agcgagcgca ggcggtcttt 600
taagtctaat gtgaaagcct tcggctcaac cgaagaagtg cattggaaac tgggagactt 660
gagtgcagaa gaggacagtg gaactccatg tgtagcggtg aaatgcgtag atatatggaa 720
gaacaccagt ggcgaaggcg gctgtctggt ctgcaactga cgctgaggct cgaaagcatg 780
ggtagcgaac aggattagat accctggtag tccatgccgt aaacgatgaa tgctaagtgt 840
tggagggttt ccgcccttca gtgctgcagc taacgcatta agcattccgc ctggggagta 900
cgaccgcaag gttgaaactc aaaagaattg acgggggccc gcacaagcgg tggagcatgt 960
ggtttaattc gaagctacgc gaagaacctt accaggtctt gacatcttct gacagtctaa 1020
gagattagag gttcccttcg ggacagaat gacaggtggt gcatggttgt cgtcagctcg 1080
tgtcgtgaga tgttgggtta agtcccgcaa cgagcgcaac ccttattact agttgccagc 1140
atttagttgg gcactctagt gagactgccg gtgacaaacc ggaggaaggt ggggacgacg 1200
tcaaatcatc atgcccctta tgacctgggc tacacacgtg ctacaatgga tgatacaacg 1260
agtcgcgaaa ccgcgaggtt tagctaatct cttaaaatca ttctcagttc ggactgtagg 1320
ctgcaactcg ccyacacgaa gtcggaatcg ctagtaatcg cggatcagca tgccgcggtg 1380
aatacgttcc cgggccttgt acacaccgcc cgtcacacca tgagagtttg taacacccaa 1440
agccggtggg gtaacctttt aggagctagc cgtctaaggt gggacagatg attagggtga 1500
agtcgtaaca aggtagccgt aagaaaacc 1529

<210> SEQ ID NO 56
<211> LENGTH: 20
<212> TYPE: DNA
<213> ORGANISM: Bifidobacterium longum subsp. infantis

<400> SEQUENCE: 56
atacagcaga accttggcct 20

<210> SEQ ID NO 57
<211> LENGTH: 20
<212> TYPE: DNA
<213> ORGANISM: Bifidobacterium longum subsp. infantis

<400> SEQUENCE: 57
gcgatcacat ggacgagaac 20

<210> SEQ ID NO 58
<211> LENGTH: 27
<212> TYPE: DNA
<213> ORGANISM: Bifidobacterium longum subsp. infantis
<220> FEATURE:
<221> NAME/KEY: misc_feature
<222> LOCATION: (1)..(1)
<223> OTHER INFORMATION: FAM dye
<220> FEATURE:
<221> NAME/KEY: misc_feature
<222> LOCATION: (10)..(10)
<223> OTHER INFORMATION: n = ZEN quencher
<220> FEATURE:
<221> NAME/KEY: misc_feature
<222> LOCATION: (11)..(11)

<223> OTHER INFORMATION: n is a, c, g, or t
<220> FEATURE:
<221> NAME/KEY: misc_feature
<222> LOCATION: (25)..(25)
<223> OTHER INFORMATION: n = IABkFQ quencher
<220> FEATURE:
<221> NAME/KEY: misc_feature
<222> LOCATION: (27)..(27)
<223> OTHER INFORMATION: n is a, c, g, or t

<400> SEQUENCE: 58
ntttcacgga ntcaccggac catacgn 27

<210> SEQ ID NO 59
<211> LENGTH: 1113
<212> TYPE: DNA
<213> ORGANISM: Bifidobacterium longum subsp. infantis

<400> SEQUENCE: 59
gtgataattg gaaaacgtct cggtgaagat cggttcaaat tttacaaaac cgtccttgcc 60
ggaaatacag atcagctgct attcgacgag gaatttaatg catggtttgt gttcaatgtg 120
cgtaaccttc atactttgat aagagatgag cggctcaaag ccaacactaa aactgtcata 180
gataaactcc ctctgaagat agaaactata cggacattaa agaattttta ttccaactgg 240
gttatgttca ccgacggaga gtctcataaa cagcttcgtc gcctagtggg aacaatcatt 300
aatactcgtt atcacgccat aaattacaca tggccgcaaa tcaataaaaa ttgtgacttc 360
actacagagt atgcaaggcc ttatgtgtac ggtatccttg ctcaactggt gggtgtctct 420
gtagaagaca tttcaagaat ggtctcggca tcggaaacca ttaactcgtt cttactgcgc 480
gaacggctta cgctagacga tatcgaacaa gtcgcgcatt caatcgaata cgcgtatcag 540
gttgtcaaag aaatcgaaga taagcatgta ggggagccgc tgtacatagg caacgaattg 600
cttgacttgc ctcaggagac acgatatccc ctcatcatta atctagtaac cgatggtttt 660
gccccattcg tagctgcgct tgatttcctg gcgttcaatc tgttgactca cccatattta 720
gaggaagagc tcaatgcaaa agcagggcaa atatcccttg aaagtcttcg gttgttccct 780
ccattcacga caataagcag gacatgcgtg catgaaatac cttttaagga aaaaattatt 840
agaccaaggc agttggtaat ttttgattta tacagcatta atcgcgaccc ggaagttttt 900
cccgatccgg aaaaatttaa ccttgagaac actgcaagag catactcctt tggggctgcg 960
cagcatctat gctccggaaa cccgctggtg agaaaagccc tggaacaagt aacgcgccaa 1020
agcgaatcac tatataaata caagatacag tcttattgct tcaaaaattc atacggtttt 1080
accgacatga atttgtctat tgaattaaaa taa 1113

<210> SEQ ID NO 60
<211> LENGTH: 333
<212> TYPE: DNA
<213> ORGANISM: Bifidobacterium longum subsp. infantis

<400> SEQUENCE: 60
atggaaccca tcaaagactg gctgaccggc ctcgaccgag aatccaaact gcagatcctc 60
gccgccgtcg aagtcctgaa agaacaagga cccaacctca gacgaccact ggtaggcaaa 120
atcgaaggct ccaaaatcaa atcgatgaag gaactccgac ccggctccgc aggcaaaagc 180
gaaatacgaa tactgttcgt gttcgacccg aaccggcagg cgataatgct cgtcggcgga 240
gacaagcaaa acaaatggtc gaaatggtac aaaacggcca taccggaagc ggaagaccgg 300
tatgaggcgt ggcttaaaca gaacaacaaa tga 333

<210> SEQ ID NO 61
<211> LENGTH: 1101
<212> TYPE: DNA
<213> ORGANISM: Bifidobacterium longum subsp. infantis

<400> SEQUENCE: 61
atggacgatg cgcagtacat gggactcgcg atcgagctgg cgaagcgagg ggccggatac 60
gtgaacccca atcccatggt cggcgcggtg atcgtcaagg acgatcggat catcgggcag 120
gggtatcacg agatgttcgg cggattgcac gccgagagga acgcgttgcg gcattgcacg 180
cagtcacccg ccggggcgac gttgtacgtc acgcttgagc cgtgctgcca ttacggcaaa 240
acgccgccat gcacggaggc gatcgtggaa agcggcatcg caagggtcgt cgtcggaacc 300
ttggactgca atcccgtggt gtccggcaag ggcgtgcgca tgctcgaaga ccacggcata 360
cgggtcgatg tgggggtgct ggccgacgag tgccggcatc tgatacgggt gttcagcaaa 420
tacatcacca cgcatacgcc gtatgtcatc atgaaatacg ccatgacgat ggacgggaag 480
atagcgaccc ataccaatca atcacggtgg atcagcggcg aggagtcgag gcgtcgggtc 540
catcagctcc gtcgatccgt cgcggcggtc atggtggggg tgaacacggt gatcgaggac 600
gacccgttgc tgacatgccg catggcacac ggaaggaacc cggttcgcgt cgtctgcgat 660
acgcgattga ggacgcccct cacctcgcgg atcgtgcaga cggcgaatga cgtcaggacc 720
tatatcgcca ccgcctgcga tgacgaacgc aaggcggagg actaccggcg gcacggctgc 780
gaaatactcg ccgtcggaag gaagggcgac cacgtcgatc tggcggacgt ggtgcggcgc 840
ctgggggata tgcagatgga cagcgtgctg ctggaaggcg ggagcgcgat gaattggagc 900
gccctcgaac agcggatcgt cgatgaggcg cacgtgtaca tcgcgccgaa gatattcggc 960
ggcaccgcga aaagcccggt gggcggccaa ggggtcgccc tgccttccga cgccgtcatg 1020
ctccggcccc gcgcctgctc ccgagtggga gaggattatc tggtggaaag cgaggtggtg 1080
tattcatgtt cacgggaata g 1101

<210> SEQ ID NO 62
<211> LENGTH: 1638
<212> TYPE: DNA
<213> ORGANISM: Bifidobacterium longum subsp. infantis

<400> SEQUENCE: 62
atgactttca tcaaacagat gatgccgcgt tatgtggcgt ctatgaccgc aggcatcgta 60
gcggcagcga tggccgcaac atgcgcgttt gcaccggtag cgaatgcgga cgccgtttct 120
ccgacacagg aaaccataca atcgaccggt cgccatttca tggtgtacta ccgcgcgtgg 180
cgtgatgtca cgatgaaggg tgtcaacacc gaccttccag acgataactg gatttcgatg 240
tacgatattc cgtacggcgt cgacgtggtc aatatattca gctatgttcc atcgggacag 300
gaagaacagg cgcaaccgtt ctacgataag ctcaaatctg attatgcacc gtacttgcat 360
tcgcgtggca tcaagctggt tcggggcatt gattacaccg gcgtggcggt caatggtttt 420
cgtactttca tgaaagagca gaacaaaacc gagagcgagg cgaccgaagc tgattatgat 480
gcctatgcta agcaagtaat cgataaatac atgatctccg ttggcttgga tggtctggat 540
atcgacatgg aggcgcaccc gaatgatgcc gatgtgaaga tctccgacaa tgtgattcgt 600
gcactgtcca aacacatcgg tcccaaatcc gccaagccgg ataccacgat gttcctttat 660
gacacgaatg gatcttatct caatccgttc aagaatgtgg cggaatgctt tgactacgtg 720

-continued gcataccagc agtacggttc ttcctccgat cgcaccgcta gggccgccgc cgattatcag 780
ccttatatcg gcaacgagtt tgtgccgggc ctgacgttcc ccgaagaagg ggacatgaac 840
aatcgctggt atgatgccac cgagccgtat gaagaaagcc atttctatca agtggcgtca 900
tatgtgcgtg agcataatct tggcggcatg ttcgtttacg cgctcgaccg agacggtcgc 960
aactatgatg aagacctgcg tcggattgta ccgtccaact tgctgtggac caagaccgcc 1020
attgcggaga gcgagggcat ggcgttggat acggcaaaga ctgcagcgaa ccattacctt 1080
gatcgcatgt cgttgcgtca ggtgattgac gacaacgccg catccgcgga taaggcgcgg 1140
gatatggtgg ggaaggccgc taacctatac gagacaaata aagcagtcct tggtggtgac 1200
tacggagaag gtttctccaa cacatatgat ccgacattgg aagctggatt attagggatt 1260
gacatctccg tgttgcaaca gcagattgat aaatccagtg agatcattgg tgccgatacg 1320
gcggaatcgg atgcaaaaac tgcactccgt atggcacgtg atgccgccat cgatggtttg 1380
accggcaaga tctacacagc ggaccaagta tcagcgtggt cgcaggcatt gaaggcggcg 1440
cttgatgcca ccgtgccggt tccgacgcca gattccaccg atcagaatgg caaccgtgac 1500
aaggttacca atcacaaagt gcaaggccaa ccgaagcaac tgagtgcgac cggcatctcg 1560
acggatatta tcgttgccgt aggcgtgact cttgccatcg caggggtggc tctgtctcta 1620
tcacgtaagc tctcctga 1638

<210> SEQ ID NO 63
<211> LENGTH: 876
<212> TYPE: DNA
<213> ORGANISM: Bifidobacterium longum subsp. infantis

<400> SEQUENCE: 63
atgcagtacg ttaagggcac caatcaggaa ctattgacca catcaccgca gttccctgcc 60
ctggtcatcg cacatcaggg attcgacaaa gccaggttgc attggcatga aggcttcgag 120
gtggtatacg tccgacgctg tcgggccaca gtgatgaaag gcacccaacg ttcgatgcat 180
catgccggtg atgtagtact gattcctcca cgctgcctgc atagcatcga acttattcag 240
gatcttcggc aaccatcagc tgtaccgcag gcgctttccg taacgatctc gcccacggag 300
ttgctaccgt catatccgta tattacccaa atccaacaac agctggatta cgactacatt 360
ggcgaaaaag atcatcaaca attgctgaaa tgctgcgaac aaatgtttgc ggcactgatc 420
agtggcaagc agacacggtt ccttgaagcg aattcctggt tctacaccat gcttaccaat 480
gtttttgact acgccaaacc attggctgca gcgaaccaag aagacaccga ggatgaaacc 540
atactccagg atggacgagt cattagacga atacgccact acgtgcaacg tcattatcgc 600
gagcccctat ccaccgcaca ggtgtcgcag aaattcggat attcacgaga gcatttttca 660
aggatattca gcaaatattc tggagtgaca tttaaagact acgtaacgcg tgtacgtctg 720
ctggcggcct gcgatttgct caccaacacg gatatgccaa tcaatcaaat cgtccgggaa 780
tccggattcc ccagttctca aaccatgcga ggatcgtttg accgcgaatt cgcatgcacg 840
cccagcgaat atcgctctcg ttcgatggaa gaataa 876

<210> SEQ ID NO 64
<211> LENGTH: 696
<212> TYPE: DNA
<213> ORGANISM: Bifidobacterium longum subsp. infantis

<400> SEQUENCE: 64
atgaatacta acgatactta ttcgaaacgt cttattgatt cgctccacgg cacactgata 60
gtcagctgtc aagcatatcc cggcgagcca atgcggcatc ccgaaaccat ggcccaagtc 120
gctcaatcag tagtaatcgg cggcgctgcc gccattcgat gccaaggtct tgccgatatc 180
agcgccatca aaggccaagt aaaagttcca gtcatcggca tatggaagga aggcgataac 240
ggcgtataca tcacgccaac gttacgccac gccagagcct gcattatggc gggagccgac 300
attgtggcac tcgatgctac agatcggcct cggccagacg gtctaactct gcagcagacc 360
gcgcggcaac tcaaaagcga gggcgcaata ctgatggccg actgcggctg catcgaagac 420
tccgatgcag ccgtggatgc aggattcgac atcatctcca ccacgctggc tggatacacc 480
gattcccgcg ccaaaacaga aggaccggat tacgagctcc tcgctcaaat gctggagcgg 540
cacccccacg taccggtgat atgcgagggt aggatacata ctccgtccga tgcggccaaa 600
gccatagaaa tgggtgcctg ggcagccgta gtcggtaccg ccatcaccca ccccatgacg 660
ataacgtcat ggttcgccga tgcagtaagg tcctga 696

<210> SEQ ID NO 65
<211> LENGTH: 1020
<212> TYPE: DNA
<213> ORGANISM: Bifidobacterium longum subsp. infantis

<400> SEQUENCE: 65
atgagttttg caagcataat ccatcagcat acggtgatat ccgtggacat cggcggcacc 60
aaaatcgccg ctggtctcat gtgcgtagac ctcgacgaac aaggaagacc gcgggacatg 120
ccagcgttga ttcgacggta cgtcataccg acgaaagcac gtctcggcgg cacctccgta 180
ttgcaacgcg tcgttcaagc cattcgccag tgtctggacg atggtgagat tcctttccca 240
ctattgggga tcggtgtagc gagcgcagga gtcattgacg gcaacggttc ggtggtatca 300
gccacttcgt tgattcccgg ttgggccggt attcaactgc aagccgaatt atcggcaacg 360
ttcaacgtgc ctgccatcgt catcggagat gttcaggcac acgcccttgg tgaagcgcac 420
tggggatgcg gacgacaata ccaatcacta ctggtcgccg ccatcggcac cggtatcgga 480
ggcgcgataa tcatcgacgg gaaactggta cgcggcgtcc acggagcctg tggccatatc 540
ggccatctgc cgcatcccga cgccattggt atatcctgct catgtggatg tgagggccat 600
gtggagtcaa tcgcctcagg taccggcatt gccgataatt atcgacgtgc tctgcaacag 660
aacggacaca atactctccc caccgacatc aatggacgcg ctatcgccga actggccagt 720
caaggtagta cggaagccgt aaccagtatc actctggccg gcacgagtct cggcgatgtt 780
cttggcggac taatcaatgc ccttgatccc gatgccgtga tcctttccgg ctccgtagtc 840
cattctggag agctatggat gaaatctgtg aaacaaggca tccaaagaca gaccttgggc 900
attctttccc gaacaccggt tttgacagga acactcggcg gcagagcccc tctcatcgga 960
gcaacatcag ctctgtgcgc cgacctcaga tcaaataagg agcagaaata tgaatactaa 1020

<210> SEQ ID NO 66
<211> LENGTH: 948
<212> TYPE: DNA
<213> ORGANISM: Bifidobacterium longum subsp. infantis

<400> SEQUENCE: 66
atggaagaga ggcgcgagaa gtcgattgcg gtgactgccc tgaatgaggg cgggggaggg 60
aaatctcatc gctcaggtcg atattccgcc gagcggcagc cccatgcgtg gctgttgctg 120
ttcccggcct tggcgctgat caccgtgttc aatctgcttc cctggtgcg tatcttcatc 180

-continued atgtcgctgc agggcgggac gttgacccgt caacggtttg tgggaatgcg taattttgtt 240
ttcgtgttcg cggatcccga attccgcaag gccatcgcca atacggcgct gttcgcattc 300
gtcgtggtgt cggtcgggct ggtgctgtcg atggcggtgg ccgtggccat caatggaaag 360
cttcgcggag gcagggtctt cgaaatcctg ttcttcatcc cctatctgac ctcggtgatc 420
gccatcggca tggtgttccg gtatctgttc aacggcgatt acggtcttgt caattacgtg 480
ttgggtctgt gcggccttgg accctatgat tttctcaacg atccgaagtt caatatgccc 540
acgctcatca tcttcggcat atggtcgtcc ctggcgttca acatcatcat tctgttgtcg 600
ggcctgcgcg gcatagacaa ggaatattac aaggtggccg acatgttcgg cgccacggcc 660
tgggagaagt tccgccggat cacgttgccg cagatggtgc cgattctgac gttcctgtcc 720
atcgtggatt tcatcaattc cttcaaggtg tatacggagg tgtacgcctt gttcaacggg 780
aaggccggta tcggcgatag cgccacgacg gcggtgttct acgtgttcaa caagttctac 840
gtggacaaca agtatgggca gggcatggcc gcggcggtgg tgctgttcct ggtgattctg 900
gctttcacca tcatccaagg catcgtattg aggaggctgg cgaagtga 948

<210> SEQ ID NO 67
<211> LENGTH: 1185
<212> TYPE: DNA
<213> ORGANISM: Bifidobacterium longum subsp. infantis

<400> SEQUENCE: 67
atgacggaga acgggatgat gaatacgaac aatactgtgt gcggcgcgaa ccatgacgga 60
gcgatgagtc tggcggcccc aggcgattac ggtgtggcct gctaccggat tccggccctt 120
gccgaggcgc ccaacggctg gatcctcgcg gcgttcgacg cgcggcccca taactgccag 180
gatgccccgc aagccaattc gatcgtgcag cgtatctcca aagacggcgg ccggtcattc 240
gagccgcagc atgttgtggc cgccgggcat gatggcgtcg acaaatacgg gtattccgat 300
ccgtcctatg tggtggaccg gcagacggga gaggtgttcc tgttcttcgt caaatcctat 360
gacgccggtt tcggaacctc ccaggcgggc gtcgatccct ctgcgcgtga ggtgcttcaa 420
gccgccgtca ccagttccat cgacaatggc gtgacgtgga gcgagccgcg catcatcacc 480
gccgacatca cgaacagcga atcatggatt tcacggttcg cttcttccgg tgccggcatc 540
cagctcacgt atggcgagca tgcggggcgc ctgatccagc agtacaccat caaggagctc 600
gacggccgct accgtgcggt atcggtcttc tccgacgatc acggtgcaac ctggcatgca 660
ggcacccccg tcggcgatca catggacgag aacaaagtcg tggaactttc cgatggccgt 720
gtgatgctga actcgcgttc ctccgatgga aacggttgcc gctatgtcgc catctcccgg 780
gacggtggcg ccacgtatgg tccggtgatc cgtgaaacgc agctgcccga tcccgagaac 840
aacgcgcaga ttgcccgtgc gttccccgat gcccccgagg ggtcggcgca ggccaaggtt 900
ctgctgtatt cctcctcgtc gccttcggac aggatcgatg gtctggtgcg cgtctcgatc 960
gatgacggca agacctggag tgccggccga cggttcacga cagggccgat ggcgtattcg 1020
gtgatcgccg cattgagcca caaggccggc ggcggctatg gcctgctgta tgaaggtgat 1080
aataataaca ttatgtacac ccgtatctcg ctcgactggc tcaacggcca gctgaacgtc 1140
gacggaatcg gcggttttcc gctgtctggt gagggagggt gctga 1185

<210> SEQ ID NO 68
<211> LENGTH: 438
<212> TYPE: DNA
<213> ORGANISM: Bifidobacterium longum subsp. infantis

<400> SEQUENCE: 68
atgctgaagg gaataccgcc gatcatacag cccgatctgc tgaagatact cagcgagatg 60
ggccacggcg atgccatagt ccttgcggac gcccactttc ccgccgaatc ggtgggcgtc 120
cgatcccacg tgatcaggta tgacggccag cccatcgagc cgctgctcga cgcggtgctg 180
cagctgatac cgctggacca atacacggaa cacccggtgc tgctgatgga caaggttccc 240
ggagacaccg tggacacccc gatatgggac cggtaccgtc aggtcatcga caggcacgag 300
cccggcaagc aagcgggcat cgggatgctg gaacggttcg ccttctacga ggaggccggc 360
aggtcctatt gcatcgtcgc caccggcgaa caatcgcagt atgcgaacat catcatcaga 420
aaaggcgtca ttcgctaa 438

<210> SEQ ID NO 69
<211> LENGTH: 705
<212> TYPE: DNA
<213> ORGANISM: Bifidobacterium longum subsp. infantis

<400> SEQUENCE: 69
atgtccgtac gaaaaacgtc tatcatgtgc actatgggga acccaaatga aatcagactg 60
gcgatagtcg ataacgacga cttcgtgctg atgggtttgg cagcgttctt gtcgcgtcat 120
ctgccgaatg ttcggttagc ttggaaggcg aataccggaa ccgatgctct ggaatatgcg 180
acggatcccg caaatgaagc ggacattctg ctggttgaca tgagtctgga ggacatgccc 240
ggagacatgg tgtgccggga aatcagaagt cgtaacagga tgttgccgtt gctggcggtg 300
acatcgttca gtttaactcg ctatgcgcga cgtgctgctg agggtggtgc tcaaggcatt 360
gtgtcaaaag ctgattttcc agtactgtgt aaagcggtca agctcgtcag cgatggtcat 420
actctctgtg ttcgagtagg aggggagact attggattcg aggatgtaga tgctgcatat 480
catcgtctgg ttcgacttcc cgtgaataga atcgaaagat tgtcggaacg ggaaaaatat 540
gccatggaac tatattcaca gtcgtataag cccactcaga ttgcccggat gatggatgtt 600
tcggcaggga cggtgaaaac ctatcttgac cgtgctcaga acaaactcca tcttacttcc 660
agagccgaac tgattgccta ttggtggagg cgggaacgat gctga 705

<210> SEQ ID NO 70
<211> LENGTH: 1722
<212> TYPE: DNA
<213> ORGANISM: Bifidobacterium longum subsp. infantis

<400> SEQUENCE: 70
atgagaacca tcaccagaag cgactatgcg ggcatgttcg ggccgaccac cggcgatcgg 60
gtgcgcttgg gggatacggg tctgctgatc gaggtcgaga aggattacgc gcgttatggc 120
gatgaattga aattcggcgg cggaaaatcc ttccgggacg gcatggggca gtcatccgtc 180
cagaaggact ccgaatcgcc ggacacggtc atcaccaacg cgctcgtcgt cgattacacc 240
ggcatctaca aagcggatat cggcatcaag gatgggaaga tcagcgcgat cggcaaggcc 300
ggcaacccgc agaccatgga cggggtgacc ccgggtcttg cagtcggcgc gtgcacggag 360
gcaatcgccg gtgaagggct catcctcacc gccggcggca tcgacaccca tattcatttc 420
atcgcgccgc agcaagtccg cacggctctt gccggtggcg tcaccaccat ggtcggcggc 480
ggcaccgggc cggctgacgg caccaacgcc accacatgct cgccgggcgc gttccacatc 540
gcccgcatga tcgaagccgc cgaagccatg ccggtgaaca tcgcgtatct gggcaaaggc 600
aacggatcat cgccggaacc attgcgcgag cagattcgtg cgggagcggc cggattgaag 660
atccacgagg attggggcgc gaccccggcc gtcatcgaca cgtgcctcgg tgtcgccgac 720
gacatggacg tgcaggtggc catccatacg gacaccctga atgagggagg atgcgtcgaa 780
gacaccatcg ccgcattcaa gggccggacc atccacacct atcacaccga aggggcgggc 840
ggcggccacg cgcccgacat catccgcgcg gccagtttcc ccaacgtgct cccgagctcc 900
acgaacccga ccatgccgtt cacccgtaac accatcgatg aacatctcga catgatgatg 960
gtcacgcatc atcttgaccg caatgtgccg gaagacatcg ccttcgccga ttcgcgtatt 1020
cgccccgaga ccatcggggc cgaggatgtg cttcatgacc ttgggctgat ctccatgatg 1080
agttcggact cgcaggccat gggacgggtc ggagaggtca tcacccgtac ctggcagacg 1140
gccgacaaga tgaaaaagca acgcggcccg ctccccgagg atgcgcacga cgacaaccgc 1200
aacgacaatt tccgtgtgaa gcggtacgtg tcgaaataca ccatcaatcc ggccatcacg 1260
cacggcatct ccgactacgt cggttccgtc gaagtcggga aaatggccga tctggtgctt 1320
tggcagccgg cgctgttcgg cgccaaaccg gagatgatca tcaagggagg atcgatcctc 1380
catgcgcgta tgggcgacgc gaatgcgtcc atacctactc ccgagccggt gctgtaccgc 1440
gacatgttcg gcgcgatggg caaagccttg ggctcctcat gcgccacatt cgtctcgcag 1500
gccgcccatg acgacgacat cgccggccgg ctcggtctcg aacggcaggt gcttccggtg 1560
cgccactgcc gtggcatcgg taagaaggat ctgaagttca atgacaccat cgcggatatt 1620
caggtcaacc ccgagacgtt ccaagtgagc gtcgacggcg agccgattca cagcgaaccg 1680
gtggcggaac tgccgttggc gcagcggtac ttcctgttct ag 1722

<210> SEQ ID NO 71
<211> LENGTH: 963
<212> TYPE: DNA
<213> ORGANISM: Bifidobacterium longum subsp. infantis

<400> SEQUENCE: 71
atgacaagca catccatcaa tccggcgccg gtccgcggcg cggggtcgga cgacatcccg 60
ttcaacccga agctgaggca gaggaggagc gtgtccgact gggtcgtcga catcgtgatc 120
tggctgttga tcgcgttggt cgtggtggcg atcgtctatc cgatctggtt catcgtgatc 180
gcctcggtct cggaccagac gatggtcagc cagggcaagg tgttcctgtt gcccgcgaag 240
atgaacttcg gcggttacgc caaggtgttc accgattcga ggatctgggt cggctaccgc 300
aacaccatct tctattcggt ggcgggcacg gccctgaaca tgctggtcac gatcccggcg 360
gcgttcgcgt tgtctcgccg cgagttcaag ccgcgccgcg tgatcctgtt cctgatgacg 420
ttcacgatgt tcttctcggg cggcatgatc ccgagcttcc tgctgtacaa gcagctgggt 480
ctgctgaact cggtgtgggt gttcatcctt ccgggcgcgg tgagcgtgtg gaacctgatc 540
gtggcgcgtt cgttcttcga gagctcgatc ccggagagcc tgcatgacgc cgcgcagatc 600
gacggcctgg ggtatttcgg gtatttcctg cggatcgtgc tgccgttgag ctccgcgatc 660
ctggcggtga tgacgttgta ttacttcgtg ggtcattgga acgacttctt cactggcttg 720
gtgtacatcc gcgacgcgga caagctgccg ttgcagaacg tgttgcgttc catcctgttg 780
tcgaaccaga cgaacatcac cggtcagagt tcgggtggca tggacgtggt gcagcagcgt 840
gatttcgcga accagatcaa gtacggcgtg atcatcgtgt cgacgttgcc gttgctggtg 900
ttgtatccgt tcctgcagaa gtatttcaac aagggcgtga tgatcggtgc cgtgaagggc 960
tga 963

<210> SEQ ID NO 72
<211> LENGTH: 954
<212> TYPE: DNA
<213> ORGANISM: Bifidobacterium longum subsp. infantis

<400> SEQUENCE: 72
atgtctgtgg tgaagcaggg tgaagtggtg gataacgcgt tggcggctcg ttccgcgccg 60
ttgccggtgc ggttggggcg tcatttccgt cggtacggcg cgttgtggct gatgacgttg 120
ccggcgttgg tgttcgtcgg tctgttcgcg tacgtgccga tgtacggtct tcgtctcgcg 180
ttctatgatt tcgatccggt cgagggtctg atgggcggca ggttcgcggg gctgcggtat 240
ttcgagcagt tcttccggtc gggcatgttc gtgaacatca tggtcaacac gttgcggatc 300
agcctgtgga cgctggtcat ggggttcatc gccccgatcg tgctggcgtt gctgatcaac 360
cagatctcgt cgtcgaagat caaggggttc gtgcagacgg tgacgtacat gccgcacttc 420
atctcgacgg tcgtgatcgt gtcgatgatc aacatcttcc tgtcgccgag cacgggcatg 480
atcgggcgcc tgttcccggg caccgacctg ttgggcgagc cggggctgtt cacgccgatc 540
tactggatca gcgaggtgtg gcagcacatg ggttggaact gcatcatcta tctggcggcg 600
ttgagttcgg tggacctgtc cctgtacgag gccgcgaaga tcgacggggc cggtcgtctg 660
cagctcatcc gctacgtcga catcccggcg atcatgccga cggtgggcat catgctgatc 720
atgaacatgg gttccgtgct caacgtgggc ttcgagaagg tgctgttgat gcagaacccg 780
atgaacctgt ccgtgtcgga ggtcatcgcg acgtacacgt accgcatggg tattctgggc 840
aaccagttca gctacacgac ggccataggc ctgttcaaca ccgtggtcaa cttcttcttc 900
ctggtgctcg ccaacttcat ttcgaagagg gcgtcggaca ccagcatctt ctag 954

<210> SEQ ID NO 73
<211> LENGTH: 1395
<212> TYPE: DNA
<213> ORGANISM: Bifidobacterium longum subsp. infantis

<400> SEQUENCE: 73
atgactgata cacatgattt cacgtcattg cccagattga accgcgcaga gcacggccgc 60
gccgcagcgc cggtgcgcat catccatctt ggtatcggca atttcaccag ggcgcatcaa 120
gcctggtaca cggaacatgc gccggacacc gcgcagtggg gcatcgccgg tttcaccgga 180
cgttctcgcc gaatggtcga caagctggcc cctcaggaca acgtctacac gctgatcacc 240
tcggcaccgg aaggcgattc gttcgaagtc atctcttcga tttcatcgat gcatgagggc 300
ggcgacatgg cggcactgca caagtacttc gcggatccga acgtgtccat cgtcacctcc 360
acggttaccg aagctggata caaaaggaac gcccacggtg atctagatgt caacgacacc 420
gacgtgtcgg aggacctcgc caaactgcgt aacgatgtga acgtgtccga acttgccacc 480
gtgcctgcac gcattgtggc cgggctggag gcgcgtcgcg cggcaaacgc cggagcgatc 540
actatccttc cctgcgacaa cctcgcaggc aacggagccg cgttccgtcg cgtcgtcgag 600
caggccattg aggccgtgga ccccaccttg ctggaatgga ctcgcgacaa cgtggcatgg 660
gccacttcga tggtcgaccg catcacgccg gccaccaccg acgccgaact gcagaccgtg 720
gcacaggacg agggatggta cgacgtggcg ccggtgcgca cggaaccgtt cctcgaatgg 780
gtcatccgag gcgacttccc gaagggacgt cctgcatggg acaaggccgg tgccgttatc 840
acggatgatg tggaacccta cgagcagcgc aaactgtgga tgctcaatgg ttcgcattcc 900

```
actctcgcct atgtcggccc gctgttcggt catgagtcgg tggccgaggc catcgctgac    960

ccgcagctgc gggcatgggt gaatgaatgg tgggatctgg ccggatcata cctgtccgtc   1020

tccagtgacg actaccgtgc caagctgttg gagcgattct ccaatccgcg cattcaccat   1080

caccttttcc aaatcgccac cgatggttcg caaaagctgc cggtacgaat cgtgcctgtc   1140

gccaagcacg cgcttgcgga cggtcgcgac atcacggctc cggcacgtgc tgtcgccgca   1200

tggatcgtgt tcctgcgtcg atttggaaac acggaggcca aggacgtgaa tctcgacgag   1260

gtgaggaaac ttgccgtcaa cgatgacgtc accccagccg tgtcctacct ggacaaggat   1320

cttggcgcca acgccacttt caccaacaag gtgagcgaac tcgtcaacga gctgtcttcg   1380

gcgacagccg cgtga                                                    1395
```

<210> SEQ ID NO 74
<211> LENGTH: 1431
<212> TYPE: DNA
<213> ORGANISM: Bifidobacterium longum subsp. infantis

<400> SEQUENCE: 74

```
atggtatccg cgctcaatga agatcgccta ttcccaacgg atccggaaca acgtttaatc     60

gcacgtcgac tgtacgaggc aatcaaggat cgtcccatca tctcccctca cggacacgtc    120

cctatcgact ggttcgcgga agacaagcat ttcaagaacc ccaccgatct attcatcact    180

cctgatcact acgtgacccg tatcatgcac ggacatagtg ttcctttcag cgagctgggt    240

gtgggccaga agaacttcac cgaagaacaa tctcgcaacg ccttccgcct ccttggaaag    300

tactggtatg cctatgctgg cacgccgatg cgttactgga tggaggattc gctgtccaat    360

gtgttcggca tcaacaagcc actcaatgaa gacaccgcag acagcatcta cgatgagctc    420

aacgagctcc ttgcctccga cgatttcacc acccgcaagc ttgtgaagcg tttcaacatc    480

ggcttcatct ccaccaccga tgaccccacc gatgacctgg tcctgcacga taaggtgcgc    540

gccgacgcca atttcccggc gcgtcttgca ccgtgtttcc gtccggatcg ctaccttgcg    600

gtcgatcgtg tggattgggc tcagctctgc gaccagctgg gtgaatcggc tggcgtaaac    660

accgccactt atgaaggatt cgtagaggcc atgcgccgtc gtcgtctgtt cttcaagcag    720

catggcgcag tcgccgccga ttacggtgtg gatccttcgc ttgacgaagt caattggtcc    780

ggcgacacca cacgcctgtc ggatgatgtg gcgattcgct tgtacaccaa ggctcgtagt    840

ggcagcctga cttccgatga ggcacgcaag ctgcacgccc atctgctcaa cgaccaggca    900

aagctcgcgc aggacgacgg tctggtaatg accttgcacc ccggcgtgat gcgcaaccac    960

taccgcaagc agctcgtcaa ctacggtccg gactgtggag cggattgccc gatgccggct   1020

gattgggctc actggctgcg ccccatgctc aacgaatacg gcgagaatcc tgatttccac   1080

cttgtggcat tcaccatgga tgagaccgca tactcccgcg agctcgctcc aatggcggca   1140

tactacccgg cgctgtacat cggagccccg tggtggttcc tggatgcgcc tgagccgatt   1200

ctgcgctact acgaggatgt cgttccgtac gctggtttcg ccaagctgtc gggattcatc   1260

gatgacaccc gtgcgctgtg ctccatcccc gcccgccacg acatgaaccg tcgtctgacc   1320

gcacgttaca tctccggtct ggtcgccgac caccggttga gttatgagga aggcgagcag   1380

atcgccattc gttccgtgga cggtcagcct tctgacgtgt tcaagctctg a            1431
```

<210> SEQ ID NO 75
<211> LENGTH: 1536
<212> TYPE: DNA
<213> ORGANISM: Bifidobacterium longum subsp. infantis

<400> SEQUENCE: 75
atgggagata agaaacaact gcttgtgaac atggtcgcaa gtttggtgaa tttcacggtt 60
tccgttggaa tcggtctggt gcttacgcca tatatcgtgc gtagcatcgg cgctgaagcc 120
tatgggttcg tcggattggc gaacacgttc gtgagctatg cgcagctgct taccatcgca 180
ttgaattcgg tggccgggcg cttcatcacg gtcgcatacc atgaaggcga tgattccaag 240
gcgaacgggt attattcgtc tacgcttgcg gcaaacggcg tcatggtcgc catactggtg 300
gtcgtcgcgg ttccggtggt gacgttcctt gacaagctgg tgaacatctc tccacatctt 360
gtgggagacg tgaaggctct gttcgtcttc atattcctga atttcatgct ttcgaccatc 420
gccacggtgt attccgtcgc cacattcgtg aagaacaagc tgtatctgag cagtatcgcg 480
aatctcgcgt tttccttggt acgtgtggtg gccatggtcg cgcttttcgg gattctgccg 540
ccaaaggtct actacgtggg cttggccgta tgcttggcga cggcggtgat gacgctgatg 600
aatcgctcgt atacgcgcag attacttccc gacatttcct tcgacaggaa atcggtatcg 660
tggacgagca ttcgtgagat gctttccgcc ggcgtgtgga acgtggtcac gaaactccag 720
cagattatga tgttcggatt gcagttgctg gtggcgaacc tgatgatcag cccgtatctt 780
atgggtatgc tctccatcgc ccagaccgtt ccgaaccaga tcagcggact aatgtggact 840
gtgtcgagcc tgttttatcc tgaacagacg aaatactatg cgcagggcaa gcataaggaa 900
ctcatcgaag acctcaaatc gggcatgaag gtgaccggtt tcttcacgaa tattattttt 960
gtggcgatgc ttgttgcagg atatgatttc atgagtttgt ggcagcatgg tcaggatacg 1020
gagctgttgt atcagttgct taccettacc atgctgggct tgctgatttc cggtgtcgct 1080
acgacgttgc agaatctgcc gctgatcgtc aaccgtttga agaagtattc tatcggatgg 1140
ctcgtctaca gtgcgatatc catggtcgtg ctgattgcct ttatcgaggt tcttccgaag 1200
tggggcgttt tcctcgtggc ggcgattccg cctctgtttg agattttggc aaatgtgaca 1260
ttcgtgcccg tttatgcctc cagatgcttg ggcatcggga aattcgagtt ctatcccatc 1320
tatattcggt acttcgcctc cacagcggtg gctgccgccg tctgctgggg aatcaggcat 1380
gtgttcgcgc tggtcgccaa tggctgggtc tcgttgattc tgacgtgttg cctgtatgca 1440
ttggtcacaa tgcttttgga tgtagtgttg ttgctcggaa agaaagaacg ttccatgttg 1500
gtaggtatgc tgaagaagaa gctacatatc aactag 1536

<210> SEQ ID NO 76
<211> LENGTH: 897
<212> TYPE: DNA
<213> ORGANISM: Bifidobacterium longum subsp. infantis

<400> SEQUENCE: 76
atgaccagca acgccatgtt cgaaggcgtg ttctgcccct ccatcaccat catgaacgcg 60
gacggaacca tagattacga caactggggc aagcacctcg accacctcgt cgacgcaggc 120
gtcgacggcg tgctgctgtt cggcagcatc ggcgaattct acgccatcga cgtcaagacg 180
aaggcggaag cggctcgctt cgccgtctcg aaggtcgccg gacgcatgaa ggtgctcgtc 240
ggcgtgggag acaccaacct ggacaacgtg aaggcgttgg cggcggaaag cgaagcggcc 300
ggagtcgacg cgctgctcgc cgtgtccccg tactatttcg gcccgtcccc ggattgcgcg 360
aaacggtact tctcggcggt ggccaaggcg acgaccctgc ccgtcatcct gtacaacttc 420
ccggcccgaa cgggcaacga cctcacgccc gagctggtgg ccgaactcgc cggcgagaac 480
ccgaacatcg tcggcatcaa agacaccgtc gacaccatca gtcacaccag gaaggtcatc 540
gcggccgtcc gcaaggtgaa cccgtcgttc agcgtgctgt ccggattcga cgaatactac 600
atcgtcaacc ggatcagcgg cggcaacggc gtgctgagtg gtctgaccaa cgtggaaccc 660
gagacgttcg tcaaactgca ccgcgcatgg gaggccggcg accacgccgc ggtcgtcgaa 720
gcggccgagc gcgtctccta cctgatgcgc ctgtacgaca ccgccgacct gttcatcagc 780
gccatcaagg gcgcggtcaa ggccaaggga ctacccatcg acacgtccgt ccacgagccc 840
gccgtgcagc tgaccgacga gcagtatcgc accatccgcg ccatcctgga caagtga 897

<210> SEQ ID NO 77
<211> LENGTH: 1266
<212> TYPE: DNA
<213> ORGANISM: Bifidobacterium longum subsp. infantis

<400> SEQUENCE: 77
atgacatttc ccgaaggatt ccagtttggt acggccacgg cctcgtatca gatcgaaggc 60
ggcgccaccg agggcggccg cgcgccatcg atttgggaca cgttctccca cacgcccggc 120
aaaaccgtga acggcgatac cggtgatgtg gcctgtgatt cctaccattt gtggcagaag 180
gacatcgatt tgctcgccga tctgggcgtg gactcctacc gtctgtctgt ggccatgccg 240
cgtgtgatgc cgaccgagga cggcccggtc aacgaggagg gccttgacta ctacgagcgc 300
gtggtcgacg cgttgctcga caagggcatc aagcccacgg tcacgctcta ccactgggat 360
ctgccgcagt acctcggcga tgggaacggt tggctcaacc gcgacaccgc ctacaaactg 420
gccgactatg cgcgcatcgt ggctcaccgt ctgggcgacc gcgtcgaaac ctacaccacg 480
ttgaacgagc cgtggtgctc ctcctacctg agctacggcg ccaccgagca cgcacccggt 540
ctgggccttg gtcccggtgc cttcccggcc gtgcatcatc tgaatctggc tcatggtctg 600
atggcccagg cggtgcgtag cgaggtcggc gacaggtcgc agctgtcggt cacgctgaac 660
ctgcagttca accgtggcga cgccgacgcc gtgcaccgtc tcgacctgat cggcaaccgc 720
gtgtggctcg acccgatgct gcgcggctac tacccgaacg agctgttcgc catcaccaag 780
ggcatctgcg attgggagtt cgtcaaggac ggcgacctcg aacagatcca tcagccgctg 840
gacgtgctcg gcatcaacta ctattcctcc ggcttggtca cgatgagcgg acgcccgcag 900
ttcccgcagt ccacgggccc gagcaccgcg cctggtgcca gcgacgtcga ctggctgccg 960
acgcccggcg agcacaccga catgggctgg aacatcgatc cgaagggcct atatgacctg 1020
ctgatgcgcg tgcataacga ttatccagag attccgctga tggtcaccga aaacggcatc 1080
gcggtcgagg gcggcgaccg ggtcgtcacc gaggcggatg gcaccaaggc cgtgcacgac 1140
cccaagcgca tcgactacct gaagcggcac ttcgaggccg cactcaaggc tatcgaggac 1200
ggcgtggatt tgcgcggcta cttcgtgtgg tccatcgcac cagctgccaa gcagtccggc 1260
tactga 1266

<210> SEQ ID NO 78
<211> LENGTH: 165
<212> TYPE: DNA
<213> ORGANISM: Bifidobacterium longum subsp. infantis -continued

```
<400> SEQUENCE: 78

atgacattgc cgccgcaatc gcgaaaagac gatgactgcg gcggcatcct caacatcact     60

ccaacagaaa gcatgaccca cggcaccacg cgtcaggcgc tcagtctcat caccaatccc    120

atcatcacca tcgtgctttt tgcgctcgcc gtgttcgcct gctga                    165
```